United States Patent
Lu et al.

(10) Patent No.: US 8,530,443 B2
(45) Date of Patent: Sep. 10, 2013

(54) MIR-150 FOR THE TREATMENT OF BLOOD DISORDERS

(71) Applicants: Jun Lu, North Haven, CT (US); Shangqin Guo, North Haven, CT (US); Benjamin Ebert, Brookline, MA (US); David Scadden, Weston, MA (US); Todd Golub, Newton, MA (US)

(72) Inventors: Jun Lu, North Haven, CT (US); Shangqin Guo, North Haven, CT (US); Benjamin Ebert, Brookline, MA (US); David Scadden, Weston, MA (US); Todd Golub, Newton, MA (US)

(73) Assignees: The General Hospital Corporation, Boston, MA (US); Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/652,672

(22) Filed: Oct. 16, 2012

(65) Prior Publication Data
US 2013/0039895 A1  Feb. 14, 2013

Related U.S. Application Data

(63) Continuation of application No. 12/363,016, filed on Jan. 30, 2009, now abandoned.

(60) Provisional application No. 61/062,931, filed on Jan. 30, 2008, provisional application No. 61/086,556, filed on Aug. 6, 2008.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................ 514/44 A; 536/24.5

(58) Field of Classification Search
USPC ........................ 514/44 A; 536/24.5
See application file for complete search history.

(56) References Cited

U.S. PATENT DOCUMENTS
7,683,036 B2  3/2010  Esau et al.

OTHER PUBLICATIONS

Barroga, C.F. et al., Experimental Hematology, 36:1585-1592 (2008). "Thrombopoietin regulates c-MyB expression by modulating micro RNA 150 expression."
Bruchova, H. et al., Experimental Hematology, 35:1657-1667 (2007). "Regulated expression of microRNAs in normal and polycythemia vera erythropoiesis."
Bruchova, H. et al., Haematologica, 93(7):1009-1016 (2008). "Aberrant expression of microRNA in polycythemia vera."
Dai, Y. et al., Lupus, 16:939-946 (2007). "Microarray analysis of microRNA expression in peripheral blood cells of systemic lupus erythematosus patients."
Emambokus, N. et al., The EMBO Journal, 22(17):4478-4488 (2003). "Progression through key stages of haemopoiesis is dependent on distinct threshold levels of c-Myb."
Lu, J. et al., Developmental Cell, 14:843-853 (2008). "MicroRNA-Mediated Control of Cell Fate in Megakaryocyte-Erythrocyte Progenitors."
Merkerova, M. et al., European Journal of Haematology, 81:304-310 (2008). "Differential expression of microRNAs in hematopoietic cell lineages."

(Continued)

*Primary Examiner* — Terra Cotta Gibbs
(74) *Attorney, Agent, or Firm* — David S. Resnick; Nixon Peabody LLP

(57) ABSTRACT

The invention provides methods of treating certain blood related disorders, in particular, thrombocytopenia and anemia comprising increasing miR-150 expression or inhibiting miR-150 in progenitor cells respectively.

5 Claims, 24 Drawing Sheets

(56) References Cited

OTHER PUBLICATIONS

Mukai, H.Y. et al., Molecular and Cellular Biology, 26(21):7953-7965 (2006). "Transgene Insertion in Proximity to the c-myb Gene Disrupts Erythroid-Megakaryocytic Lineage Bifurcation."

Xiao, C. et al., Cell, 131:146-159 (2007). "MiR-150 Controls B Cell Differentiation by Targeting the Transcription Factor c-Myb."

Zhou, B. et al., PNAS, 104(17):7080-7085 (2007). "miR-150, a microRNA expressed in mature B and T cells, blocks early B cell development when expressed prematurely."

Lin et al., Molecular Biology and Evolution, 25(10):2189-98 (2008).

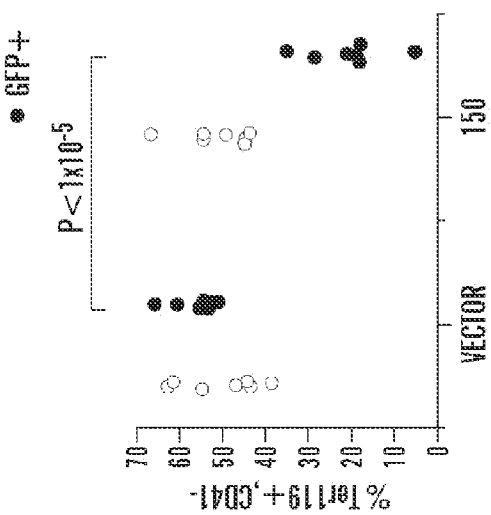
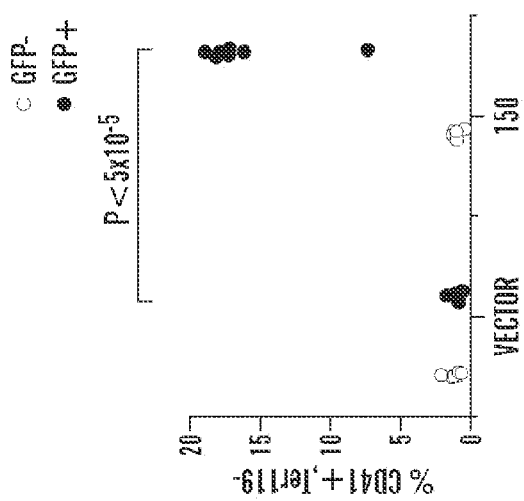
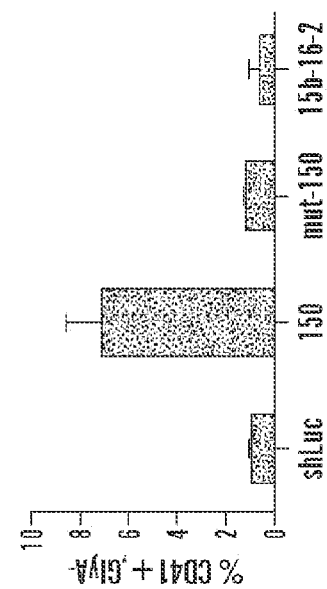
FIG. 2D
FIG. 2C
FIG. 2B

```
    Human: UCUCCCAACCCUUGUACCAGUG
    Mouse: UCUCCCAACCCUUGUACCAGUG
      Rat: UCUCCCAACCCUUGUACCAGUG
      Cow: UCUCCCAACCCUUGUACCAGUGU
     Frog: UCUCCCAACCCUUGUACCAGAG
Zebrafish: UCUCCCAAUCCUUGUACCAGUG
```

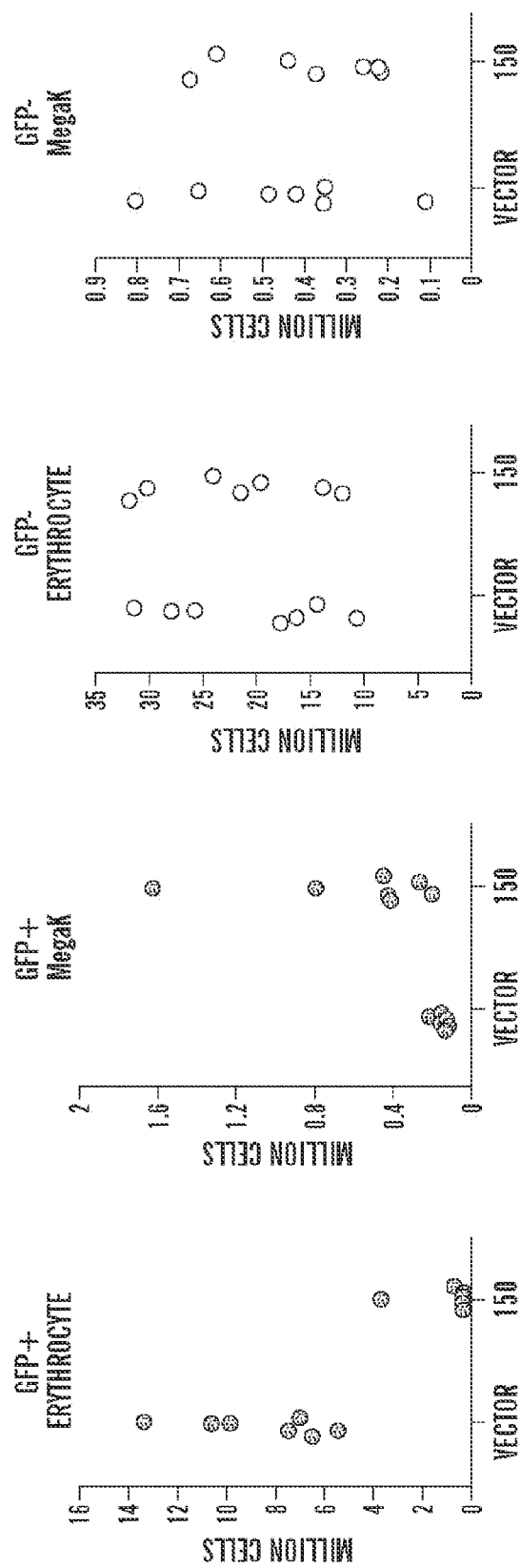

Human Myo 3' UTR

GACATTTCCAGAAAAGCATTATGTGTTTCAGAACACTTCAAGTTGACTTGGGATATATCATTCCTCAACATGAAACTTTTCATGAATGGGAGAA
GAACCTATTTTTGTTGTGTACAACAGTTGAGAGCAGCACCAAGTGCATTTAGTTGAATGAAGTCTTCTTGATTCACCAACTAAAAGGATT
TTTAAAAATAAATAACAGTCTTACCTAAATTATTAGGTAATGAATTGTAGCCAGTTGTTGTAATATCCAGATTTTGAAATTGACACATTAAAAGTACTCCAGT
AAATGATTTATCTGTATTTTAAGGATCCAACAGATCAGTATTTTTCCTGTGATGGGTTTTTGAAATTGACACATTAAAAGTACTCCAGT
ATTTCACTTTTCTGATCACTAAACATATGCATATATTTTAAAAATCAGTAAAAACATTACTCTAGTGTAGACTAATACCATGACATT
AATCCAGATTGTAAATGCTCATTTATGGTTAATGACATTGAAGGTACATTATTGTACCAAACCATTTATGAGTTTTTCTGTTAGCTTGCTTTA
AAAATTATTACTGTAAGAAATAGTTTTATAAAAATATTATTTATTCAGTAATTAATTGTAAATGCAAATGGTGTTAGTAATTGACTAT
CTAGGTCTTAGCCTGTAGACATGCTGCTAGTATCAGAGGGCCAGTAGAGCTGGACAGAAAGAAAAGAAACTGGTGTTAGTAATTGACTAT
GCACTAGTATTTCAGACTTTTTAATTT-ATAT-TATATACATTTTTTTTCCTCTGCAATACATTGAAAACTTGTTTGGAGACTCTGCATT
TTTATTGTGTTTTTTGTATTGTTGGTTTATACAAGCATGCGTTCGCATTTGATCCGCATCCCTGTGTTTCTAAGTGTATGGTCTCAGAACTGTTGCA
TTGAGTGTAGCCTGACTGTTTTATAATTGGAGTTCTGCATTTGATCCGCATCCCTGTGTTTCTAAGTGTATGGTCTCAGAACTGTTGCA
GGACCCTGTGTTTGCAACTGGGACGTACTACTCCTTGTAGCAAATAAAGATGTGCCCTTATTTACCT
TTTGAGATATGACGGTACTTACTCCTTGTAGCAAATAAAGATGTGCCCTTATTTACCT

FIG. 17A

| | | | | |
|---|---|---|---|---|
| Human | atcaatggagagaa | -ttgtttgggagac-- | ---tttgggaga--t | -aatttgggac---t |
| Mouse | atcgctcagagagag | -ttatttgggagaa-- | t--tttgggaga--t | ccgttggcgtttt |
| Rat | gtcactcagggggaga- | -ttatttgggagaa-- | ttcttgggaga-tt | ccgttggca-ctt |
| Dog | atcaatggcagagag | -ttgtttgggagat-- | ---tttgggaga--t | -aattcagagg---t |
| Opossum | atcaatggcagat-gga | ttttttcttggatt-- | ---tttgggaga--t | -aatccaaat---t |
| Chicker | gtcaatggcagacgag | tgttcctgggagt-- | ---tttgggaaca | -acctttgggtc---t |
| Xenopus tropicalis | atcattggcaga---- | -tgatgtgggagt-gg | -tctgtatga--t | aaacccaaga---c |

FIG. 17B

SEQUENCE LISTING

<160> NUMBER OF SEQ ID NOS: 798

<210> SEQ ID NO 1
<211> LENGTH: 84
<212> TYPE: RNA
<213> ORGANISM: Homo sapiens

<400> SEQUENCE: 1
cuccccaugg cccugucucc caacccuugu accagugcug ggcucagacc cugguacagg    60 ccuggggac agggaccugg ggac    84

<210> SEQ ID NO 2
<211> LENGTH: 22
<212> TYPE: RNA
<213> ORGANISM: Homo sapiens

<400> SEQUENCE: 2
ucucccaacc cuuguaccag ug    22

<210> SEQ ID NO 3
<211> LENGTH: 22
<212> TYPE: RNA
<213> ORGANISM: Homo sapiens

<400> SEQUENCE: 3
cugguacagg ccuggggac ag    22

<210> SEQ ID NO 4
<211> LENGTH: 22
<212> TYPE: RNA
<213> ORGANISM: Homo sapiens

<400> SEQUENCE: 4
cacugguaca aggguuggga ga    22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cagcataggg tggagtgggt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tactttgcgc atcacacaga                                                 20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tttcctcaaa acaggaagg                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ccaccaagta agtcattttc                                                 20

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ccccatggcc ctgtctggga acccttgtac cagtg                                35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cactggtaca agggttccca gacagggcca tgggg                                35

```
<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccctggtaca ggcctcccgg acagggacct g                                          31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caggtccctg tccgggaggc ctgtaccagg g                                          31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taactcgaga catttccaga aaagcattat g                                          31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atagcggccg caggtaaaat aagggcacat c                                          31

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acttttcatg aatcccagaa gaacctat                                              28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataggttctt ctgggattca tgaaaagt                                              28

<210> SEQ ID NO 17
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgaaaacttg tttcccagac tctgcatt                                          28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aatgcagagt ctgggaaaca agttttca                                          28

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgcacttctt ttttcccaga tgtgtgttgt                                        30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acaacacaca tctgggaaaa aagaagtgca                                        30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctgttttata atttcccagt tctgcatttg                                        30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaatgcaga actgggaaat tataaaacag                                        30

<210> SEQ ID NO 23
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'O-Methyl-cytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 2'O-Methyl-adenine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (3)..(3)
<223> OTHER INFORMATION: 2'O-Methyl-cytosine
<220> FEATURE:
<221> NAME/KEY: modified_base
<222> LOCATION: (4)..(4)
<223> OTHER INFORMATION: 2'O-Methyl-uracil
<220> FEATURE:
<221> NAME/KEY: modified_base
<222> LOCATION: (5)..(6)
<223> OTHER INFORMATION: 2'O-Methyl-guanine
<220> FEATURE:
<221> NAME/KEY: modified_base
<222> LOCATION: (7)..(7)
<223> OTHER INFORMATION: 2'O-Methyl-uracil
<220> FEATURE:
<221> NAME/KEY: modified_base
<222> LOCATION: (8)..(8)
<223> OTHER INFORMATION: 2'O-Methyl-adenine
<220> FEATURE:
<221> NAME/KEY: modified_base
<222> LOCATION: (9)..(9)
<223> OTHER INFORMATION: 2'O-Methyl-cytosine
<220> FEATURE:
<221> NAME/KEY: modified_base
<222> LOCATION: (10)..(11)
<223> OTHER INFORMATION: 2'O-Methyl-adenine
<220> FEATURE:
<221> NAME/KEY: modified_base
<222> LOCATION: (12)..(14)
<223> OTHER INFORMATION: 2'O-Methyl-guanine
<220> FEATURE:
<221> NAME/KEY: modified_base
<222> LOCATION: (15)..(16)
<223> OTHER INFORMATION: 2'O-Methyl-uracil
<220> FEATURE:
<221> NAME/KEY: modified_base
<222> LOCATION: (17)..(19)
<223> OTHER INFORMATION: 2'O-Methyl-guanine
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: modified_base
<222> LOCATION: (20)..(20)
<223> OTHER INFORMATION: 2'O-Methyl-adenine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (21)..(21)
<223> OTHER INFORMATION: 2'O-Methyl-guanine
<220> FEATURE:
<221> NAME/KEY: misc_feature
<222> LOCATION: (21)..(22)
<223> OTHER INFORMATION: Phosphorothioate linkage
<220> FEATURE:
```

```
<221> NAME/KEY: modified_base
<222> LOCATION: (22)..(22)
<223> OTHER INFORMATION: 2'O-Methyl-adenine

<400> SEQUENCE: 23
cacugguaca aggguuggga ga                                              22

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'O-Methyl-cytosine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 2'O-Methyl-uracil
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (3)..(3)
<223> OTHER INFORMATION: 2'O-Methyl-cytosine
<220> FEATURE:
<221> NAME/KEY: modified_base
<222> LOCATION: (4)..(4)
<223> OTHER INFORMATION: 2'O-Methyl-guanine
<220> FEATURE:
<221> NAME/KEY: modified_base
<222> LOCATION: (5)..(5)
<223> OTHER INFORMATION: 2'O-Methyl-cytosine
<220> FEATURE:
<221> NAME/KEY: modified_base
<222> LOCATION: (6)..(6)
<223> OTHER INFORMATION: 2'O-Methyl-guanine
<220> FEATURE:
<221> NAME/KEY: modified_base
<222> LOCATION: (7)..(7)
<223> OTHER INFORMATION: 2'O-Methyl-uracil
<220> FEATURE:
<221> NAME/KEY: modified_base
<222> LOCATION: (8)..(8)
<223> OTHER INFORMATION: 2'O-Methyl-adenine
<220> FEATURE:
<221> NAME/KEY: modified_base
<222> LOCATION: (9)..(9)
<223> OTHER INFORMATION: 2'O-Methyl-guanine
<220> FEATURE:
<221> NAME/KEY: modified_base
<222> LOCATION: (10)..(11)
<223> OTHER INFORMATION: 2'O-Methyl-adenine
<220> FEATURE:
<221> NAME/KEY: modified_base
<222> LOCATION: (12)..(12)
<223> OTHER INFORMATION: 2'O-Methyl-guanine
<220> FEATURE:
<221> NAME/KEY: modified_base
<222> LOCATION: (13)..(13)
<223> OTHER INFORMATION: 2'O-Methyl-adenine
<220> FEATURE:
<221> NAME/KEY: modified_base
<222> LOCATION: (14)..(14)
<223> OTHER INFORMATION: 2'O-Methyl-guanine
<220> FEATURE:
<221> NAME/KEY: modified_base
<222> LOCATION: (15)..(15)
<223> OTHER INFORMATION: 2'O-Methyl-uracil
```

```
<220> FEATURE:
<221> NAME/KEY: modified_base
<222> LOCATION: (16)..(16)
<223> OTHER INFORMATION: 2'O-Methyl-adenine
<220> FEATURE:
<221> NAME/KEY: modified_base
<222> LOCATION: (17)..(18)
<223> OTHER INFORMATION: 2'O-Methyl-guanine
<220> FEATURE:
<221> NAME/KEY: modified_base
<222> LOCATION: (19)..(19)
<223> OTHER INFORMATION: 2'O-Methyl-uracil
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: modified_base
<222> LOCATION: (20)..(21)
<223> OTHER INFORMATION: 2'O-Methyl-guanine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: misc_feature
<222> LOCATION: (21)..(22)
<223> OTHER INFORMATION: Phosphorothioate linkage
<220> FEATURE:
<221> NAME/KEY: modified_base
<222> LOCATION: (22)..(22)
<223> OTHER INFORMATION: 2'O-Methyl-adenine

<400> SEQUENCE: 24
cucgcguaga agaguaggug ga                                              22

<210> SEQ ID NO 25
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25 aauaaa                                                                 6

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
actcagaagg acaagtagag tttt                                            24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
gtggtaatcc ctggcaatgt gat                                             23

<210> SEQ ID NO 28
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 28
acactctaaa gggaaccatt tt                                              22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ggaaatccct ggcaatgtga t                                               21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
aaagaagtgc accatgtttg ttt                                             23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
aaagtgtcag atacggtgtg g                                               21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aagaagtgca ccgcgaatgt                                                 20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
acagttcttc aactggcagc tt                                              22

<210> SEQ ID NO 34
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 34
aacactctga agggaagcgc                                                    20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ctacctgcac tataagcact tta                                                23

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
cactctaaaa ggatgcactt t                                                  21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
tcagttttgc atggatttgc aca                                                23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ttcaccaaag ggaagcactt t                                                  21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
cccaacaaca tgaaactacc ta                                                 22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 40
acactctaaa gggaagtgcg tt                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
acaaagttct gtagtgcact ga                                              22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
ctcccttctt tcctcccgtc                                                 20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ctagtacatc atctatactg ta                                              22

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
ctcacaccta ggttccaagg att                                             23

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
tgagctacag tgcttcatct ca                                              22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
```
ttacagatgg ataccgtgca att                                      23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ccatctttac cagacagtgt t                                        21

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
ccacgaccga cgccacgcc                                           19

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ctaccatagg gtaaaaccac t                                        21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
cctctaaaag gaagcacttt ct                                       22

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tggagacacg tgcactgtag a                                        21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
gaacatacaa agggtatcct ct                                       22

```
<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
ttcacatagg aataaaaagc cata                                          24

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
cgaatataac acggtcgatc t                                             21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
acagctggtt gaaggggacc aa                                            22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
cctccagccc ctccagggct                                               20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
ggggtatttg acaaactgac a                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
tcaatcacag atagcacccc t                                             21
```

```
<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
gcaaaaatgt gctagtgcca aa                                              22

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
gtagtgcaac tatgcaaaac t                                               21

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
tcatacagct agataaccaa aga                                             23

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
tggtggcagt ggtgggat                                                   18

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
cttccagtcg gggatgttta ca                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
acactctaaa gggatgcacg at                                              22

<210> SEQ ID NO 65
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
acacaaattc ggttctacag gg                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
aaagtgcttc ttacctccag at                                              22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
accctccacc atgcaaggga tg                                              22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
acctctaaag gggagcgctt                                                 20

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
cctatctccc ctctggacc                                                  19

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
acactctaaa gggaggcact tt                                              22

<210> SEQ ID NO 71
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 71
ggctgtcaat tcataggtca g                                                 21

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
tccaggagct cacaatctag tg                                                22

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
cggctgcaac acaagacacg a                                                 21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
gttaccgcag gctgctctgg                                                   20

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
cagtgaattc taccagtgcc ata                                               23

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
agaaagcgct tccctgtaga g                                                 21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 77
tgtgagttct accattgcca aa                                              22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
agccaagtaa tggagaacag g                                               21

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
cgaaggcaac acggataacc ta                                              22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
agaaagcgct tccctctaga g                                               21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
tcacttttgt gactatgcaa                                                 20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
acagaaaggg cttccctttg c                                               21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 83
ccaagttctg tcatgcactg a                                          21

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tcggtccctc gggccaggg                                             19

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
ggagtgaaga cacggagcca ga                                         22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
tctaagccac catgtgaaac ca                                         22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
acaaagttct gtgatgcact ga                                         22

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
gcaaggcagt ggcctgtaca                                            20

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
```
gctgagagtg taggatgttt aca                                    23

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
tccagcaaag ggaagcgctt                                        20

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
aaccgatttc agatggtgct ag                                     22

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
accctctata gggaagcgcg t                                      21

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
gtcatcatta ccaggcagta tta                                    23

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
caggtaacaa ctcgccgctc                                        20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
aaccaatgtg cagactactg ta                                     22

-continued

```
<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96 actgcactttt tatgaataag ctc                                          23

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
gctgggtgga gaaggtggtg aa                                            22

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
aacgctccaa aagaaggcac t                                             21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99 gccaatatttt ctgtgctgct a                                            21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
accagaactg agtccacagg g                                             21

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
cgcaaggtcg gttctacggg tg                                            22

<210> SEQ ID NO 102
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tcccgtcgcc agcggaggc                                                19

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
acaccgagga gcccatcatg at                                            22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
actgaaacca agtatgggtc gc                                            22

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
cctgcatgac ggcctgcaag aca                                           23

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
cagccctcct ggtggctgg                                                19

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
ataaggattt ttaggggcat ta                                            22

<210> SEQ ID NO 108
<211> LENGTH: 21
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 108
atctacactg gctactgagc c                                            21

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
tattaggaac acatcgcaaa aa                                           22

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
cgcgactgcg tcaccggcc                                               19

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
accagctaac aatacactgc ca                                           22

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
cctgcgccat ctcctctac                                               19

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
atgggacatc ctacatatgc aa                                           22

<210> SEQ ID NO 114
<211> LENGTH: 23
<212> TYPE: DNA
<213> ORGANISM: Artificial Sequence
<220> FEATURE:

-continued

<223> OTHER INFORMATION: Description of Artificial Sequence: Synthetic
      probe

<400> SEQUENCE: 114
actgtgtttc agctcagtag gca                                           23

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
ttcaaaacat gaattgctgc tg                                            22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
cgaacacagc agggataacc ac                                            22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
gtacccctgg agattctgat aa                                            22

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
actgcagaac tgttcccgct g                                             21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
tcacgcgagc cgaacgaaca aa                                            22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 120
agaaaatgcc cctcagtttt ga                                              22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
acaaaagttg cctttgtgtg at                                              22

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
agacgggagg agaggagtga                                                 20

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
acacaggacc tggagtcagg ag                                              22

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
atcgggaggg gactgagcct                                                 20

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
cctacgttcc atagtctacc a                                               21

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
```
ctcggggcag ctcagtacag                                           20

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
gcgcatgttc tatggtcaac ca                                        22

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
cgagccggtc gaggtccggt                                           20

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
acagagagct tgcccttgta ta                                        22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
tctcgtgaca tgatgatccc cg                                        22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
tatgaacaat ttctaggaat                                           20

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
agaaagcgct ttcctttgta ga                                        22

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
ggcggacacg acattcccga t                                             21

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
cacatggcca aaacagagaa ga                                            22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
gtctcagttt cctctgcaaa ca                                            22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
ccacccaatg acctactcca ag                                            22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
gctgtaaaca tccgactgaa ag                                            22

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
tcatctcgcc cgcaaagacc                                               20

```
<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139 atgcttttg gggtaagggc tt                                              22

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
agaaagtgct ttcttttgga gaa                                            23

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
acggcattac cagacagtat ta                                             22

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
gaaagtgctt ctttcctcga gaa                                            23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
tctctgcagg ccctgtgctt tgc                                            23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
cacaggttaa agggtctcag gga                                            23

<210> SEQ ID NO 145
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
tgttgcagcg cttcatgttt                                                   20

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
acaaattcgg ttctacaggg ta                                                22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
agccacagtc accttctgat ct                                                22

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
tgatagccct gtacaatgct gct                                               23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
catgcataca tgcacacata cat                                               23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
tcatagccct gtacaatgct gct                                               23

<210> SEQ ID NO 151
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 151
caacaaacat ttaatgaggc c                                              21

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
aactatacaa tctactacct ca                                             22

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
tgatggacaa caaattaggt a                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
actatgcaac ctactacctc t                                              21

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
tatctcacag aataaacttg gta                                            23

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
ttcagctatc acagtactgt a                                              21

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

```
    probe

<400> SEQUENCE: 157
tcacatcagt gccattctaa ata                                          23

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
ctatacaacc tcctacctca                                              20

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
gtcttatgtg tgcgtgtatg tat                                          23

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
ctcaatagac tgtgagctcc tt                                           22

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
gtgtaggtgt gtgtatgtat at                                           22

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
aacctatcct gaattacttg aa                                           22

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 163
cagacacacg cacatcagtc ata                                           23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
tccatcatca aaacaaatgg agt                                           23

<210> SEQ ID NO 165
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
ggacaccaag atcaatgaaa gaggca                                        26

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
aggcaaagga tgacaaaggg aa                                            22

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
tcaccagtgc cagtccaaga a                                             21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
gaacaggtag tctaaacact ggg                                           23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
```

```
tgtgaaaagc actatactac gta                                              23
```

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170

```
atccagtcag ttcctgatgc agta                                             24
```

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171

```
agactagata tggaagggtg a                                                21
```

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172

```
gctgcaaaca tccgactgaa ag                                               22
```

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173

```
tctgggcaca cggagggaga                                                  20
```

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174

```
taaccgattt caaatggtgc ta                                               22
```

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175

```
acggtcaggc tttggctaga t                                                21
```

```
<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
aacaatacaa cttactacct ca                                              22

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
agaggcaggc actcaggcag a                                               21

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
atacatactt ctttacattc ca                                              22

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
tgggcgaccc agagggaca                                                  19

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
gctgagtgta ggatgtttac a                                               21

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
agaggttaag acagcagggc tg                                              22

<210> SEQ ID NO 182
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
atgccctttt aacattgcac tg                                              22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
ggttcaaacc atgagtcgag ct                                              22

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
ctacgcgtat tcttaagcaa taa                                             23

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
ggagtcgagt gatggttcaa a                                               21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
agaacaatgc cttactgagt a                                               21

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
gaataatgac aggctcaccg ta                                              22

<210> SEQ ID NO 188
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 188
tcttcccatg cgctatacct ct                                              22

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
tactatgcaa cctactactc t                                               21

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
ccacacactt ccttacattc ca                                              22

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
ctgaggggcc tcagaccgag ct                                              22

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
gagggaggag agccaggaga agc                                             23

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
taactgcact agatgcacct ta                                              22

<210> SEQ ID NO 194
<211> LENGTH: 22
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 194
acaagctttt tgctcgtctt at                                              22

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ctacctgcac tatgagcact ttg                                             23

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
ggccgtgact ggagactgtt a                                               21

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
ggggacgaaa tccaagcgca gc                                              22

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
cacagttgcc agctgagatt a                                               21

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
aataggtcaa ccgtgtatga tt                                              22

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 200
acatggttag atcaagcaca a                                              21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
gcagaagcat ttccacacac                                                20

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
acaaccagct aagacactgc ca                                             22

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
cccctatcac gattagcatt aa                                             22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
aggcgaagga tgacaaaggg aa                                             22

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
acaagtgcct tcactgcagt                                                20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
```
gtctgtcaat tcataggtca t                                                 21

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
tccagcactg tccggtaaga tg                                                22

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
atccaatcag ttcctgatgc agta                                              24

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
aaagcaagta catccacgtt ta                                                22

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
actacctgca ctgtaagcac tttg                                              24

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
aagcggttta ccatcccaca ta                                                22

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
tatctgcact agatgcacct ta                                                22

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
tagttggcaa gtctagaacc a                                              21

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
aacccaccga cagcaatgaa tgtt                                           24

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
ctactaaaac atggaagcac tta                                            23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
gaacaggtag tctgaacact ggg                                            23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
agaaagcact tccatgttaa agt                                            23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
gaacagatag tctaaacact ggg                                            23

```
<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
ccactgaaac atggaagcac tta                                              23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
tcagttttgc atagatttgc aca                                              23

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
cagcaggtac ccccatgtta                                                  20

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ctagtggtcc taaacatttc ac                                               22

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
acactcaaac atggaagcac tta                                              23

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
aggcatagga tgacaaaggg aa                                               22

<210> SEQ ID NO 225
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
acttactgga cacctactag g                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
cagccgctgt cacacgcaca g                                              21

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
aaaggcatca taggagct gga                                              23

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
ctgcctgtct gtgcctgctg t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
gccctggact aggagtcagc a                                              21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
cacaagttcg gatctacggg tt                                             22

<210> SEQ ID NO 231
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 231
agaggcaggc atgcgggcag                                                    20

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
gctacctgca ctgtaagcac tttt                                               24

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
tcaccattgc taaagtgcaa tt                                                 22

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
cacaaattcg gatctacagg gta                                                23

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
aaacgtggaa tttcctctat gt                                                 22

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
acaaacacca ttgtcacact cca                                                23

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 237
aaagatcaac catgtattat t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
cgcgtaccaa aagtaataat g                                              21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
agccacaatc accttctgat ct                                             22

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
gccctttcat cattgcactg                                                20

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
tctctgcagg ccgtgtgctt tgc                                            23

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
tccctctggt caaccagtca ca                                             22

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 243
acggttttac cagacagtat ta                                          22

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
gtagtgcttt ctactttatg                                             20

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
acgtggattt tcctctatga t                                           21

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
cccctatcac aattagcatt aa                                          22

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
ggccttctga ctccaagtcc ag                                          22

<210> SEQ ID NO 248
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
tgtaaaccat gatgtgctgc ta                                          22

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
```
aagatgtgga ccatattaca ta                                              22

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
actcaccgac aggttgaatg tt                                              22

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
ggccttctga ccctaagtcc ag                                              22

<210> SEQ ID NO 252
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
cacaaaccat tatgtgctgc ta                                              22

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
aaagaggtta accaggtgtg tt                                              22

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
taactgtaca aactactacc tca                                             23

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
cgaactcacc acggacaacc tc                                              22

```
<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
acaggccggg acaagtgcaa tat                                              23

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
cttctttgca gatgagactg a                                                21

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
taacccatgg aattcagttc tca                                              23

<210> SEQ ID NO 259
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
tgcaaagttg ctcgggtaac ct                                               22

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
aaccatacaa cctactacct ca                                               22

<210> SEQ ID NO 261
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
aacatggatt ttcctctatg at                                               22

<210> SEQ ID NO 262
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
aacaacaaaa tcactagtct tcca                                              24

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
gaattcatca cggccagcct ct                                                22

<210> SEQ ID NO 264
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
actttcggtt atctagcttt at                                                22

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
agaggagagc cgtgtatgac                                                   20

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
acagcacaaa ctactacctc a                                                 21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
ttgagagtgc cattatctgg g                                                 21

<210> SEQ ID NO 268
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 268
aactatacaa cctactacct ca                                              22

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
gctgccgtat atgtgatgtc act                                             23

<210> SEQ ID NO 270
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
aaccacacaa cctactacct ca                                              22

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
cagcatggag tcctccaggt tg                                              22

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
ccgaccatgg ctgtagactg tta                                             23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
tcctcatgga agggttcccc act                                             23

<210> SEQ ID NO 274
<211> LENGTH: 23
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 274
acaccaatgc cctaggggat gcg                                              23

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
tgactgcaga gcaaaagaca c                                                21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
tggcattcac cgcgtgcctt a                                                21

<210> SEQ ID NO 277
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
agcctatgga attcagttct ca                                               22

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
tcacaagtta gggtctcagg ga                                               22

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
aaagaagtat atgcatagga aa                                               22

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 280
cacaagatcg gatctacggg t                                            21

<210> SEQ ID NO 281
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
ttttcccatg ccctatacct ct                                           22

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
cgccaatatt tacgtgctgc ta                                           22

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
aagaatcttg tcccgcaggt cct                                          23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
aacactgatt tcaaatggtg cta                                          23

<210> SEQ ID NO 285
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
aatgaaagcc taccatgtac aa                                           22

<210> SEQ ID NO 286
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
```
cttcagttat cacagtactg ta                                             22

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
agacatggag gagccatcca g                                              21

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
acaggagtct gagcatttga                                                20

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 289
aagaggtttc ccgtgtatgt ttca                                           24

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
atctgcactg tcagcacttt a                                              21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
ggagattggc catgtaatac t                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
gcattattac tcacggtacg a                                              21

```
<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
acaaaccaca gtgtgctgct g                                              21

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
agccaagctc agacggatcc ga                                             22

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 295
aacccaccga caacaatgaa tgtt                                           24

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
actgatatca gctcagtagg cac                                            23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
gaaagtgccc tcaaggctga gtg                                            23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298
tccatcatta cccggcagta tta                                            23
```

```
<210> SEQ ID NO 299
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 299
gacctcagct atgacagcac tt                                              22

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
taaacggaac cactagtgac ttg                                             23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301
gaaaaacgcc ccctggcttg aaa                                             23

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
tcagaccgag acaagtgcaa tg                                              22

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
ccctcaaaaa ggaagcactt t                                               21

<210> SEQ ID NO 304
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
ggcggaactt agccactgtg aa                                              22

<210> SEQ ID NO 305
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 305
gaaagtgctc cctttggag aa                                              22

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
acaggattga gggggggccc t                                              21

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
acactctaaa aggaggcact tt                                             22

<210> SEQ ID NO 308
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
atgtatgtgg gacggtaaac ca                                             22

<210> SEQ ID NO 309
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 309
atcctctaaa aagatgcact tt                                             22

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 310
gctttgacaa tactattgca ctg                                            23

<210> SEQ ID NO 311
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 311
agaaagtact tccctctgga g                                            21

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 312
tcaccaaaac atggaagcac tta                                          23

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 313
acagtccaaa gggaagcact tt                                           22

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
gcttccagtc gaggatgttt aca                                          23

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 315
aacagaaagt gcttccctca agag                                         24

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 316
tccagtcaag gatgtttaca                                              20

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                                    probe

<400> SEQUENCE: 317
gcctctaaaa ggaagcactt t                                          21

<210> SEQ ID NO 318
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 318
cagctatgcc agcatcttgc ct                                         22

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 319
aaacctctaa aaggatgcac ttt                                        23

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320
gcaacttagt aatgtgcaat a                                          21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 321
agaaagtgca tccctctgga g                                          21

<210> SEQ ID NO 322
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 322
caatcagcta atgacactgc ct                                         22

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 323
gctctaaagg gaagcgcctt c                                             21

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 324
gcaatcagct aactacactg cct                                           23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 325
agagaaagtg cttccctcta gag                                           23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 326
ctacctgcac gaacagcact ttg                                           23

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 327
tcctctaaag agaagcgctt t                                             21

<210> SEQ ID NO 328
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 328
tgctcaataa atacccgttg aa                                            22

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 329
```

-continued

```
cagaaagtgc ttccctccag aga                                           23

<210> SEQ ID NO 330
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 330
agcaagccca gaccgcaaaa ag                                            22

<210> SEQ ID NO 331
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 331
cactctaaag agaagcgctt tg                                            22

<210> SEQ ID NO 332
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 332
agaaaggcag caggtcgtat ag                                            22

<210> SEQ ID NO 333
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 333
gagaaagtgc ttccctttgt ag                                            22

<210> SEQ ID NO 334
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 334
tacctgcact gttagcactt tg                                            22

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 335
actccaaagg gaagcgcctt c                                             21
```

<210> SEQ ID NO 336
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 336
cacataggaa tgaaaagcca ta                                          22

<210> SEQ ID NO 337
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 337
agacagtgct tccatctaga gg                                          22

<210> SEQ ID NO 338
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 338
cctcaaggag cctcagtcta gt                                          22

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 339
cagaaagggc ttccctttgt aga                                         23

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 340
acaagtgccc tcactgcagt                                             20

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 341
aacccaccaa agagaagcac ttt                                         23

<210> SEQ ID NO 342

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 342
taaacggaac cactagtgac tta                                              23

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 343
acactctaaa gggaagcact ttgt                                             24

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 344
aaaaagtgcc cccatagttt gag                                              23

<210> SEQ ID NO 345
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 345
aaccctctga aaggaagcac tt                                               22

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 346
ggcacacaaa gtggaagcac ttt                                              23

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 347
gctccaaagg gaagcgcttt g                                                21

<210> SEQ ID NO 348
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 348
agagagggcc tccactttga tg                                              22

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 349
aaagggcttc cctttgcaga                                                 20

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 350
acactcaaaa cctggcggca ctt                                             23

<210> SEQ ID NO 351
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 351
acactctaaa aggatgcacg at                                              22

<210> SEQ ID NO 352
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
caaaagagcc cccagtttga gt                                              22

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
ttaaacatca ctgcaagtct taa                                             23

<210> SEQ ID NO 354
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 354
acactacaaa ctctgcggca ct                                             22

<210> SEQ ID NO 355
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 355
cagaatcctt gcccaggtgc at                                             22

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
acacacaaaa gggaagcact tt                                             22

<210> SEQ ID NO 357
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 357
tctcacccag ggacaaagga tt                                             22

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 358
agactcaaaa gtagtagcac ttt                                            23

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 359
tagcacccag atagcaagga t                                              21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 360
catgcacatg cacacataca t                                            21

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 361
ctgcagaact gttcccgctg cta                                          23

<210> SEQ ID NO 362
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 362
ggaagaacag ccctcctctg cc                                           22

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 363
atagagtgca gaccagggtc t                                            21

<210> SEQ ID NO 364
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
gaagagagct tgcccttgca ta                                           22

<210> SEQ ID NO 365
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 365
ataaatgaca cctccctgtg aa                                           22

<210> SEQ ID NO 366
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 366
```
agaggtcgac cgtgtaatgt gc                                            22

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 367
tctactcaga agggtgcctt a                                             21

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 368
ccagcagcac ctggggcagt                                               20

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 369
ttcactccaa aaggtgcaaa a                                             21

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 370
acacttactg agcacctact agg                                           23

<210> SEQ ID NO 371
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 371
tctactccaa aaggctacaa tca                                           23

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 372
actggaggaa gggcccagag g                                             21

<210> SEQ ID NO 373
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 373
tctacccaca gacgtaccaa tca         23

<210> SEQ ID NO 374
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 374
acggaagggc agagagggcc ag         22

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 375
tgtgattgcc actctcctga gta         23

<210> SEQ ID NO 376
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 376
aaaaaggtta gctgggtgtg tt         22

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 377
ctactcacag aagtgtcaat         20

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 378
ttctaggata ggcccagggg c         21

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 379
ttcaatttct gccgcaaaag                                              20

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 380
aaaggcatca tataggagct gaa                                          23

<210> SEQ ID NO 381
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 381
gctatctgct gcaacagaat tt                                           22

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 382
ggctataaag taactgagac gga                                          23

<210> SEQ ID NO 383
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 383
gtgtgcttac acacttcccg tta                                          23

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 384
actgaccgac cgaccgatcg a                                            21

<210> SEQ ID NO 385
<211> LENGTH: 21

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 385
agcacgtcac ttccactaag a                                              21

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 386
acagtcaggc tttggctaga tca                                            23

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 387
gcaagggcga atgcagaaaa                                                20

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 388
gcactggact aggggtcagc a                                              21

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 389
aactccgggg ctgatcaggt                                                20

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 390
agaggcaggc actcgggcag a                                              21

<210> SEQ ID NO 391
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 391
cttgtaccag ttatctgcaa                                              20

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 392
caatcagcta attacactgc cta                                          23

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
ttgtacgttt acatggaggt c                                            21

<210> SEQ ID NO 394
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394
gtgaaagtgt atgggctttg tgaa                                         24

<210> SEQ ID NO 395
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395
ctgactgact gactgactga ctg                                          23

<210> SEQ ID NO 396
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 396
caggctcaaa gggctcctca gg                                           22

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 397
ccataaagta ggaaacacta                                                  20

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 398
aacaaaatca caagtcttcc a                                                21

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 399
tcaccgacag cgttgaatgt                                                  20

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 400
tgtaagtgct cgtaatgcag t                                                21

<210> SEQ ID NO 401
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 401
cgggactttg agggccagt                                                   19

<210> SEQ ID NO 402
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 402
accctcatgc ccctcaagg                                                   19

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 403
gaatccacca cgaacaactt                                               20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 404
aaaagtaact agcacaccac                                               20

<210> SEQ ID NO 405
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 405
agagaccggt tcactgtga                                                19

<210> SEQ ID NO 406
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
acatttttcg ttattgctct t                                             21

<210> SEQ ID NO 407
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
agagaccggt tcactgtga                                                19

<210> SEQ ID NO 408
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 408
tatggcagac tgtgatttgt tg                                            22

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 409
```

```
cctgattcac aacaccagct                                                20

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
catcgttacc agacagtgtt a                                              21

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 411
ggattcctgg gaaaactgga                                                20

<210> SEQ ID NO 412
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 412
tccacatgga gttgctgtta ca                                             22

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 413
actggtacaa gggttgggag                                                20

<210> SEQ ID NO 414
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 414
aacagctgct tttgggattc tg                                             22

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 415
ctgggacttt gtaggccagt                                                20
```

```
<210> SEQ ID NO 416
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
acctaatata tcaaacatat ca                                               22

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 417
agactccggt ggaatgaagg                                                  20

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 418
aagcccaaaa ggagaattct ttg                                              23

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 419
caacatcagt ctgataagct a                                                21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 420
aggaactgcc tttctctcca a                                                21

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 421
gtacaatcaa cggtcgatgg                                                  20

<210> SEQ ID NO 422
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
acccttatca gttctccgtc ca                                              22

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 423
agaattgcgt ttggacaatc                                                 20

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 424
tagctggttg aagggqacca a                                               21

<210> SEQ ID NO 425
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
acccagcaga caatgtagc                                                  19

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
cctcaaggag cttcagtcta gt                                              22

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
acccagtagc cagatgtagc                                                 20

<210> SEQ ID NO 428
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 428
ccaacaacag gaaactacct a                                                   21

<210> SEQ ID NO 429
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
gccctctcaa cccagcttt                                                      19

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 430
ccaggttcca ccccagcagg                                                     20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 431
gcaatgcaac tacaatgcac                                                     20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 432
acactcaaaa gatggcggca                                                     20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 433
aacaaaatca ctgatgctgg                                                     20

<210> SEQ ID NO 434
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 434
acgctcaaat gtcgcagcac                                              20

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 435
gagctcctgg aggacaggg                                               19

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 436
acaccccaaa atcgaagcac                                              20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 437
gggtgcgatt tctgtgtgag                                              20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 438
ggaaagcgcc cccattttga                                              20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 439
actcagtaat ggtaacggtt                                              20

<210> SEQ ID NO 440
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 440
cacttatcag gttgtattat aa                                              22

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 441
gaggaaacca gcaagtgttg                                                 20

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 442
gtctgtcaaa tcataggtca t                                               21

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 443
gcaatgcaac agcaatgcac                                                 20

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 444
ggggttcacc gagcaacatt c                                               21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 445
gtccgtggtt ctaccctgtg g                                               21

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 446
```
caggccatct gtgttatatt                                          20

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 447
atactagact gtgagctcct cga                                      23

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 448
agtggatgtt cctctatgat                                          20

<210> SEQ ID NO 449
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 449
ccagaaggag cacttagggc ag                                       22

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 450
cgtggatttt cctctacgat                                          20

<210> SEQ ID NO 451
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 451
gctggatgca aacctgcaaa ac                                       22

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 452
gagggttagt ggaccgtgtt                                          20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 453
aatcccatcc ccaggaaccc                                         20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 454
gatgtggacc atactacata                                         20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 455
cggctctgtc gtcgaggcgc                                         20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 456
ggctagtgga ccaggtgaag                                         20

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 457
aaagtctcgc tctctgcccc t                                       21

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 458
cagaacttag ccactgtgaa                                         20

```
<210> SEQ ID NO 459
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 459
tcaacgggag tgatcgtgtc at                                            22

<210> SEQ ID NO 460
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 460
agcctatcct ggattacttg aa                                            22

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 461
agcattgcaa ccgatcccaa c                                             21

<210> SEQ ID NO 462
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 462
ctgttcctgc tgaactgagc ca                                            22

<210> SEQ ID NO 463
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 463
gcagcaaaca tctgactgaa ag                                            22

<210> SEQ ID NO 464
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 464
acaaattcgg ttctacaggg ta                                            22

<210> SEQ ID NO 465
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 465
tgatagccct gtacaatgct gct                                               23

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 466
tcatagccct gtacaatgct gct                                               23

<210> SEQ ID NO 467
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 467
aactatacaa tctactacct ca                                                22

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 468
actatgcaac ctactacctc t                                                 21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 469
ttcagctatc acagtactgt a                                                 21

<210> SEQ ID NO 470
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 470
tcgccctctc aacccagctt tt                                                22

<210> SEQ ID NO 471
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 471
ctatacaacc tcctacctca                                                    20

<210> SEQ ID NO 472
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 472
ctcaatagac tgtgagctcc tt                                                 22

<210> SEQ ID NO 473
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
aacctatcct gaattacttg aa                                                 22

<210> SEQ ID NO 474
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 474
tccatcatca aaacaaatgg agt                                                23

<210> SEQ ID NO 475
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 475
aggcaaagga tgacaaaggg aa                                                 22

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 476
gaacaggtag tctaaacact ggg                                                23

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 477
atccagtcag ttcctgatgc agta                                          24

<210> SEQ ID NO 478
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 478
gctgcaaaca tccgactgaa ag                                            22

<210> SEQ ID NO 479
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 479
taaccgattt caaatggtgc ta                                            22

<210> SEQ ID NO 480
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 480
aacaatacaa cttactacct ca                                            22

<210> SEQ ID NO 481
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 481
atacatactt ctttacattc ca                                            22

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 482
gctgagtgta ggatgtttac a                                             21

<210> SEQ ID NO 483
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 483
atgccctttt aacattgcac tg                                               22

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 484
tccataaagt aggaaacact aca                                              23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 485
ctacgcgtat tcttaagcaa taa                                              23

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 486
agaacaatgc cttactgagt a                                                21

<210> SEQ ID NO 487
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 487
tcttcccatg cgctatacct ct                                               22

<210> SEQ ID NO 488
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 488
ccacacactt ccttacattc ca                                               22

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 489
```

```
gagggaggag agccaggaga agc                                              23

<210> SEQ ID NO 490
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 490
acaagctttt tgctcgtctt at                                               22

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 491
ggccgtgact ggagactgtt a                                                21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 492
cacagttgcc agctgagatt a                                                21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 493
acatggttag atcaagcaca a                                                21

<210> SEQ ID NO 494
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 494
acaaccagct aagacactgc ca                                               22

<210> SEQ ID NO 495
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 495
aggcgaagga tgacaaaggg aa                                               22
```

```
<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 496
gtctgtcaat tcataggtca t                                              21

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 497
atccaatcag ttcctgatgc agta                                           24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 498
actacctgca ctgtaagcac tttg                                           24

<210> SEQ ID NO 499
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
tatctgcact agatgcacct ta                                             22

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
actcaccgac agcgttgaat gtt                                            23

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 501
aacccaccga cagcaatgaa tgtt                                           24

<210> SEQ ID NO 502
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 502
gaacaggtag tctgaacact ggg                                             23

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 503
gaacagatag tctaaacact ggg                                             23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 504
tcagttttgc atagatttgc aca                                             23

<210> SEQ ID NO 505
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 505
ctagtggtcc taaacatttc ac                                              22

<210> SEQ ID NO 506
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 506
aggcatagga tgacaaaggg aa                                              22

<210> SEQ ID NO 507
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 507
cagactccgg tggaatgaag ga                                              22

<210> SEQ ID NO 508
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 508
cagccgctgt cacacgcaca g                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 509
ctgcctgtct gtgcctgctg t                                              21

<210> SEQ ID NO 510
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 510
cacaagttcg gatctacggg tt                                             22

<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 511
gctacctgca ctgtaagcac tttt                                           24

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 512
cacaaattcg gatctacagg gta                                            23

<210> SEQ ID NO 513
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 513
acaaacacca ttgtcacact cca                                            23

<210> SEQ ID NO 514
<211> LENGTH: 21
<212> TYPE: DNA
<213> ORGANISM: Artificial Sequence
<220> FEATURE:
```

<223> OTHER INFORMATION: Description of Artificial Sequence: Synthetic
       probe

<400> SEQUENCE: 514
cgcgtaccaa aagtaataat g                                          21

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 515
gccctttcat cattgcactg                                            20

<210> SEQ ID NO 516
<211> LENGTH: 22
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 516
tccctctggt caaccagtca ca                                         22

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 517
gtagtgcttt ctactttatg                                            20

<210> SEQ ID NO 518
<211> LENGTH: 22
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 518
cccctatcac aattagcatt aa                                         22

<210> SEQ ID NO 519
<211> LENGTH: 22
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 519
tgtaaaccat gatgtgctgc ta                                         22

<210> SEQ ID NO 520
<211> LENGTH: 22
<212> TYPE: DNA
<213> ORGANISM: Artificial Sequence
<220> FEATURE:
<223> OTHER INFORMATION: Description of Artificial Sequence: Synthetic
       probe -continued

<400> SEQUENCE: 520
actcaccgac aggttgaatg tt                                                  22

<210> SEQ ID NO 521
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 521
cacaaaccat tatgtgctgc ta                                                  22

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 522
taactgtaca aactactacc tca                                                 23

<210> SEQ ID NO 523
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 523
acaggccggg acaagtgcaa tat                                                 23

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 524
taacccatgg aattcagttc tca                                                 23

<210> SEQ ID NO 525
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 525
aaccatacaa cctactacct ca                                                  22

<210> SEQ ID NO 526
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 526
aacaacaaaa tcactagtct tcca                                              24

<210> SEQ ID NO 527
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 527
actttcggtt atctagcttt at                                                22

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 528
acagcacaaa ctactacctc a                                                 21

<210> SEQ ID NO 529
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 529
aactatacaa cctactacct ca                                                22

<210> SEQ ID NO 530
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 530
aaccacacaa cctactacct ca                                                22

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 531
ccgaccatgg ctgtagactg tta                                               23

<210> SEQ ID NO 532
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 532
acaccaatgc cctaggggat gcg                                               23

```
<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 533
tggcattcac cgcgtgcctt a                                              21

<210> SEQ ID NO 534
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 534
tcacaagtta gggtctcagg ga                                             22

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 535
cacaagatcg gatctacggg t                                              21

<210> SEQ ID NO 536
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 536
cgccaatatt tacgtgctgc ta                                             22

<210> SEQ ID NO 537
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 537
aacactgatt tcaaatggtg cta                                            23

<210> SEQ ID NO 538
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 538
cttcagttat cacagtactg ta                                             22
```

-continued

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 539
acaggagtct gagcatttga                                              20

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 540
atctgcactg tcagcacttt a                                            21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 541
gcattattac tcacggtacg a                                            21

<210> SEQ ID NO 542
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 542
agccaagctc agacggatcc ga                                           22

<210> SEQ ID NO 543
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 543
actgatatca gctcagtagg cac                                          23

<210> SEQ ID NO 544
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 544
tccatcatta cccggcagta tta                                          23

<210> SEQ ID NO 545
<211> LENGTH: 23

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 545
taaacggaac cactagtgac ttg                                               23

<210> SEQ ID NO 546
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 546
tcagaccgag acaagtgcaa tg                                                22

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 547
agactagata tggaagggtg a                                                 21

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 548
tctgggcaca cggagggaga                                                   20

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 549
acggtcaggc tttggctaga t                                                 21

<210> SEQ ID NO 550
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 550
tgctcaataa atacccgttg aa                                                22

<210> SEQ ID NO 551
<211> LENGTH: 22
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 551
agcaagccca gaccgcaaaa ag                                          22

<210> SEQ ID NO 552
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 552
agaaaggcag caggtcgtat ag                                          22

<210> SEQ ID NO 553
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 553
tacctgcact gttagcactt tg                                          22

<210> SEQ ID NO 554
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 554
cacataggaa tgaaaagcca ta                                          22

<210> SEQ ID NO 555
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 555
cctcaaggag cctcagtcta gt                                          22

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 556
acaagtgccc tcactgcagt                                             20

<210> SEQ ID NO 557
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 557
taaacggaac cactagtgac tta                                              23

<210> SEQ ID NO 558
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 558
aaaaagtgcc cccatagttt gag                                              23

<210> SEQ ID NO 559
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 559
ggcacacaaa gtggaagcac ttt                                              23

<210> SEQ ID NO 560
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 560
agagagggcc tccactttga tg                                               22

<210> SEQ ID NO 561
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 561
acactcaaaa cctggcggca ctt                                              23

<210> SEQ ID NO 562
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 562
caaaagagcc cccagtttga gt                                               22

<210> SEQ ID NO 563
<211> LENGTH: 22
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 563
acactacaaa ctctgcggca ct                                              22

<210> SEQ ID NO 564
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 564
acacacaaaa gggaagcact tt                                              22

<210> SEQ ID NO 565
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 565
agactcaaaa gtagtagcac ttt                                             23

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 566
catgcacatg cacacataca t                                               21

<210> SEQ ID NO 567
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 567
ggaagaacag ccctcctctg cc                                              22

<210> SEQ ID NO 568
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 568
gaagagagct tgcccttgca ta                                              22

<210> SEQ ID NO 569
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 569
```

```
agaggtcgac cgtgtaatgt gc                                               22
```

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 570

```
ccagcagcac ctggggcagt                                                  20
```

<210> SEQ ID NO 571
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 571

```
acacttactg agcacctact agg                                              23
```

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 572

```
actggaggaa gggcccagag g                                                21
```

<210> SEQ ID NO 573
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 573

```
acggaagggc agagagggcc ag                                               22
```

<210> SEQ ID NO 574
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 574

```
aaaaaggtta gctgggtgtg tt                                               22
```

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 575

```
ttctaggata ggcccagggg c                                                21
```

```
<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 576
aaaggcatca tataggagct gaa                                              23

<210> SEQ ID NO 577
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 577
tcaacaaaat cactgatgct gga                                              23

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 578
tgagctcctg gaggacaggg a                                                21

<210> SEQ ID NO 579
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 579
ggctataaag taactgagac gga                                              23

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 580
actgaccgac cgaccgatcg a                                                21

<210> SEQ ID NO 581
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 581
gacgggtgcg atttctgtgt gaga                                             24

<210> SEQ ID NO 582
```

<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 582
acagtcaggc tttggctaga tca                                              23

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 583
gcactggact aggggtcagc a                                                21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 584
agaggcaggc actcgggcag a                                                21

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 585
caatcagcta attacactgc cta                                              23

<210> SEQ ID NO 586
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 586
gtgaaagtgt atgggctttg tgaa                                             24

<210> SEQ ID NO 587
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 587
caggctcaaa gggctcctca gg                                               22

<210> SEQ ID NO 588
<211> LENGTH: 21
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 588
aacaaaatca caagtcttcc a                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 589
tgtaagtgct cgtaatgcag t                                              21

<210> SEQ ID NO 590
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 590
accctcatgc ccctcaagg                                                 19

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 591
aaaagtaact agcacaccac                                                20

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 592
acatttttcg ttattgctct t                                              21

<210> SEQ ID NO 593
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 593
tatggcagac tgtgatttgt tg                                             22

<210> SEQ ID NO 594
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 594
catcgttacc agacagtgtt a                                              21

<210> SEQ ID NO 595
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 595
tccacatgga gttgctgtta ca                                             22

<210> SEQ ID NO 596
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 596
aacagctgct tttgggattc tg                                             22

<210> SEQ ID NO 597
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 597
acctaatata tcaaacatat ca                                             22

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 598
aagcccaaaa ggagaattct ttg                                            23

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 599
aggaactgcc tttctctcca a                                              21

<210> SEQ ID NO 600
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 600
acccttatca gttctccgtc ca                                                  22

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 601
tagctggttg aaggggacca a                                                   21

<210> SEQ ID NO 602
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 602
cctcaaggag cttcagtcta gt                                                  22

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 603
ccaacaacag gaaactacct a                                                   21

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 604
ccaggttcca ccccagcagg                                                     20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 605
acactcaaaa gatggcggca                                                     20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 606
```
acgctcaaat gtcgcagcac                                               20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 607
acaccccaaa atcgaagcac                                               20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 608
ggaaagcgcc cccatttga                                                20

<210> SEQ ID NO 609
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 609
cacttatcag gttgtattat aa                                            22

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 610
gtctgtcaaa tcataggtca t                                             21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 611
ggggttcacc gagcaacatt c                                             21

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
caggccatct gtgttatatt                                               20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 613
agtggatgtt cctctatgat                                              20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 614
cgtggatttt cctctacgat                                              20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 615
gagggttagt ggaccgtgtt                                              20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 616
gatgtggacc atactacata                                              20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 617
ggctagtgga ccaggtgaag                                              20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 618
cagaacttag ccactgtgaa                                              20

-continued

```
<210> SEQ ID NO 619
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 619
agcctatcct ggattacttg aa                                                22

<210> SEQ ID NO 620
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 620
ctgttcctgc tgaactgagc ca                                                22

<210> SEQ ID NO 621
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 621
gtggtaatcc ctggcaatgt gat                                               23

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 622
ggaaatccct ggcaatgtga t                                                 21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 623
aaagtgtcag atacggtgtg g                                                 21

<210> SEQ ID NO 624
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 624
acagttcttc aactggcagc tt                                                22

<210> SEQ ID NO 625
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 625
ggtacaatca acggtcgatg gt                                              22

<210> SEQ ID NO 626
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 626
tcaacatcag tctgataagc ta                                              22

<210> SEQ ID NO 627
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 627
ctacctgcac tataagcact tta                                             23

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 628
tcagttttgc atggatttgc aca                                             23

<210> SEQ ID NO 629
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 629
cccaacaaca tgaaactacc ta                                              22

<210> SEQ ID NO 630
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 630
acaaagttct gtagtgcact ga                                              22

<210> SEQ ID NO 631
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 631
aagggattcc tgggaaaact ggac                                              24

<210> SEQ ID NO 632
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 632
ctagtacatc atctatactg ta                                                22

<210> SEQ ID NO 633
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 633
tgagctacag tgcttcatct ca                                                22

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 634
agaggcaggc actcaggcag a                                                 21

<210> SEQ ID NO 635
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 635
tgggcgaccc agagggaca                                                    19

<210> SEQ ID NO 636
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 636
agaggttaag acagcagggc tg                                                22

<210> SEQ ID NO 637
<211> LENGTH: 22
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 637
tgcaatgcaa ctacaatgca cc                                               22

<210> SEQ ID NO 638
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 638
gcaaaaatgt gctagtgcca aa                                               22

<210> SEQ ID NO 639
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 639
tcatacagct agataaccaa aga                                              23

<210> SEQ ID NO 640
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 640
cttccagtcg gggatgttta ca                                               22

<210> SEQ ID NO 641
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 641
acacaaattc ggttctacag gg                                               22

<210> SEQ ID NO 642
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 642
accctccacc atgcaaggga tg                                               22

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 643
ctgggacttt gtaggccagt t                                            21

<210> SEQ ID NO 644
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 644
cctatctccc ctctggacc                                               19

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 645
ggctgtcaat tcataggtca g                                            21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 646
cggctgcaac acaagacacg a                                            21

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 647
cagtgaattc taccagtgcc ata                                          23

<210> SEQ ID NO 648
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 648
tgtgagttct accattgcca aa                                           22

<210> SEQ ID NO 649
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 649
```
cgaaggcaac acggataacc ta                                              22

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 650
tcacttttgt gactatgcaa                                                 20

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 651
ccaagttctg tcatgcactg a                                               21

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 652
acactggtac aagggttggg aga                                             23

<210> SEQ ID NO 653
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 653
ggagtgaaga cacggagcca ga                                              22

<210> SEQ ID NO 654
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 654
acaaagttct gtgatgcact ga                                              22

<210> SEQ ID NO 655
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 655
gctgagagtg taggatgttt aca                                             23

```
<210> SEQ ID NO 656
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 656
aaccgatttc agatggtgct ag                                              22

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 657
gtcatcatta ccaggcagta tta                                             23

<210> SEQ ID NO 658
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 658
aaccaatgtg cagactactg ta                                              22

<210> SEQ ID NO 659
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 659
gctgggtgga gaaggtggtg aa                                              22

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 660
gccaatattt ctgtgctgct a                                               21

<210> SEQ ID NO 661
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 661
cgcaaggtcg gttctacggg tg                                              22

<210> SEQ ID NO 662
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 662
acaccgagga gcccatcatg at                                              22

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 663
cctgcatgac ggcctgcaag aca                                             23

<210> SEQ ID NO 664
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 664
ataaggattt ttagggcat ta                                               22

<210> SEQ ID NO 665
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 665
tattaggaac acatcgcaaa aa                                              22

<210> SEQ ID NO 666
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 666
accagctaac aatacactgc ca                                              22

<210> SEQ ID NO 667
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 667
atgggacatc ctacatatgc aa                                              22

<210> SEQ ID NO 668
<211> LENGTH: 22
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 668
ttcaaaacat gaattgctgc tg                                              22

<210> SEQ ID NO 669
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 669
gtacccctgg agattctgat aa                                              22

<210> SEQ ID NO 670
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 670
tcacgcgagc cgaacgaaca aa                                              22

<210> SEQ ID NO 671
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 671
acaaaagttg cctttgtgtg at                                              22

<210> SEQ ID NO 672
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 672
acacaggacc tggagtcagg ag                                              22

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 673
cctacgttcc atagtctacc a                                               21

<210> SEQ ID NO 674
<211> LENGTH: 22
<212> TYPE: DNA
<213> ORGANISM: Artificial Sequence
<220> FEATURE:

-continued

<223> OTHER INFORMATION: Description of Artificial Sequence: Synthetic
      probe

<400> SEQUENCE: 674
gcgcatgttc tatggtcaac ca                                              22

<210> SEQ ID NO 675
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 675
acagagagct tgcccttgta ta                                              22

<210> SEQ ID NO 676
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 676
cgaatccacc acgaacaact tc                                              22

<210> SEQ ID NO 677
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 677
tatgaacaat ttctaggaat                                                 20

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 678
ggcggacacg acattcccga t                                               21

<210> SEQ ID NO 679
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 679
gtctcagttt cctctgcaaa ca                                              22

<210> SEQ ID NO 680
<211> LENGTH: 22
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 680
gctgtaaaca tccgactgaa ag                                              22

<210> SEQ ID NO 681
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 681 atgcttttg gggtaagggc tt                                               22

<210> SEQ ID NO 682
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 682
acggcattac cagacagtat ta                                              22

<210> SEQ ID NO 683
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 683
tctctgcagg ccctgtgctt tgc                                             23

<210> SEQ ID NO 684
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 684
tgttgcagcg cttcatgttt                                                 20

<210> SEQ ID NO 685
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 685
agccacagtc accttctgat ct                                              22

<210> SEQ ID NO 686
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 686
aaactcagta atggtaacgg ttt                                              23

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 687
caacaaacat ttaatgaggc c                                                21

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 688
tgatggacaa caaattaggt a                                                21

<210> SEQ ID NO 689
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 689
tatctcacag aataaacttg gta                                              23

<210> SEQ ID NO 690
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 690
tcacatcagt gccattctaa ata                                              23

<210> SEQ ID NO 691
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 691
gtcttatgtg tgcgtgtatg tat                                              23

<210> SEQ ID NO 692
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 692
gtgtaggtgt gtgtatgtat at                                               22

```
<210> SEQ ID NO 693
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 693
cagacacacg cacatcagtc ata                                              23

<210> SEQ ID NO 694
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 694
ggacaccaag atcaatgaaa gaggca                                           26

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 695
tcaccagtgc cagtccaaga a                                                21

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 696
tgtgaaaagc actatactac gta                                              23

<210> SEQ ID NO 697
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 697
ggcggaactt agccactgtg aa                                               22

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 698
acaggattga gggggggccc t                                                21
```

<210> SEQ ID NO 699
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 699
atgtatgtgg gacggtaaac ca                                              22

<210> SEQ ID NO 700
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 700
gctttgacaa tactattgca ctg                                             23

<210> SEQ ID NO 701
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 701
tcaccaaaac atggaagcac tta                                             23

<210> SEQ ID NO 702
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 702
gcttccagtc gaggatgttt aca                                             23

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 703
tccagtcaag gatgtttaca                                                 20

<210> SEQ ID NO 704
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 704
cagctatgcc agcatcttgc ct                                              22

<210> SEQ ID NO 705
<211> LENGTH: 21

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 705
gcaacttagt aatgtgcaat a                                            21

<210> SEQ ID NO 706
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 706
caatcagcta atgacactgc ct                                           22

<210> SEQ ID NO 707
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 707
gcaatcagct aactacactg cct                                          23

<210> SEQ ID NO 708
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 708
ctacctgcac gaacagcact ttg                                          23

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 709
ccatctttac cagacagtgt t                                            21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 710
ctaccatagg gtaaaaccac t                                            21

<210> SEQ ID NO 711
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 711
tggagacacg tgcactgtag a                                              21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 712
cctgattcac aacaccagct g                                              21

<210> SEQ ID NO 713
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 713
ttcacatagg aataaaaagc cata                                           24

<210> SEQ ID NO 714
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 714
acagctggtt gaagggacc aa                                              22

<210> SEQ ID NO 715
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 715
gaaagagacc ggttcactgt ga                                             22

<210> SEQ ID NO 716
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 716
aaaagagacc ggttcactgt ga                                             22

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

```
      probe

<400> SEQUENCE: 717
agaattgcgt ttggacaatc a                                             21

<210> SEQ ID NO 718
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 718
gaaacccagc agacaatgta gct                                           23

<210> SEQ ID NO 719
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 719
gagacccagt agccagatgt agct                                          24

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 720
ggggtatttg acaaactgac a                                             21

<210> SEQ ID NO 721
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 721
ggttcaaacc atgagtcgag ct                                            22

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 722
ggagtcgagt gatggttcaa a                                             21

<210> SEQ ID NO 723
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 723
gaataatgac aggctcaccg ta                                            22

<210> SEQ ID NO 724
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 724
acactctaaa gggaaccatt tt                                            22

<210> SEQ ID NO 725
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 725
aaagaagtgc accatgtttg ttt                                           23

<210> SEQ ID NO 726
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 726
catgcataca tgcacacata cat                                           23

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 727
aacactctga agggaagcgc                                               20

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 728
cactctaaaa ggatgcactt t                                             21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 729
```

```
ttcaccaaag ggaagcactt t                                              21
```

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 730

```
gtccgtggtt ctaccctgtg g                                              21
```

<210> SEQ ID NO 731
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 731

```
acactctaaa gggaagtgcg tt                                             22
```

<210> SEQ ID NO 732
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 732

```
ctcacaccta ggttccaagg att                                            23
```

<210> SEQ ID NO 733
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 733

```
ccagaaggag cacttagggc ag                                             22
```

<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 734

```
ttacagatgg ataccgtgca att                                            23
```

<210> SEQ ID NO 735
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 735

```
gctggatgca aacctgcaaa ac                                             22
```

```
<210> SEQ ID NO 736
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 736
cctctaaaag gaagcactttt ct                                              22

<210> SEQ ID NO 737
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 737
aatcccatcc ccaggaaccc                                                  20

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 738
cgaatataac acggtcgatc t                                                21

<210> SEQ ID NO 739
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 739
cggctctgtc gtcgaggcgc                                                  20

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 740
tcaatcacag atagcacccc t                                                21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 741
gtagtgcaac tatgcaaaac t                                                21

<210> SEQ ID NO 742
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 742
acactctaaa gggatgcacg at                                              22

<210> SEQ ID NO 743
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 743
aaagtgcttc ttacctccag at                                              22

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 744
acctctaaag gggagcgctt                                                 20

<210> SEQ ID NO 745
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 745
acactctaaa gggaggcact tt                                              22

<210> SEQ ID NO 746
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 746
atactagact gtgagctcct cga                                             23

<210> SEQ ID NO 747
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 747
tccaggagct cacaatctag tg                                              22

<210> SEQ ID NO 748
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 748
agaaagcgct tccctgtaga g                                               21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 749
agccaagtaa tggagaacag g                                               21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 750
agaaagcgct tccctctaga g                                               21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 751
acagaaaggg cttccctttg c                                               21

<210> SEQ ID NO 752
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 752
tctaagccac catgtgaaac ca                                              22

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 753
gcaaggcagt ggcctgtaca                                                 20

<210> SEQ ID NO 754
<211> LENGTH: 20
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 754
tccagcaaag ggaagcgctt                                                  20

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 755
accctctata gggaagcgcg t                                                21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 756
aacgctccaa aagaaggcac t                                                21

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 757
accagaactg agtccacagg g                                                21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 758
atctacactg gctactgagc c                                                21

<210> SEQ ID NO 759
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 759
actgtgtttc agctcagtag gca                                              23

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 760
actgcagaac tgttcccgct g                                          21

<210> SEQ ID NO 761
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 761
agaggaaacc agcaagtgtt ga                                         22

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 762
aaagtctcgc tctctgcccc t                                          21

<210> SEQ ID NO 763
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 763
ccacccaatg acctactcca ag                                         22

<210> SEQ ID NO 764
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 764
tcaacgggag tgatcgtgtc at                                         22

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 765
agcattgcaa ccgatcccaa c                                          21

<210> SEQ ID NO 766
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 766
tcatctcgcc cgcaaagacc                                               20

<210> SEQ ID NO 767
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 767
agaaagtgct ttcttttgga gaa                                           23

<210> SEQ ID NO 768
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 768
gaaagtgctt ctttcctcga gaa                                           23

<210> SEQ ID NO 769
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 769
gcagcaaaca tctgactgaa ag                                            22

<210> SEQ ID NO 770
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 770
ctacctgcac tatgagcact ttg                                           23

<210> SEQ ID NO 771
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 771
ggggacgaaa tccaagcgca gc                                            22

<210> SEQ ID NO 772
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 772
aataggtcaa ccgtgtatga tt                                              22

<210> SEQ ID NO 773
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 773
gcagaagcat ttccacacac                                                 20

<210> SEQ ID NO 774
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 774
cccctatcac gattagcatt aa                                              22

<210> SEQ ID NO 775
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 775
acaagtgcct tcactgcagt                                                 20

<210> SEQ ID NO 776
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 776
tccagcactg tccggtaaga tg                                              22

<210> SEQ ID NO 777
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 777
aaagcaagta catccacgtt ta                                              22

<210> SEQ ID NO 778
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 778
aagcggttta ccatcccaca ta                                              22

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 779
tagttggcaa gtctagaacc a                                               21

<210> SEQ ID NO 780
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 780
ctactaaaac atggaagcac tta                                             23

<210> SEQ ID NO 781
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 781
agaaagcact tccatgttaa agt                                             23

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 782
tactatgcaa cctactactc t                                               21

<210> SEQ ID NO 783
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 783
ctgaggggcc tcagaccgag ct                                              22

<210> SEQ ID NO 784
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 784
taactgcact agatgcacct ta					22

<210> SEQ ID NO 785
<211> LENGTH: 1191
<212> TYPE: DNA
<213> ORGANISM: Homo sapiens

<400> SEQUENCE: 785
gacatttcca gaaaagcatt atggttttca gaacacttca agttgacttg ggatatatca	60
ttcctcaaca tgaaactttt catgaatggg agaagaacct attttgttg tggtacaaca	120
gttgagagca gcaccaagtg catttagttg aatgaagtct tcttggattt cacccaacta	180
aaaggatttt taaaaataaa taacagtctt acctaaatta ttaggtaatg aattgtagcc	240
agttgttaat atcttaatgc agatttttt aaaaaaaaca taaaatgatt tatctgtatt	300
ttaaaggatc caacagatca gtatttttc ctgtgatggg ttttttgaaa tttgacacat	360
taaaaggtac tccagtattt cacttttctc gatcactaaa catatgcata tattttaaa	420
aatcagtaaa agcattactc taagtgtaga cttaatacca tgtgacattt aatccagatt	480
gtaaatgctc atttatggtt aatgacattg aaggtacatt tattgtacca aaccatttta	540
tgagttttct gttagcttgc tttaaaaatt attactgtaa gaatagttt tataaaaaat	600
tatatttta ttcagtaatt taattttgta aatgccaaat gaaaaacgtt ttttgctgct	660
atggtcttag cctgtagaca tgctgctagt atcagagggg cagtagagct tggacagaaa	720
gaaaagaaac ttggtgttag gtaattgact atgcactagt atttcagact tttaatttt	780
atatatatat acattttttt tccttctgca atacatttga aaacttgttt gggagactct	840
gcattttta ttgtggtttt tttgttattg ttggtttata caagcatgcg ttgcacttct	900
tttttgggag atgtgtgttg ttgatgttct atgttttgtt ttgagtgtag cctgactgtt	960
ttataatttg ggagttctgc atttgatccg catcccctgt ggtttctaag tgtatggtct	1020
cagaactgtt gcatggatcc tgtgtttgca actggggaga cagaaactgt ggttgatagc	1080
cagtcactgc cttaagaaca tttgatgcaa gatggccagc actgaacttt tgagatatga	1140
cggtgtactt actgccttgt agcaaaataa agatgtgccc ttatttacc t	1191

<210> SEQ ID NO 786
<211> LENGTH: 22
<212> TYPE: RNA
<213> ORGANISM: Homo sapiens

<400> SEQUENCE: 786
ucucccaacc cuuguaccag ug					22

<210> SEQ ID NO 787
<211> LENGTH: 22
<212> TYPE: RNA
<213> ORGANISM: Mus sp.

<400> SEQUENCE: 787
ucucccaacc cuuguaccag ug					22

<210> SEQ ID NO 788
<211> LENGTH: 22
<212> TYPE: RNA
<213> ORGANISM: Rattus sp.

-continued

<400> SEQUENCE: 788
ucucccaacc cuuguaccag ug                                        22

<210> SEQ ID NO 789
<211> LENGTH: 23
<212> TYPE: RNA
<213> ORGANISM: Bos sp.

<400> SEQUENCE: 789
ucucccaacc cuuguaccag ugu                                       23

<210> SEQ ID NO 790
<211> LENGTH: 22
<212> TYPE: RNA
<213> ORGANISM: Unknown
<220> FEATURE:
<223> OTHER INFORMATION: Description of Unknown: Unknown frog sequence

<400> SEQUENCE: 790
ucucccaacc cuuguaccag ag                                        22

<210> SEQ ID NO 791
<211> LENGTH: 22
<212> TYPE: RNA
<213> ORGANISM: Danio rerio

<400> SEQUENCE: 791
ucucccaauc cuuguaccag ug                                        22

<210> SEQ ID NO 792
<211> LENGTH: 52
<212> TYPE: DNA
<213> ORGANISM: Homo sapiens

<400> SEQUENCE: 792
atgaatggga gaagaattgt ttgggagact tttgggagat taatttggga gt        52

<210> SEQ ID NO 793
<211> LENGTH: 56
<212> TYPE: DNA
<213> ORGANISM: Mus sp.

<400> SEQUENCE: 793
atggctgaga gaagagttat ttgggagaat ttttgggaga tccgtttggg cgtttt    56

<210> SEQ ID NO 794
<211> LENGTH: 58
<212> TYPE: DNA
<213> ORGANISM: Rattus sp.

<400> SEQUENCE: 794
gtgactgagg ggagatttat ttgggagaat ttctttggga gattccgttt gggcactt  58

<210> SEQ ID NO 795
<211> LENGTH: 52
<212> TYPE: DNA
<213> ORGANISM: Canis familiaris

<400> SEQUENCE: 795
atgaatggga gaagagttgt ttgggagatt tttgggagat taattcagag gt        52

```
<210> SEQ ID NO 796
<211> LENGTH: 53
<212> TYPE: DNA
<213> ORGANISM: Didelphis virginiana

<400> SEQUENCE: 796
atgaatggga gatggatttt tcttgcagat ttttgggaga ttaatccaaa ttt            53

<210> SEQ ID NO 797
<211> LENGTH: 55
<212> TYPE: DNA
<213> ORGANISM: Gallus sp.

<400> SEQUENCE: 797
gtgaatggga gacgagtgtt cctgggagat ttttgggaga acataccttg ggtct          55

<210> SEQ ID NO 798
<211> LENGTH: 50
<212> TYPE: DNA
<213> ORGANISM: Xenopus tropicalis

<400> SEQUENCE: 798
atgattggga gatgatgtgg gagattggtc tgtatgataa acccaagaac                50
```

MIR-150 FOR THE TREATMENT OF BLOOD DISORDERS

CROSS REFERENCE TO RELATED APPLICATIONS

This application is a continuation application of U.S. patent application Ser. No. 12/363,016 filed on Jan. 30, 2009, which is now abandoned and which claims benefit under 35 U.S.C. §119(e) of U.S. Provisional Application No. 61/062,931 filed on Jan. 30, 2008, and U.S. Provisional Application No. 61/086,556 filed on Aug. 6, 2008, the contents of which are incorporated herein by reference in their entireties.

GOVERNMENT SUPPORT

This invention was made with Government support under No. 219335 awarded by the National Institute of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 15, 2012, is named 20121016_SequenceListing-TextFile_030258_061192_C and is 185,582 bytes in size.

BACKGROUND OF INVENTION

Blood disorders such as thrombocytopenia and anemia affect a significant population, with anemia being the most common disorder of the two. At least 50% of new patients admitted to a hospital's intensive care unit will develop thrombocytopenia during their stay. The development of thrombocytopenia correlates with mortality, longer duration of mechanical ventilation, and an increased need for blood product transfusion.

Anemia occurs when the level of healthy red blood cells (RBCs) in the body becomes too low. RBCs contain hemoglobin, which carries oxygen to the body's tissues. Thus, low levels of healthy RBCs can cause a variety of complications, including fatigue and stress on bodily organs. More than 3 million people in the United States have anemia. Women and people with chronic diseases are at the greatest risk for anemia. A person presents with anemia when the body loses too much blood (such as with heavy periods, certain diseases, and trauma); or the body has problems making red blood cells; or red blood cells break down or die faster than the body can replace them with new ones; or more than one of these problems happen at the same time.

Aplastic anemia occurs when the bone marrow cannot make enough RBCs. This can be due to a viral infection, or exposure to certain toxic chemicals, radiation, or medications (such as antibiotics, antiseizure drugs, or cancer treatments). Some childhood cancers can also cause aplastic anemia, as can certain chronic diseases that affect the ability of the bone marrow to make blood cells. Vitamin B12 and iron deficiencies also contribute to anemia.

Thrombocytopenia is a deficiency of platelets (thrombocytes). The blood usually contains about 140,000 to 440,000 platelets per microliter. Bleeding can occur with relatively minor trauma when the platelet count falls below about 50,000 platelets per microliter of blood. The most serious risk of bleeding, however, generally does not occur until the platelet count falls below 10,000 to 20,000 platelets per microliter. At these very low levels, bleeding may occur without any injury.

Abnormal reductions in the number of platelets are caused when abnormalities occur in any of the following three processes: decreased platelet production by the bone marrow; increased trapping of platelets by the spleen; or a more rapid than normal destruction of platelets. Persons with this condition easily bruise and can have episodes of excess bleeding (a hemorrhage).

Many diseases can cause thrombocytopenia. Thrombocytopenia can occur when the bone marrow does not produce enough platelets, as happens in leukemia, lymphoma and some anemias—aplastic, megaloblastic, vitamin B12 deficiency, and folic acid deficiency. Excessive alcohol consumption can also impede platelet production. Infection with the human immunodeficiency virus (HIV), the virus that causes AIDS, often results in thrombocytopenia. Platelets can become entrapped in an enlarged spleen, as happens in myelofibrosis and Gaucher's disease, reducing the number of platelets in the bloodstream. Massive blood transfusions can dilute the concentration of platelets in the blood. Finally, the body may use or destroy too many platelets, as occurs in many disorders, three of the most notable being idiopathic thrombocytopenic purpura, thrombotic thrombocytopenic purpura, and hemolytic-uremic syndrome.

Currently, the treatment options for anemia and thrombocytopenia are directed at the immediate increase of circulating RBC and platelet respectively, followed by identifying the underlying causes. Alternative treatment methods aimed at boosting the innate production of RBCs and platelets, for example, the use of erythropoietin and thrombopoietin to stimulate the bone marrow to produce more red blood cells, are still needed and will be useful in complementing existing treatments for anemia and thrombocytopenia.

SUMMARY OF THE INVENTION

Embodiments of the invention provide methods of treating certain blood related disorders, in particular, thrombocytopenia and anemia. Thrombycytopenia is a condition where there is low platelet count in the blood. Anemia is a condition where there is a low number of red blood cells (RBC) in the blood. Embodiments of the inventions are based on the discovery that miR-150 is involved in the differentiation of megakaryocyte-erythrocyte progenitor cells (MEPs) from the bone marrow. Overexpression of miR-150 can shift more MEPs toward megakaryocyte differentiation and also block erythrocyte maturation. In contrast, a lower level of miR-150 expression shift more MEPs towards erythrocyte differentiation. Accordingly, embodied in the invention is a method of treating thrombocytopenia in a host in need thereof, the method comprising administering to a host an effective amount of an agent that increases miR-150 expression in a cell.

The cell being administered an effective amount of an agent that increases miR-150 expression is a progenitor cell, preferably, a hematopoietic progenitor cell. The increase in miR-150 expression promotes megakaryocyte differentiation from the hematopoietic progenitor cell and consequently more platelets are produced.

In one embodiment, the agent that increases miR-150 expression in a cell comprises a vector comprising a nucleic acid sequence that is at least 90% identical to SEQ. ID. No. 1. In other embodiments, the nucleic acid is at least 92%, at least 93% at least 94%, at least 95%, at least 96%, at least 97%, at least 98%, at least 99%, and all the intermediate percentages between 90% and 100%, identical to SEQ. ID. No. 1. The differences from SEQ. ID. No. 1 should be such that the overall hairpin structure of the pri-miR-150 is maintained. The agent serves to increase the basal level of miR-150 in hematopoietic progenitor cells. The vector can be a virus or a non-virus.

In another embodiment, the agent that increases miR-150 expression in a cell comprises a nucleic acid sequence that is at least 90% identical to SEQ. ID. No. 1. In other embodiments, the nucleic acid is at least 92%, at least 94%, at least 95%, at least 97%, at least 99%, and all the intermediate percentages between 90% and 100%, identical to SEQ. ID. No. 1. The differences from SEQ. ID. No. 1 should be such that the overall hairpin structure of the pri-miR-150 is maintained.

Embodied herein is a method of treating thrombocytopenia in a host in need thereof, the method comprising: (a) obtaining a sample of hematopoietic progenitor cells from the host; (b) contacting the hematopoietic progenitor cells with a vector comprising a nucleic acid sequence that is at least 90% identical to SEQ. ID. No. 1; and (c) introducing the cell from step b into the host.

Also embodied herein is a method of treating anemia in a host in need thereof, the method comprising administering to a host an effective amount of an agent that inhibits miR-150 in a cell.

The cell being administered an effective amount of an agent that inhibits miR-150 expression is a progenitor cell, preferably, a hematopoietic progenitor cell. By inhibiting miR-150 expression in the cells, the repression associated with the miR-150 is relieved and erythrocyte differentiation from the progenitor cells is promoted.

In one embodiment, the agent comprises a vector comprising a nucleic acid sequence that is at least 90% identical to SEQ. ID. No. 3. In another embodiment, the agent is an antagomir of miR-150, an anti-miR-150 oligonucleotide, an antisense oligonucleotide to miR-150, a locked nucleic acid that anneals to miR-150, or a double strand RNA. Nucleic acid sequences similar to SEQ. ID. No. 3, antagomir of miR-150, an anti-miR-150 oligonucleotide, an antisense oligonucleotide to miR-150, a locked nucleic acid that anneals to miR-150, or a double strand RNA all complementary basepair with miR-150, although not necessarily perfectly, and can thus inhibit miR-150 from complexing with the miRISC. The vector comprising a nucleic acid sequence can be virus or a non-virus.

Embodied herein is a method of treating anemia in a host in need thereof, the method comprising: (a) obtaining a sample of hematopoietic progenitor cells from said host; (b) contacting the hematopoietic progenitor cells with a vector comprising a nucleic acid sequence that is at least 90% identical to SEQ. ID. No. 3; and (c) introducing the cell from step b into the same host.

BRIEF DESCRIPTION OF THE DRAWINGS

FIG. 2B shows the histograms of the data obtained for FIG. 2A. Error bars reflect standard deviation. n=3

FIG. 2C shows the percentage of bone marrow GFP+ or GFP− megakaryocytes (CD41+Ter119−)−J) in mice transduced with either miR-150 and a GFP marker or with control retroviral vector and analyzed 5 to 8 weeks post-transplantation. Each dot represents data from one recipient mouse. n=7.

FIG. 2D shows the percentage of bone marrow GFP+ or GFP− erythrocyte (CD41−Ter119+) in mice transduced with either miR-150 and a GFP marker or with control retroviral vector and analyzed 5 to 8 weeks post-transplantation. Each dot represents data from one recipient mouse. n=7.

FIG. 12A shows the absolute cell numbers of GFP+ erythrocytes in the bone marrow of vector control or miR-150 recipient mice. Data reflect cell numbers from two legs of each mouse. Cell number was calculated based on total bone marrow cell yield, GFP status and megakaryocyte and erythrocyte percentage as determined by CD41 and Ter119 staining.

FIG. 12B shows the absolute cell numbers of GFP+ megakaryocytes in the bone marrow of vector control or miR-150 recipient mice.

FIG. 12C shows the absolute cell numbers of GFP− erythrocytes in the bone marrow of vector control or miR-150 recipient mice.

FIG. 12D shows the absolute cell numbers of GFP− megakaryocytes in the bone marrow of vector control or miR-150 recipient mice.

FIG. 17A shows the human MYB 3'UTR sequence (SEQ ID NO: 785) with four putative miR-150 binding sites in boxes.

FIG. 17B shows the conservation of the four putative miR-150 targeting sites across several shown species (SEQ ID NOS: 792-798, respectively, in order of appearance). Conservation data were obtained from UCSC genome browser.

DETAILED DESCRIPTION OF THE INVENTION

Definitions of Terms

Figure 1A:
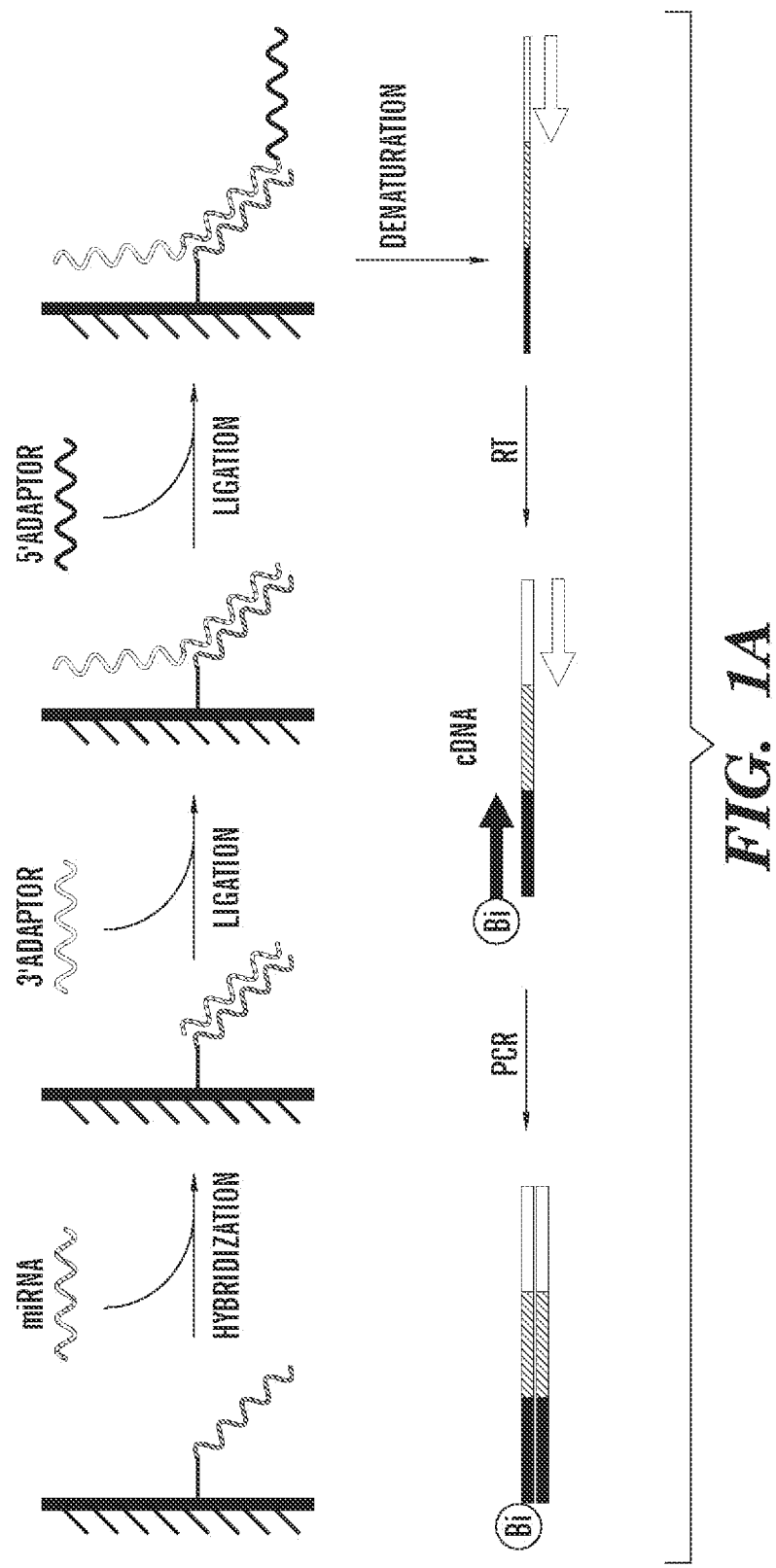
FIG. 1A shows the schematic of a novel, sensitive and high-throughput miRNA labeling methodology for expression profiling. RT: reverse transcription; Bi: biotin; arrows: primers.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

As used herein, the term "therapeutically effective amount" refers to an amount of an agent that is sufficient to effect a therapeutically significant increase in the circulating platelet count in a host diagnosed with thrombocytopenia to at least above $1.6 \times 10^5$ platelets/mm$^3$ or an amount of an agent that is sufficient to effect a therapeutically significant increase in the circulating RBC count in a host diagnosed with anemia to at least above $4.0 \times 10^{12}$ red cells/L in adults and $4.6 \times 10^{12}$ red cells/L in children.

As used herein, the term "treating thrombocytopenia" refers to a means of increasing the number of circulating platelets in a host who has low platelet count, less than about $1.6 \times 10^5$ platelets/mm$^3$.

As used herein, the term "agent" refers to a nucleic acid sequence or a vector. The nucleic acid sequence can have modifications such as 2'O-methylation and 3' end cholesterol found in antagomirs and locked nucleic acid oligonucleotides.

As used herein, the term "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uracil (U).

As used herein, the term "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, ie., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

The term "vector", as used herein, refers to a nucleic acid construct designed for delivery to a host cell or transfer between different host cells. As used herein, a vector can be viral or non-viral.

As used herein, the term "expression vector" refers to a vector that has the ability to incorporate and express heterologous nucleic acid fragments in a cell. An expression vector may comprise additional elements, for example, the expression vector may have two replication systems, thus allowing it to be maintained in two organisms, for example in human cells for expression and in a prokaryotic host for cloning and amplification.

As used herein, the term "heterologous nucleic acid fragments" refers to nucleic acid sequences that are not naturally occurring in that cell. For example, when a miR-150 gene is inserted into the genome of a bacteria or virus, that miR-150 gene is heterologous to that recipient bacteria or virus because the bacteria and viral genome do not naturally have the miR-150 gene.

As used herein, the term "viral vector" refers to a nucleic acid vector construct that includes at least one element of viral origin and has the capacity to be packaged into a viral vector particle. The viral vector can contain the miR-150 gene in place of non-essential viral genes. The vector and/or particle may be utilized for the purpose of transferring any nucleic acids into cells either in vitro or in vivo. Numerous forms of viral vectors are known in the art.

The term "replication incompetent" as used herein means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins from packaging the virus) and viral particles cannot be formed in the patient's cells.

The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, "identity", in the context of two or more nucleic acids sequences, refers to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) when the sequences are aligned to maximize sequence matching, i.e., taking into account gaps and insertions, such as when using a BLAST or BLAST 2.0 sequence comparison algorithms with default parameters described below, or by manual alignment and visual inspection. Such sequences are then said to be "substantially identical." This term also refers to, or can be applied to, the complement of a test sequence. The term also includes sequences that have deletions and/or additions, as well as those that have substitutions. As described below, the preferred algorithms can account for gaps and the like. Preferably, identity exists over a region that is at least about 25 nucleotides in length, or more preferably over a region that is 50-100 nucleotides in length. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2: 482, 1981, by the homology alignment algorithm of Needleman & Wunsch, J. Mol. Biol. 48: 443, 1970, by the search for similarity method of Pearson & Lipman, Proc. Nat'l. Acad. Sci. USA 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement)).

Identity can be readily calculated by known methods, including but not limited to those described in (Computational Molecular Biology, Lesk, A. M., ea., Oxford University Press, New York, 1988; Biocomputing: Informatics and −14 Genome Projects, Smith, D. W., ea., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988)). Methods to determine identity are designed to give the largest match between the sequences tested. Moreover, methods to determine identity are codified in publicly available computer programs such as BLASTP.

Where necessary or desired, optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

As used herein, the term "a progenitor cell" refers to refer to an immature or undifferentiated cell that has the potential later on to mature (differentiate) into a specific cell type, for example, a blood cell, a skin cell, a bone cell, or a hair cells. A progenitor cell also can proliferate to make more progenitor cells that are similarly immature or undifferentiated.

As used herein, the term "hematopoietic progenitor cell" refers to progenitor cells that can differentiate into the hematopoietic lineage and give rise to all blood cell types such as white blood cells and red blood cells.

As used herein, the term "microRNA or miRNA" refers to a microRNA molecule found in eukaryotes that is involved in RNA-based gene regulation. See, e.g., Carrington and Ambros, 2003, Science, 301(5631):336-8 which is hereby incorporated by reference in its entirety. miRNA are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. The term will be used to refer to the RNA molecule processed from a precursor pre-miRNA.

Unless otherwise explained, all technical and scientific terms used herein have the same meaning as commonly understood by one of ordinary skill in the art to which this disclosure belongs. Definitions of common terms in hematology and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Current Protocols in Immunology (CPI) (John E. Coligan, et. al., ed. John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); Animal Cell Culture Methods (Methods in Cell Biology, Vol 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and, as such, may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the Inventions

Embodiments of the methods disclosed herein are based on the discovery that a microRNA (miRNAs), miR-150, regulates the differentiation of megakaryocyte-erythrocyte progenitor cells (MEPs) from the bone marrow. The regulation of the developmental fate of multi-potential cells is not well known and the process by which bipotential hematopoietic progenitor cells are driven to become either red blood cells or platelets is not understood. The inventors discovered that miRNAs control mammalian cell fate of the multi-potential MEPs, in particular, miR-150 modulates lineage fate in MEPs. The inventors found that miR-150 is preferentially expressed in the megakaryocytic lineage and that miR-150 expression in MEPs drives MEP differentiation toward megakaryocytes at the expense of erythroid cells in vitro and in vivo.

In experiments using human bone marrow hematopoietic progenitor cells, overexpression of the miR-150 gene resulted in a significant increase in megakaryocyte colony forming units (CFU-Mk) differentiating from MEPs with a concomitant decrease in erythroid colony forming units. When similar miR-150 overexpression experiments were conducted with murine bone marrow hematopoietic progenitor cells and the resultant miR-150 overexpressing progenitor cells were transplanted back into the animal, the mice exhibited a larger population of megakaryocytes and a greater number of platelets compared to control mice. miR-150 expression led to a bona fide increase in bone marrow megakaryocytes that were competent to produce mature platelets in circulation. MiR-150 expression induces a blockage in the earliest definable stage of erythropoiesis, in addition to causing a significant reduction in the total erythroid population. Accordingly, an increase amount of miR-150 regulates the differentiation of MEPs and the post-commitment megakaryocyte expansion.

While overexpression of miR-150 leads to pro-megakaryocyte differentiation and an increase in platelet count, the inhibition of miR-150 expression results in more erythroid colony forming units, more erythrocytes production and a corresponding decrease in CFU-Mk. In an artificial model of induced anemia, an inhibition of miR-150 with a specific antagomir elevated the erythrocyte count in the model animal. Clearly, one of the roles of miR-150 is in vivo is to regulate the differentiation of bi-potential MEPs and the production of RBCs and platelets.

MicroRNAs (miRNAs) are a class of 18-24 nt non-coding RNAs (ncRNAs) that exist in a variety of organisms, including mammals, and are conserved in evolution. miRNAs are transcribed as 5'-capped large polyadenylated transcripts (pri-miRNA), primarily in a Pol II-dependent manner. Approximately 40% of human miRNAs are co-transcribed as clusters encoding up to eight distinct miRNA sequences in a single pri-microRNA transcript. Many miRNAs can be encoded in intergenic regions, hosted within introns of pre-mRNAs or within ncRNA genes. Many miRNAs also tend to be clustered and transcribed as polycistrons and often have similar spatial temporal expression patterns. mRNAs have been found to have roles in a variety of biological processes including developmental timing, differentiation, apoptosis, cell proliferation, organ development, and metabolism (Kloosterman, et al., 2006 Dev Cell 11:441-50, and Krutzfeldt, et al., 2006 Cell Metab 4:9-12). Furthermore, miRNAs have been implicated in diseases such as cancer (Esquela-Kerscher, et al., 2006 Nat Rev Cancer 6:259-69) and hepatitis C (Jopling, et al., 2005 Science 309:1577-81), which make them attractive new drug targets. In contrast to the widely used RNAi technology using small interfering RNA (siRNA) duplexes, strategies to inhibit miRNAs have been less well investigated. Reverse-complement 2'-O-methyl sugar modified RNA is frequently being used to block miRNA function in cell-based systems (Krutzfeldt, et al., 2006 Nat Genet. 38:S14-9).

Pri-miRNAs are cleaved within the nucleus by the microprocessor complex consisting of Drosha, an RNaseIII-type nuclease and a protein co-factor, DGCR8 (DiGeorge syndrome critical region 8 gene) in humans, Pasha in *Drosophila*. The resulting 60-70 nucleotide hairpin structure (pre-miRNA) encodes for a single miRNA sequence that is exported from the nucleus to the cytoplasm by Exportin5 in a Ran-GTP dependent manner. Cytoplasmic pre-miRNAs are further cleaved, by another RNaseIII-nuclease, Dicer in concert with cofactors (TRBP and PACT in humans), to remove the loop sequence forming a short-lived asymmetric duplex intermediate (miRNA: miRNA *). The microRNA: microRNA * duplex is in turn loaded into the miRISC complex in which Argonaut (Ago) proteins appear to be the key effector molecules. The strand that becomes the active mature microRNA appears to be dependent upon which has the lowest free energy 5' end and the other strand is degraded by an unknown nuclease.

Accordingly, in one embodiment, disclosed herein is a method of treating thrombocytopenia in a host in need thereof, the method comprising administering to a host an effective amount of an agent that increases miR-150 expression in a cell.

Thrombocytopenia is a deficiency of platelets (thrombocytes). Platelets come from megakaryocytes, which are produced in the bone marrow from hematopoietic progenitor cells. When abnormalities develop in the marrow, the marrow cells can lose their ability to produce platelets in correct amounts. The result is a lower than normal level of platelets in the blood. Drugs used in cancer chemotherapy can cause the marrow to malfunction in this way, as can the presence of tumor cells in the marrow itself.

Normally, the spleen holds about one-third of the body's platelets as part of this organ's function to recycle aging or damaged RBCs. When liver disease or cancer of the spleen is present, the spleen can enlarge, resulting in a greater number of platelets staying in the organ. This condition then results in abnormally low numbers of platelets in the blood.

Platelets can break down in unusually high amounts in persons with abnormalities in their blood vessel walls; with blood clots; or with man-made replacement heart valves. Devices placed inside blood vessels to keep them from closing (stents) due to weakened walls or fat build-up can also cause platelets to break down. In addition, infections and other changes in the immune system can speed up the removal of platelets from the circulation.

Thrombocytopenia generally means a circulating platelet count of less than the normal circulating range, e.g., less than about $1.6 \times 10^5/mm^3$, less than about $1.5 \times 10^5/mm^3$, less than about $1.3 \times 10^5/mm^3$ or less than about $1.0 \times 10^5/mm^3$. Under the common terminology criteria for adverse events, version 3.0, grade 1 thrombocytopenia is the lower normal limit to 75,000 platelets/$mm^3$, grade 2 thrombocytopenia is <75,000–50,000 platelets/$mm^3$, grade 3 thrombocytopenia is <50,000–25,000 platelets/$mm^3$ and grade 4 is <25,000 platelets/$mm^3$.

The host needing treatment for thrombocytopenia can be any animal that has platelets, the platelets are produced from megakaryocytes, and the megakaryocytes are differentiated from hematopoietic progenitor cells. In one embodiment, the host is a mammal, such as a dog, cat, horse, and monkey, preferably a human.

A platelet count is performed to determine the number of platelets in circulation and on the basis of the platelet counts, the physician can determine whether the host has thrombocytopenia. A platelet count is part of the complete blood count test (CBC) routinely ordered by physicians. A platelet count is a test to measure platelets that are present in the peripheral circulating blood of a host. This test can be performed by skilled medical personnel such as physicians, nurses and trained laboratory technicians by methods known in the art. For example, a sample of peripheral blood is drawn into anticoagulaent to prevent the blood from clotting. The larger and heavier cells: white blood cells and RBCs are sedimented by low speed centrifugation (1000×G, 10 min) and the platelet-rich liquid fraction of the blood is collected and counted. Other manual methods of determining platelet counts include visual evaluation of blood smears on microscope slides and methods using RBCs-lysing agents followed by visual platelet counting. In one embodiment, platelets are determined using automated blood counting machines that include but are not limited to the Sysmex XE-2100, the Abbott Cell-Dyn range (e.g. Cell-Dyn 3500), Boule Nordic AB Ca530 Vet and Melet Schloesing MS4. In one embodiment, the platelet count is performed according to the European Patent EP1123510 and U.S. Pat. No. 6,872,572, both of which are hereby incorporated by reference in their entirety.

In one embodiment, the cell from a host needing treatment for thrombocytopenia wherein the miR-150 expression is increased is a progenitor cell. In another embodiment, the progenitor cell is a hematopoietic progenitor cell.

In one aspect, an agent that increases the miR-150 expression in a cell of a host comprises a vector comprising a nucleic acid sequence that is at least 90% identical to SEQ. ID. No. 1. In other aspects, the nucleic acid is at least 92%, at least 94%, at least 95%, at least 97%, at least 99%, and all the intermediate percentages between 90% and 100%, identical to SEQ. ID. No. 1. The differences from SEQ. ID. No 1 should be such that the overall hairpin structure of the pri-miR-150 is maintain.

In another aspect, the vector is a virus. In yet another aspect, the vector is a non-viral vector.

In one embodiment, an agent that increases miR-150 expression in a cell of a host comprises a nucleic acid sequence that is at least 90% identical to SEQ. ID. No. 1. In another embodiment, the nucleic acid is at least 92%, at least 94%, at least 95%, at least 97%, at least 99%, and all the intermediate percentages between 90% and 100%, identical to SEQ. ID. No. 1.

The SEQ. ID. No 1 provides the *Homo sapiens* miR-150 stem-loop pri-miRNA which is also known as has-mir-150, MI0000479, NT_011109, or miRBase:MI0000479 at the miRBase at the Sanger Institute (world wide web "period" microRNA "period" Sanger "period" ac "period" uk).

While not wishing to be bound by theory, expression of the miR-150 gene or a nucleic acid that is at least 90% identical to SEQ. ID. No. 1 by gene transcription produces a primary transcript, pre-miR-150, that can fold into a stem-loop structure. The pre-miR-150 can be exported out of the nucleus and be processed in the cytoplasm into a duplex miR-150 from which a mature miR-150 (SEQ. ID. 2) (miRBase:MI-MAT0000451) becomes available for upload into the miRISC (the miRNA gene inhibition complex). A vector comprising a nucleic acid that is at least 90% identical to SEQ. ID. No. 1, when transfected into a host cell, introduces the miR-150 gene as a transgene into the host cell. In this transfected host cell harboring the miR1-50 transgene, overexpression of the miR-150 transgene increases the amount of miR-150 in the cell. Excess amounts of miR-150 can lead to enhanced repression of genes naturally regulated by miR-150.

In one embodiment, a vector comprising a nucleic acid that is at least 90% identical to SEQ. ID. No. 1 is an expression vector. The expression vector can have a strong promoter sequence driving the robust mammalian transcription of the miR-150 transgene in the host cell. Strong promoter sequences include but are not limited to the Moloney murine leukemia virus promoter, cytomegalovirus promoter, the simian virus 40 early region promoter, the lymphotropic papovavirus, and the human beta-globin gene promoter sequences. In one embodiment, the promoter can be chimeric sequences from several promoter types as described in U.S. Pat. No. 6,136,536 which is incorporated hereby reference in its entirety. In another embodiment, the promoter can be the human osteocalcin (hOC) promoter (McCarthy H. O., et. al., 2007, J. Gene Medicine, 9: 511-20).

In one embodiment, the expression vector can be a virus such as an adenovirus, an adeno-associated virus, or lentivirus, for example, MDH.xdna murine retroviral vector. Viral vectors provide an additional advantage of ease of transfecting the host cell by viral infection. In another embodiment, the expression in a non-viral vector. Such vectors can be transfected into host cells using known transfection methods known in the art, such as cationic lipid transfection.

By increasing the miR-150 expression in the hematopoietic progenitor cells of a host, the differentiation of the hematopoietic progenitor cells can be shifted to producing more megakaryocytes, from which platelets are derived, eventually increasing the platelet count.

In one embodiment, disclosed herein is a method of treating thrombocytopenia in a host in need thereof, comprises: (a) contacting the hematopoietic progenitor cells with a vector comprising a nucleic acid sequence that is at least 90% identical to SEQ. ID. No. 1; and (b) introducing the cell carrying the transgene into the host.

The method comprises obtaining a sample of hematopoietic progenitor cells from a host.

In one embodiment, the hematopoietic progenitor cells are isolated from host, transfected, cultured, and transplanted back into the same host, i.e. an autologous cell transplant. In another embodiment, the hematopoietic progenitor cells are isolated from a donor who is an HLA-type match with a host (recipient) who is diagnosed with thrombocytopenia. Donor-recipient antigen type-matching is well known in the art. The HLA-types include HLA-A, HLA-B, HLA-C, and HLA-D. These represent the minimum number of cell surface antigen matching required for transplantation. The donor's hematopoietic progenitor cells can be transfected with a vector or nucleic acid comprising the nucleic acid that is at least 90% identical to SEQ. ID. No. 1 (the miR-150 transgene), culture expanded, and then transplanted into the host.

In one embodiment, the method disclosed herein includes monitoring the platelet count of a host before and after the administration of the agent for treatment of thrombocytopenia. The platelet count performed before treatment provides the data for a physician to make a diagnosis of thrombocytopenia and the platelet count also serves a reference number from which after the treatment platelet counts can be compared. Routine platelet count of samples of peripheral blood should be performed at 1, 2, 3 months or every bi-monthly after treatment or according to physician's decision in order to monitor the efficacy of the treatment.

In one embodiment, disclosed herein is a method of treating anemia in a host in need thereof, the method comprising administering an effective amount of an agent that inhibits miR-150 expression in a cell to a host.

Anemia generally means a red cell mass corresponding to less than about $4.0 \times 10^{12}$ red cells/L in adult females and less than about $4.5 \times 10^{12}$ red cells/L in adult males (a hemoglobin level of less than about 12.0 g/dL in adult females and less than about 13.5 g/dL in adult males). Anemia may occur as a result of bleeding (including internal), hemolysis, kidney disease, leukemia, multiple myeloma, bone marrow failure, erythropoietin deficiency, or deficiencies in iron, folate, vitamin B12, or vitamin B6.

The RBCs count is also a part of the complete blood count test (CBC) routinely ordered by physicians. A sample of peripheral blood can be collected and mixed with anticoagulant. For RBC counting by the manual visual method, a small, fixed volume of blood is diluted, applied to a hemacytometer and counted under a microscope. Alternatively, RBCs are counted with automated cell counters described herein.

In one embodiment, a host needing treatment for anemia can be any animal that has RBCs (erythrocytes), and the RBCs are differentiated from hematopoietic progenitor cells. In one embodiment, the host is a mammal, such as a dog, cat, horse, and monkey, preferably a human.

In one embodiment, the cell in a host wherein the miR-150 activity is inhibited, is a progenitor cell. In another embodiment, a progenitor cell wherein the miR-150 activity is inhibited is a hematopoietic progenitor cell.

In one embodiment, an agent that inhibits miR-150 activity in a cell comprises a nucleic acid sequence that can form complementary base-pairing with SEQ. ID. No. 2, the mature miR-150, for at least 90% of the bases of SEQ. ID. No. 2. In one aspect, the nucleic acid can form complementary base-pairing with at least 92%, at least 94%, at least 95%, at least 97%, at least 99%, and all the intermediate percentages between 90% and 100%, to SEQ. ID. No. 2. In another embodiment, an agent is a vector comprising a nucleic acid sequence that is at least 90% identical to SEQ. ID. No. 3 (miRBase:MIMAT0004610). The nucleic acid is at least 92%, at least 94%, at least 95%, at least 97%, at least 99%, and all the intermediate percentages between 90% and 100%, identical to SEQ. ID. No. 3. In yet another embodiment, an agent is a nucleic acid sequence that is at least 90% identical to SEQ. ID. No. 3.

In some aspects, an agent that inhibits miR-150 activity in a cell can be referred to as a miR-150 inhibitor, the miR-150 inhibitor functions by blocking, preventing, and/or antagonizing the normal cellular activity of the mature miR-150 which is to down regulate the expressions of certain genes. A miR-150 inhibitor can be an antagomir of miR-150, an anti-sense oligonucleotide to miR-150, a locked nucleic acid that anneals to miR-150, and double-stranded RNA corresponding to miR-150 (dsRNA).

In one embodiment, a miR-150 inhibitor is between 17 and 25 nucleotides in length and that comprises a 5' to 3' sequence that is at least 90% complementary to the 5' to 3' sequence of SEQ. ID. No. 2. In another embodiment, a miR-150 inhibitor is a synthetic RNA molecule of between 17 and 125 residues in length comprising i) an miRNA region whose sequence from 5' to 3' is identical to a mature miR-150 sequence, and ii) a complementary region whose sequence from 5' to 3' is between 60% and 100% complementary to the mature miR-150 sequence.

Antagomirs are a novel class of chemically engineered oligonucleotides that block the activity of miRNAs and essentially "silence" the miRNA (Krützfeldt J, et. al., 2005, Nature 438: 685-9). Antagomirs are single-stranded RNA that are perfectly complementary to their miRNA except that they are 2'-O-methyl (2'-OMe) oligoribonucleotides and are also linked to cholesterol at the 3' end. Both these modifications, 2'-OMe and cholesterol, aid in the antagomir stability in vivo and ease of entry into the cells. Methods of designing and synthesizing antagomirs and the various modifications (e.g. 2'-O-Methoxyethyl) are described in US Pat. Application 20070213292 and is hereby incorporated by reference in its entirety. An example of a miR-150 antagomir is 5' mC(*)mA(*)mCmUmGmGmUmAmCmAmAmGmGmGmUmUm GmGmG(*)mA(*)mG (*)mA (*)(3'-Chl) 3' (SEQ. ID. No. 23). The mN: 2'OMe base; *: phosphorothioate linkage; Chl: cholesterol.

In one embodiment, the miR-150 inhibitor is a miR-150 antagomir. In one embodiment, the miR-150 inhibitor is SEQ. ID. No. 23. In another embodiment, the miR-150 inhibitor consist essentially of SEQ. ID. No. 23. In another embodiment, the miR-150 inhibitor consist of SEQ. ID. No. 23. In another embodiment, the miR-150 inhibitor comprises SEQ. ID. No. 23.

Locked nucleic acid (LNA)-modified oligonucleotides are distinctive 2'-O-modified RNA in which the 2'-O-oxygen is bridged to the 4'-position via a methylene linker to form a rigid bicycle, locked into a C3'-endo (RNA) sugar conformation (Vester B., et. al., Biochemistry 2004; 43: 13233-13241). The LNA modification leads to the thermodynamically strongest duplex formation with complementary RNA known. Consequently, a biological activity is often attained with very short LNA oligonucleotides. For example, an 8 nt fully-modified LNA oligomer complementary to a structural loop inhibited 50% of self-splicing of group I introns from rRNA genes in pathogenic organisms whereas DNA and RNA oligonucleotides were ineffective. Short fully-modified LNA oligonucleotides designed against telomerase were active in cellular assays, compared to mismatched negative controls. Furthermore, LNAs display excellent mismatch discrimination. Mouritzen et al. (Expert Rev Mol Diagn 2003; 3: 27-38) showed single-nucleotide specificity against complementary DNA using fully modified 12 nucleotide LNA probes coupled to glass slides during the development of a microarray used to probe samples for single-nucleotide polymorphisms (SNPs) associated with human dysmetabolic syndrome. The synthesis and incorporation of LNA bases can be achieved by using standard DNA synthesis chemistry and described in U.S. Pat. No. 6,268,490 and is hereby incorporated by reference in its entirety.

An anti-sense oligonucleotide of miR-150 has a sequence that perfectly complementary to SEQ. ID. No. 2, the mature miR-150. Complementary pairing between an anti-sense oligonucleotide of miR-150 and miR-150 produces a duplex RNA that is highly susceptible to RNase degradation. An anti-sense oligonucleotide of miR-150 comprises the sequence 5'-CACUGGUACAAGGGUUGGGAGA-3' (SEQ. ID. No. 4).

One skilled in the art can also readily determine an appropriate dosage regimen for administering a compound that inhibits miRNA expression to a given subject, as described herein. Suitable compounds for inhibiting miRNA gene expression include double-stranded RNA (such as short- or small-interfering RNA or "siRNA"), antisense nucleic acids, and enzymatic RNA molecules, such as ribozymes. Each of these compounds can be targeted to a given miRNA gene product and interfere with the expression (e.g., by inhibiting translation, by inducing cleavage and/or degradation) of the target miRNA gene product. For example, expression of a given miRNA gene can be inhibited by inducing RNA interference of the miRNA gene with an isolated double-stranded RNA ("dsRNA") molecule which has at least 90%, for example at least 95%, at least 98%, at least 99%, or 100%, sequence homology with at least a portion of the miRNA gene product. In a particular embodiment, the dsRNA molecule is a "short or small interfering RNA" or "siRNA." siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired")—The sense strand comprises a nucleic acid sequence that is substantially identical to a nucleic acid sequence contained within the target miRNA gene product.

In one embodiment, an agent that inhibits miR-150 activity is a vector that comprises an anti-sense oligonucleotide to miR-150 (SEQ. ID. No. 4). The anti-sense oligonucleotide sequence can be cloned into a vector for the expression in a host cell by any means known to one skilled in the art. In one embodiment, the vector is a virus. In another embodiment, the vector is a non-virus. Designing, cloning, transfection, and expression of anti-sense oligonucleotides against miRNAs are described in Scherr M. et. al., 2007, Nucleic Acid Research 35(22):e149 and is incorporated hereby reference in its entirety.

In one embodiment, the agent can be various combinations of an antagomir of miR-150, an antisense oligonucleotide to miR-150, dsRNA to miR-150, or a locked nucleic acid that anneals to miR-150.

In one embodiment, disclosed herein is a method of treating anemia in a host in need thereof, the method comprising: (a) contacting the hematopoietic progenitor cells with a vector comprising a nucleic acid sequence that is at least 90% identical to SEQ. ID. No. 3 or 4; and (b) introducing the cell from step b into the same host. The method comprises obtaining a sample of hematopoietic progenitor cells from a host. Methods of isolating, transfecting, culturing, screening for strong expression of transgene, and transplantation can be performed as described herein.

In one embodiment, the method disclosed herein includes monitoring the RBC count of a host before and after the administration of the agent for treatment of anemia. The RBC count performed before treatment provide the data for a physician to make a diagnosis of anemia and the RBC count also serve a reference number from which after treatment RBC counts can be compared with. Routine RBC count of samples of peripheral blood should be performed at 1, 2, 3 months or every bi-monthly after treatment or according to physician's decision in order to monitor the efficacy of the treatment.

In one embodiment, the method disclosed herein comprises treating anemia in conjunction with other known treatments such as with erythropoietin (EPO) and peptide mimetics of EPO. EPO is a hormone produced by the kidney that promotes the formation of red blood cells in the bone marrow. The kidney cells that make EPO are specialized and are sensitive to low oxygen levels in the blood. These cells release EPO when the oxygen level is low in the kidney. EPO then stimulates the bone marrow to produce more red cells and thereby increase the oxygen-carrying capacity of the blood. EPO is the prime regulator of red blood cell production. Its major functions are to promote the differentiation and development of red blood cells and to initiate the production of hemoglobin, the molecule within red cells that transports oxygen.

In one embodiment, the methods described herein can be implemented with other therapeutics associated with thrombocytopenia and anemia.

The present invention can be defined in any of the following alphabetized paragraphs:

[A] The use of an agent that increases miR-150 expression in a cell for the treatment of thrombocytopenia in a host in need thereof.

[B] The use of an agent that increases miR-150 expression in a cell in the manufacture of a medicament for the treatment of thrombocytopenia.

[C] The use of paragraph [A] or [B], wherein the cell is a progenitor cell.

[D] The use of paragraph [C], wherein the progenitor cell is a hematopoietic progenitor cell.

[E] The use of paragraph [A] or [B], wherein the agent is a vector comprising a nucleic acid sequence that is at least 90% identical to SEQ. ID. No. 1.

[F] The use of paragraph [E], wherein the vector is a virus.

[G] The use of paragraph [A] or [B], wherein the agent is a nucleic acid sequence that is at least 90% identical to SEQ. ID. No. 1.

[H] A method of treating thrombocytopenia in a host in need thereof, the method comprising administering an effective amount of an agent that increases miR-150 expression in a cell to a host.

[I] The method of paragraph [H], wherein the cell is a progenitor cell.

[J] The method of paragraph [I], wherein the progenitor cell is a hematopoietic progenitor cell.

[K] The method of paragraph [H], wherein the agent is a vector comprising a nucleic acid sequence that is at least 90% identical to SEQ. ID. No. 1.

[L] The method of paragraph [K], wherein the vector is a virus.

[M] The method of paragraph [H], wherein the agent is a nucleic acid sequence that is at least 90% identical to SEQ. ID. No. 1.

[N] A method of treating thrombocytopenia in a host in need thereof, the method comprising:
  a. obtaining a sample of hematopoietic progenitor cells from said host;
  b. contacting the hematopoietic progenitor cells with a vector comprising a nucleic acid sequence that is at least 90% identical to SEQ. ID. No. 1; and
  c. introducing the cell from step b into the host.

[O] The use of an agent that inhibits miR-150 in a cell for the treatment of anemia in a host in need thereof.

[P] The use of an agent that inhibits miR-150 in a cell in the manufacture of a medicament for the treatment of anemia.

[Q] The use of either paragraph [O] or [P], wherein the cell is a progenitor cell.

[R] The use of paragraph [Q], wherein the progenitor cell is a hematopoietic progenitor cell.

[S] The use of paragraph [O] or [P], wherein the agent is an antagomir of miR-150, an anti-miR-150 oligonucleotide, an antisense oligonucleotide to miR-150 or a locked nucleic acid that anneals to miR-150.

[T] The use of paragraph [O] or [P], wherein the agent is a vector comprising a nucleic acid sequence that is at least 90% identical to SEQ. ID. No. 3.

[U] The use of paragraph [T], wherein the vector is a virus.

[V] A method of treating anemia in a host in need thereof, the method comprising administering an effective amount of an agent that inhibits miR-150 in a cell to a host.

[W] The method of paragraph [V], wherein the cell is a progenitor cell.

[X] The method of paragraph [W], wherein the progenitor cell is a hematopoietic progenitor cell.

[Y] The method of paragraph [V], wherein the agent is a vector comprising a nucleic acid sequence that is at least 90% identical to SEQ. ID. No. 3.

[Z] The method of paragraph [V], wherein the agent is an antagomir of miR-150, an anti-miR-150 oligonucleotide, an antisense oligonucleotide to miR-150 or a locked nucleic acid that anneals to miR-150.

[AA] A method of paragraph [Y], wherein the vector is a virus.

[BB] A method of treating anemia in a host in need thereof, the method comprising:
  a. obtaining a sample of hematopoietic progenitor cells from said host;
  b. contacting the hematopoietic progenitor cells with a vector comprising a nucleic acid sequence that is at least 90% identical to SEQ. ID. No. 3; and
  c. introducing the cell from step b into the same host.

Hematopoietic Progenitor Cells

Peripheral blood progenitor cells (PBPC) have become the preferred source of hematopoetic progenitor cells for allogeneic and autologous transplantation because of technical ease of collection and shorter time required for engraftment. Traditionally, granulocyte-colony stimulating factor (G-CSF) has been used to stimulate more PBPC and release of hematopoetic progenitor cells from the bone marrow. Although regimens using G-CSF usually succeed in collecting adequate numbers of PBPC from healthy donors, 5%-10% will mobilize stem cells poorly and may require multiple large volume apheresis or bone marrow harvesting.

AMD3100, is a bicyclam compound that inhibits the binding of stromal cell derived factor-1 (SDF-1) to its cognate receptor CXCR4. CXCR4 is present on CD34+ hematopoetic progenitor cells and its interaction with SDF-1 plays a pivotal role in the homing of CD34+ cells in the bone marrow. Inhibition of the CXCR4-SDF1 axis by AMD3100 releases CD34+ cells into the circulation, which can then be collected easily by apheresis. Recently, a published report demonstrated that large numbers of CD34+ cells were rapidly mobilized in healthy volunteers following a single subcutaneous injection of AMD3100.

The hematopoietic progenitor cells can be isolated fresh and frozen mononuclear cells of peripheral blood, cord blood, and bone marrow using its pan-hematopoietic antigen CD34 or by other methods that are known to one skilled in the art. For example, antibodies against CD34 can be used for immuno-isolating the CD34(+) hematopoietic progenitor cells from the mononuclear cell fraction. The anti-CD34 antibodies can be conjugated with fluorophores or to magnetic beads for ease of separation by FACS or magnets respectively.

Hematopoietic progenitor cells bearing the pan-hematopoietic antigen CD34 can also be isolated by using taking advantage of the cells ability to bind galactose-conjugated proteins. This lectin-positive sub-population represents approximately 0.1 to 0.5% of the total bone marrow cells, and contains 100% of the hematopoietic progenitor cells. The galactose-binding lectin on these cells is specific for this sugar. Additionally, highly proliferative hematopoietic progenitor cells with very primitive phenotypes, including a newly identified progenitor cell that produces multiple lineages, express this lectin. (Pipia and Long, Nature Biotechnology 15, 1007-1011 (1997)).

In vitro transfection of isolated hematopoietic progenitor cells from a host facilitates targeted transfection of the miR-150 transgene into specific progenitor cells. Transfection of progenitor cells can be accomplished by any transfection methods known in the art, for example, calcium phosphate-mediated, DEAE-Dextran-mediated, calcium alginate microbeads, cation lipid-mediated, scrape-loading, and ballistic bombardment of nucleic acid gold particles. In one embodiment, isolation and culturing of progenitor cells is performed using the methods well known in to those skilled in the art, e.g. as described in U.S. Pat. Nos. 5,199,942, 5,474,687, 5,589,368, 5,612,211, 5,905,041, 6,355,237, and 7,345,025, which are hereby incorporated by reference in their entirety. The identity of the isolated hematopoietic progenitor cells can be confirmed by transglutaminase expression in culture as described in WO2000/006766, which is also hereby incorporated by reference in its entirety. After in vitro transfection, the miR-150 transfection level can be monitored by quantitative real-time PCR with specific primer pairs to the pre-miR-150 and the mature miR-150. The transfected progenitor cells carrying the transgene can be expanded in culture according to methods described in U.S. Pat. Nos. 5,744,361, 5,905,041, and 6,326,198, which are hereby incorporated by reference in their entirety. The expanded progenitor cells with the miR-150 transgene can then be transplanted back into the original host. Transplantation of progenitor cells are described in U.S. Pat. Nos. 5,817,773, 5,858,782, and U.S. patent application Ser. No. 10/730,334 and they are hereby incorporated by reference in their entirety.

In one embodiment, the SEQ. ID. No. 1 (miR-150 gene) is cloned into the MDH.xdna murine retroviral vector and miR-150 retroviral vectors can be transfected into isolated hematopoietic progenitor cells. Forty-eight hours after transfection, total RNAs were isolated and loaded onto a 10% denaturing polyacrylamide gel. DNA oligo probes that were complementary to each of the selected miRNAs were labeled and hybridized to the membrane to detect mature miR-150s that can be efficiently processed (20- to 24-nt). Constructs with high processing efficiency can be selected for bone marrow transplantation.

Expression Vectors and Expression Systems for Expression

Isolated nucleic acid sequences that are at least 90% identical to SEQ. ID. No. 1, 3 and 4 can be obtained using a number of standard techniques. For example, the nucleic acids can be chemically synthesized or recombinantly produced using methods known in the art. In one embodiment, the nucleic acids are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the nucleic acids and their complementary strands can be synthesized as single strand DNA initially and then subsequently anneal together to form duplex for cloning into vectors for gene expression as described in Scheer M. et. al. supra. Restriction enzyme sites can be designed and incorporated at the ends of the eventual duplex to facilitate ligating the duplex into a vector.

The human miR-150 stem loop (hsa-miR-150) is contained within a 473 bp genomic fragment that includes the hairpin region of hsa-miR-150 and ~200 bp of flanking sequence on each side. This genomic expression cassette can be PCR amplified from human genomic DNA (Roche Applied Science) with primers containing 5' linker sequences harboring relevant digestion sites (core primer sequences: 5' CAGCAT-AGGGTGGAGTGGGT3' (Seq. ID. No. 5); 5'TACTTTGCG-CATCACACAGA3' (SEQ. ID. No. 6).

Once ligated into a vector, the nucleic acid can be subcloned into several expression vectors, such as a viral expression vector or a mammalian expression vector by PCR cloning, restriction digestion followed by ligation, or recombination reaction such as those of the lambda phage-based site-specific recombination using the GATEWAY® LR and BP CLONASE™ enzyme mixtures. Subcloning should be unidirectional such that the 5' transcription start nucleotide of the nuclei acid sequence is downstream of the promoter in the expression vector. Alternatively, when the nucleic acid sequence is cloned into pENTR/D-TOPO®, pENTR/SD/D-TOPO® (directional entry vectors), or any of the INVITROGEN's GATEWAY® Technology pENTR (entry) vectors, the nucleic acid sequence can be transferred into the various GATEWAY® expression vectors (destination) for protein expression in host cells in one single recombination reaction. Some of the GATEWAY® destination vectors are designed for the constructions of baculovirus, adenovirus, adeno-associated virus (AAV), retrovirus, and lentiviruses, which upon infecting their respective host cells, facilitating ease of introducing the transgene into the host cells. The GATEWAY® Technology uses lambda phage-based site-specific recombination instead of restriction endonuclease and ligase to insert a gene of interest into an expression vector. The DNA recombination sequences (attL, attR, attB, and attP) and the LR and BP CLONASE™ enzyme mixtures that mediate the lambda recombination reactions are the foundation of GATEWAY® Technology. Transferring a gene into a destination vector is accomplished in just two steps: Step 1: Clone the nucleic acid sequence of interest into an entry vector such as pENTR/D-TOPO®. Step 2: Mix the entry clone containing the nucleic acid sequence of interest in vitro with the appropriate GATEWAY® expression vector (destination vector) and GATEWAY® LR CLONASE™ enzyme mix. There are GATEWAY® expression vectors for protein expression in *E. coli*, insect cells, mammalian cells, and yeast. Site-specific recombination between the att sites (attR×attL and attB×attP) generates an expression vector and a by-product. The expression vector contains the nucleic acid sequence of interest recombined into the destination vector backbone. Following transformation and selection in *E. coli*, the expression vector is ready to be used for expression in the appropriate host.

The nucleic acid sequence of interest can be expressed from recombinant circular or linear DNA vector using any suitable promoter. Suitable promoters for expressing RNA from a vector include, e.g., the U6 or H1 RNA pol III promoter sequences, or the cytomegalovirus promoters. Selection of other suitable promoters is within the skill in the art. The expression vector should have the necessary 5' upstream and 3' downstream regulatory elements such as promoter sequences, ribosome recognition and binding TATA box, and 3' UTR AAUAAA (SEQ. ID. No. 25) transcription termination sequence for the efficient gene transcription and translation in its respective host cell. The recombinant vectors can also comprise inducible or regulatable promoters for expression of the nucleic acid sequence of interest in hematopoietic progenitor cells. The nucleic acids that are expressed from recombinant vectors can also be delivered to, and expressed directly in, cells. In one embodiment, the nucleic acids are expressed as RNA precursor molecules from a single vector, and the precursor molecules are processed into the functional miR gene product by a suitable processing system, including, but not limited to, processing systems extant within a cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of vectors suitable for expressing the nucleic acid sequence, methods for inserting nucleic acid sequences into vector to express the gene products, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee ei al. (2002), Nat. Biotechnol. 20:500-505; and Paul et al. (2002), Nat. Biotechnol. 20:505-508, the entire disclosures of which are incorporated herein by reference.

Examples of expression vectors for mammalian host cells include but are not limited to the strong CMV promoter-based pcDNA3.1 (INVITROGEN) and pClneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (INVITROGEN) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLENTI4/V5-DEST™, pLenti6/V5-DESTT™, and pLENTI6.2/V5-GW/lacZ (INVITROGEN) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells;

A simplified system for generating recombinant adenoviruses is presented by He T C. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli*. BJ5183 cells with an adenoviral backbone plasmid, e.g. pAdEasy-1 of Stratagene's AdEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

In one embodiment, a recombinant lentivirus can be used for the delivery and expression of a nucleic acid sequence that is at least 90% identical to SEQ. ID. No. 1, 3 or 4 in either dividing and non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLENTI4/V5-DEST™, pLENTI6/V5-DEST™ or pLenti vectors together with ViraPower™ Lentiviral Expression systems from Invitrogen.

In one embodiment, a recombinant adeno-associated virus (rAAV) vector can be used for the expression of a nucleic acid sequence that is at least 90% identical to SEQ. ID. No. 1, 3 or 4. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-

$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the chimeric DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients. Delivery vectors can also included but are not limited to replication-defective adenoviral vectors, cationic liposomes and protein-cationic peptides. For example, one study reports a system to deliver DNA in vitro by covalently attaching the surfactant associated protein B (SP-B) to a 10 kDa polylysine. See, Baatz, J., et al., PNAS USA, 91:2547-2551 (1994). See, e.g., Longmuir, et al., 1992 ASBMB/Biophysical Society abstract; Longmuir, et al., 1993 Biophysical Society abstract.

Therapeutic Uses and Administration

In one embodiment, a nucleic acid or vector administered to the host cells comprise a non-cationic lipid for cytoplasmic and/or nuclear delivery, wherein the nucleic acid or vector is stable and is used in biological extracellular fluids typically found in animals, particularly blood serum.

Liposomes, spherical, self-enclosed vesicles composed of amphipathic lipids, have been widely studied and are employed as vectors for in vivo administration of therapeutic agents. In particular, the so-called long circulating liposomes formulations which avoid uptake by the organs of the mononuclear phagocyte system, primarily the liver and spleen, have found commercial applicability. Such long-circulating liposomes include a surface coat of flexible water soluble polymer chains, which act to prevent interaction between the liposome and the plasma components which play a role in liposome uptake. Alternatively, hyaluronan has been used as a surface coating to maintain long circulation.

In one embodiment, the liposome encapsulate the nucleic acid sequences, vectors or even the viral particles. In one embodiment, the nucleic acid sequences or vectors are condensed with a cationic polymer, e.g., PEI, polyamine spermidine, and spermine, or a cationic peptide, e.g., protamine and poly-lysine, and encapsulated in the lipid particle. The liposomes can comprise multiple layers assembled in a step-wise fashion.

Lipid materials well known and routinely utilized in the art to produce liposomes. Lipids may include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. Preferred lipids for producing liposomes according to the invention include phosphatidylethanolamine (PE) and phosphatidylcholine (PC) in further combination with cholesterol (CH). According to one embodiment of the invention, a combination of lipids and cholesterol for producing the liposomes of the invention comprise a PE:PC:Chol molar ratio of 3:1:1. Further, incorporation of polyethylene glycol (PEG) containing phospholipids is also contemplated by the present invention.

In addition, in order to prevent the uptake of the liposomes into the cellular endothelial systems and enhance the uptake of the liposomes into the tissue of interest, the outer surface of the liposomes may be modified with a long-circulating agent. The modification of the liposomes with a hydrophilic polymer as the long-circulating agent is known to enable to prolong the half-life of the liposomes in the blood Liposomes encapsulating the nucleic acid sequences described herein can be obtained by any method known to the skilled artisan. For example, the liposome preparation of the present invention can be produced by reverse phase evaporation (REV) method (see U.S. Pat. No. 4,235,871), infusion procedures, or detergent dilution. A review of these and other methods for producing liposomes may be found in the text Liposomes, Marc Ostro, ed., Marcel Dekker, Inc., New York, 1983, Chapter 1. See also Szoka Jr. et al., (1980, Ann. Rev. Biophys. Bioeng., 9:467).

The use of an therapeutically effective amount of the nucleic acid sequences or vectors disclosed herein for the treatment of thrombocytopenia and anemia should preferably include but is not limited to a composition of the nucleic acid segments in lactated Ringer's solution and the composition is sterile. Lactated Ringer's solution is a solution that is isotonic with blood and intended for intravenous administration. Include are antioxidants, buffers, antibiotics and solutes that render the compositions substantially isotonic with the blood of an intended recipient. In another embodiment, the composition comprise gene delivery vectors described herein. In another embodiment, the composition also include water, polyols, glycerine and vegetable oils, and nutrients for cells, for example. Compositions adapted for parenteral administration can be presented in unit-dose or multi-dose containers, in a pharmaceutically acceptable dosage form. Such dosage forms, along with methods for their preparation, are known in the pharmaceutical and cosmetic art. Harry's Cosmeticology (Chemical Publishing, 7th ed. 1982); Remington's Pharmaceutical Sciences (Mack Publishing Co., 18th ed. 1990).

In one embodiment, dosage forms include pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients can be added, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the administration of the nucleic acid segments or gene delivery vectors disclosed herein are by any suitable route, and means, for example, parenterally, intravenous, intra-arterial, intracranial, intracerebrospinal, intratumoral, peritoneal, by injection, by catheter, by implantation with or without a matrix or gel material, or by gradual delivery device. In one embodiment, the nucleic acid segments or gene delivery vectors described herein can be administered directly by injection.

The therapeutically effective amount amounts to be administered will depend on the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art; however, that a lower dose or tolerable dose may be administered for medical reasons, psychological reasons or for virtually any other reason.

This invention is further illustrated by the following example which should not be construed as limiting. The contents of all references cited throughout this application, as well as the figures and table are incorporated herein by reference.

EXAMPLES

Materials and Methods mRNA expression profiling and data analysis—miRNA expression profiling was performed using the plate capture method unless otherwise stated. 96-well PCR plates with N-oxysuccinimide surface (DNA-BIND plates, Corning Costar) were coated at room temperature for 1 hour with 5 μM mixture of 5' amino-antisense oligonucleotides (see Table 4) at 20 μl per well according to manufacturer's protocol. Coated plates were successively washed with (100 mM Tris-HCl, pH8.0, 150 mM NaCl, 1 mM EDTA) and (10 mM Tris-HCl, pH 8.0, 1 mM EDTA). Total RNA (10 ng or higher) was diluted to 20 μl in 50 mM Tris-HCl, pH 8.0, 1 M NaCl, 1 mM EDTA, 1×RNAsecure (Ambion), containing pre-control synthetic miRNA mixture at the ratio previously described (1). miRNAs were captured in the coated wells by denaturing at 80° C. for 5 minutes and gradually cooling to room temperature in 1.5 hours in a PCR machine, followed by three 2×SSC washes. 3' adaptor ligation and 5' adaptor ligations were carried out as described (1) in 20 μl reaction volumes, with four 2×SSC washes after each ligation. Ligated miRNA were denatured for 5 minutes at 80° C. in 20 μl water with 2 μM adaptor-specific RT primer, chilled on ice, and reverse transcribed as described (1). RT products were denatured at 95° C. for 5 minutes before 2 rounds of PCR amplification with described conditions (1), for 26 and 27 cycles respectively, to incorporate biotin labels for low input RNA profiling. Labeled miRNAs were hybridized to a bead-based detection platform (1), with updated detection probes (Table 5). Median fluorescence intensities were quantitated on a Luminex 100S machine (Luminex Corp).

Data were normalized as described (1) with modifications. Average readings from 5 water-only labeled samples were used for probe-specific background subtraction.

Linear normalization among different bead sets for the same sample was performed using readings from 2 post-control probes with equal contribution. Sample normalization was subsequently carried out assuming equal total fluorescence readings. To identify markers, all ERY samples were compared to all MEGA samples, with median-based t-test and 50,000 permutations, using the Comparative Marker Selection module in GENEPATTERN (2).

Cell sorting and flow cytometry—Human umbilical cord blood was harvested at Brigham and Women's Hospital with informed patient consent under an IRB approved protocol. Adult human bone marrow cells were obtained from AllCells, LLC. Mononuclear cells were purified by Ficoll Hypaque sedimentation. Lineage depletion was performed using antibodies against CD2, CD3, CD4, CD5, CD8, CD11b, CD14C, CD19, and CD56 with a magnetic column (Miltenyi Biotec). Populations were defined as follows: MEP (CD34+ CD38iL¬ 13Ra–CD45RA–), ERY1 (CD34+CD71+GlyA–), ERY2 (CD34–CD71+GlyA–), ERY3 (CD34–CD71+ GlyA+). Megakaryocytes were purified without lineage depletion according to the following immunophenotypes: MEGA1 (CD34+CD61+CD41+CD45–), MEGA2 (CD34– CD61+CD41+CD45–). Adult human bone marrow cells were similarly sorted according to CD34–CD61+CD41+ and CD34–CD71+GlyA+. Sorting was performed with a Vantage SE Diva or with an Aria (BD Biosciences). RNA was extracted using TRIZOL (INVITROGEN).

For the in vitro human primary culture experiment, approximately 500,000 cells were stained with CD41-FITC, Ter119-PE and CD71-PE-Cy5 antibodies for 15 minutes on ice and washed twice before flow cytometry. For analysis of transplant recipients, murine bone marrow cells were labeled with CD41-PE and Ter119-APC, or Ter119-APC and CD71-PE. Peripheral blood cells were harvested into 0.38% sodium citrate and stained with CD41-PE.

Mouse MEPs were purified as described in (3). Briefly, bone marrow cells were harvested from 8- to 10-week old C57B16/J mice and stained with an antibody cocktail containing biotinylated lineage markers including Ter119, CD3, CD4, CD8, CD11b/Mac-1 Gr-1 and B220, and followed by staining with a second antibody cocktail containing streptavidin-PerCP, Sca-PE, cKit-APC, CD16/32 PE-Cy7 and CD34-FITC. MEPs are defined as the Lin−cKit+Sca−CD34−CD16/32− population. Antibodies used for cell surface markers are found in Table 2.

Constructs—Expression vectors for hsa-miR-150 contain a 473 bp genomic fragment that includes the hairpin region of hsa-miR-150 and ~200 bp of flanking sequence on each side. This genomic expression cassette was PCR amplified from human genomic DNA (Roche Applied Science) with primers containing 5' linker sequences harboring relevant digestion sites (core primer sequences: 5' CAGCATAGGGTG-GAGTGGGT3' (SEQ. ID. No. 5); 5'TACTTTGCGCATCA-CACAGA3' (SEQ. ID. No. 6)). For the human CD34+ primary culture experiment, the lenti-viral vector pLKO. 1 (obtained from The RNAi Consortium, Broad Institute) was used, with the miR-150 expression cassette, or an shRNA against luciferase (shLuc), cloned into the AgeI and EcoRI sites. hsa-miR-15b-16-2 was similarly cloned with a genomic DNA fragment through PCR amplification (core primer sequences: 5'TTTCCTCAAAACAGGAAGG3' (SEQ. ID. No. 7); 5'CCACCAAGTAAGTCATTTTC3' (SEQ. ID. No. 8)). For expression in cell lines, the miR-150 expression cassette, or EGFP coding sequence, was cloned into the pMSCV-puro vector through the BglII and MluI sites. For in vivo transplantation assays, the pMSCV-puro vector was substituted with pMSCV-EGFP, in which the EGFP coding sequence replaced that of the puromycin resistance gene in pMSCV-puro.

Mutant miR-150 constructs were created by PCR-mediated site-directed mutagenesis. Mutations were introduced into the 5' seed region of mature hsa-miR-150, as well as into the opposite arm of the hairpin to maintain overall hairpin structure. Primers used are listed below:

```
                                        (SEQ. ID. No. 9)
5'CCCCATGGCCCTGTCTGGGAACCCTTGTACCAGTG3'

(SEQ. ID. No. 10)
5' CACTGGTACAAGGGTTCCCAGACAGGGCCATGGGG3'

(SEQ. ID. No. 11)
5' CCCTGGTACAGGCCTCCCGGACAGGGACCTG3'

(SEQ. ID. No. 12)
5' CAGGTCCCTGTCCGGGAGGCCTGTACCAGGG3'.
```

The MYB cDNA clone, containing only the coding sequence and Kozak sequence, was obtained from Invitrogen (Ultimate ORF collection) in the form of a Gateway entry vector. This clone, as well as a Gateway entry clone without insert (vector control), were recombined into pLenti6.2/V5DEST vector using LR recombination reactions (Invitrogen).

MYB 3'UTR luciferase reporter was created by inserting human MYB 3' UTR (according to RefSeq NM_005375) into the XhoI and NotI sites in the psiCHECK2 vector (Promega), downstream of the renilla luciferase coding sequence. MYB 3'UTR was amplified from human genomic DNA with the following primers:

```
                                        (SEQ. ID. No. 13)
5'TAACTCGAGACATTTCCAGAAAAGCATTATG3',
and
                                        (SEQ. ID. No. 14)
5'ATAGCGGCCGCAGGTAAAATAAGGGCACATC3'.
```

Mutations of putative miR-150 binding sites were created by PCR-mediated site-directed mutagenesis. Primers used are listed below.

```
Site 1:
                                        (SEQ. ID. No. 15)
5'ACTTTTCATGAATCCCAGAAGAACCTAT3'

(SEQ. ID. No. 16)
5'ATAGGTTCTTCTGGGATTCATGAAAAGT3'

Site 2:
                                        (SEQ. ID. No. 17)
5'TGAAAACTTGTTTCCCAGACTCTGCATT3'

(SEQ. ID. No. 18)
5'AATGCAGAGTCTGGGAAACAAGTTTTCA3'

Site 3:
                                        (SEQ. ID. No. 19)
5'TGCACTTCTTTTTTCCCAGATGTGTGTTGT3'

(SEQ. ID. No. 20)
5'ACAACACACAT CT GGGAAAAAAGAAGT GCA3'

Site 4:
                                        (SEQ. ID. No. 21)
5'CTGTTTTATAATTTCCCAGTTCTGCATTTG3'

(SEQ. ID. No. 22)
5' CAAAT GCAGAAC T GGGAAAT TATAAAACAG3'
```

Short hairpin RNAs against human MYB were obtained from The RNAi Consortium (world wide web "period" broad "period" mit "period" edu "forward slash" genome "underscore" bio "forward slash" trc "forward slash"). The IDs of the shMYB-1 and shMYB-2 clones are TRCN0000040058 and TRCN0000009853.

Quantitative RT-PCR—Quantitative RT-PCR primers and probes were all obtained from Applied Biosystems. Reverse transcription reactions were performed following the manufacturer's protocol with minor modifications. Briefly, 1 ng to 10 ng of total RNA were reverse transcribed using the MultiScribe cDNA synthesis system (Applied Biosystems) in 5 µl volume with either miRNA gene specific RT primers, or with 6.25 ng random primers (Invitrogen). Duplicate or triplicate RT reactions were performed for each sample and each RT primer. RT products were diluted 2.5 fold before PCR. PCR reactions were performed in duplicate for each RT product, following the manufacturer's protocol and using assays from Applied Biosystems on an ABI HT7900 real time PCR machine. Reactions for eukaryotic 18S ribosomal RNA and messenger RNAs were performed with random-primer-based RT products, whereas reactions for miRNAs used corresponding gene-specific RT products. Threshold cycles (using a manual cutoff of 0.2) or genes of interest were normalized by Ct values of corresponding 18S rRNA reactions. ΔCt values (Ct of 18S minus Ct of gene of interest) were used unless specified otherwise. Quantitative RT-PCR assays used in this study are found in Table 1.

In vitro primary culture of human CD34+ cells-Cryopreserved human adult bone marrow CD34+ cells were obtained from Cambrex (Poietics; Cambrex). Cells were cultured in Serum Free Expansion Medium (SFEM, Stem Cell Technologies) supplemented with 100 U/mL penicillin/streptomycin, 2 mM glutamine, and 40 µg/mL lipids (SIGMA ALDRICH). Erythroid and megakaryocytic differentiation were supported in a single liquid culture, similarly as described (4), in the presence of 50 ng/mL TPO, 100 ng/mL SCF, 10 ng/mL IL-3, 10 ng/mL IL-6, and 0.5 U/mL EPO. The concentration of EPO was increased to 3 IU/mL on day 7. Cells were harvested for flow cytometry following 10 days of liquid culture. Lentiviral infection was performed starting one day after thawing cells. Where indicated, cDNA construct and miRNA construct were infected on consecutive days. Cells were selected with 2 μg/mL puromycin or 3 μg/mL blasticidin one day after infection.

Murine bone marrow transplant—All mice were purchased from the Jackson Laboratory. Murine bone marrow transplant was performed similarly as previously described (5), and approved by the MGH Subcommittee on Research Animal Care. Donor C57B16/J mice (~8 weeks) were primed with 150 mg/kg 5FU for four days. Bone marrow cells were purified by Ficoll (GE Healthcare) density gradient centrifugation, following the manufacturer's protocol. Cells were transduced with empty vector or miR-150 retrovirus in X-VIVO 15 medium (Biowhittaker) supplemented with 100 ng/mL SCF, 50 ng/mL TPO, 50 ng/mL Flt3 ligand and 20 ng/mL IL3 by centrifugation onto plates coated with retronectin (TAKARA). Lethally irradiated (9.5 Gy) recipient mice were transplanted with 2.5-4 million cells the day after infection. Hematopoeitic recovery was monitored by complete blood count. Bone marrow cells of 7 pairs of recipients were analyzed at 5 to 8 weeks post-transplantation respectively. Platelets were analyzed 7-weeks post-transplantation.

Cell culture—K562 and 293T cells were obtained from ATCC, and were cultured according to ATCC instructions.

Mouse bone marrow cells were treated with antagomir (50 μg/ml) or PBS for three days in X-VIVO 15 medium (Biowhittaker) supplemented with 50 ng/mL SCF, 50 ng/mL TPO, 50 ng/mL Flt3 ligand and 20 ng/mL IL3. Cells were then harvested for RNA analysis.

Oligonucleotides and antagomirs-DNA oligonucleotides were synthesized by IDT Technology. RNA oligonucleotides, including antagomirs and DNA-RNA hybrids, were synthesized by Dharmacon. Antagomir stock solution was prepared in PBS.

```
Antagomir-150:
                                         (SEQ. ID. No. 23)
5' mC(*)mA(*)mCmUmGmGmUmAmCmAmAmGmGmGmUmUmGmGmG(*)

mA(*)mG(*)mA(*)(3'-Chl) 3'.

Antagomir-scrambled:
                                         (SEQ. ID. No. 24)
5'mC(*)mU(*)mCmGmCmGmUmAmGmAmAmGmAmGmUmAmGmGmU(*)

mG(*)mG(*)mA(*)(3'-Chl) 3'.

(mN: 2'OMe base; *: phosphorothioate linkage;
Chl: cholesterol).
```

Colony assay—Megakaryocyte colony assay was performed using the MegaCult-C kit (Stem Cell Technology) according to the manufacturer's protocol. Bone marrow cells from recipient mice 7 to 10 weeks after transplantation were sorted into GFP− and GFP+ populations. Two recipient mice were analyzed for each construct, and each population of cells was assayed in duplicates with 100,000 sorted bone marrow cells per well. Cultures were maintained for 8 days before stained for acetylcholinesterase activity and scored. For antagomir treatment, 1000 LKS cells or 4000 MEPs were FACS-sorted and assayed in the presence of antagomir (50 μg/ml) or PBS and maintained in culture for 11 days before staining and scoring. In all cases, a colony with ≧3 acetylcholinesterase-positive cells was scored as a megakaryocyte colony.

For erythoid colony assay, 5FU primed wild type C57B16/J marrow was transduced as described above. Forty-eight hours after viral transduction, 30,000 GFP+ cells were FACS-sorted and plated into methylcellulose (StemCell Technologies, M3334) which only contains EPO.

Anemic response—Phenylhydrazine hydrochloride (Sigma) solution in PBS was injected intraperitoneally into 10- to 12-week wild type C57B16/J mouse (60 mg/kg body weight) on each of days 0, 1, and 2. On the 3rd day, mice were euthanized by CO2 inhalation and bone marrow was harvested and stained with a lineage marker antibody cocktail as described in cell sorting and flow cytometry. Lineage negative cells were FACS sorted into TRIZOL reagent for RNA preparation.

Western blot analysis—Western blot analysis was performed as previously described (6). MYB antibody (clone 1-1) was from Upstate Biotechnology. Beta tubulin antibody (ab6046) was from Abcam.

Luciferase reporter assay—293T cells were plated in 96 well plates at 5000 cells per well the day before transfection. Transfection was carried out in 8 replicates using FuGENE 6 (Roche), with 100 ng of plasmid mixture (90 ng of expression vector and 10 ng of reporter vector in the psiCHECK2 backbone). Luciferase assays for both firefly and renilla luciferase were performed 2 days after transfection, using the Dual-Glo Luciferase assay kit (Promega). Luminescence was quantitated on a Tecan Spectrafluor Plus machine. *Renilla* luciferase readings were normalized against the firefly luciferase activity in the corresponding well.

Statistical Analysis—Student's t-test (2 tailed, unequal variance) was used for statistical analysis on experiments, unless otherwise specified.

Example 1 miRNA Expression in Hematopoietic Progenitor Cells

Mammalian developmental cell fate can be guided at least in part by different mechanism of gene regulation, such as by miRNAs. These recently discovered ~22 nt non-coding RNAs negatively regulate the expression of target proteins either by inhibiting translation of their cognate mRNAs, or by inducing mRNA degradation, primarily through sites in the 3'UTR (see review (6)). Previous miRNA expression patterns encode developmental history supports a role of miRNAs in lineage specification (7). Here, MEP differentiation was used as a model system to test that miRNA can regulate cell fate, starting with the profiling of the expression of miRNAs in MEPs, erythroid and megakaryocytic primary cells.

Figure 5B:
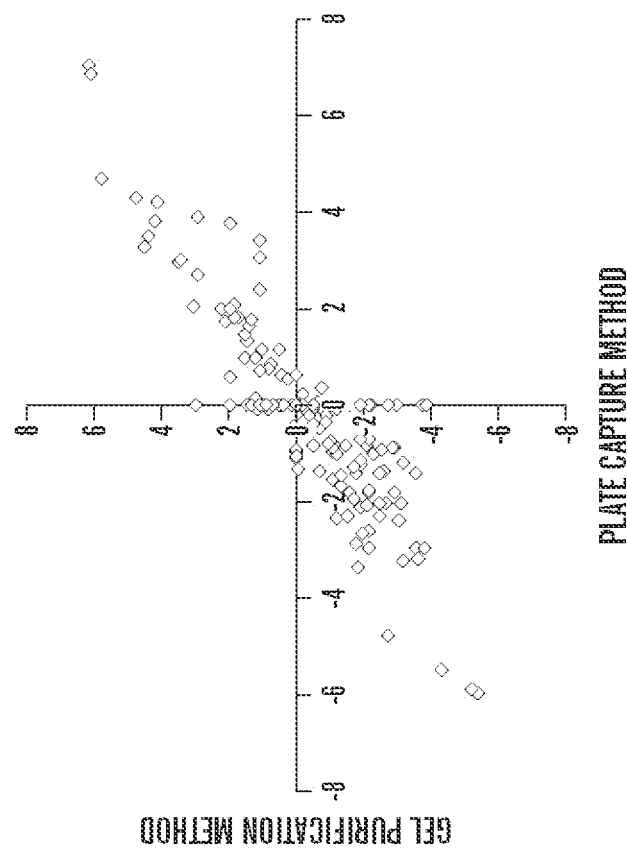
FIG. 5B shows the comparison of methods. miRNA expression profiling was performed on the same MCF-7 and 293T total RNA using either the plate capture method, or the previously reported method involving multiple denaturing acrylamide gel purification of small RNAs ("gel purification method").
Figure 5A:
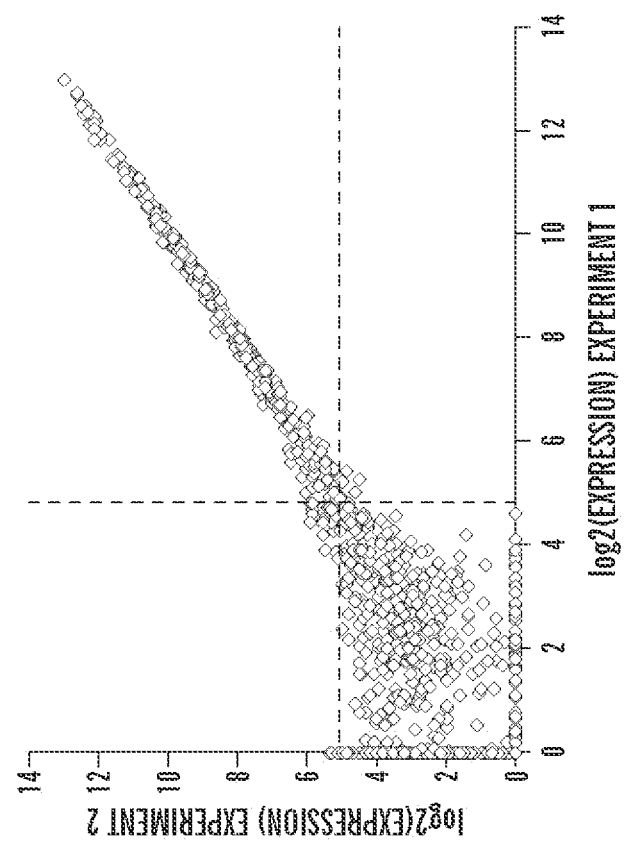
FIG. 5A shows the reproducibility performance of the plate capture method of miRNA labeling.

Unfortunately, the small number of precursor cells obtainable from human donors has precluded a thorough analysis of miRNA expression in hematopoiesis (and other systems) using conventional miRNA profiling methods, which generally require either large amounts of input RNA, or are not amenable to genome-wide, high throughput applications. To address this technical challenge, a method was developed in which mature miRNAs are captured in 96-well plates using immobilized 5'-amino-modified oligonucleotides complementary to the mature miRNA sequence of more than 300 human miRNAs (from the miRBASE (8) release 7.0). This plate-based capture obviates the need for gel-purification of small RNAs which, in addition to being labor-intensive, results in significant loss of input miRNAs. The captured miRNAs were ligated with adaptors on 3' and 5' ends successively, reverse transcribed, and amplified via PCR (FIG. 1A). The biotinylated PCR products were then detected by hybridization to fluorescent beads coupled to capture oligonucleotides complementary to the mature miRNA sequence. The beads were then analyzed by flow cytometry, where the color of the bead indicates the identity of the miRNA and the phycoerythrin channel indicates the abundance of that particular miRNA (7). In contrast to previously reported method (7) that required ~10 μg of input RNA, the present method yields similarly informative results with as little as 10 ng of total RNA (FIG. 5). FIG. 5A shows the reproducibility performance of the plate capture method of miRNA labeling. Two experiments of miRNA profiling with the plate capture method were performed on total RNA from MCF-7, 293T or K562 cells. Data were normalized and log 2-transformed. Data from experiment 1 were plotted against data from experiment 2. Each dot represents the reading of one miRNA in one sample. FIG. 5B shows data that were normalized and log 2-transformed. The differences of log 2-transformed data between MCF-7 and 293T cells, which reflect the fold change, were plotted to compare the two labeling methods. Each dot represents one miRNA. Note that most dots are close to the diagonal, indicating the two labeling methods captured similar results.

Figure 1B:
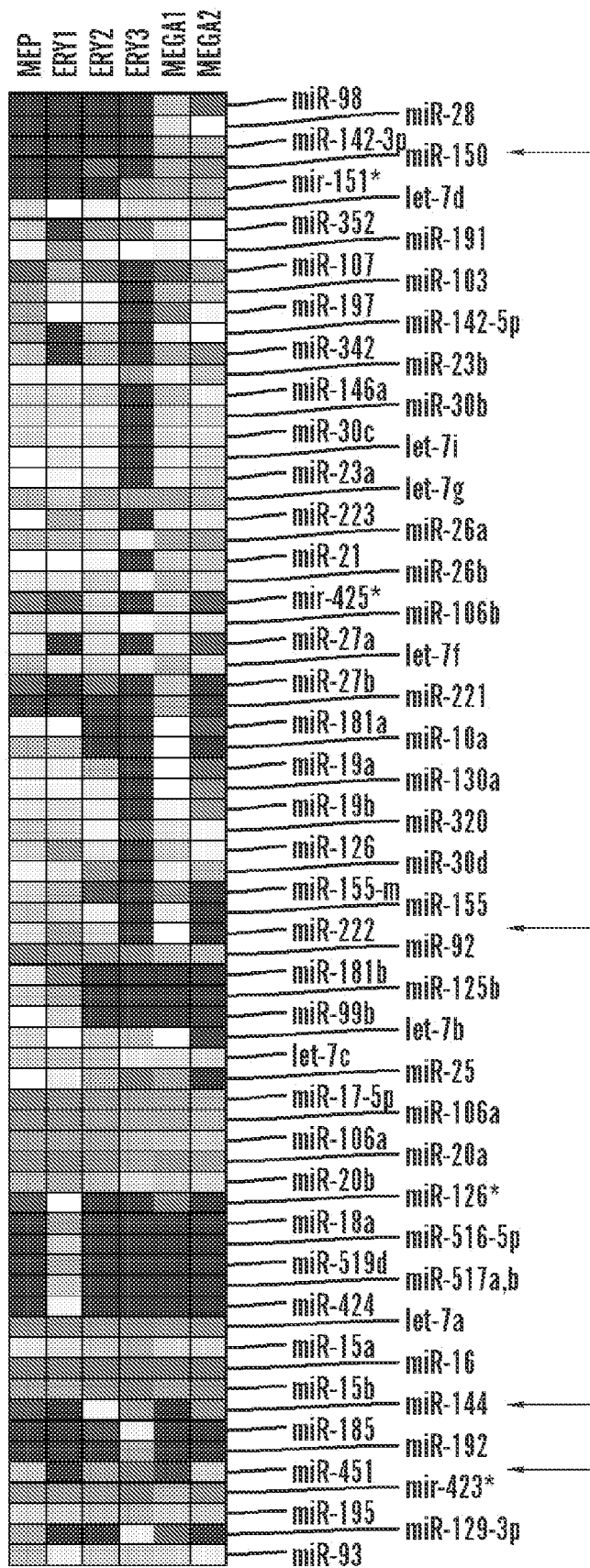
FIG. 1B shows a heatmap on log 2-transformed data, with black color indicating higher expression and light grey for lower expression. Data reflect the median expression of miRNAs within corresponding populations. Arrows point to miRNAs mentioned in text. Multiple harvests of MEP (n=8), MEGA1 (n=4), MEGA2 (n=6), ERY1 (n=4), ERY2 (n=3), and ERY3 (n=2) populations were purified from human umbilical cord blood cells (23) and profiled for miRNA expression.
Figure 1D:
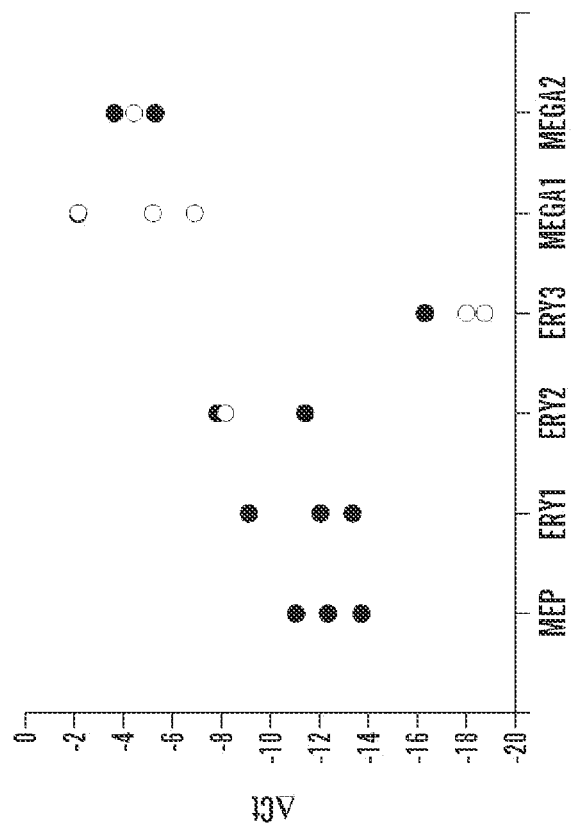
FIG. 1D shows miR-150 expression measured using quantitative RT-PCR on multiple harvests of MEP (n=3), MEGA1 (n=4), MEGA2 (n=3), ERY1 (n=3), ERY2 (n=3) and ERY3 (n=3) populations. The ΔCt values (Ct (threshold cycle) of 18S minus Ct of miR-150) are shown for all samples. Note that ΔCt reflects log scale of expression. Samples indicated with black dots were also used in miRNA profiling in FIGS. 1B and 1C, whereas those with open circles were additional samples.
Figure 1C:
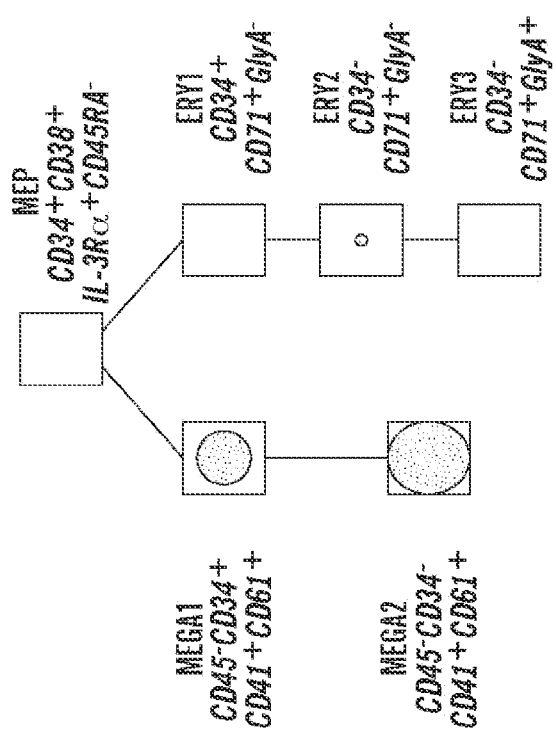
FIG. 1C shows the median expression of miR-150 was plotted for each population, with the oval area proportional to the expression level.

With a suitable miRNA profiling method in hand, the miRNA expression pattern in MEPs and early megakaryocytic and erythroid populations obtained from FACS-sorted human umbilical cord blood samples were examined. Using well-established surface markers, 6 populations of cells were purified, and them are referred to as MEP (CD34+, CD38+, IL-3Rα−, CD45RA−), MEGA1 (CD34+, CD41+, CD61+, CD45−), MEGA2 (CD34−, CD41+, CD61+, CD45−), ERY1 (CD34+, CD71+, GlyA−), ERY2 (CD34−, CD71+, GlyA−) and ERY3 (CD34−, CD71+, GlyA+). These 6 populations thus capture the bifurcation of the megakaryocytic and erythroid lineages with fine granularity (FIG. 1C).

Figure 6B:
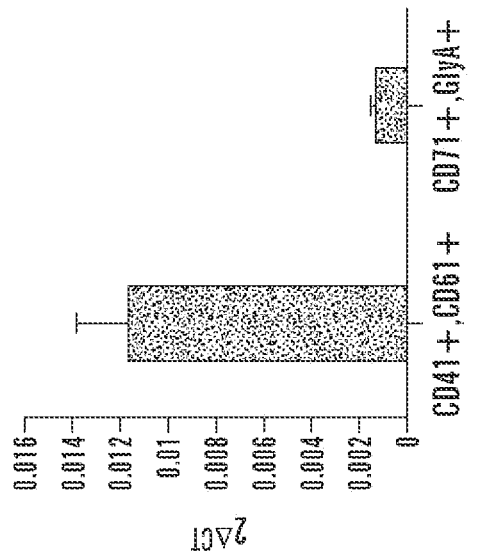
FIG. 6B shows the histogram of miR-150 expression in CD41+CD61+ and CD71+GlyA+ cells FACS-sorted from the bone marrow of a healthy adult human donor. miR-150 expression was measured using quantitative RT-PCR. $2^{\Delta Ct}$ values are shown. Error bars represent standard deviation of measurement.
Figure 6A:
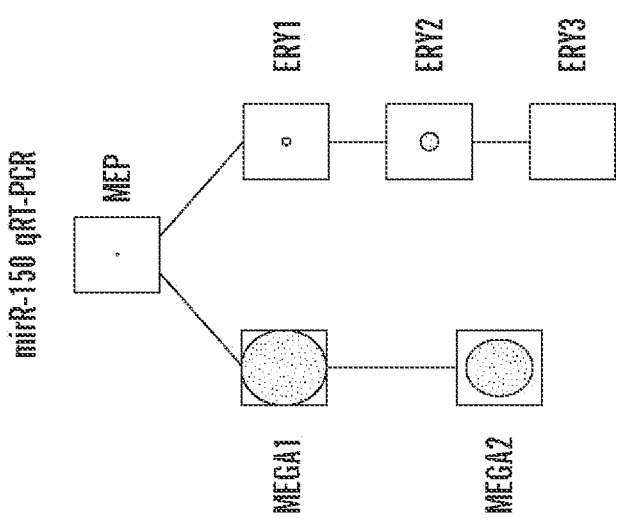
FIG. 6A shows the expression of miR-150 in FACS-sorted umbilical cord blood populations. Expression is measured by quantitative RT-PCR analysis as in FIG. 1D were plotted in an oval plot with the oval area proportional to the median value of $2^{\Delta Ct}$ for each of the populations.
Figure 16B:
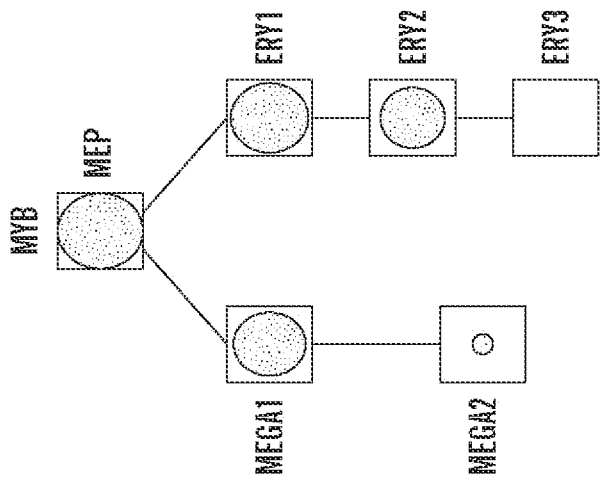
FIG. 16B shows the data plotted in an oval plot with the oval area proportional to the median value of $2^{\Delta Ct}$ for each of the MEP, MEGA1, MEGA2, ERY1, ERY2 and ERY3 populations.
Figure 16A:
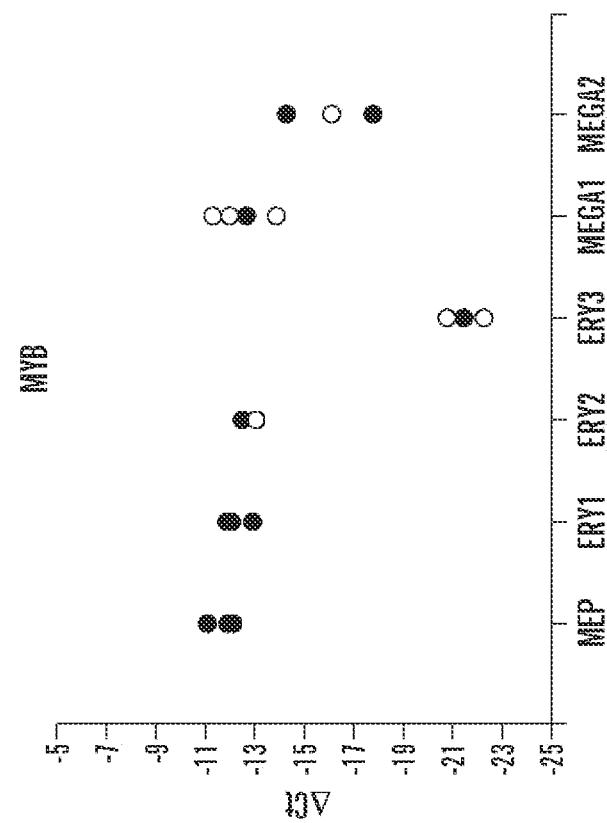
FIG. 16A shows the MYB expression as measured using quantitative RT-PCR on multiple harvests of MEP (n=3), MEGA1 (n=4), MEGA2 (n=3), ERY1 (n=3), ERY2 (n=3) and ERY3 (n=3) populations. The ΔCt values (Ct of 18S minus Ct of MYB) are shown for all samples. Samples with black dots were used in miRNA profiling in FIGS. 1B and 1C, whereas those with open circles are additional samples.

Profiling of 320 miRNAs was performed to identify those most differentially expressed across the megakaryocytic and erythroid populations. The profiling result (FIG. 1B, Table 6) captured and extended known miRNA expression patterns. For example, miR-451 and miR-144 were highly expressed in CD71+GlyA+ erythrocytes, and miR-222 was down-regulated during erythropoiesis (9, 10) (FIG. 1B). Among all miRNAs, differential analysis (Table 3) identified miR-150 with the most divergent expression between early megakaryocytic and erythroid cells, being expressed >15-fold higher in megakaryocytes (FIG. 1C). Quantitative RT-PCR analysis in sorted umbilical cord blood cells confirmed miR-150 as being highly expressed in megakaryocytes, weakly expressed in erythrocytes and moderately expressed in MEPs (FIG. 1D, FIG. 16). Similarly, miR-150 was expressed more highly in CD41+CD61+ megakaryocytes than in CD71+ GlyA+ erythrocytes in human adult bone marrow (FIG. 6B).

Example 2

Function of miR-150 in Differentiation of Progenitor Cells

Figures 7, 8:
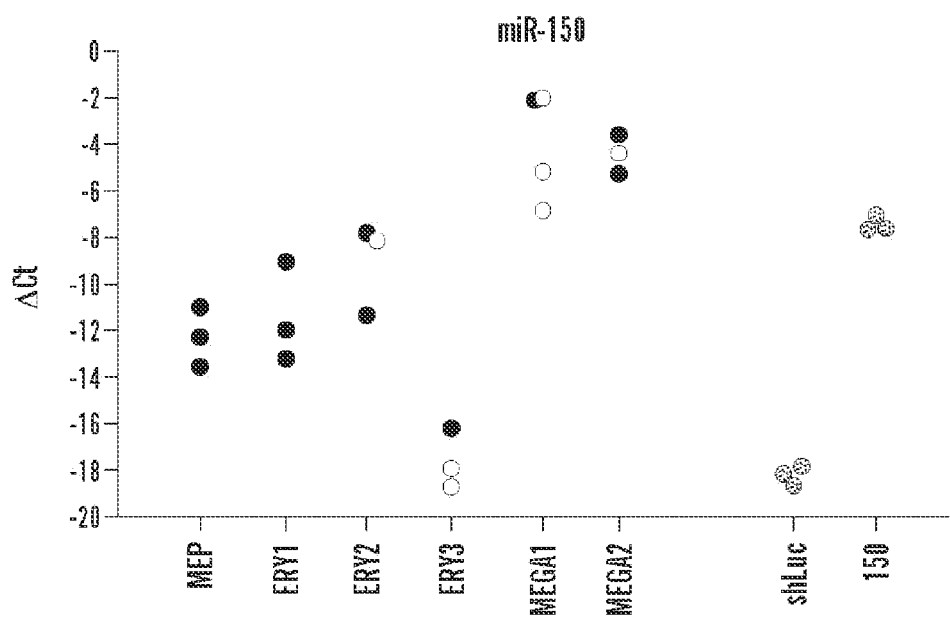
FIG. 7 shows the evolutionary conservation of mature miR-150 sequences of across multiple species (SEQ ID NOS: 786-791, respectively, in order of appearance). Sequence data were from miRBASE. Big and bold letters indicate non-conserved bases.
FIG. 8 shows the miR-150 expression in cultured human CD34+ bone marrow cells transduced with a control vector (shLuc, n=3) or a m-iR150 construct (n=3), and in multiple harvests of MEP, ERY1, ERY2, ERY3, MEGA1 and MEGA2 populations (as described in FIG. 1D). Threshold cycle values were normalized against 18S ribosomal RNA levels. ΔCt values are plotted

While high level expression of miR-150 was observed in the megakaryocytic lineage, it is conceivable that it may not play a functional role in the specification of megakaryocytes versus erythrocytes. Arguing for its functional importance is its exquisite sequence conservation across organisms with functional erythrocytic and thrombocytic systems, exhibiting identical sequence in the 5' seed region that mediates target recognition (FIG. 7). To assess a potential causal role of miR-150 in the specification of megakaryocytes versus erythrocytes, a series of gain- and loss-of-function experiments were performed.

First, a bi-lineage primary cell culture was used, in which human CD34+ hematopoietic progenitor cells isolated from adult human bone marrow, when cultured in the presence of thrombopoietin and erythropoietin, differentiate along the megakaryocytic and erythroid lineages in vitro. This system allowed the quantitative perturbation in the balance of megakaryocytic and erythroid development from progenitor cells. CD34+ cells were transfected with a lentiviral construct harboring miR-150, resulting in a physiological level of miR-150 expression that is similar to that observed in primary megakaryocytes (FIG. 8).

Figure 2A:
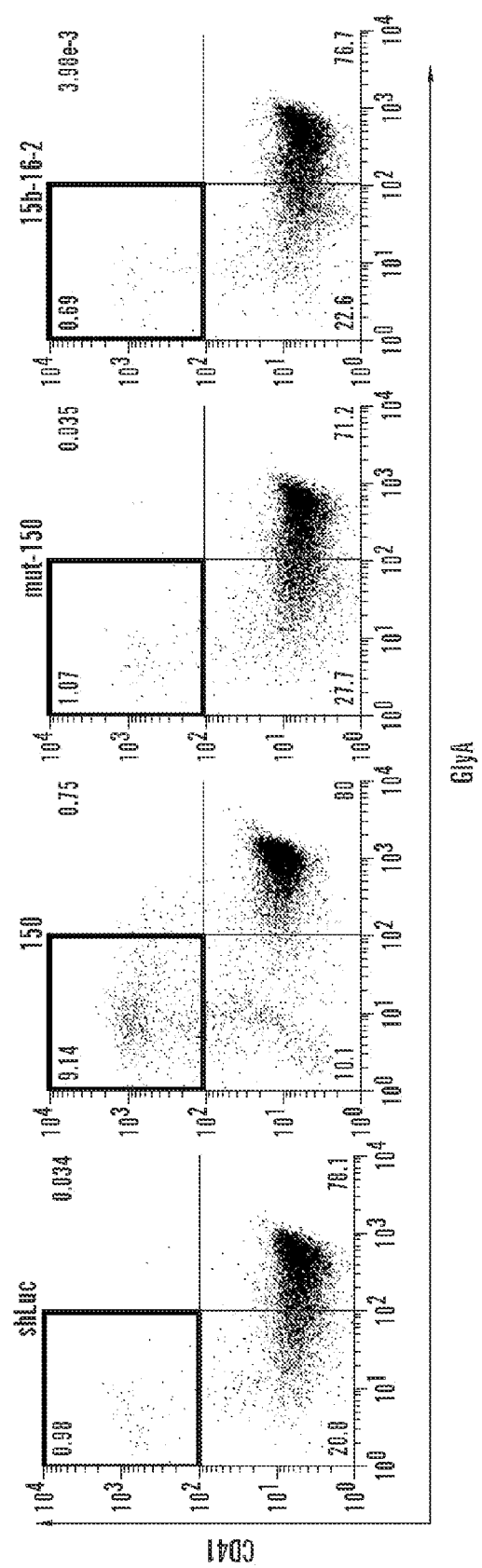
FIG. 2A shows representative flow cytometry plots of the differentiation lineage of CD34+ hematopoietic progenitors cells transduced with constructs expressing a control hairpin (shLuc), miR-150, a mutant miR-150 or miR-15b-16-2. Plots represents lineage markers CD41 (megakaryocytic) and GlyA (erythroid).

The function of miR-150 was assayed in an in vitro primary culture. CD34+ hematopoietic progenitors derived from human adult bone marrow cells were transduced with constructs expressing a control hairpin (shLuc), miR-150, a mutant miR-150 or miR-15b-16-2. The culture was analyzed after 10 days of differentiation, using flow cytometry with lineage markers CD41 (megakaryocytic) and GlyA (erythroid). Transduced cells were allowed to differentiate. Megakaryocytes were then enumerated by flow cytometry measuring the CD41+GlyA− population. Compared to CD34+ cells transduced with a control vector (shLuc, expressing a short hairpin RNA against luciferase), mutant miR-150, or an irrelevant miRNA construct (miR-15b-16-2), the miR-150 expressing cells yielded an average of 8-fold enrichment of megakaryocytes (FIG. 2A, 2B). This result indicates that miR-150 shifts the balance of megakaryocytic-erythroid differentiation towards megakaryocytes, and further indicates its role in governing the fate of MEPs.

Example 3

Function of miR-150 in in vivo Differentiation of Progenitor Cells

Figure 2E:
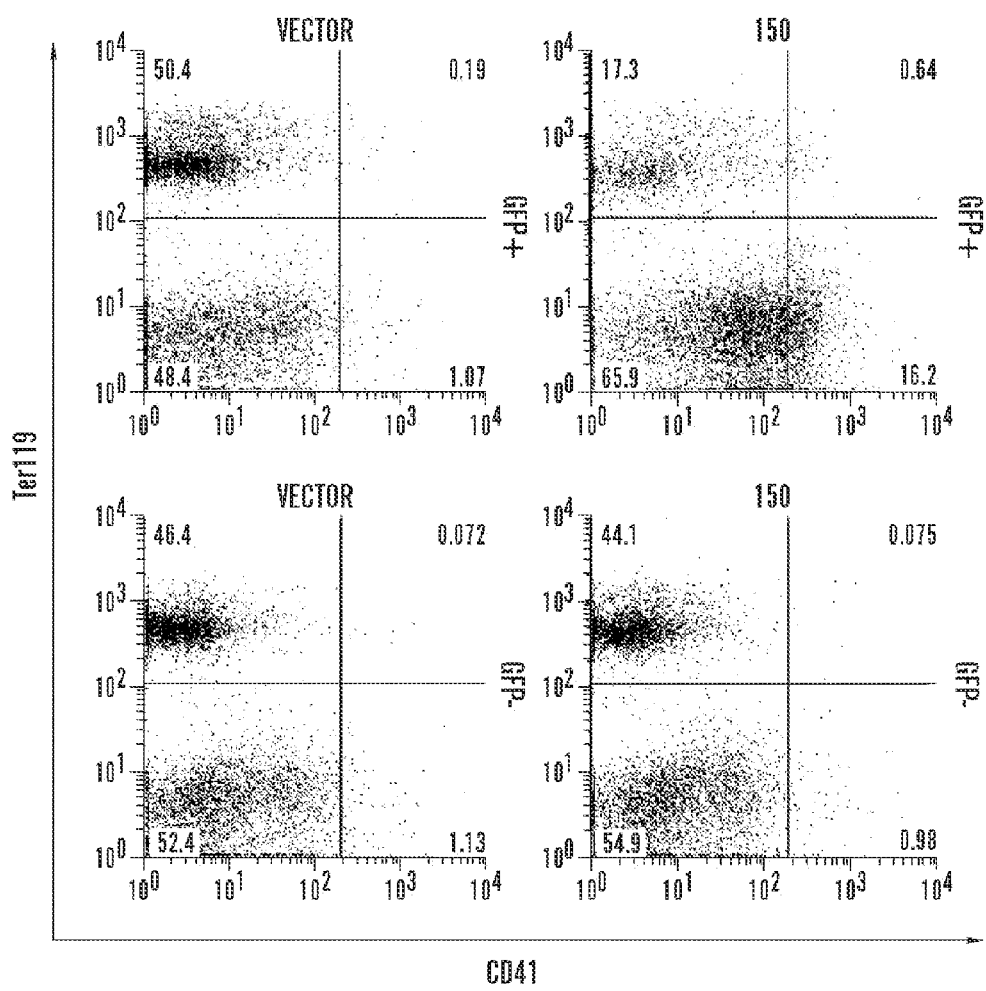
FIG. 2E shows representative flow cytometry plots on bone marrow cells with megakaryocytic (CD41) and erythroid (Ter119) markers from data of FIGS. 2C and 2D.
Figure 2F:
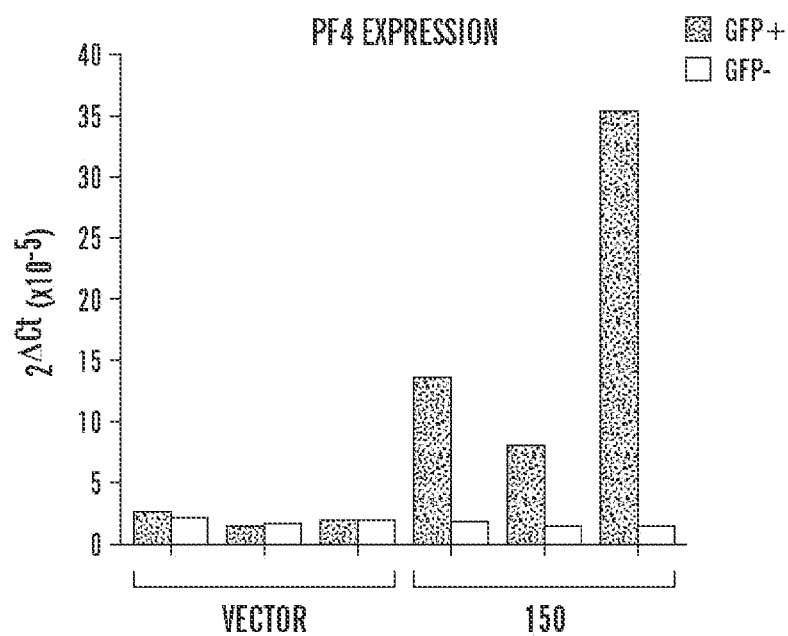
FIG. 2F shows the PF4 expression of recipient bone marrow cells that are GFP+ and GFP−. Each pair of bars represents data from one recipient mouse.
Figure 2G:
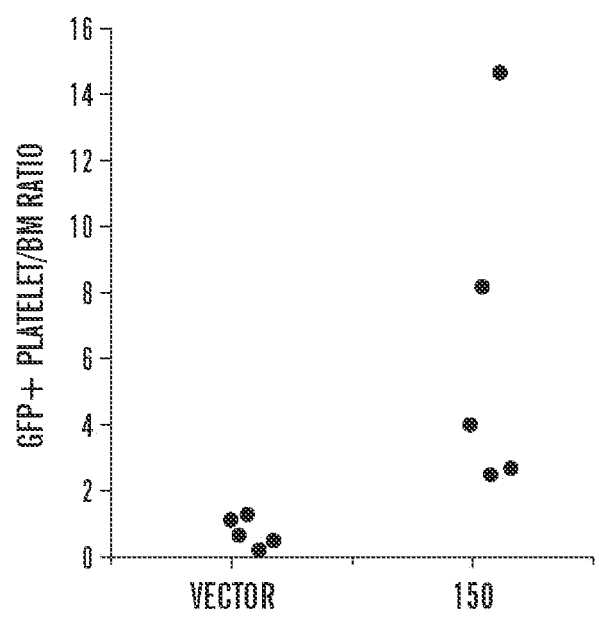
FIG. 2G shows the ratio of GFP+ platelet percentage to the percentage of GFP+ bone marrow cells in the peripheral blood of recipient animals 7-week post-transplantation. T was plotted to reflect the thrombocytogenic potential of bone marrow cells. n=5.
Figure 9:
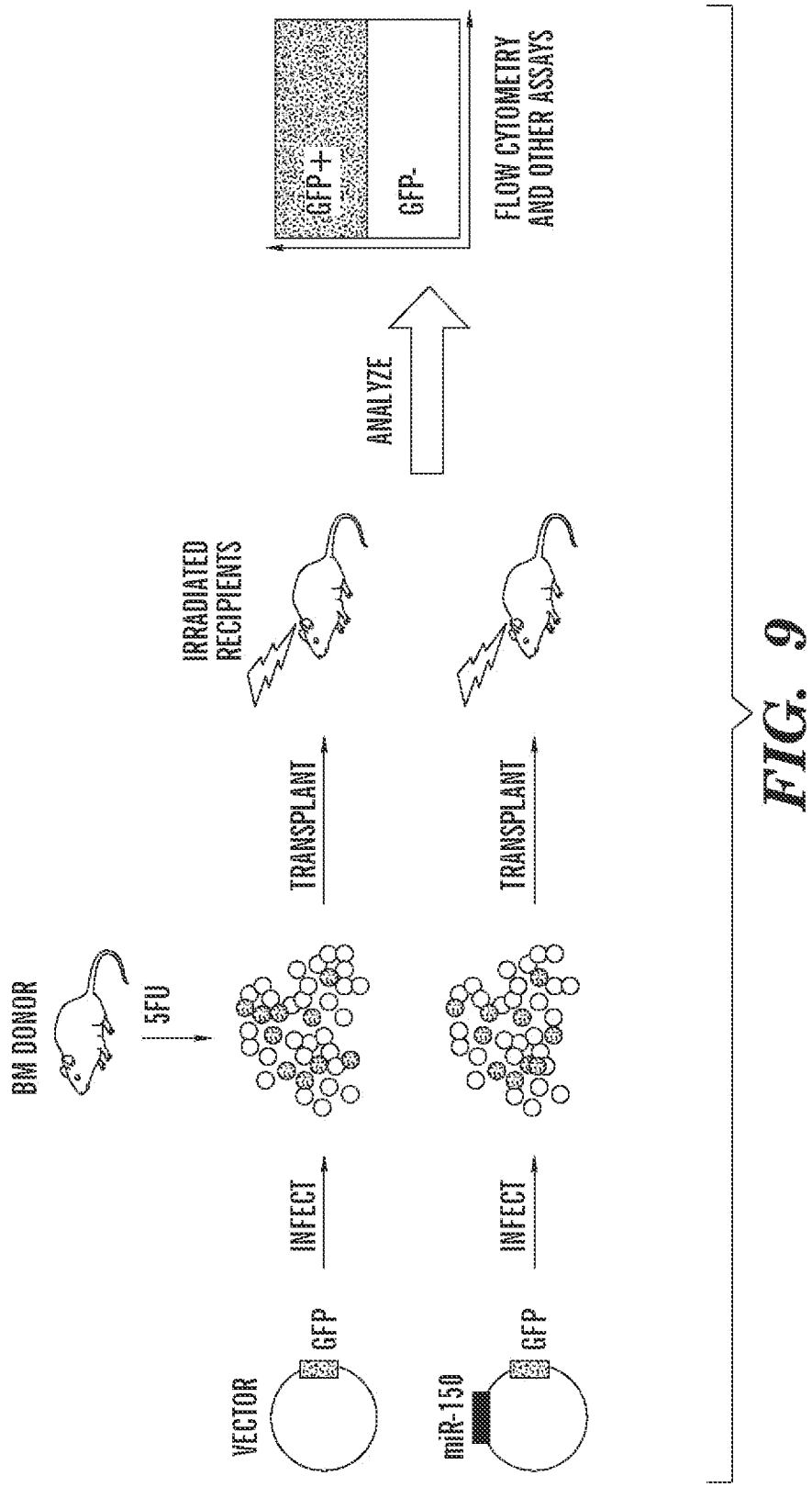
FIG. 9 shows a schematic model for murine bone marrow transplantation.
Figure 10A:
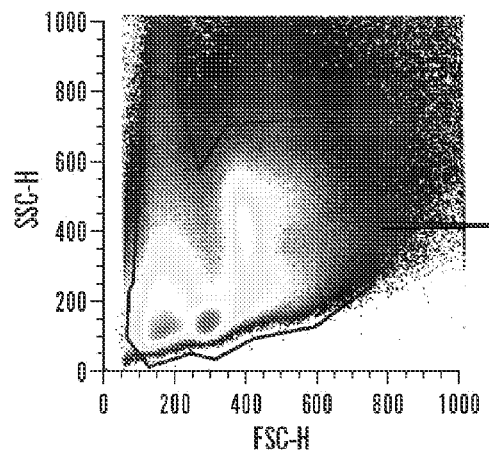
FIG. 10A shows the gated forward and side scattering flow cytometry analysis of bone marrow cells from wild-type mouse and recipient mice 5-8 weeks after transplantation with vector control or miR-150 vector. GFP gating was determined on cells from wild-type animal.
Figure 10B:
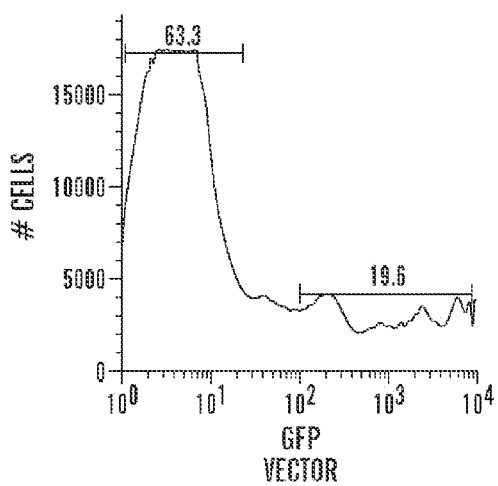
FIG. 10B shows the GFP gated flow cytometry analysis of bone marrow cells from recipient mice 5-8 weeks after transplantation with vector control.
Figure 10C:
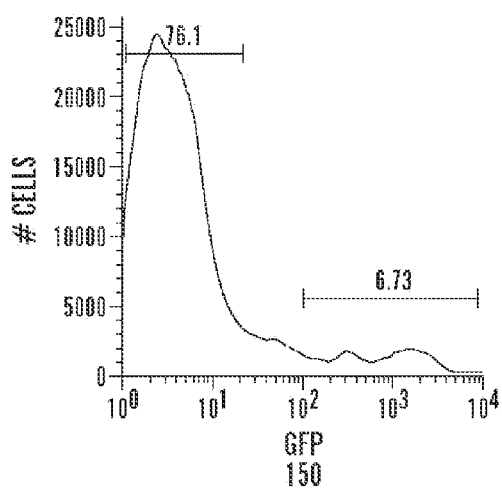
FIG. 10C shows the GFP gated flow cytometry analysis of bone marrow cells from recipient mice 5-8 weeks after transplantation with miR-150 vector.
Figure 10D:
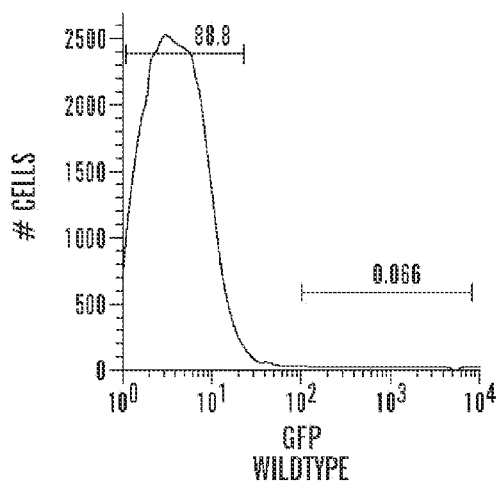
FIG. 10D shows the GFP gated flow cytometry analysis of bone marrow cells from wild-type mouse.
Figure 11A:
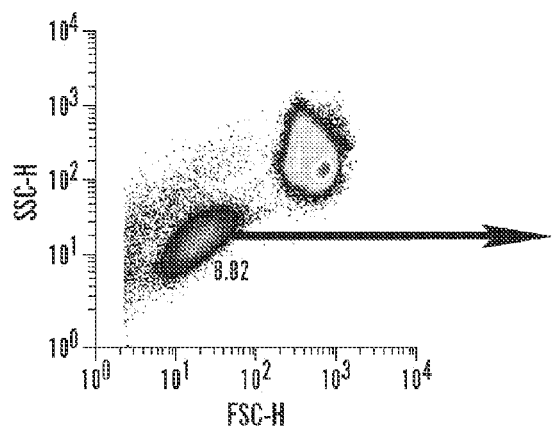
FIG. 11A shows the gated sensitized forward and side scattering flow cytometry analysis of platelets in peripheral blood of wild-type mouse and from recipients 7 weeks after transplantation with vector control or miR-150 vector. Peripheral blood cells were stained with CD41 antibody.
Figure 11B:
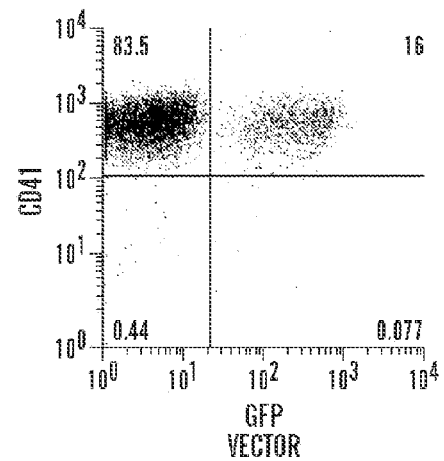
FIG. 11B shows the GFP and CD41 flow cytometry analysis of platelets in peripheral blood from recipients 7 weeks after transplantation with vector control.
Figure 11C:
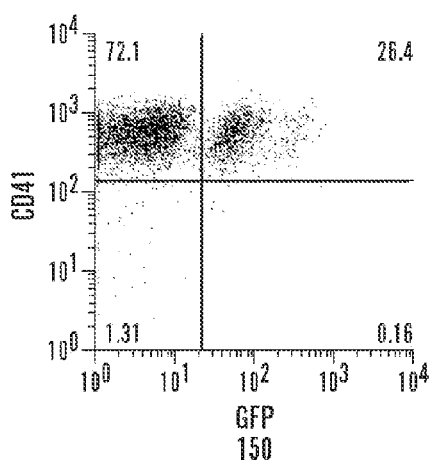
FIG. 11C shows the GFP and CD41 flow cytometry analysis of platelets in peripheral blood from recipients 7 weeks after transplantation with miR-150 vector.
Figure 11D:
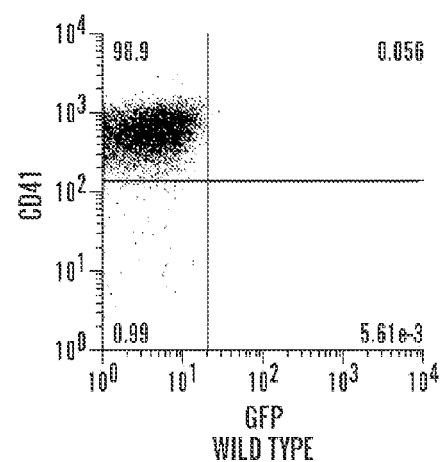
FIG. 11D shows the GFP and CD41 flow cytometry analysis of platelets in peripheral blood from wild-type mouse.

Having established a functionally important role of miR-150 in a human in vitro model of MEP differentiation, the functions of miR-150 in vivo were examined to address whether miR-150 inhibits the erythroid lineage, promotes the megakaryocytic lineage, or both. To this end, a murine bone marrow transplantation model was used, in which stem/progenitor-cell-enriched bone marrow cells from donor mice were transduced with either miR-150 retrovirus or control virus at low titer. The vectors carry a GFP marker, thus labeling transduced cells and cells derived from them with green fluorescence. The mixture of transduced and non-transduced donor cells was transplanted into lethally irradiated recipients. Bone marrow and peripheral blood of recipients were analyzed 5 to 8 weeks post transplantation, when the hematopoietic system had largely recovered in the hosts. Both viral vectors carry GFP as a marker, allowed the distinguishing between donor-derived cells that were transduced from those that were not (FIG. 9).

miR-150 was expressed from a retroviral vector with a GFP marker. This construct, or a control vector, was assayed by murine bone marrow transplant. Recipient mice were analyzed 5 to 8 weeks post-transplantation on transduced (GFP+) and non-transduced (GFP−) cells. Flow cytometry was used to assay the bone marrow cells with megakaryocyte-(CD41) and erythrocyte-(Ter119) specific markers. Strikingly, compared to either non-transduced (GFP−) cells in miR-150 recipients, or vector control recipient mice, miR-150 transduced (GFP+) bone marrow cells exhibited a dramatic (>15-fold on average) expansion of megakaryocytes (CD41+ Ter119−) in relation to all transduced cells in the bone marrow (FIG. 2C, 2E, 10). Recipient bone marrow cells were FACS sorted into GFP+ and GFP− populations, and measured for PF4 expression using quantitative RT-PCR. Each pair of bars represents data from one recipient mouse. It was observed that a strong elevation in the expression of the megakaryocyte-specific gene PF4 (11) occurred in miR-150 transduced bone marrow cells (FIG. 2F). In addition, the circulating platelets were analyzed in the peripheral blood of recipient animals 7-week post-transplantation. The ratio of GFP+ platelet percentage to the percentage of GFP+ bone marrow cells was plotted to reflect the thrombocytogenic potential of bone marrow cells. n=5. There was a consistent 2- to 14-fold enrichment in GFP+ circulating platelets in miR-150 animals compared to control vector recipients (FIG. 2G, 11). These results proved that miR-150 expression led to a bona fide increase in bone marrow megakaryocytes that were competent to produce mature platelets in circulation.

Figure 2H:
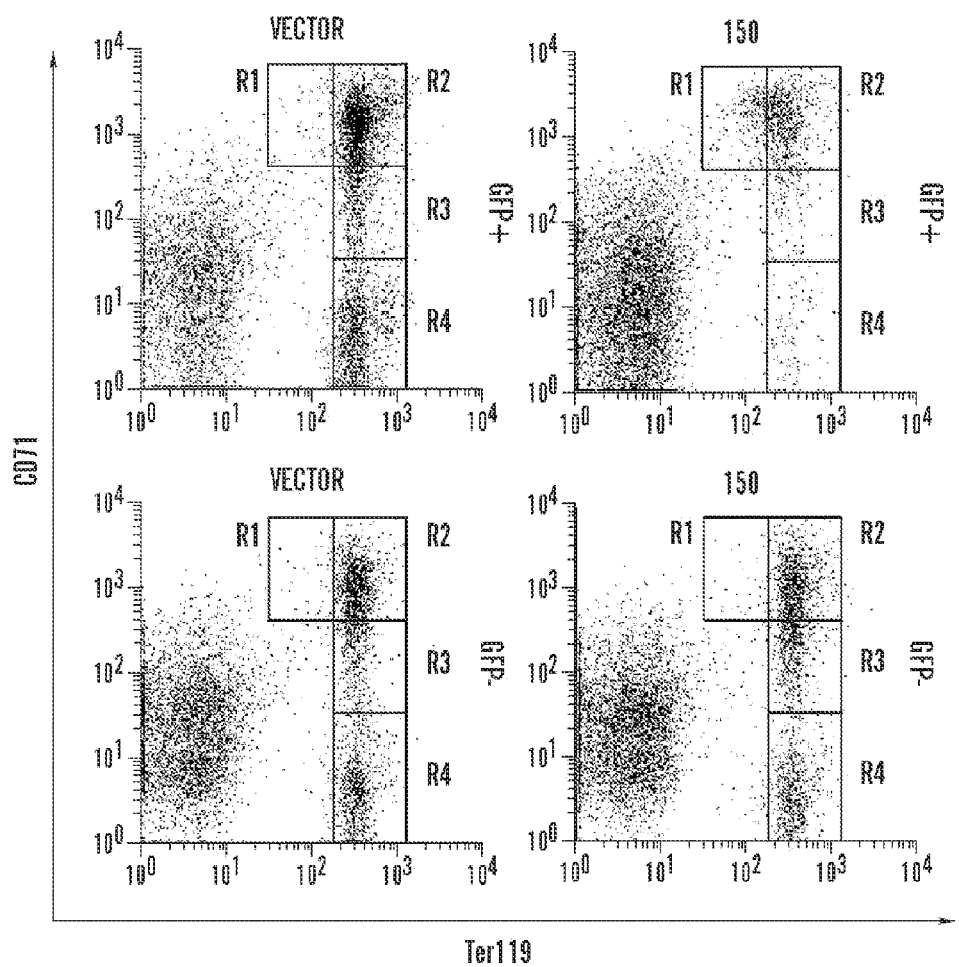
FIG. 2H show the representative flow cytometry plots of bone marrow cells assayed with CD71 and Ter119. The gates R1 to R4 represent immature to mature erythrocytes.
Figure 2I:
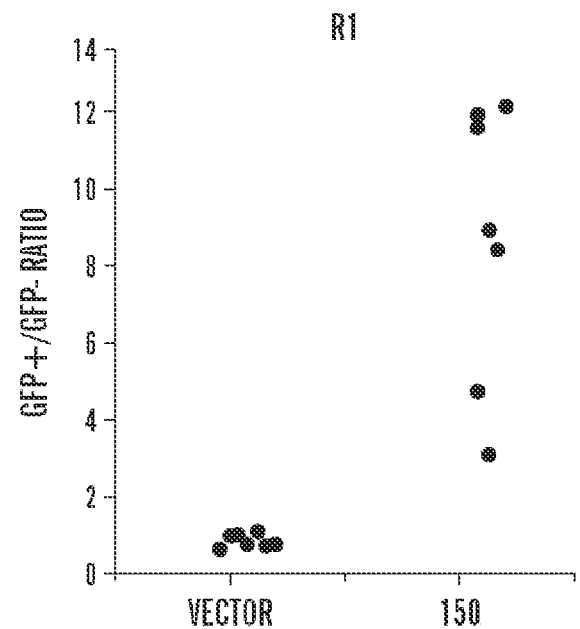
FIG. 2I shows a ratio between GFP+ and GFP− population within the same recipient mouse based upon the percentage of R1 population among all erythrocytes (sum of R1 to R4), n=7. P<0.002.
Figure 2J:
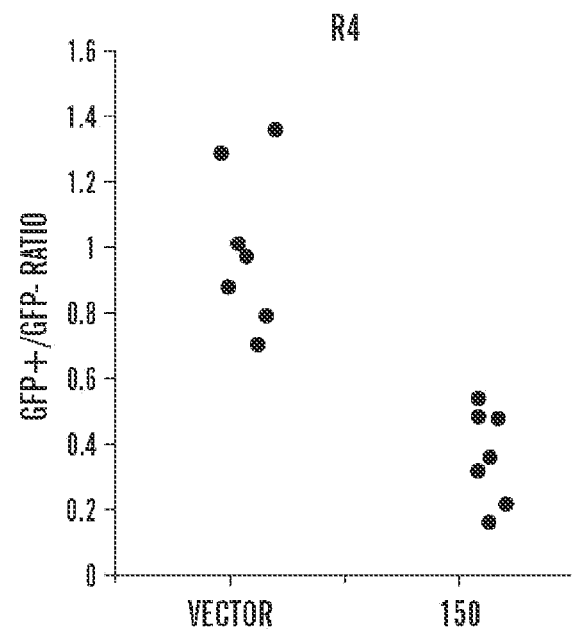
FIG. 2J shows a ratio between GFP+ and GFP− population within the same recipient mouse based on data for R4 population. P<2×10-4.

In contrast, an over 60% decrease in GFP+ erythrocytes (Ter119+CD41−) was observed, again in relation to all GFP+ cells in the bone marrow (FIG. 2D, 2E). Importantly, the absolute numbers of GFP+ megakaryocytes in the bone marrow increased, whereas that of erythrocytes decreased in the presence of miR-150 expression (FIG. 12). Bone marrow cells with CD71 and Ter119 were examined, which distinguish different stages of murine erythroid differentiation (12). The R1 to R4 gates on CD71/Ter119 plot show that miR-150 expressing cells displayed a strong shift toward an earlier (immature) erythroid state, compared to controls (FIG. 2H, 2I, 2J). The percentage of R1 population among all erythrocytes (sum of R1 to R4) was used to derive a ratio between GFP+ and GFP− population within the same recipient mouse. n=7. P<0.002. Specifically, miR-150 expression led to an average of 8-fold increase in the immature R1 population, and a more than 60% decrease in the late R4 stage. These experiments indicate that ectopic miR-150 expression induces a blockage in the earliest definable stage of murine adult erythropoiesis, in addition to causing a significant reduction in the total erythroid population.

Figure 3A:
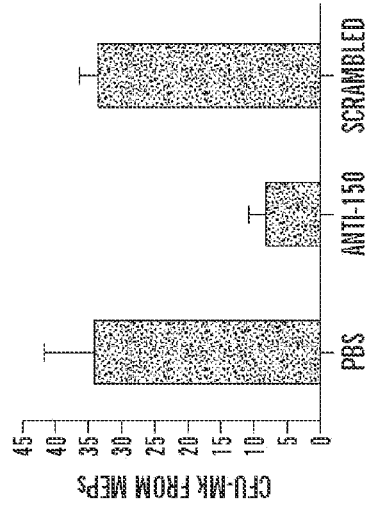
FIG. 3A shows the megakaryocyte colony forming units (CFU-Mks) formed from GFP+ and GFP− populations of bone marrow cells isolated from mice transduced with miR-150 retroviral vector or vector control. CFU-Mks were quantitated from 100,000 sorted cells. n=4.
Figure 13:
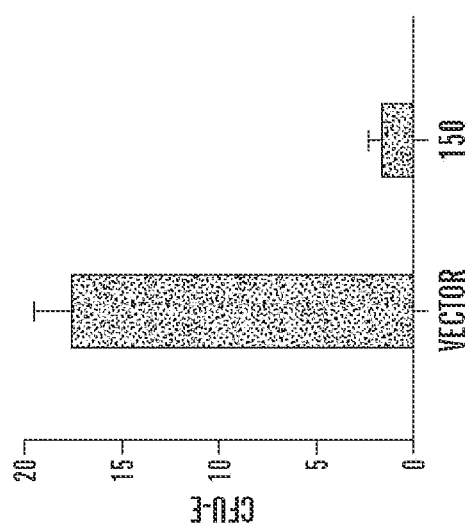
FIG. 13 shows that miR-150 decreases erythroid colony formation.

The megakaryocyte-promoting effect of miR-150 could be due to its effect on MEP commitment, or simply an effect on post-commitment megakaryocytic proliferation or survival. To address this, colony formation assay was used to quantify the megakaryocytic potential of progenitor cells at the single cell level. Erythroid colony formation assays were performed with 30,000 transduced bone marrow cells. Bone marrow cells from 5FU treated mice were transduced with a control vector or miR-150. GFP+ cells were sorted two days after transduction and assayed for erythroid colony forming units (CFU-E). Using the bone marrow cells from the transplant recipients, it was found that miR-150 overexpression resulted in a statistically significant increase in megakaryocyte colony-forming units (CFU-Mk) (FIG. 3A), coupled with a dramatic decrease in erythroid colony formation (FIG. 13). Representative erythroid colonies from control vector- or miR-150-transduced bone marrow cells. Note that rare erythroid colonies formed from miR-150 transduced cells showed reduced cell number. These gain of function experiments indicate that miR-150 regulates MEP fate, and not simply post-commitment megakaryocyte expansion.

Example 4

Figure 3B:
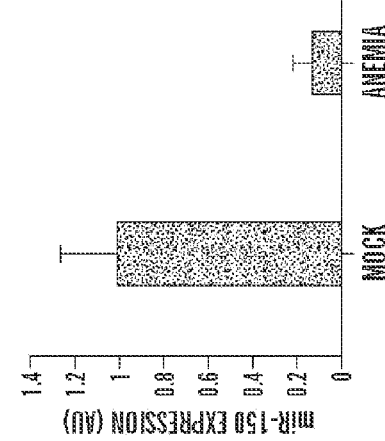
FIG. 3B shows the effects of solvent (PBS), antagomir against miR-150 (anti-150) or a scrambled antagomir on the differentiation of CFU-Mk from MEP cells sorted from wild-type C57BL/6J mice. 4000 cells were analyzed per assay. n=4.
Figure 3C:
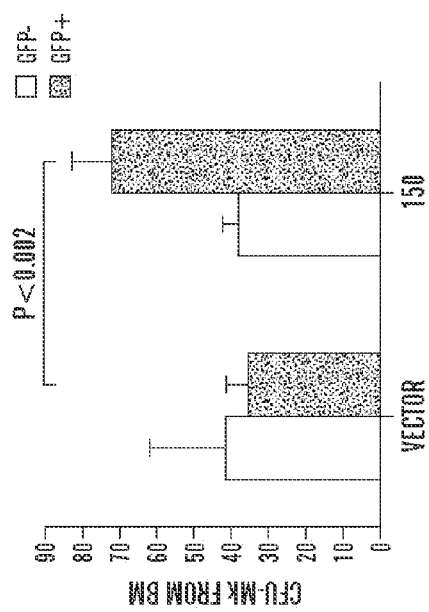
FIG. 3C shows the effects of solvent (PBS), antagomir against miR-150 (anti-150) or a scrambled antagomir on the differentiation of CFU-Mk from Lin-Kit+Sca+ (LKS) stem cells. 1000 cells were analyzed per assay. n=4.
Figure 3D:
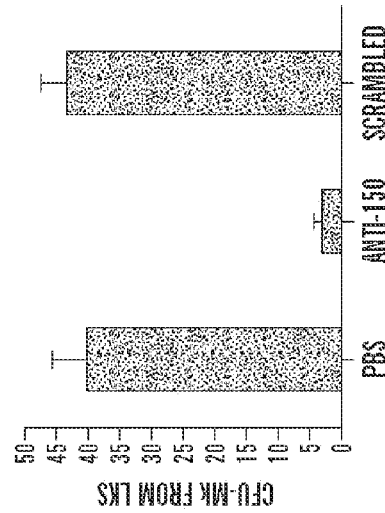
FIG. 3D shows the miR-150 expression in mice were treated with phenylhydrazine to induce anemia, or in mice were treated with PBS (mock). miR-150 expression was assayed by qRT-PCR in lineage negative cells purified from bone marrow. n=3. Error bars represent standard deviation.
Figure 15:
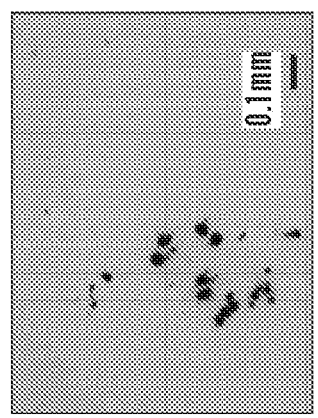
FIG. 15 shows the formation of megakaryocyte colony in the presence of antagomir-150. Brown color reflects megakaryocyte-specific acetylchol inesterase activity.
Figure 14:
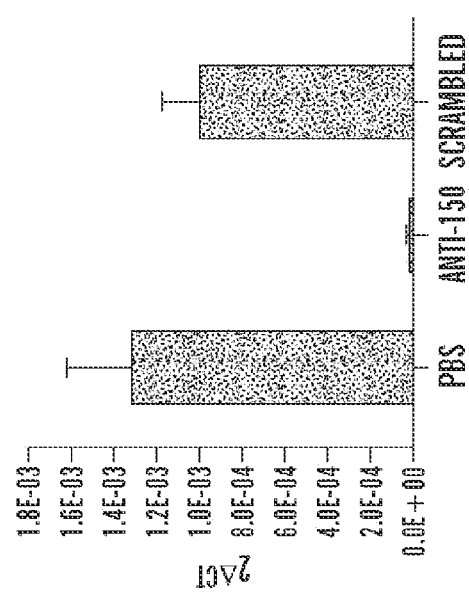
FIG. 14 shows that antagomir-150 knocks down miR-150 expression.

Effects of Loss of Function of miR-150 in in vitro Differentiation of Progenitor Cells To complement these miR-150 forced expression studies, a loss-of-function approach was used. MEP cells were isolated from bone marrow, and assayed for megakaryocyte colony formation in the presence or absence of an antagomir (a cholesterol-modified antisense oligonucleotide (13) directed against miR-150. Murine bone marrow cells were cultured in the presence of solvent (PBS), antagomir against miR-150 (anti-150) or a scrambled antagomir. miR-150 expression was measured with quantitative RT-PCR after 3 days of treatment (FIG. 14). Data represent 2ΔCt. Error bars represent standard deviation of measurement. MEPs treated with antagomir-150 showed more than a 4-fold decrease in CFU-Mk, compared to controls (see FIG. 3B). A similar effect was observed using purified uncommitted Lin-Kit+Sca+ hematopoietic stem cells (FIG. 3C). Interestingly, miR-150 knockdown megakaryocyte colonies showed normal morphology and acetylcholinesterase activity (FIG. 15), indicating that miR-150 might be dispensable once MEP commitment to the megakaryocyte lineage is established. To confirm a role of miR-150 in the physiological regulation of MEP fate, we treated mice with the anemia-inducing drug phenylhydrazine, and then measured miR-150 expression in lineage-negative bone marrow cells. miR-150 expression was significantly decreased in this setting of increased demand for erythropoiesis, consistent with miR-150's role in promoting megakaryopoiesis at the expense of erythropoiesis (FIG. 3D).

Example 5 miR-150 Regulates the c-myc Gene

Figures 4A, 4B:
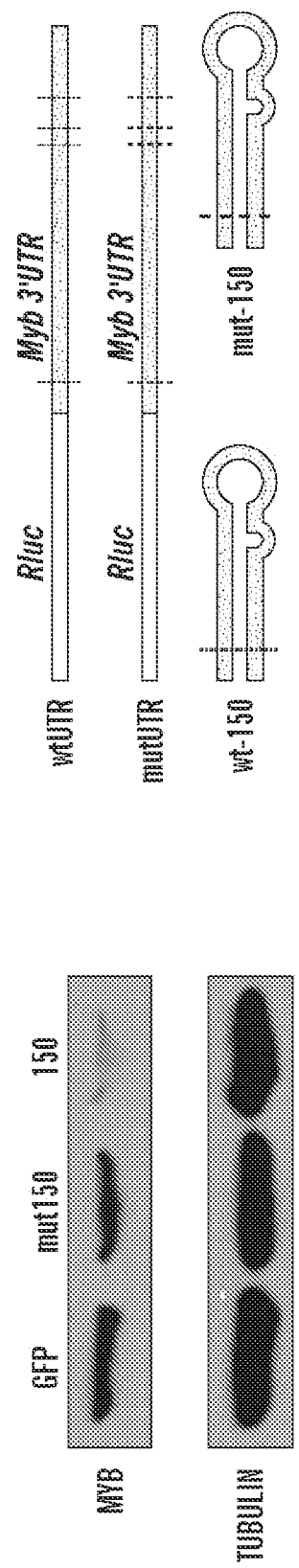
FIG. 4A shows the Western blot analysis for MYB and beta-Tubulin expressed in K562 cells transduced with constructs expressing GFP, mutant miR-150 or miR-150.
FIG. 4B shows the design of luciferase reporters for human MYB 3' UTR, with grey vertical bar indicating wild-type (wt) sites and black indicating mutant (mut) sites. The mutant miRNA site and mutant 3'UTR sites are complementary.
Figure 4C:
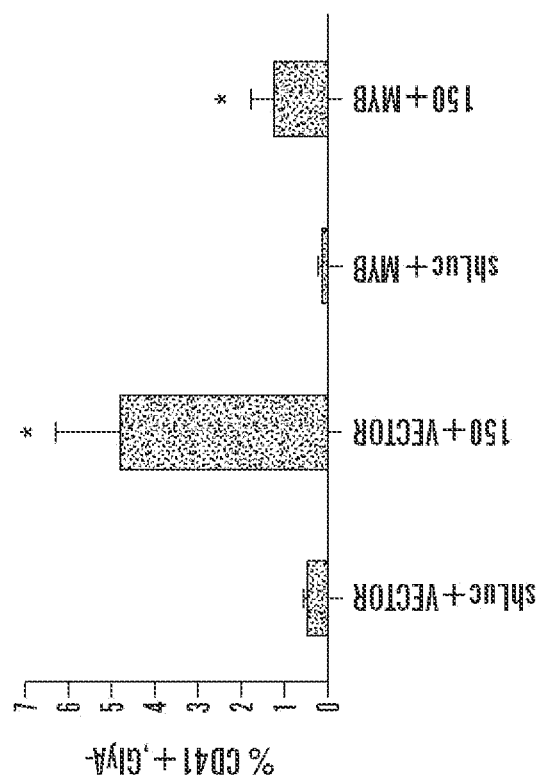
FIG. 4C shows a normalized plot of luciferase activities in 293T cells transduced with constructs expressing GFP, mutant miR-150 or miR-150. Error bars represent standard deviation. n=8.

The experiments described above firmly establish an important role of miR-150 in the specification of megakaryocytes from MEPs. To determine the mRNA targets of miR-150 that explain its effect on megakaryocytic/erythroid outcome, the targets predicted in common among several sequence-based prediction algorithms (14-16) were analyzed. MYB (also known as c-myb) was tested as a candidate because several recently reported mouse models, in which MYB activity was reduced due to either mutation or the serendipitous integration of a transgene near the MYB locus, displayed thrombocytosis and anemia (17-21). The expression of MYB messenger RNA, however, is not immediately indicative of a role in MEP differentiation, as similar expression in MEPs and early erythroid and megakaryocyte populations were noted (FIG. 16). Examination of the human MYB 3'UTR, however, identified multiple conserved miR-150 putative sites (FIG. 17). To establish miR-150 as a functional negative regulator of MYB, the erythroblastic cell line K562 was experimented in, which has the potential to be induced to differentiate into erythroid or megakaryocytic cells. A dramatic reduction in MYB protein level upon ectopic expression of miR-150 (FIG. 4A) was observed. Next, the MYB 3' UTR was cloned into a luciferase reporter, and it was found that miR-150 repressed reporter activity by more than 6-fold, again consistent with miR-150 targeting MYB. Importantly, mutation of the 4 candidate miR-150 binding sites abrogated miR-150 repression, and a mutant miR-150 construct designed to be complementary to the mutant MYB 3'UTR binding sites restored miR-150 mediated repression, but did not affect the wild-type MYB 3'UTR (FIG. 4B, 4C). These experiments establish that miR-150 negatively regulates the protein level of MYB directly through its 3' UTR.

Figure 4D:
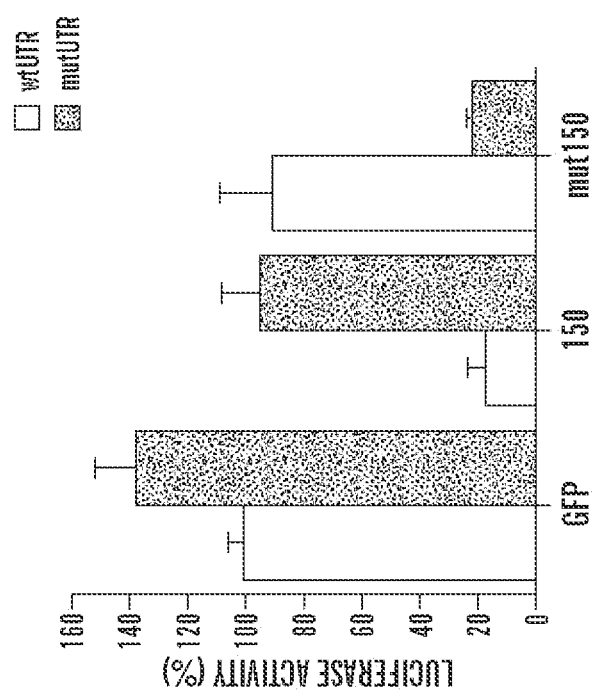
FIG. 4D shows the histograms of the differentiation lineages of cells transduced with miR-150 and MYB expression constructs and their corresponding vector controls (shLuc, Vector). The lineage markers are CD41 (megakaryocytic) and GlyA (erythroid). n=3. Error bars reflect standard deviation. *P=0.04.
Figure 4E:
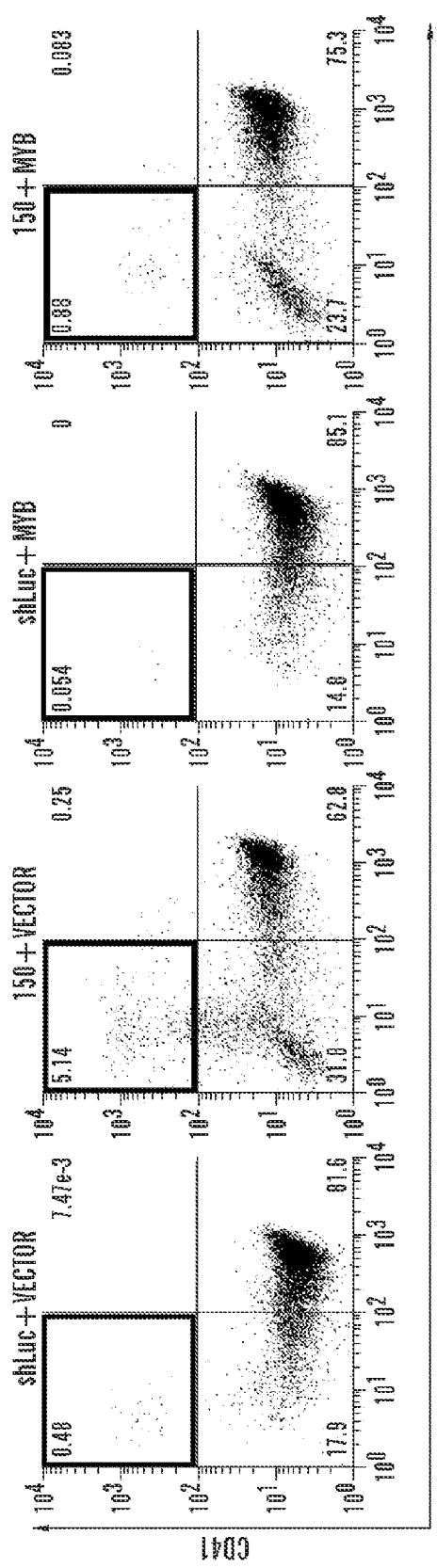
FIG. 4E shows the representative flow cytometry plots of the differentiation lineages in FIG. 4D. Plots represents lineage markers CD41 (megakaryocytic) and GlyA (erythroid).
Figure 18B:
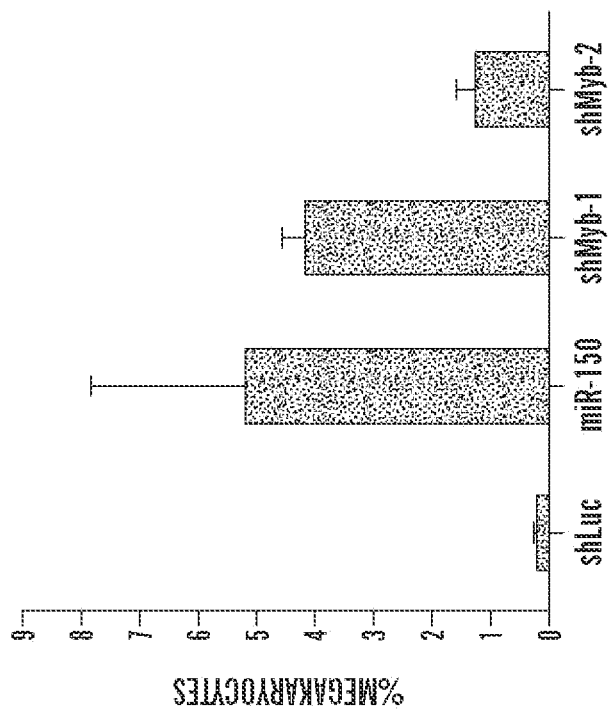
FIG. 18B shows the percentage of differentiated megakaryocytes (CD41+GlyA−) from CD34+ human adult bone marrow cells transduced with control vector (shLuc), miR-150 or shRNAs against MYB in an in vitro culture. n=3. Error bars represent standard deviation.
Figure 18A:
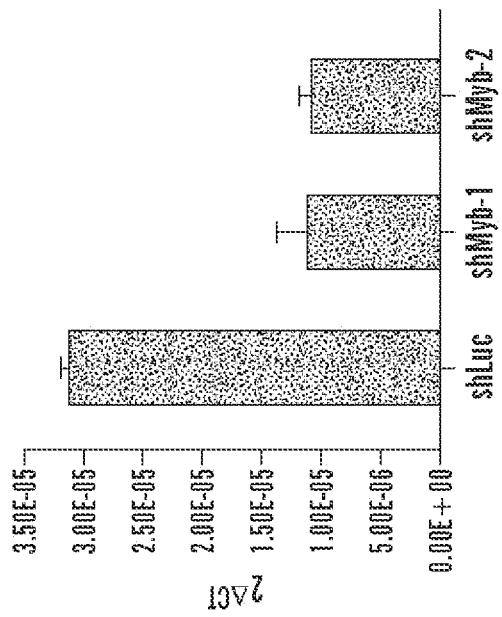
FIG. 18A shows the knockdown efficiency of two independent shRNAs against MYB expression in MYB-expressing K562 cells. MYB expression was measured by quantitative RT-PCR. The values of $2^{\Delta Ct}$ are shown.

Lastly, the question of whether miR-150 repression of MYB explains miR-150's erythroid/megakaryocytic effects was addressed. Using the in vitro CD34+ human bone marrow cell culture, consistent with reports that mice with reduced MYB activity display megakaryocytosis (17-21), two independent shRNA constructs that knocked down MYB expression (FIG. 18A) promoted megakaryocyte development (FIG. 18B). In contrast, forced expression of a MYB cDNA construct lacking its 3'UTR resulted in a decrease in megakaryocytes (FIG. 4D, 4E). Moreover, the MYB expression construct rescued the megakaryocytopoiesis-promoting effect of miR-150 to a large extent, indicating that MYB is a functionally relevant downstream effector of miR-150 (FIG. 4D, 4E). This MYB effect is consistent with a recent study showing MEPs with reduced MYB activity favor decision towards megakaryocytic as opposed to erythroid differentiation (20). In contrast to total loss of MYB function, which results in complete hematopoietic failure (19), our data indicate that modest modulation of MYB expression levels by miRNA can have important effects on lineage specification. These results are particularly interesting in light of the recent report of miR-150 regulation of MYB activity in B-lineage lymphocytes (22). It has been generally assumed that miRNAs have a plethora of targets that vary depending on cellular context. Remarkably, MYB appears to be a critical target of miR-150 both in establishing MEP fate and in regulating the differentiation of lineage-committed B-cells. This observation indicates that a single mRNA target of miRNAs might explain much of the miRNAs function, even in completely different developmental contexts. Our studies, of course, do not exclude the possibility that additional factors may also contribute to the establishment of MEP fate.

References
1. J. Zhu, S. G. Emerson, Oncogene 21, 3295 (May 13, 2002).
2. A. B. Cantor, S. H. Orkin, Oncogene 21, 3368 (May 13, 2002).
3. A. D. Friedman, Oncogene 21, 3377 (May 13, 2002).
4. M. Ye, T. Graf, Curr Opin Immunol 19, 123 (April 2007).
5. W. Zheng, R. A. Flavell, Cell 89, 587 (May 16, 1997).
6. D. P. Bartel, Cell 116, 281 (Feb. 23, 2004).
7. J. Lu et al., Nature 435, 834 (Jun. 9, 2005).
8. S. Griffiths-Jones, R. J. Grocock, S. van Dongen, A. Bateman, A. J. Enright, Nucleic Acids Res 34, D140 (Jan. 1, 2006).
9. N. Felli et al., Proc Natl Acad Sci USA 102, 18081 (Dec. 13, 2005).
10. M. Zhan, C. P. Miller, T. Papayannopoulou, G. Stamatoyannopoulos, C. Z. Song, Exp Hematol 35, 1015 (July, 2007).
11. K. Ravid, D. L. Beeler, M. S. Rabin, H. E. Ruley, R. D. Rosenberg, Proc Natl Acad Sci USA 88, 1521 (Feb. 15, 1991).
12. M. Socolovsky et al., Blood 98, 3261 (Dec. 1, 2001).
13. J. Krutzfeldt et al., Nature 438, 685 (Dec. 1, 2005).
14. A. Krek et al., Nat Genet. 37, 495 (May, 2005).
15. B. P. Lewis, C. B. Burge, D. P. Bartel, Cell 120, 15 (Jan. 14, 2005).
16. X. Xie et al., Nature 434, 338 (Mar. 17, 2005).
17. N. Emambokus et al., Embo J 22, 4478 (Sep. 1, 2003).
18. L. H. Kasper et al., Nature 419, 738 (Oct. 17, 2002).
19. M. L. Mucenski et al., Cell 65, 677 (May 17, 1991).
20. H. Y. Mukai et al., Mol Cell Biol 26, 7953 (November 2006).
21. M. L. Sandberg et al., Dev Cell 8, 153 (February 2005).
22. C. Xiao et al., Cell 131, 146 (Oct. 5, 2007).

TABLE 1

Quantitative RT-PCR assays used in this study

| Gene of interest | Assay |
|---|---|
| Human Myb | Hs00193527_m1 |
| Eukaryotic 18S | 4333760T |
| miR-150 | 4373127 |
| Mouse PF4 | Mm00451315_g1 |

TABLE 2

Antibodies for cell surface markers

| Antigen | Fluorophore | Clone | Source |
|---|---|---|---|
| Mouse CD71 | PE | C2 | BD Pharmingen |
| Mouse Ter119 | APC | TER-119 | BD Pharmingen |
| Mouse CD41 | PE | MWReg30 | BD Pharmingen |
| Mouse CD3ε | biotin | 145-2C11 | BD Pharmingen |
| Mouse CD4 | biotin | L3T4 | BD Pharmingen |
| Mouse CD8a | biotin | 53-6.7 | BD Pharmingen |
| Mouse CD45R/B220 | biotin | RA3-6B2 | BD Pharmingen |
| Mouse Ter119 | biotin | TER-119 | BD Pharmingen |
| Mouse CD11b | biotin | M1/70 | BD Pharmingen |
| Mouse Gr1 | biotin | RB6-8C5 | BD Pharmingen |
| Mouse c-Kit | APC | 2B8 | BD Pharmingen |
| Mouse Sca-1 | PE | Cat # MSCA04-3 | Caltag |
| Mouse CD34 | Pacific blue | RAM34 | eBioscience |
| Mouse CD16/32 | PE-Cy7 | 93 | eBioscience |
| Streptavidine | PerCP | Cat # 554064 | BD Pharmingen |
| Human CD71 | FITC and PE-Cy5 | C2 | BD Pharmingen |
| Human CD34 | APC | 581 | BD Pharmingen |
| Humn CD61 | FITC | 2C9.G2 | BD Pharmingen |
| Human CD41 | PE and FITC | HIP8 | BD Pharmingen |
| Human CD45 | APC-Cy7 | 2D1 | BD Pharmingen |
| Human CD45RA | FITC | L48 | BD Pharmingen |
| Human GlyA | PE | CLB-ery-1 (AME-1) | CALTAG/Invitrogen |

TABLE 3

Comparative marker selection result for ERY samples vs. MEGA samples

| Feature | Description | TTEST_Score | Feature P | FDR(BH) | Q Value | FWER |
|---|---|---|---|---|---|---|
| EAM217 | hmr-miR-150_rfam7.0 | −6.134193365 | 6.00E−04 | 0.00373 | 0.00197 | 0.00148 |
| EAM161 | hmr-miR-28_rfam7.0 | −4.939403406 | 7.60E−04 | 0.00441 | 0.00225 | 0.02214 |
| EAM163 | hmr-miR-142-3p_rfam7.0 | −3.738371725 | 0.0012 | 0.00653 | 0.00333 | 0.26634 |
| EAM371 | hmr-miR-342_rfam7.0 | −3.42554054 | 6.00E−04 | 0.00373 | 0.00197 | 0.45006 |
| EAM278 | hmr-miR-98 rfam7.0 | −2.987417405 | 0.00524 | 0.02682 | 0.01368 | 0.76548 |
| EAM263 | hmr-miR-26a_rfam7.0 | −2.93748816 | 0 | 0 | 0 | 0.79334 |

TABLE 3-continued

Comparative marker selection result for ERY samples vs. MEGA samples

| Feature | Description | TTEST_Score | Feature P | FDR(BH) | Q Value | FWER |
|---|---|---|---|---|---|---|
| EAM224 | hmr-miR-17-5p__rfam7.0 | 2.052993319 | 0.00604 | 0.02919 | 0.01489 | 0.99828 |

Normalized miRNA expression data for ERY populations (ERY1, ERY2, ERY3) and MEGA populations (MEGA1, MEGA2) were log 2 transformed, thresholded at 6, and filtered to retain miRNAs with maximum expression over 8. Markers were selected using the ComparativeMarkerSelection module in GenePattern, with median-based t-test and 50,000 permutations. The table below shows features with BH-FDR of less than 0.05. Negative TTEST_Score means higher expression in MEGA samples, whereas positive number reflects higher expression in ERY samples. The table was sorted according to TTEST_Score. Feature: miRNA detection probe ID; Description: Detection probe annotation based on miRBASE 7.0; TTEST_Score: Median-based t-test score; Feature P: Nominal P value, after 50,000 permutations; FDR (BH): Benjamini-Hochberg false discovery rate; Q Value: q-value; FWER: Family-wise error rate.

TABLE 4

List of capture probes for initial miRNA capture
/5AmMC6/indicates 5' amino modification. Probes were synthesized by IDT.

/5AmMC6/ACTCAGAAGGACAAGTAGAGTTTT (SEQ. ID. No. 26)   /5AmMC6/GTGGTAATCCCTGGCAATGTGAT (SEQ. ID. No. 27)

/5AmMC6/ACACTCTAAAGGGAACCATTTT (SEQ. ID. No. 28)   /5AmMC6/GGAAATCCCTGGCAATGTGAT (SEQ. ID. No. 29)

/5AmMC6/AAAGAAGTGCACCATGTTTGTTT (SEQ. ID. No. 30)   /5AmMC6/AAAGTGTCAGATACGGTGTGG (SEQ. ID. No. 31)

/5AmMC6/AAGAAGTGCACCGCGAATGT (SEQ. ID. No. 32)   /5AmMC6/ACAGTTCTTCAACTGGCAGCTT (SEQ. ID. No. 33)

/5AmMC6/AACACTCTGAAGGGAAGCGC (SEQ. ID. No. 34)   /5AmMC6/CTACCTGCACTATAAGCACTTTA (SEQ. ID. No. 35)

/5AmMC6/CACTCTAAAAGGATGCACTTT (SEQ. ID. No. 36)   /5AmMC6/TCAGTTTTGCATGGATTTGCACA (SEQ. ID. No. 37)

/5AmMC6/TTCACCAAAGGGAAGCACTTT (SEQ. ID. No. 38)   /5AmMC6/CCCAACAACATGAAACTACCTA (SEQ. ID. No. 39)

/5AmMC6/ACACTCTAAAGGGAAGTGCGTT (SEQ. ID. No. 40)   /5AmMC6/ACAAAGTTCTGTAGTGCACTGA (SEQ. ID. No. 41)

/5AmMC6/CTCCCTTCTTTCCTCCCGTC (SEQ. ID. No. 42)   /5AmMC6/CTAGTACATCATCTATACTGTA (SEQ. ID. No. 43)

/5AmMC6/CTCACACCTAGGTTCCAAGGATT (SEQ. ID. No. 44)   /5AmMC6/tgAGCTACAGTGCTTCATCTCA (SEQ. ID. No. 45)

/5AmMC6/TTACAGATGGATACCGTGCAATT (SEQ. ID. No. 46)   /5AmMC6/CCATCTTTACCAGACAGTGTT (SEQ. ID. No. 47)

/5AmMC6/CCACGACCGACGCCACGCC (SEQ. ID. No. 48)   /5AmMC6/CTACCATAGGGTAAAACCACT (SEQ. ID. No. 49)

/5AmMC6/CCTCTAAAAGGAAGCACTTTCT (SEQ. ID. No. 50)   /5AmMC6/TGGAGACACGTGCACTGTAGA (SEQ. ID. No. 51)

/5AmMC6/GAACATACAAAGGGTATCCTCT (SEQ. ID. No. 52)   /5AmMC6/TTCACATAGGAATAAAAAGCCATA (SEQ. ID. No. 53)

/5AmMC6/CGAATATAACACGGTCGATCT (SEQ. ID. No. 54)   /5AmMC6/ACAGCTGGTTGAAGGGGACCAA (SEQ. ID. No. 55)

/5AmMC6/CCTCCAGCCCCTCCAGGGCT (SEQ. ID. No. 56)   /5AmMC6/GGGGTATTTGACAAACTGACA (SEQ. ID. No. 57)

/5AmMC6/TCAATCACAGATAGCACCCCT (SEQ. ID. No. 58)   /5AmMC6/GCAAAAATGTGCTAGTGCCAAA (SEQ. ID. No. 59)

/5AmMC6/GTAGTGCAACTATGCAAAACT (SEQ. ID. No. 60)   /5AmMC6/TCATACAGCTAGATAACCAAAGA (SEQ. ID. No. 61)

/5AmMC6/TGGTGGCAGTGGTGGGAT (SEQ. ID. No. 62)   /5AmMC6/CTTCCAGTCGGGGATGTTTACA (SEQ. ID. No. 63)

/5AmMC6/ACACTCTAAAGGGATGCACGAT (SEQ. ID. No. 64)   /5AmMC6/ACACAAATTCGGTTCTACAGGG (SEQ. ID. No. 65)

/5AmMC6/AAAGTGCTTCTTACCTCCAGAT (SEQ. ID. No. 66)   /5AmMC6/ACCCTCCACCATGCAAGGGATG (SEQ. ID. No. 67)

/5AmMC6/ACCTCTAAAGGGGAGCGCTT (SEQ. ID. No. 68)   /5AmMC6/CCTATCTCCCCTCTGGACC (SEQ. ID. No. 69)

/5AmMC6/ACACTCTAAAGGGAGGCACTTT (SEQ. ID. No. 70)   /5AmMC6/GGCTGTCAATTCATAGGTCAG (SEQ. ID. No. 71)

/5AmMC6/TCCAGGAGCTCACAATCTAGTG (SEQ. ID. No. 72)   /5AmMC6/CGGCTGCAACACAAGACACGA (SEQ. ID. No. 73)

/5AmMC6/GTTACCGCAGGCTGCTCTGG (SEQ. ID. No. 74)   /5AmMC6/CAGTGAATTCTACCAGTGCCATA (SEQ. ID. No. 75)

/5AmMC6/AGAAAGCGCTTCCCTGTAGAG (SEQ. ID. No. 76)   /5AmMC6/TGTGAGTTCTACCATTGCCAAA (SEQ. ID. No. 77)

/5AmMC6/AGCCAAGTAATGGAGAACAGG (SEQ. ID. No. 78)   /5AmMC6/CGAAGGCAACACGGATAACCTA (SEQ. ID. No. 79)

/5AmMC6/AGAAAGCGCTTCCCTCTAGAG (SEQ. ID. No. 80)   /5AmMC6/TCACTTTTGTGACTATGCAA (SEQ. ID. No. 81)

TABLE 4-continued

List of capture probes for initial miRNA capture
/5AmMC6/indicates 5' amino modification. Probes were synthesized by IDT.

| | |
|---|---|
| /5AmMC6/ACAGAAAGGGCTTCCCTTTGC (SEQ. ID. No. 82) | /5AmMC6/CCAAGTTCTGTCATGCACTGA (SEQ. ID. No. 83) |
| /5AmMC6/TCGGTCCCTCGGGCCAGGG (SEQ. ID. No. 84) | /5AmMC6/GGAGTGAAGACACGGAGCCAGA (SEQ. ID. No. 85) |
| /5AmMC6/TCTAAGCCACCATGTGAAACCA (SEQ. ID. No. 86) | /5AmMC6/ACAAAGTTCTGTGATGCACTGA (SEQ. ID. No. 87) |
| /5AmMC6/GCAAGGCAGTGGCCTGTACA (SEQ. ID. No. 88) | /5AmMC6/GCTGAGAGTGTAGGATGTTTACA (SEQ. ID. No. 89) |
| /5AmMC6/TCCAGCAAAGGGAAGCGCTT (SEQ. ID. No. 90) | /5AmMC6/AACCGATTTCAGATGGTGCTAG (SEQ. ID. No. 91) |
| /5AmMC6/ACCCTCTATAGGGAAGCGCGT (SEQ. ID. No. 92) | /5AmMC6/GTCATCATTACCAGGCAGTATTA (SEQ. ID. No. 93) |
| /5AmMC6/CAGGTAACAACTCGCCGCTC (SEQ. ID. No. 94) | /5AmMC6/AACCAATGTGCAGACTACTGTA (SEQ. ID. No. 95) |
| /5AmMC6/ACTGCACTTTTATGAATAAGCTC (SEQ. ID. No. 96) | /5AmMC6/GCTGGGTGGAGAAGGTGGTGAA (SEQ. ID. No. 97) |
| /5AmMC6/AACGCTCCAAAAGAAGGCACT (SEQ. ID. No. 98) | /5AmMC6/GCCAATATTTCTGTGCTGCTA (SEQ. ID. No. 99) |
| /5AmMC6/ACCAGAACTGAGTCCACAGGG (SEQ. ID. No. 100) | /5AmMC6/CGCAAGGTCGGTTCTACGGGTG (SEQ. ID. No. 101) |
| /5AmMC6/TCCCGTCGCCAGCGGAGGC (SEQ. ID. No. 102) | /5AmMC6/ACACCGAGGAGCCCATCATGAT (SEQ. ID. No. 103) |
| /5AmMC6/ACTGAAACCAAGTATGGGTCGC (SEQ. ID. No. 104) | /5AmMC6/CCTGCATGACGGCCTGCAAGACA (SEQ. ID. No. 105) |
| /5AmMC6/CAGCCCTCCTGGTGGCTGG (SEQ. ID. No. 106) | /5AmMC6/ATAAGGATTTTTAGGGGCATTA (SEQ. ID. No. 107) |
| /5AmMC6/ATCTACACTGGCTACTGAGCC (SEQ. ID. No. 108) | /5AmMC6/TATTAGGAACACATCGCAAAAA (SEQ. ID. No. 109) |
| /5AmMC6/CGCGACTGCGTCACCGGCC (SEQ. ID. No. 110) | /5AmMC6/ACCAGCTAACAATACACTGCCA (SEQ. ID. No. 111) |
| /5AmMC6/CCTGCGCCATCTCCTCTAC (SEQ. ID. No. 112) | /5AmMC6/ATGGGACATCCTACATATGCAA (SEQ. ID. No. 113) |
| /5AmMC6/ACTGTGTTTCAGCTCAGTAGGCA (SEQ. ID. No. 114) | /5AmMC6/TTCAAAACATGAATTGCTGCTG (SEQ. ID. No. 115) |
| /5AmMC6/CGAACACAGCAGGGATAACCAC (SEQ. ID. No. 116) | /5AmMC6/GTACCCCTGGAGATTCTGATAA (SEQ. ID. No. 117) |
| /5AmMC6/ACTGCAGAACTGTTCCCGCTG (SEQ. ID. No. 118) | /5AmMC6/TCACGCGAGCCGAACGAACAAA (SEQ. ID. No. 119) |
| /5AmMC6/AGAAAATGCCCCTCAGTTTTGA (SEQ. ID. No. 120) | /5AmMC6/ACAAAAGTTGCCTTTGTGTGAT (SEQ. ID. No. 121) |
| /5AmMC6/AGACGGGAGGAGAGGAGTGA (SEQ. ID. No. 122) | /5AmMC6/ACACAGGACCTGGAGTCAGGAG (SEQ. ID. No. 123) |
| /5AmMC6/ATCGGGAGGGGACTGAGCCT (SEQ. ID. No. 124) | /5AmMC6/CCTACGTTCCATAGTCTACCA (SEQ. ID. No. 125) |
| /5AmMC6/CTCGGGGCAGCTCAGTACAG (SEQ. ID. No. 126) | /5AmMC6/GCGCATGTTCTATGGTCAACCA (SEQ. ID. No. 127) |
| /5AmMC6/CGAGCCGGTCGAGGTCCGGT (SEQ. ID. No. 128) | /5AmMC6/ACAGAGAGCTTGCCCTTGTATA (SEQ. ID. No. 129) |
| /5AmMC6/TCTCGTGACATGATGATCCCCG (SEQ. ID. No. 130) | /5AmMC6/TATGAACAATTTCTAGGAAT (SEQ. ID. No. 131) |
| /5AmMC6/AGAAAGCGCTTTCCTTTGTAGA (SEQ. ID. No. 132) | /5AmMC6/GGCGGACACGACATTCCCGAT (SEQ. ID. No. 133) |
| /5AmMC6/CACATGGCCAAAACAGAGAAGA (SEQ. ID. No. 134) | /5AmMC6/GTCTCAGTTTCCTCTGCAAACA (SEQ. ID. No. 135) |
| /5AmMC6/CCACCCAATGACCTACTCCAAG (SEQ. ID. No. 136) | /5AmMC6/GCTGTAAACATCCGACTGAAAG (SEQ. ID. No. 137) |
| /5AmMC6/TCATCTCGCCCGCAAAGACC (SEQ. ID. No. 138) | /5AmMC6/ATGCTTTTTGGGGTAAGGGCTT (SEQ. ID. No. 139) |
| /5AmMC6/AGAAAGTGCTTTCTTTTGGAGAA (SEQ. ID. No. 140) | /5AmMC6/ACGGCATTACCAGACAGTATTA (SEQ. ID. No. 141) |
| /5AmMC6/GAAAGTGCTTCTTTCCTCGAGAA (SEQ. ID. No. 142) | /5AmMC6/TCTCTGCAGGCCCTGTGCTTTGC (SEQ. ID. No. 143) |
| /5AmMC6/CACAGGTTAAAGGGTCTCAGGGA (SEQ. ID. No. 144) | /5AmMC6/TGTTGCAGCGCTTCATGTTT (SEQ. ID. No. 145) |
| /5AmMC6/ACAAATTCGGTTCTACAGGGTA (SEQ. ID. No. 146) | /5AmMC6/AGCCACAGTCACCTTCTGATCT (SEQ. ID. No. 147) |
| /5AmMC6/TGATAGCCCTGTACAATGCTGCT (SEQ. ID. No. 148) | /5AmMC6/CATGCATACATGCACACATACAT (SEQ. ID. No. 149) |
| /5AmMC6/TCATAGCCCTGTACAATGCTGCT (SEQ. ID. No. 150) | /5AmMC6/CAACAAACATTTAATGAGGCC (SEQ. ID. No. 151) |
| /5AmMC6/AACTATACAATCTACTACCTCA (SEQ. ID. No. 152) | /5AmMC6/TGATGGACAACAAATTAGGTA (SEQ. ID. No. 153) |
| /5AmMC6/ACTATGCAACCTACTACCTCT (SEQ. ID. No. 154) | /5AmMC6/TATCTCACAGAATAAACTTGGTA (SEQ. ID. No. 155) |
| /5AmMC6/TTCAGCTATCACAGTACTGTA (SEQ. ID. No. 156) | /5AmMC6/TCACATCAGTGCCATTCTAAATA (SEQ. ID. No. 157) |
| /5AmMC6/CTATACAACCTCCTACCTCA (SEQ. ID. No. 158) | /5AmMC6/GTCTTATGTGTGCGTGTATGTAT (SEQ. ID. No. 159) |

TABLE 4-continued

List of capture probes for initial miRNA capture
/5AmMC6/indicates 5' amino modification. Probes were synthesized by IDT.

| | |
|---|---|
| /5AmMC6/CTCAATAGACTGTGAGCTCCTT (SEQ. ID. No. 160) | /5AmMC6/GTGTAGGTGTGTGTATGTATAT (SEQ. ID. No. 161) |
| /5AmMC6/AACCTATCCTGAATTACTTGAA (SEQ. ID. No. 162) | /5AmMC6/CAGACACACGCACATCAGTCATA (SEQ. ID. No. 163) |
| /5AmMC6/TCCATCATCAAAACAAATGGAGT (SEQ. ID. No. 164) | /5AmMC6/GGACACCAAGATCAATGAAAGAGGCA (SEQ. ID. No. 165) |
| /5AmMC6/AGGCAAAGGATGACAAAGGGAA (SEQ. ID. No. 166) | /5AmMC6/TCACCAGTGCCAGTCCAAGAA (SEQ. ID. No. 167) |
| /5AmMC6/GAACAGGTAGTCTAAACACTGGG (SEQ. ID. No. 168) | /5AmMC6/TGTGAAAAGCACTATACTACGTA (SEQ. ID. No. 169) |
| /5AmMC6/ATCCAGTCAGTTCCTGATGCAGTA (SEQ. ID. No. 170) | /5AmMC6/AGACTAGATATGGAAGGGTGA (SEQ. ID. No. 171) |
| /5AmMC6/GCTGCAAACATCCGACTGAAAG (SEQ. ID. No. 172) | /5AmMC6/TCTGGGCACACGGAGGGAGA (SEQ. ID. No. 173) |
| /5AmMC6/TAACCGATTTCAAATGGTGCTA (SEQ. ID. No. 174) | /5AmMC6/ACGGTCAGGCTTTGGCTAGAT (SEQ. ID. No. 175) |
| /5AmMC6/AACAATACAACTTACTACCTCA (SEQ. ID. No. 176) | /5AmMC6/AGAGGCAGGCACTCAGGCAGA (SEQ. ID. No. 177) |
| /5AmMC6/ATACATACTTCTTTACATTCCA (SEQ. ID. No. 178) | /5AmMC6/TGGGCGACCCAGAGGGACA (SEQ. ID. No. 179) |
| /5AmMC6/GCTGAGTGTAGGATGTTTACA (SEQ. ID. No. 180) | /5AmMC6/AGAGGTTAAGACAGCAGGGCTG (SEQ. ID. No. 181) |
| /5AmMC6/ATGCCCTTTTAACATTGCACTG (SEQ. ID. No. 182) | /5AmMC6/GGTTCAAACCATGAGTCGAGCT (SEQ. ID. No. 183) |
| /5AmMC6/CTACGCGTATTCTTAAGCAATAA (SEQ. ID. No. 184) | /5AmMC6/GGGAGTCGAGTGATGGTTCAAA (SEQ. ID. No. 185) |
| /5AmMC6/AGAACAATGCCTTACTGAGTA (SEQ. ID. No. 186) | /5AmMC6/GAATAATGACAGGCTCACCGTA (SEQ. ID. No. 187) |
| /5AmMC6/TCTTCCCATGCGCTATACCTCT (SEQ. ID. No. 188) | /5AmMC6/TACTATGCAACCTACTACTCT (SEQ. ID. No. 189) |
| /5AmMC6/CCACACACTTCCTTACATTCCA (SEQ. ID. No. 190) | /5AmMC6/CTGAGGGGCCTCAGACCGAGCT (SEQ. ID. No. 191) |
| /5AmMC6/GAGGGAGGAGAGCCAGGAGAAGC (SEQ. ID. No. 192) | /5AmMC6/TAACTGCACTAGATGCACCTTA (SEQ. ID. No. 193) |
| /5AmMC6/ACAAGCTTTTTGCTCGTCTTAT (SEQ. ID. No. 194) | /5AmMC6/CTACCTGCACTATGAGCACTTTG (SEQ. ID. No. 195) |
| /5AmMC6/GGCCGTGACTGGAGACTGTTA (SEQ. ID. No. 196) | /5AmMC6/GGGGACGAAATCCAAGCGCAGC (SEQ. ID. No. 197) |
| /5AmMC6/CACAGTTGCCAGCTGAGATTA (SEQ. ID. No. 198) | /5AmMC6/AATAGGTCAACCGTGTATGATT (SEQ. ID. No. 199) |
| /5AmMC6/ACATGGTTAGATCAAGCACAA (SEQ. ID. No. 200) | /5AmMC6/GCAGAAGCATTTCCACACAC (SEQ. ID. No. 201) |
| /5AmMC6/ACAACCAGCTAAGACACTGCCA (SEQ. ID. No. 202) | /5AmMC6/CCCCTATCACGATTAGCATTAA (SEQ. ID. No. 203) |
| /5AmMC6/AGGCGAAGGATGACAAAGGGAA (SEQ. ID. No. 204) | /5AmMC6/ACAAGTGCCTTCACTGCAGT (SEQ. ID. No. 205) |
| /5AmMC6/GTCTGTCAATTCATAGGTCAT (SEQ. ID. No. 206) | /5AmMC6/TCCAGCACTGTCCGGTAAGATG (SEQ. ID. No. 207) |
| /5AmMC6/ATCCAATCAGTTCCTGATGCAGTA (SEQ. ID. No. 208) | /5AmMC6/AAAGCAAGTACATCCACGTTTA (SEQ. ID. No. 209) |
| /5AmMC6/ACTACCTGCACTGTAAGCACTTTG (SEQ. ID. No. 210) | /5AmMC6/AAGCGGTTTACCATCCCACATA (SEQ. ID. No. 211) |
| /5AmMC6/TATCTGCACTAGATGCACCTTA (SEQ. ID. No. 212) | /5AmMC6/TAGTTGGCAAGTCTAGAACCA (SEQ. ID. No. 213) |
| /5AmMC6/AACCCACCGACAGCAATGAATGTT (SEQ. ID. No. 214) | /5AmMC6/CTACTAAAACATGGAAGCACTTA (SEQ. ID. No. 215) |
| /5AmMC6/GAACAGGTAGTCTGAACACTGGG (SEQ. ID. No. 216) | /5AmMC6/AGAAAGCACTTCCATGTTAAAGT (SEQ. ID. No. 217) |
| /5AmMC6/GAACAGATAGTCTAAACACTGGG (SEQ. ID. No. 218) | /5AmMC6/CCACTGAAACATGGAAGCACTTA (SEQ. ID. No. 219) |
| /5AmMC6/TCAGTTTTGCATAGATTTGCACA (SEQ. ID. No. 220) | /5AmMC6/CAGCAGGTACCCCCATGTTA (SEQ. ID. No. 221) |
| /5AmMC6/CTAGTGGTCCTAAACATTTCAC (SEQ. ID. No. 222) | /5AmMC6/ACACTCAAACATGGAAGCACTTA (SEQ. ID. No. 223) |
| /5AmMC6/AGGCATAGGATGACAAAGGGAA (SEQ. ID. No. 224) | /5AmMC6/ACTTACTGGACACCTACTAGG (SEQ. ID. No. 225) |
| /5AmMC6/CAGCCGCTGTCACACGCACAG (SEQ. ID. No. 226) | /5AmMC6/AAAGGCATCATATAGGAGCTGGA (SEQ. ID. No. 227) |
| /5AmMC6/CTGCCTGTCTGTGCCTGCTGT (SEQ. ID. No. 228) | /5AmMC6/GCCCTGGACTAGGAGTCAGCA (SEQ. ID. No. 229) |
| /5AmMC6/CACAAGTTCGGATCTACGGGTT (SEQ. ID. No. 230) | /5AmMC6/AGAGGCAGGCATGCGGGCAG (SEQ. ID. No. 231) |
| /5AmMC6/GCTACCTGCACTGTAAGCACTTTT (SEQ. ID. No. 232) | /5AmMC6/TCACCATTGCTAAAGTGCAATT (SEQ. ID. No. 233) |
| /5AmMC6/CACAAATTCGGATCTACAGGGTA (SEQ. ID. No. 234) | /5AmMC6/AAACGTGGAATTTCCTCTATGT (SEQ. ID. No. 235) |
| /5AmMC6/ACAAACACCATTGTCACACTCCA (SEQ. ID. No. 236) | /5AmMC6/AAAGATCAACCATGTATTATT (SEQ. ID. No. 237) |

TABLE 4-continued

List of capture probes for initial miRNA capture
/5AmMC6/indicates 5' amino modification. Probes were synthesized by IDT.

| | |
|---|---|
| /5AmMC6/CGCGTACCAAAAGTAATAATG (SEQ. ID. No. 238) | /5AmMC6/AGCCACAATCACCTTCTGATCT (SEQ. ID. No. 239) |
| /5AmMC6/GCCCTTTCATCATTGCACTG (SEQ. ID. No. 240) | /5AmMC6/TCTCTGCAGGCCGTGTGCTTTGC (SEQ. ID. No. 241) |
| /5AmMC6/TCCCTCTGGTCAACCAGTCACA (SEQ. ID. No. 242) | /5AmMC6/ACGGTTTTACCAGACAGTATTA (SEQ. ID. No. 243) |
| /5AmMC6/GTAGTGCTTTCTACTTTATG (SEQ. ID. No. 244) | /5AmMC6/ACGTGGATTTTCCTCTATGAT (SEQ. ID. No. 245) |
| /5AmMC6/CCCCTATCACAATTAGCATTAA (SEQ. ID. No. 246) | /5AmMC6/GGCCTTCTGACTCCAAGTCCAG (SEQ. ID. No. 247) |
| /5AmMC6/TGTAAACCATGATGTGCTGCTA (SEQ. ID. No. 248) | /5AmMC6/AAGATGTGGACCATATTACATA (SEQ. ID. No. 249) |
| /5AmMC6/ACTCACCGACAGGTTGAATGTT (SEQ. ID. No. 250) | /5AmMC6/GGCCTTCTGACCCTAAGTCCAG (SEQ. ID. No. 251) |
| /5AmMC6/CACAAACCATTATGTGCTGCTA (SEQ. ID. No. 252) | /5AmMC6/AAAGAGGTTAACCAGGTGTGTT (SEQ. ID. No. 253) |
| /5AmMC6/TAACTGTACAAACTACTACCTCA (SEQ. ID. No. 254) | /5AmMC6/CGAACTCACCACGGACAACCTC (SEQ. ID. No. 255) |
| /5AmMC6/ACAGGCCGGGACAAGTGCAATAT (SEQ. ID. No. 256) | /5AmMC6/CTTCTTTGCAGATGAGACTGA (SEQ. ID. No. 257) |
| /5AmMC6/TAACCCATGGAATTCAGTTCTCA (SEQ. ID. No. 258) | /5AmMC6/TGCAAAGTTGCTCGGGTAACCT (SEQ. ID. No. 259) |
| /5AmMC6/AACCATACAACCTACTACCTCA (SEQ. ID. No. 260) | /5AmMC6/AACATGGATTTTCCTCTATGAT (SEQ. ID. No. 261) |
| /5AmMC6/AACAACAAAATCACTAGTCTTCCA (SEQ. ID. No. 262) | /5AmMC6/GAATTCATCACGGCCAGCCTCT (SEQ. ID. No. 263) |
| /5AmMC6/ACTTTCGGTTATCTAGCTTTAT (SEQ. ID. No. 264) | /5AmMC6/AGAGGAGAGCCGTGTATGAC (SEQ. ID. No. 265) |
| /5AmMC6/ACAGCACAAACTACTACCTCA (SEQ. ID. No. 266) | /5AmMC6/TTGAGAGTGCCATTATCTGGG (SEQ. ID. No. 267) |
| /5AmMC6/AACTATACAACCTACTACCTCA (SEQ. ID. No. 268) | /5AmMC6/GCTGCCGTATATGTGATGTCACT (SEQ. ID. No. 269) |
| /5AmMC6/AACCACACAACCTACTACCTCA (SEQ. ID. No. 270) | /5AmMC6/CAGCATGGAGTCCTCCAGGTTG (SEQ. ID. No. 271) |
| /5AmMC6/CCGACCATGGCTGTAGACTGTTA (SEQ. ID. No. 272) | /5AmMC6/TCCTCATGGAAGGGTTCCCCACT (SEQ. ID. No. 273) |
| /5AmMC6/ACACCAATGCCCTAGGGGATGCG (SEQ. ID. No. 274) | /5AmMC6/TGACTGCAGAGCAAAAGACAC (SEQ. ID. No. 275) |
| /5AmMC6/TGGCATTCACCGCGTGCCTTA (SEQ. ID. No. 276) | /5AmMC6/AGCCTATGGAATTCAGTTCTCA (SEQ. ID. No. 277) |
| /5AmMC6/TCACAAGTTAGGGTCTCAGGGA (SEQ. ID. No. 278) | /5AmMC6/AAAGAAGTATATGCATAGGAAA (SEQ. ID. No. 279) |
| /5AmMC6/CACAAGATCGGATCTACGGGT (SEQ. ID. No. 280) | /5AmMC6/TTTTCCCATGCCCTATACCTCT (SEQ. ID. No. 281) |
| /5AmMC6/CGCCAATATTTACGTGCTGCTA (SEQ. ID. No. 282) | /5AmMC6/AAGAATCTTGTCCCGCAGGTCCT (SEQ. ID. No. 283) |
| /5AmMC6/AACACTGATTTCAAATGGTGCTA (SEQ. ID. No. 284) | /5AmMC6/AATGAAAGCCTACCATGTACAA (SEQ. ID. No. 285) |
| /5AmMC6/CTTCAGTTATCACAGTACTGTA (SEQ. ID. No. 286) | /5AmMC6/AGACATGGAGGAGCCATCCAG (SEQ. ID. No. 287) |
| /5AmMC6/ACAGGAGTCTGAGCATTTGA (SEQ. ID. No. 288) | /5AmMC6/AAGAGGTTTCCCGTGTATGTTTCA (SEQ. ID. No. 289) |
| /5AmMC6/ATCTGCACTGTCAGCACTTTA (SEQ. ID. No. 290) | /5AmMC6/GGAGATTGGCCATGTAATACT (SEQ. ID. No. 291) |
| /5AmMC6/GCATTATTACTCACGGTACGA (SEQ. ID. No. 292) | /5AmMC6/ACAAACCACAGTGTGCTGCTG (SEQ. ID. No. 293) |
| /5AmMC6/AGCCAAGCTCAGACGGATCCGA (SEQ. ID. No. 294) | /5AmMC6/AACCCACCGACAACAATGAATGTT (SEQ. ID. No. 295) |
| /5AmMC6/ACTGATATCAGCTCAGTAGGCAC (SEQ. ID. No. 296) | /5AmMC6/GAAAGTGCCCTCAAGGCTGAGTG (SEQ. ID. No. 297) |
| /5AmMC6/TCCATCATTACCCGGCAGTATTA (SEQ. ID. No. 298) | /5AmMC6/GACCTCAGCTATGACAGCACTT (SEQ. ID. No. 299) |
| /5AmMC6/TAAACGGAACCACTAGTGACTTG (SEQ. ID. No. 300) | /5AmMC6/GAAAAACGCCCCCTGGCTTGAAA (SEQ. ID. No. 301) |
| /5AmMC6/TCAGACCGAGACAAGTGCAATG (SEQ. ID. No. 302) | /5AmMC6/CCCTCAAAAAGGAAGCACTTT (SEQ. ID. No. 303) |
| /5AmMC6/GGCGGAACTTAGCCACTGTGAA (SEQ. ID. No. 304) | /5AmMC6/GAAAGTGCTCCCTTTTGGAGAA (SEQ. ID. No. 305) |
| /5AmMC6/ACAGGATTGAGGGGGGGCCCT (SEQ. ID. No. 306) | /5AmMC6/ACACTCTAAAAGGAGGCACTTT (SEQ. ID. No. 307) |
| /5AmMC6/ATGTATGTGGGACGGTAAACCA (SEQ. ID. No. 308) | /5AmMC6/ATCCTCTAAAAAGATGCACTTT (SEQ. ID. No. 309) |
| /5AmMC6/GCTTTGACAATACTATTGCACTG (SEQ. ID. No. 310) | /5AmMC6/AGAAAGTACTTCCCTCTGGAG (SEQ. ID. No. 311) |
| /5AmMC6/TCACCAAAACATGGAAGCACTTA (SEQ. ID. No. 312) | /5AmMC6/ACAGTCCAAAGGGAAGCACTTT (SEQ. ID. No. 313) |
| /5AmMC6/GCTTCCAGTCGAGGATGTTTACA (SEQ. ID. No. 314) | /5AmMC6/AACAGAAAGTGCTTCCCTCAAGAG (SEQ. ID. No. 315) |

TABLE 4-continued

List of capture probes for initial miRNA capture
/5AmMC6/ indicates 5' amino modification. Probes were synthesized by IDT.

/5AmMC6/TCCAGTCAAGGATGTTTACA (SEQ. ID. No. 316)  /5AmMC6/GCCTCTAAAAGGAAGCACTTT (SEQ. ID. No. 317)

/5AmMC6/CAGCTATGCCAGCATCTTGCCT (SEQ. ID. No. 318)  /5AmMC6/AAACCTCTAAAAGGATGCACTTT (SEQ. ID. No. 319)

/5AmMC6/GCAACTTAGTAATGTGCAATA (SEQ. ID. No. 320)  /5AmMC6/AGAAAGTGCATCCCTCTGGAG (SEQ. ID. No. 321)

/5AmMC6/CAATCAGCTAATGACACTGCCT (SEQ. ID. No. 322)  /5AmMC6/GCTCTAAAGGGAAGCGCCTTC (SEQ. ID. No. 323)

/5AmMC6/GCAATCAGCTAACTACACTGCCT (SEQ. ID. No. 324)  /5AmMC6/AGAGAAAGTGCTTCCCTCTAGAG (SEQ. ID. No. 325)

/5AmMC6/CTACCTGCACGAACAGCACTTTG (SEQ. ID. No. 326)  /5AmMC6/TCCTCTAAAGAGAAGCGCTTT (SEQ. ID. No. 327)

/5AmMC6/TGCTCAATAAATACCCGTTGAA (SEQ. ID. No. 328)  /5AmMC6/CAGAAAGTGCTTCCCTCCAGAGA (SEQ. ID. No. 329)

/5AmMC6/AGCAAGCCCAGACCGCAAAAAG (SEQ. ID. No. 330)  /5AmMC6/CACTCTAAAGAGAAGCGCTTTG (SEQ. ID. No. 331)

/5AmMC6/AGAAAGGCAGCAGGTCGTATAG (SEQ. ID. No. 332)  /5AmMC6/GAGAAAGTGCTTCCCTTTGTAG (SEQ. ID. No. 333)

/5AmMC6/TACCTGCACTGTTAGCACTTTG (SEQ. ID. No. 334)  /5AmMC6/ACTCCAAAGGGAAGCGCCTTC (SEQ. ID. No. 335)

/5AmMC6/CACATAGGAATGAAAAGCCATA (SEQ. ID. No. 336)  /5AmMC6/AGACAGTGCTTCCATCTAGAGG (SEQ. ID. No. 337)

/5AmMC6/CCTCAAGGAGCCTCAGTCTAGT (SEQ. ID. No. 338)  /5AmMC6/CAGAAAGGGCTTCCCTTTGTAGA (SEQ. ID. No. 339)

/5AmMC6/ACAAGTGCCCTCACTGCAGT (SEQ. ID. No. 340)  /5AmMC6/AACCCACCAAAGAGAAGCACTTT (SEQ. ID. No. 341)

/5AmMC6/TAAACGGAACCACTAGTGACTTA (SEQ. ID. No. 342)  /5AmMC6/ACACTCTAAAGGGAAGCACTTTGT (SEQ. ID. No. 343)

/5AmMC6/AAAAAGTGCCCCCATAGTTTGAG (SEQ. ID. No. 344)  /5AmMC6/AACCCTCTGAAAGGAAGCACTT (SEQ. ID. No. 345)

/5AmMC6/GGCACACAAAGTGGAAGCACTTT (SEQ. ID. No. 346)  /5AmMC6/GCTCCAAAGGGAAGCGCTTTG (SEQ. ID. No. 347)

/5AmMC6/AGAGAGGGCCTCCACTTTGATG (SEQ. ID. No. 348)  /5AmMC6/AAAGGGCTTCCCTTTGCAGA (SEQ. ID. No. 349)

/5AmMC6/ACACTCAAAACCTGGCGGCACTT (SEQ. ID. No. 350)  /5AmMC6/ACACTCTAAAAGGATGCACGAT (SEQ. ID. No. 351)

/5AmMC6/CAAAAGAGCCCCCAGTTTGAGT (SEQ. ID. No. 352)  /5AmMC6/TTAAACATCACTGCAAGTCTTAA (SEQ. ID. No. 353)

/5AmMC6/ACACTACAAACTCTGCGGCACT (SEQ. ID. No. 354)  /5AmMC6/CAGAATCCTTGCCCAGGTGCAT (SEQ. ID. No. 355)

/5AmMC6/ACACACAAAAGGGAAGCACTTT (SEQ. ID. No. 356)  /5AmMC6/TCTCACCCAGGGACAAAGGATT (SEQ. ID. No. 357)

/5AmMC6/AGACTCAAAAGTAGTAGCACTTT (SEQ. ID. No. 358)  /5AmMC6/TAGCACCCAGATAGCAAGGAT (SEQ. ID. No. 359)

/5AmMC6/CATGCACATGCACACATACAT (SEQ. ID. No. 360)  /5AmMC6/CTGCAGAACTGTTCCCGCTGCTA (SEQ. ID. No. 361)

/5AmMC6/GGAAGAACAGCCCTCCTCTGCC (SEQ. ID. No. 362)  /5AmMC6/ATAGAGTGCAGACCAGGGTCT (SEQ. ID. No. 363)

/5AmMC6/GAAGAGAGCTTGCCCTTGCATA (SEQ. ID. No. 364)  /5AmMC6/ATAAATGACACCTCCCTGTGAA (SEQ. ID. No. 365)

/5AmMC6/AGAGGTCGACCGTGTAATGTGC (SEQ. ID. No. 366)  /5AmMC6/TCTACTCAGAAGGGTGCCTTA (SEQ. ID. No. 367)

/5AmMC6/CCAGCAGCACCTGGGGCAGT (SEQ. ID. No. 368)  /5AmMC6/TTCACTCCAAAAGGTGCAAAA (SEQ. ID. No. 369)

/5AmMC6/ACACTTACTGAGCACCTACTAGG (SEQ. ID. No. 370)  /5AmMC6/TCTACTCCAAAAGGCTACAATCA (SEQ. ID. No. 371)

/5AmMC6/ACTGGAGGAAGGGCCCAGAGG (SEQ. ID. No. 372)  /5AmMC6/TCTACCCACAGACGTACCAATCA (SEQ. ID. No. 373)

/5AmMC6/ACGGAAGGGCAGAGAGGGCCAG (SEQ. ID. No. 374)  /5AmMC6/TGTGATTGCCACTCTCCTGAGTA (SEQ. ID. No. 375)

/5AmMC6/AAAAAGGTTAGCTGGGTGTGTT (SEQ. ID. No. 376)  /5AmMC6/CTACTCACAGAAGTGTCAAT (SEQ. ID. No. 377)

/5AmMC6/TTCTAGGATAGGCCCAGGGGC (SEQ. ID. No. 378)  /5AmMC6/TTCAATTTCTGCCGCAAAAG (SEQ. ID. No. 379)

/5AmMC6/AAAGGCATCATATAGGAGCTGAA (SEQ. ID. No. 380)  /5AmMC6/GCTATCTGCTGCAACAGAATTT (SEQ. ID. No. 381)

/5AmMC6/GGCTATAAAGTAACTGAGACGGA (SEQ. ID. No. 382)  /5AmMC6/GTGTGCTTACACACTTCCCGTTA (SEQ. ID. No. 383)

/5AmMC6/ACTGACCGACCGACCGATCGA (SEQ. ID. No. 384)  /5AmMC6/AGCACGTCACTTCCACTAAGA (SEQ. ID. No. 385)

/5AmMC6/ACAGTCAGGCTTTGGCTAGATCA (SEQ. ID. No. 386)  /5AmMC6/GCAAGGGCGAATGCAGAAAA (SEQ. ID. No. 387)

/5AmMC6/GCACTGGACTAGGGGTCAGCA (SEQ. ID. No. 388)  /5AmMC6/AACTCCGGGGCTGATCAGGT (SEQ. ID. No. 389)

/5AmMC6/AGAGGCAGGCACTCGGGCAGA (SEQ. ID. No. 390)  /5AmMC6/CTTGTACCAGTTATCTGCAA (SEQ. ID. No. 391)

/5AmMC6/CAATCAGCTAATTACACTGCCTA (SEQ. ID. No. 392)  /5AmMC6/TTGTACGTTTACATGGAGGTC (SEQ. ID. No. 393)

TABLE 4-continued

List of capture probes for initial miRNA capture
/5AmMC6/indicates 5' amino modification. Probes were synthesized by IDT.

| | |
|---|---|
| /5AmMC6/GTGAAAGTGTATGGGCTTTGTGAA (SEQ. ID. No. 394) | /5AmMC6/CTGACTGACTGACTGACTGACTG (SEQ. ID. No. 395) |
| /5AmMC6/CAGGCTCAAAGGGCTCCTCAGG (SEQ. ID. No. 396) | /5AmMC6/CCATAAAGTAGGAAACACTA (SEQ. ID. No. 397) |
| /5AmMC6/AACAAAATCACAAGTCTTCCA (SEQ. ID. No. 398) | /5AmMC6/TCACCGACAGCGTTGAATGT (SEQ. ID. No. 399) |
| /5AmMC6/TGTAAGTGCTCGTAATGCAGT (SEQ. ID. No. 400) | /5AmMC6/CGGGACTTTGAGGGCCAGT (SEQ. ID. No. 401) |
| /5AmMC6/ACCCTCATGCCCCTCAAGG (SEQ. ID. No. 402) | /5AmMC6/GAATCCACCACGAACAACTT (SEQ. ID. No. 403) |
| /5AmMC6/AAAAGTAACTAGCACACCAC (SEQ. ID. No. 404) | /5AmMC6/AGAGACCGGTTCACTGTGA (SEQ. ID. No. 405) |
| /5AmMC6/ACATTTTTCGTTATTGCTCTT (SEQ. ID. No. 406) | /5AmMC6/AGAGACCGGTTCACTGTGA (SEQ. ID. No. 407) |
| /5AmMC6/TATGGCAGACTGTGATTTGTTG (SEQ. ID. No. 408) | /5AmMC6/CCTGATTCACAACACCAGCT (SEQ. ID. No. 409) |
| /5AmMC6/CATCGTTACCAGACAGTGTTA (SEQ. ID. No. 410) | /5AmMC6/GGATTCCTGGGAAAACTGGA (SEQ. ID. No. 411) |
| /5AmMC6/TCCACATGGAGTTGCTGTTACA (SEQ. ID. No. 412) | /5AmMC6/ACTGGTACAAGGGTTGGGAG (SEQ. ID. No. 413) |
| /5AmMC6/AACAGCTGCTTTTGGGATTCTG (SEQ. ID. No. 414) | /5AmMC6/CTGGGACTTTGTAGGCCAGT (SEQ. ID. No. 415) |
| /5AmMC6/ACCTAATATATCAAACATATCA (SEQ. ID. No. 416) | /5AmMC6/AGACTCCGGTGGAATGAAGG (SEQ. ID. No. 417) |
| /5AmMC6/AAGCCCAAAAGGAGAATTCTTTG (SEQ. ID. No. 418) | /5AmMC6/CAACATCAGTCTGATAAGCTA (SEQ. ID. No. 419) |
| /5AmMC6/AGGAACTGCCTTTCTCTCCAA (SEQ. ID. No. 420) | /5AmMC6/GTACAATCAACGGTCGATGG (SEQ. ID. No. 421) |
| /5AmMC6/ACCCTTATCAGTTCTCCGTCCA (SEQ. ID. No. 422) | /5AmMC6/AGAATTGCGTTTGGACAATC (SEQ. ID. No. 423) |
| /5AmMC6/TAGCTGGTTGAAGGGGACCAA (SEQ. ID. No. 424) | /5AmMC6/ACCCAGCAGACAATGTAGC (SEQ. ID. No. 425) |
| /5AmMC6/CCTCAAGGAGCTTCAGTCTAGT (SEQ. ID. No. 426) | /5AmMC6/ACCCAGTAGCCAGATGTAGC (SEQ. ID. No. 427) |
| /5AmMC6/CCAACAACAGGAAACTACCTA (SEQ. ID. No. 428) | /5AmMC6/GCCCTCTCAACCCAGCTTT (SEQ. ID. No. 429) |
| /5AmMC6/CCAGGTTCCACCCCAGCAGG (SEQ. ID. No. 430) | /5AmMC6/GCAATGCAACTACAATGCAC (SEQ. ID. No. 431) |
| /5AmMC6/ACACTCAAAAGATGGCGGCA (SEQ. ID. No. 432) | /5AmMC6/AACAAAATCACTGATGCTGG (SEQ. ID. No. 433) |
| /5AmMC6/ACGCTCAAATGTCGCAGCAC (SEQ. ID. No. 434) | /5AmMC6/GAGCTCCTGGAGGACAGGG (SEQ. ID. No. 435) |
| /5AmMC6/ACACCCCAAAATCGAAGCAC (SEQ. ID. No. 436) | /5AmMC6/GGGTGCGATTTCTGTGTGAG (SEQ. ID. No. 437) |
| /5AmMC6/GGAAAGCGCCCCCATTTTGA (SEQ. ID. No. 438) | /5AmMC6/ACTCAGTAATGGTAACGGTT (SEQ. ID. No. 439) |
| /5AmMC6/CACTTATCAGGTTGTATTATAA (SEQ. ID. No. 440) | /5AmMC6/GAGGAAACCAGCAAGTGTTG (SEQ. ID. No. 441) |
| /5AmMC6/GTCTGTCAAATCATAGGTCAT (SEQ. ID. No. 442) | /5AmMC6/GCAATGCAACAGCAATGCAC (SEQ. ID. No. 443) |
| /5AmMC6/GGGGTTCACCGAGCAACATTC (SEQ. ID. No. 444) | /5AmMC6/GTCCGTGGTTCTACCCTGTGG (SEQ. ID. No. 445) |
| /5AmMC6/CAGGCCATCTGTGTTATATT (SEQ. ID. No. 446) | /5AmMC6/ATACTAGACTGTGAGCTCCTCGA (SEQ. ID. No. 447) |
| /5AmMC6/AGTGGATGTTCCTCTATGAT (SEQ. ID. No. 448) | /5AmMC6/CCAGAAGGAGCACTTAGGGCAG (SEQ. ID. No. 449) |
| /5AmMC6/CGTGGATTTTCCTCTACGAT (SEQ. ID. No. 450) | /5AmMC6/GCTGGATGCAAACCTGCAAAAC (SEQ. ID. No. 451) |
| /5AmMC6/GAGGGTTAGTGGACCGTGTT (SEQ. ID. No. 452) | /5AmMC6/AATCCCATCCCCAGGAACCC (SEQ. ID. No. 453) |
| /5AmMC6/GATGTGGACCATACTACATA (SEQ. ID. No. 454) | /5AmMC6/CGGCTCTGTCGTCGAGGCGC (SEQ. ID. No. 455) |
| /5AmMC6/GGCTAGTGGACCAGGTGAAG (SEQ. ID. No. 456) | /5AmMC6/AAAGTCTCGCTCTCTGCCCCT (SEQ. ID. No. 457) |
| /5AmMC6/CAGAACTTAGCCACTGTGAA (SEQ. ID. No. 458) | /5AmMC6/TCAACGGGAGTGATCGTGTCAT (SEQ. ID. No. 459) |
| /5AmMC6/AGCCTATCCTGGATTACTTGAA (SEQ. ID. No. 460) | /5AmMC6/AGCATTGCAACCGATCCCAAC (SEQ. ID. No. 461) |
| /5AmMC6/CTGTTCCTGCTGAACTGAGCCA (SEQ. ID. No. 462) | /5AmMC6/GCAGCAAACATCTGACTGAAAG (SEQ. ID. No. 463) |

TABLE 5 miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM 190 | h-miR-1 0b_rfam7.0 | /5AmMC6/ACAAATTCGGTTCTACAGGGTA (SEQ. ID. No. 464) |
| EAM 187 | hmr-miR-1 07_rfam7.0 | /5AmMC6/TGATAGCCCTGTACAATGCTGCT (SEQ. ID. No. 465) |
| EAM 185 | hmr-miR-1 03_rfam7.0 | /5AmMC6/TCATAGCCCTGTACAATGCTGCT (SEQ. ID. No. 466) |
| EAM 181 | hmr-let-7f_rfam7.0 | /5AmMC6/AACTATACAATCTACTACCTCA (SEQ. ID. No. 467) |
| EAM 179 | hmr-let-7d_rfam7.0 | /5AmMC6/ACTATGCAACCTACTACCTCT (SEQ. ID. No. 468) |
| EAM 177 | mr-miR-1 01 b_rfam7.0 | /5AmMC6/TTCAGCTATCACAGTACTGTA (SEQ. ID. No. 469) |
| EAM 175 | hmr-miR-320_rfam7.0 | /5AmMC6/TCGCCCTCTCAACCCAGCTTTT (SEQ. ID. No. 470) |
| EAM 168 | hmr-let-7e_rfam7.0 | /5AmMC6/CTATACAACCTCCTACCTCA (SEQ. ID. No. 471) |
| EAM 161 | hmr-miR-28_rfam7.0 | /5AmMC6/CTCAATAGACTGTGAGCTCCTT (SEQ. ID. No. 472) |
| EAM 160 | hmr-miR-26b_rfam7.0 | /5AmMC6/AACCTATCCTGAATTACTTGAA (SEQ. ID. No. 473) |
| EAM 155 | hmr-miR-1 36_rfam7.0 | /5AmMC6/TCCATCATCAAAACAAATGGAGT (SEQ. ID. No. 474) |
| EAM283 | mr-miR-21 1_rfam7.0 | /5AmMC6/AGGCAAAGGATGACAAAGGGAA (SEQ. ID. No. 475) |
| EAM282 | m-miR-1 99b_rfam7.0 | /5AmMC6/GAACAGGTAGTCTAAACACTGGG (SEQ. ID. No. 476) |
| EAM281 | mr-miR-21 7_rfam7.0 | /5AmMC6/ATCCAGTCAGTTCCTGATGCAGTA (SEQ. ID. No. 477) |
| EAM280 | hmr-miR-30a-3p_rfam7.0 | /5AmMC6/GCTGCAAACATCCGACTGAAAG (SEQ. ID. No. 478) |
| EAM279 | hmr-miR-29c_rfam7.0 | /5AmMC6/TAACCGATTTCAAATGGTGCTA (SEQ. ID. No. 479) |
| EAM278 | hmr-miR-98_rfam7.0 | /5AmMC6/AACAATACAACTTACTACCTCA (SEQ. ID. No. 480) |
| EAM238 | hm-miR-1_rfam7.0 | /5AmMC6/ATACATACTTCTTTACATTCCA (SEQ. ID. No. 481) |
| EAM270 | hmr-miR-30b_rfam7.0 | /5AmMC6/GCTGAGTGTAGGATGTTTACA (SEQ. ID. No. 482) |
| EAM 159 | hmr-miR-1 30a_rfam7.0 | /5AmMC6/ATGCCCTTTTAACATTGCACTG (SEQ. ID. No. 483) |
| EAM 163 | hmr-miR-1 42-3p_rfam7.0 | /5AmMC6/TCCATAAAGTAGGAAACACTACA (SEQ. ID. No.484) |
| EAM 171 | hmr-miR-1 37_rfam7.0 | /5AmMC6/CTACGCGTATTCTTAAGCAATAA (SEQ. ID. No. 485) |
| EAM306 | m-miR-201_rfam7.0 | /5AmMC6/AGAACAATGCCTTACTGAGTA (SEQ. ID. No. 486) |
| EAM307 | m-miR-202_rfam7.0 | /5AmMC6/TCTTCCCATGCGCTATACCTCT (SEQ. ID. No. 487) |
| EAM308 | hmr-miR-206_rfam7.0 | /5AmMC6/CCACACACTTCCTTACATTCCA (SEQ. ID. No. 488) |
| EAM309 | m-miR-207_rfam7.0 | /5AmMC6/GAGGGAGGAGAGCCAGGAGAAGC (SEQ. ID. No. 489) |
| EAM31 0 | hmr-miR-208_rfam7.0 | /5AmMC6/ACAAGCTTTTTGCTCGTCTTAT (SEQ. ID. No. 490) |
| EAM247 | hmr-miR-21 2_rfam7.0 | /5AmMC6/GGCCGTGACTGGAGACTGTTA (SEQ. ID. No. 491) |
| EAM251 | hmr-miR-21 6_rfam7.0 | /5AmMC6/CACAGTTGCCAGCTGAGATTA (SEQ. ID. No. 492) |
| EAM253 | hmr-miR-21 8_rfam7.0 | /5AmMC6/ACATGGTTAGATCAAGCACAA (SEQ. ID. No. 493) |
| EAM275 | hmr-miR-34a_rfam7.0 | /5AmMC6/ACAACCAGCTAAGACACTGCCA (SEQ. ID. No. 494) |
| EAM246 | h-miR-21 1_rfam7.0 | /5AmMC6/AGGCGAAGGATGACAAAGGGAA (SEQ. ID. No. 495) |
| EAM250 | h-miR-21 5_rfam7.0 | /5AmMC6/GTCTGTCAATTCATAGGTCAT (SEQ. ID. No. 496) |
| EAM252 | h-miR-21 7_rfam7.0 | /5AmMC6/ATCCAATCAGTTCCTGATGCAGTA (SEQ. ID. No. 497) |
| EAM224 | hmr-miR-1 7-5p_rfam7.0 | /5AmMC6/ACTACCTGCACTGTAAGCACTTTG (SEQ. ID. No. 498) |
| EAM225 | hmr-miR-1 8a_rfam7.0 | /5AmMC6/TATCTGCACTAGATGCACCTTA (SEQ. ID. No. 499) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe. /5AmMC6/ indicates 5' amino modification.

| Probe | Annotation | Sequence |
|---|---|---|
| EAM226 | hmr-miR-181a_rfam7.0 | /5AmMC6/ACTCACCGACAGCGTTGAATGTT (SEQ. ID. No. 500) |
| EAM227 | hmr-miR-181b_rfam7.0 | /5AmMC6/AACCCACCGACAGCAATGAATGTT (SEQ. ID. No. 501) |
| EAM234 | hmr-miR-199a_rfam7.0 | /5AmMC6/GAACAGGTAGTCTGAACACTGGG (SEQ. ID. No. 502) |
| EAM235 | h-miR-199b_rfam7.0 | /5AmMC6/GAACAGATAGTCTAAACACTGGG (SEQ. ID. No. 503) |
| EAM236 | hmr-miR-19a_rfam7.0 | /5AmMC6/TCAGTTTTGCATAGATTTGCACA (SEQ. ID. No. 504) |
| EAM241 | hmr-miR-203_rfam7.0 | /5AmMC6/CTAGTGGTCCTAAACATTTCAC (SEQ. ID. No. 505) |
| EAM242 | hmr-miR-204_rfam7.0 | /5AmMC6/AGGCATAGGATGACAAAGGGAA (SEQ. ID. No. 506) |
| EAM243 | hmr-miR-205_rfam7.0 | /5AmMC6/CAGACTCCGGTGGAATGAAGGA (SEQ. ID. No. 507) |
| EAM245 | hmr-miR-210_rfam7.0 | /5AmMC6/CAGCCGCTGTCACACGCACAG (SEQ. ID. No. 508) |
| EAM249 | hmr-miR-214_rfam7.0 | /5AmMC6/CTGCCTGTCTGTGCCTGCTGT (SEQ. ID. No. 509) |
| EAM 184 | hmr-miR-100_rfam7.0 | /5AmMC6/CACAAGTTCGGATCTACGGGTT (SEQ. ID. No. 510) |
| EAM 186 | h-miR-106a_rfam7.0 | /5AmMC6/GCTACCTGCACTGTAAGCACTTTT (SEQ. ID. No. 511) |
| EAM 189 | hmr-miR-10a_rfam7.0 | /5AmMC6/CACAAATTCGGATCTACAGGGTA (SEQ. ID. No. 512) |
| EAM 191 | hmr-miR-122a_rfam7.0 | /5AmMC6/ACAAACACCATTGTCACACTCCA (SEQ. ID. No. 513) |
| EAM 192 | hmr-miR-126*_rfam7.0 | /5AmMC6/CGCGTACCAAAAGTAATAATG (SEQ. ID. No. 514) |
| EAM 198 | hmr-miR-130b_rfam7.0 | /5AmMC6/GCCCTTTCATCATTGCACTG (SEQ. ID. No. 515) |
| EAM202 | hmr-miR-134_rfam7.0 | /5AmMC6/TCCCTCTGGTCAACCAGTCACA (SEQ. ID. No. 516) |
| EAM209 | hmr-miR-142-5p_rfam7.0 | /5AmMC6/GTAGTGCTTTCTACTTTATG (SEQ. ID. No. 517) |
| EAM221 | m-miR-155_rfam7.0 | /5AmMC6/CCCCTATCACAATTAGCATTAA (SEQ. ID. No. 518) |
| EAM223 | hmr-miR-15b_rfam7.0 | /5AmMC6/TGTAAACCATGATGTGCTGCTA (SEQ. ID. No. 519) |
| EAM228 | hmr-miR-181c_rfam7.0 | /5AmMC6/ACTCACCGACAGGTTGAATGTT (SEQ. ID. No. 520) |
| EAM222 | hm-miR-15a_rfam7.0 | /5AmMC6/CACAAACCATTATGTGCTGCTA (SEQ. ID. No. 521) |
| EAM 111 | hm-let-7g_rfam7.0 | /5AmMC6/TAACTGTACAAACTACTACCTCA (SEQ. ID. No. 522) |
| EAM 131 | hmr-miR-92_rfam7.0 | /5AmMC6/ACAGGCCGGGACAAGTGCAATAT (SEQ. ID. No. 523) |
| EAM 139 | hmr-miR-146a_rfam7.0 | /5AmMC6/TAACCCATGGAATTCAGTTCTCA (SEQ. ID. No. 524) |
| EAM 145 | hmr-let-7c_rfam7.0 | /5AmMC6/AACCATACAACCTACTACCTCA (SEQ. ID. No. 525) |
| EAM 109 | hmr-miR-7_rfam7.0 | /5AmMC6/AACAACAAAATCACTAGTCTTCCA (SEQ. ID. No. 526) |
| EAM 152 | hm-miR-9*_rfam7.0 | /5AmMC6/ACTTTCGGTTATCTAGCTTTAT (SEQ. ID. No. 527) |
| JLA215 | hmr-let-7i_rfam7.0 | /5AmMC6/ACAGCACAAACTACTACCTCA (SEQ. ID. No. 528) |
| EAM 153 | hmr-let-7a_rfam7.0 | /5AmMC6/AACTATACAACCTACTACCTCA (SEQ. ID. No. 529) |
| EAM 147 | hmr-let-7b_rfam7.0 | /5AmMC6/AACCACACAACCTACTACCTCA (SEQ. ID. No. 530) |
| EAM 137 | hmr-miR-132_rfam7.0 | /5AmMC6/CCGACCATGGCTGTAGACTGTTA (SEQ. ID. No. 531) |
| EAM 133 | hmr-miR-324-5p_rfam7.0 | /5AmMC6/ACACCAATGCCCTAGGGGATGCG (SEQ. ID. No. 532) |
| EAM 103 | hmr-miR-124a_rfam7.0 | /5AmMC6/TGGCATTCACCGCGTGCCTTA (SEQ. ID. No. 533) |
| EAM 105 | hmr-miR-125b_rfam7.0 | /5AmMC6/TCACAAGTTAGGGTCTCAGGGA (SEQ. ID. No. 534) |
| EAM 121 | hmr-miR-99a_rfam7.0 | /5AmMC6/CACAAGATCGGATCTACGGGT (SEQ. ID. No. 535) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM115 | hmr-miR-1 6_rfam7.0 | /5AmMC6/CGCCAATATTTACGTGCTGCTA (SEQ. ID. No.536) |
| EAM119 | hmr-miR-29b_rfam7.0 | /5AmMC6/AACACTGATTTCAAATGGTGCTA (SEQ. ID. No. 537) |
| EAM31 1 | hmr-miR-1 01_rfam7.0 | /5AmMC6/CTTCAGTTATCACAGTACTGTA (SEQ. ID. No. 538) |
| EAM31 2 | h-miR-1 05_rfam7.0 | /5AmMC6/ACAGGAGTCTGAGCATTTGA (SEQ. ID. No. 539) |
| EAM31 3 | hmr-miR-1 06b_rfam7.0 | /5AmMC6/ATCTGCACTGTCAGCACTTTA (SEQ. ID. No. 540) |
| EAM31 4 | hmr-miR-1 26_rfam7.0 | /5AmMC6/GCATTATTACTCACGGTACGA (SEQ. ID. No. 541) |
| EAM31 5 | hmr-miR-1 27_rfam7.0 | /5AmMC6/AGCCAAGCTCAGACGGATCCGA (SEQ. ID. No. 542) |
| EAM320 | hm-miR-1 89_rfam7.0 | /5AmMC6/ACTGATATCAGCTCAGTAGGCAC (SEQ. ID. No. 543) |
| J_LA21 6 | hmr-miR-200c_rfam7.0 | /5AmMC6/TCCATCATTACCCGGCAGTATTA (SEQ. ID. No. 544 ) |
| EAM323 | h-miR-224_rfam7.0 | /5AmMC6/TAAACGGAACCACTAGTGACTTG (SEQ. ID. No. 545) |
| EAM324 | hmr-miR-25_rfam7.0 | /5AmMC6/TCAGACCGAGACAAGTGCAATG (SEQ. ID. No. 546) |
| EAM386 | r-miR-336_rfam7.0 | /5AmMC6/AGACTAGATATGGAAGGGTGA (SEQ. ID. No. 547) |
| J_LA21 8 | r-miR-343_rfam7.0 | /5AmMC6/TCTGGGCACACGGAGGGAGA (SEQ. ID. No. 548) |
| EAM388 | r-miR-344_rfam7.0 | /5AmMC6/ACGGTCAGGCTTTGGCTAGAT (SEQ. ID. No. 549) |
| EAM338 | h-miR-95_rfam7.0 | /5AmMC6/TGCTCAATAAATACCCGTTGAA (SEQ. ID. No. 550) |
| J_LA21 4 | hmr-miR-1 29_rfam7.0 | /5AmMC6/AGCAAGCCCAGACCGCAAAAAG (SEQ. ID. No. 551) |
| EAM340 | mr-let-7d*_rfam7.0 | /5AmMC6/AGAAAGGCAGCAGGTCGTATAG (SEQ. ID. No. 552) |
| EAM341 | m-miR-1 06a_rfam7.0 | /5AmMC6/TACCTGCACTGTTAGCACTTTG (SEQ. ID. No. 553) |
| EAM342 | hmr-miR-1 35b_rfam7.0 | /5AmMC6/CACATAGGAATGAAAAGCCATA (SEQ. ID. No. 554) |
| EAM343 | mr-mi R-1 51_rfam7.0 | /5AmMC6/CCTCAAGGAGCCTCAGTCTAGT (SEQ. ID. No. 555) |
| EAM344 | m-miR-1 7-3p_rfam7.0 | /5AmMC6/ACAAGTGCCCTCACTGCAGT (SEQ. ID. No. 556) |
| EAM345 | m-miR-224_rfam7.0 | /5AmMC6/TAAACGGAACCACTAGTGACTTA (SEQ. ID. No. 557) |
| EAM346 | mr-mi R-290_rfam7.0 | /5AmMC6/AAAAAGTGCCCCCATAGTTTGAG (SEQ. ID. No. 558) |
| EAM347 | mr-miR-291-3p_rfam7.0 | /5AmMC6/GGCACACAAAGTGGAAGCACTTT (SEQ. ID. No. 559) |
| EAM348 | mr-miR-291-5p_rfam7.0 | /5AmMC6/AGAGAGGGCCTCCACTTTGATG (SEQ. ID. No. 560) |
| EAM349 | mr-miR-292-3p_rfam7.0 | /5AmMC6/ACACTCAAAACCTGGCGGCACTT (SEQ. ID. No. 561) |
| EAM350 | mr-miR-292-5p_rfam7.0 | /5AmMC6/CAAAAGAGCCCCCAGTTTGAGT (SEQ. ID. No. 562) |
| EAM351 | m-miR-293_rfam7.0 | /5AmMC6/ACACTACAAACTCTGCGGCACT (SEQ. ID. No. 563) |
| EAM352 | m-miR-294_rfam7.0 | /5AmMC6/ACACACAAAAGGGAAGCACTTT (SEQ. ID. No. 564) |
| EAM353 | m-miR-295_rfam7.0 | /5AmMC6/AGACTCAAAAGTAGTAGCACTTT (SEQ. ID. No. 565) |
| EAM354 | m-miR-297_rfam7.0 | /5AmMC6/CATGCACATGCACACATACAT (SEQ. ID. No. 566) |
| EAM355 | mr-mi R-298_rfam7.0 | /5AmMC6/GGAAGAACAGCCCTCCTCTGCC (SEQ. ID. No. 567) |
| EAM356 | mr-mi R-300_rfam7.0 | /5AmMC6/GAAGAGAGCTTGCCCTTGCATA (SEQ. ID. No. 568) |
| EAM358 | hmr-miR-323_rfam7.0 | /5AmMC6/AGAGGTCGACCGTGTAATGTGC (SEQ. ID. No. 569) |
| EAM359 | hmr-miR-324-3p_rfam7.0 | /5AmMC6/CCAGCAGCACCTGGGGCAGT (SEQ. ID. No. 570) |
| EAM360 | mr-miR-325_rfam7.0 | /5AmMC6/ACACTTACTGAGCACCTACTAGG (SEQ. ID. No. 571) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM361 | hmr-miR-326_rfam7.0 | /5AmMC6/ACTGGAGGAAGGGCCCAGAGG (SEQ. ID. No. 572) |
| EAM362 | hmr-miR-328_rfam7.0 | /5AmMC6/ACGGAAGGGCAGAGAGGGCCAG (SEQ. ID. No. 573) |
| EAM363 | mr-miR-329_rfam7.0 | /5AmMC6/AAAAAGGTTAGCTGGGTGTGTT (SEQ. ID. No. 574) |
| EAM365 | hmr-miR-331_rfam7.0 | /5AmMC6/TTCTAGGATAGGCCCAGGGGC (SEQ. ID. No. 575) |
| EAM366 | mr-miR-337_rfam7.0 | /5AmMC6/AAAGGCATCATATAGGAGCTGAA (SEQ. ID. No. 576) |
| EAM367 | hmr-miR-338_rfam7.0 | /5AmMC6/TCAACAAAATCACTGATGCTGGA (SEQ. ID. No. 577) |
| EAM368 | hmr-miR-339_rfam7.0 | /5AmMC6/TGAGCTCCTGGAGGACAGGGA (SEQ. ID. No. 578) |
| EAM369 | hmr-miR-340_rfam7.0 | /5AmMC6/GGCTATAAAGTAACTGAGACGGA (SEQ. ID. No. 579) |
| EAM370 | mr-miR-341_rfam7.0 | /5AmMC6/ACTGACCGACCGACCGATCGA (SEQ. ID. No. 580) |
| EAM371 | hmr-miR-342_rfam7.0 | /5AmMC6/GACGGGTGCGATTTCTGTGTGAGA (SEQ. ID. No. 581) |
| EAM372 | m-miR-344_rfam7.0 | /5AmMC6/ACAGTCAGGCTTTGGCTAGATCA (SEQ. ID. No. 582) |
| EAM373 | mr-miR-345_rfam7.0 | /5AmMC6/GCACTGGACTAGGGGTCAGCA (SEQ. ID. No. 583) |
| EAM374 | m-miR-346_rfam7.0 | /5AmMC6/AGAGGCAGGCACTCGGGCAGA (SEQ. ID. No. 584) |
| EAM375 | mr-miR-34b_rfam7.0 | /5AmMC6/CAATCAGCTAATTACACTGCCTA (SEQ. ID. No.585) |
| JLA217 | mr-miR-350_rfam7.0 | /5AmMC6/GTGAAAGTGTATGGGCTTTGTGAA (SEQ. ID. No.586) |
| EAM377 | mr-miR-351_rfam7.0 | /5AmMC6/CAGGCTCAAAGGGCTCCTCAGG (SEQ. ID. No. 587) |
| EAM378 | mr-miR-7b_rfam7.0 | /5AmMC6/AACAAAATCACAAGTCTTCCA (SEQ. ID. No. 588) |
| EAM382 | r-miR-20*_rfam7.0 | /5AmMC6/TGTAAGTGCTCGTAATGCAGT (SEQ. ID. No. 589) |
| EAM383 | r-miR-327_rfam7.0 | /5AmMC6/ACCCTCATGCCCCTCAAGG (SEQ. ID. No. 590) |
| EAM384 | r-miR-333_rfam7.0 | /5AmMC6/AAAAGTAACTAGCACACCAC (SEQ. ID. No. 591) |
| EAM385 | hmr-miR-335_rfam7.0 | /5AmMC6/ACATTTTTCGTTATTGCTCTT (SEQ. ID. No. 592) |
| EAM393 | r-miR-7*_rfam7.0 | /5AmMC6/TATGGCAGACTGTGATTTGTTG (SEQ. ID. No. 593) |
| EAM304 | hmr-miR-200a_rfam7.0 | /5AmMC6/CATCGTTACCAGACAGTGTTA (SEQ. ID. No. 594) |
| EAM298 | hmr-miR-194_rfam7.0 | /5AmMC6/TCCACATGGAGTTGCTGTTACA (SEQ. ID. No. 595) |
| JLA221 | hmr-miR-191_rfam7.0 | /5AmMC6/AACAGCTGCTTTTGGGATTCTG (SEQ. ID. No. 596) |
| EAM295 | hmr-miR-190_rfam7.0 | /5AmMC6/ACCTAATATATCAAACATATCA (SEQ. ID. No. 597) |
| EAM292 | hmr-miR-186_rfam7.0 | /5AmMC6/AAGCCCAAAAGGAGAATTCTTTG (SEQ. ID. No. 598) |
| JLA219 | hmr-miR-185_rfam7.0 | /5AmMC6/AGGAACTGCCTTTCTCTCCAA (SEQ. ID. No. 599) |
| EAM290 | hmr-miR-184_rfam7.0 | /5AmMC6/ACCCTTATCAGTTCTCCGTCCA (SEQ. ID. No. 600) |
| EAM402 | hm-miR-133b_rfam7.0 | /5AmMC6/TAGCTGGTTGAAGGGGACCAA (SEQ. ID. No. 601) |
| EAM403 | h-miR-151_rfam7.0 | /5AmMC6/CCTCAAGGAGCTTCAGTCTAGT (SEQ. ID. No. 602) |
| EAM404 | hmr-miR-196b_rfam7.0 | /5AmMC6/CCAACAACAGGAAACTACCTA (SEQ. ID. No. 603) |
| EAM418 | hm-miR-370_rfam7.0 | /5AmMC6/CCAGGTTCCACCCCAGCAGG (SEQ. ID. No. 604) |
| EAM419 | h-miR-371_rfam7.0 | /5AmMC6/ACACTCAAAAGATGGCGGCA (SEQ. ID. No. 605) |
| EAM420 | h-miR-372_rfam7.0 | /5AmMC6/ACGCTCAAATGTCGCAGCAC (SEQ. ID. No. 606) |
| EAM421 | h-miR-373_rfam7.0 | /5AmMC6/ACACCCCAAAATCGAAGCAC (SEQ. ID. No. 607) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM422 | h-miR-373*_rfam7.0 | /5AmMC6/GGAAAGCGCCCCCATTTTGA (SEQ. ID. No. 608) |
| EAM423 | h-miR-374_rfam7.0 | /5AmMC6/CACTTATCAGGTTGTATTATAA (SEQ. ID. No. 609) |
| EAM426 | m-miR-21 5_rfam7.0 | /5AmMC6/GTCTGTCAAATCATAGGTCAT (SEQ. ID. No. 610) |
| EAM427 | hm-miR-409-3p_rfam7.0 | /5AmMC6/GGGGTTCACCGAGCAACATTC (SEQ. ID. No. 611) |
| EAM428 | hm-miR-41 0_rfam7.0 | /5AmMC6/CAGGCCATCTGTGTTATATT (SEQ. ID. No. 612) |
| EAM429 | m-miR-376b_rfam7.0 | /5AmMC6/AGTGGATGTTCCTCTATGAT (SEQ. ID. No. 613) |
| EAM430 | m-miR-376a_rfam7.0 | /5AmMC6/CGTGGATTTTCCTCTACGAT (SEQ. ID. No. 614) |
| EAM431 | m-miR-41 1_rfam7.0 | /5AmMC6/GAGGGTTAGTGGACCGTGTT (SEQ. ID. No. 615) |
| EAM432 | m-miR-380-3p_rfam7.0 | /5AmMC6/GATGTGGACCATACTACATA (SEQ. ID. No. 616) |
| EAM433 | hm-miR-41 2_rfam7.0 | /5AmMC6/GGCTAGTGGACCAGGTGAAG (SEQ. ID. No. 617) |
| EAM264 | hmr-miR-27b_rfam7.0 | /5AmMC6/CAGAACTTAGCCACTGTGAA (SEQ. ID. No. 618) |
| EAM263 | hmr-miR-26a_rfam7.0 | /5AmMC6/AGCCTATCCTGGATTACTTGAA (SEQ. ID. No. 619) |
| EAM262 | h mr-miR-24_rfam7.0 | /5AmMC6/CTGTTCCTGCTGAACTGAGCCA (SEQ. ID. No. 620) |
| EAM261 | hmr-miR-23b_rfam7.0 | /5AmMC6/GTGGTAATCCCTGGCAATGTGAT (SEQ. ID. No. 621) |
| EAM260 | hmr-miR-23a_rfam7.0 | /5AmMC6/GGAAATCCCTGGCAATGTGAT (SEQ. ID. No. 622) |
| EAM256 | h-miR-220_rfam7.0 | /5AmMC6/AAAGTGTCAGATACGGTGTGG (SEQ. ID. No. 623) |
| EAM255 | h mr-miR-22_rfam7.0 | /5AmMC6/ACAGTTCTTCAACTGGCAGCTT (SEQ. ID. No. 624) |
| EAM248 | hmr-miR-21 3_rfam7.0 | /5AmMC6/GGTACAATCAACGGTCGATGGT (SEQ. ID. No. 625) |
| EAM244 | hmr-miR-21_rfam7.0 | /5AmMC6/TCAACATCAGTCTGATAAGCTA (SEQ. ID. No. 626) |
| EAM240 | h mr-miR-20a_rfam7.0 | /5AmMC6/CTACCTGCACTATAAGCACTTTA (SEQ. ID. No. 627) |
| EAM237 | hmr-miR-1 9b_rfam7.0 | /5AmMC6/TCAGTTTTGCATGGATTTGCACA (SEQ. ID. No. 628) |
| EAM233 | hmr-miR-1 96a_rfam7.0 | /5AmMC6/CCCAACAACATGAAACTACCTA (SEQ. ID. No. 629) |
| EAM21 4 | hm-miR-1 48a_rfam7.0 | /5AmMC6/ACAAAGTTCTGTAGTGCACTGA (SEQ. ID. No. 630) |
| EAM21 2 | hmr-miR-1 45_rfam7.0 | /5AmMC6/AAGGGATTCCTGGGAAAACTGGAC (SEQ. ID. No. 631) |
| EAM21 1 | hmr-miR-1 44_rfam7.0 | /5AmMC6/CTAGTACATCATCTATACTGTA (SEQ. ID. No. 632) |
| EAM21 0 | hmr-miR-1 43_rfam7.0 | /5AmMC6/tgAGCTACAGTGCTTCATCTCA (SEQ. ID. No. 633) |
| EAM389 | r-miR-346_rfam7.0 | /5AmMC6/AGAGGCAGGCACTCAGGCAGA (SEQ. ID. No. 634) |
| EAM390 | r-miR-347_rfam7.0 | /5AmMC6/TGGGCGACCCAGAGGGACA (SEQ. ID. No. 635) |
| EAM391 | r-miR-349_rfam7.0 | /5AmMC6/AGAGGTTAAGACAGCAGGGCTG (SEQ. ID. No. 636) |
| J LA223 | h mr-miR-33_rfam7.0 | /5AmMC6/TGCAATGCAACTACAATGCACC (SEQ. ID. No. 637) |
| EAM277 | h mr-miR-96_rfam7.0 | /5AmMC6/GCAAAAATGTGCTAGTGCCAAA (SEQ. ID. No. 638) |
| EAM276 | h mr-miR-9_rfam7.0 | /5AmMC6/TCATACAGCTAGATAACCAAAGA (SEQ. ID. No. 639) |
| EAM272 | hmr-miR-30d_rfam7.0 | /5AmMC6/CTTCCAGTCGGGGATGTTTACA (SEQ. ID. No. 640) |
| EAM288 | mr-miR-1 0b_rfam7.0 | /5AmMC6/ACACAAATTCGGTTCTACAGGG (SEQ. ID. No. 641) |
| EAM293 | hm-miR-1 88_rfam7.0 | /5AmMC6/ACCCTCCACCATGCAAGGGATG (SEQ. ID. No. 642) |
| EAM297 | hmr-miR-1 93a_rfam7.0 | /5AmMC6/CTGGGACTTTGTAGGCCAGTT (SEQ. ID. No. 643) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM301 | h-miR-198_rfam7.0 | /5AmMC6/CCTATCTCCCCTCTGGACC (SEQ. ID. No. 644) |
| EAM232 | hmr-miR-192_rfam7.0 | /5AmMC6/GGCTGTCAATTCATAGGTCAG (SEQ. ID. No. 645) |
| EAM231 | hmr-miR-187_rfam7.0 | /5AmMC6/CGGCTGCAACACAAGACACGA (SEQ. ID. No. 646) |
| EAM230 | hmr-miR-183_rfam7.0 | /5AmMC6/CAGTGAATTCTACCAGTGCCATA (SEQ. ID. No. 647) |
| EAM229 | hm-miR-182_rfam7.0 | /5AmMC6/TGTGAGTTCTACCATTGCCAAA (SEQ. ID. No. 648) |
| EAM220 | hmr-miR-154_rfam7.0 | /5AmMC6/CGAAGGCAACACGGATAACCTA (SEQ. ID. No. 649) |
| EAM219 | hmr-miR-153_rfam7.0 | /5AmMC6/TCACTTTTGTGACTATGCAA (SEQ. ID. No. 650) |
| EAM218 | hmr-miR-152_rfam7.0 | /5AmMC6/CCAAGTTCTGTCATGCACTGA (SEQ. ID. No. 651) |
| EAM217 | hmr-miR-150_rfam7.0 | /5AmMC6/ACACTGGTACAAGGGTTGGGAGA (SEQ. ID. No. 652) |
| EAM216 | hm-miR-149_rfam7.0 | /5AmMC6/GGAGTGAAGACACGGAGCCAGA (SEQ. ID. No. 653) |
| EAM215 | hmr-miR-148b_rfam7.0 | /5AmMC6/ACAAAGTTCTGTGATGCACTGA (SEQ. ID. No. 654) |
| EAM271 | hmr-miR-30c_rfam7.0 | /5AmMC6/GCTGAGAGTGTAGGATGTTTACA (SEQ. ID. No. 655) |
| EAM268 | hmr-miR-29a_rfam7.0 | /5AmMC6/AACCGATTTCAGATGGTGCTAG (SEQ. ID. No. 656) |
| EAM305 | hmr-miR-200b_rfam7.0 | /5AmMC6/GTCATCATTACCAGGCAGTATTA (SEQ. ID. No. 657) |
| EAM303 | hm-miR-199a*_rfam7.0 | /5AmMC6/AACCAATGTGCAGACTACTGTA (SEQ. ID. No. 658) |
| EAM300 | h-miR-197_rfam7.0 | /5AmMC6/GCTGGGTGGAGAAGGTGGTGAA (SEQ. ID. No. 659) |
| EAM299 | hmr-miR-195_rfam7.0 | /5AmMC6/GCCAATATTTCTGTGCTGCTA (SEQ. ID. No. 660) |
| JLA91 | hmr-miR-99b_rfam7.0 | /5AmMC6/CGCAAGGTCGGTTCTACGGGTG (SEQ. ID. No. 661) |
| JLA92 | hmr-miR-433_rfam7.0 | /5AmMC6/ACACCGAGGAGCCCATCATGAT (SEQ. ID. No. 662) |
| JLA93 | hmr-miR-431_rfam7.0 | /5AmMC6/CCTGCATGACGGCCTGCAAGACA (SEQ. ID. No. 663) |
| JLA94 | hmr-miR-365_rfam7.0 | /5AmMC6/ATAAGGATTTTTAGGGGCATTA (SEQ. ID. No. 664) |
| JLA95 | hmr-miR-450_rfam7.0 | /5AmMC6/TATTAGGAACACATCGCAAAAA (SEQ. ID. No. 665) |
| JLA96 | hmr-miR-449_rfam7.0 | /5AmMC6/ACCAGCTAACAATACACTGCCA (SEQ. ID. No. 666) |
| JLA99 | hmr-miR-448_rfam7.0 | /5AmMC6/ATGGGACATCCTACATATGCAA (SEQ. ID. No. 667) |
| JLA103 | hmr-miR-424_rfam7.0 | /5AmMC6/TTCAAAACATGAATTGCTGCTG (SEQ. ID. No. 668) |
| JLA105 | hm-miR-361_rfam7.0 | /5AmMC6/GTACCCCTGGAGATTCTGATAA (SEQ. ID. No. 669) |
| JLA106 | hm-miR-375_rfam7.0 | /5AmMC6/TCACGCGAGCCGAACGAACAAA (SEQ. ID. No. 670) |
| JLA107 | hm-miR-377_rfam7.0 | /5AmMC6/ACAAAAGTTGCCTTTGTGTGAT (SEQ. ID. No. 671) |
| JLA108 | hm-miR-378_rfam7.0 | /5AmMC6/ACACAGGACCTGGAGTCAGGAG (SEQ. ID. No. 672) |
| JLA109 | hm-miR-379_rfam7.0 | /5AmMC6/CCTACGTTCCATAGTCTACCA (SEQ. ID. No. 673) |
| JLA110 | hm-miR-380-5p_rfam7.0 | /5AmMC6/GCGCATGTTCTATGGTCAACCA (SEQ. ID. No. 674) |
| JLA111 | hm-miR-381_rfam7.0 | /5AmMC6/ACAGAGAGCTTGCCCTTGTATA (SEQ. ID. No. 675) |
| JLA112 | hm-miR-382_rfam7.0 | /5AmMC6/CGAATCCACCACGAACAACTTC (SEQ. ID. No. 676) |
| JLA115 | hm-miR-384_rfam7.0 | /5AmMC6/TATGAACAATTTCTAGGAAT (SEQ. ID. No. 677) |
| JLA116 | hm-miR-425_rfam7.0 | /5AmMC6/GGCGGACACGACATTCCCGAT (SEQ. ID. No. 678) |
| JLA117 | hm-miR-452_rfam7.0 | /5AmMC6/GTCTCAGTTTCCTCTGCAAACA (SEQ. ID. No. 679) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| J_LA1_18 | hm-miR-30e-3p_rfam7.0 | /5AmMC6/GCTGTAAACATCCGACTGAAAG (SEQ. ID. No. 680) |
| J_LA1_04 | mr-miR-129-3p_rfam7.0 | /5AmMC6/ATGCTTTTTGGGGTAAGGGCTT (SEQ. ID. No. 681) |
| J_LA98 | mr-miR-429_rfam7.0 | /5AmMC6/ACGGCATTACCAGACAGTATTA (SEQ. ID. No. 682) |
| J_LA101 | mr-miR-330_rfam7.0 | /5AmMC6/TCTCTGCAGGCCCTGTGCTTTGC (SEQ. ID. No. 683) |
| J_LA102 | mr-miR-322_rfam7.0 | /5AmMC6/TGTTGCAGCGCTTCATGTTT (SEQ. ID. No. 684) |
| J_LA1_14 | m-miR-383_rfam7.0 | /5AmMC6/AGCCACAGTCACCTTCTGATCT (SEQ. ID. No. 685) |
| J_LA5 | hmr-miR-451 | /5AmMC6/AAACTCAGTAATGGTAACGGTTT (SEQ. ID. No. 686) |
| J_LA20_1 | r-miR-421_rfam7.0 | /5AmMC6/CAACAAACATTTAATGAGGCC (SEQ. ID. No. 687) |
| J_LA202 | m-miR-463_rfam7.0 | /5AmMC6/TGATGGACAACAAATTAGGTA (SEQ. ID. No. 688) |
| J_LA203 | m-miR-464_rfam7.0 | /5AmMC6/TATCTCACAGAATAAACTTGGTA (SEQ. ID. No. 689) |
| J_LA204 | m-miR-465_rfam7.0 | /5AmMC6/TCACATCAGTGCCATTCTAAATA (SEQ. ID. No. 690) |
| J_LA205 | m-miR-466_rfam7.0 | /5AmMC6/GTCTTATGTGTGCGTGTATGTAT (SEQ. ID. No. 691) |
| J_LA206 | m-miR-467_rfam7.0 | /5AmMC6/GTGTAGGTGTGTGTATGTATAT (SEQ. ID. No. 692) |
| J_LA207 | m-miR-468_rfam7.0 | /5AmMC6/CAGACACACGCACATCAGTCATA (SEQ. ID. No. 693) |
| J_LA208 | m-miR-469_rfam7.0 | /5AmMC6/GGACACCAAGATCAATGAAAGAGGCA (SEQ. ID. No. 694) |
| J_LA209 | m-miR-470_rfam7.0 | /5AmMC6/TCACCAGTGCCAGTCCAAGAA (SEQ. ID. No. 695) |
| J_LA210 | m-miR-471_rfam7.0 | /5AmMC6/TGTGAAAAGCACTATACTACGTA (SEQ. ID. No. 696) |
| EAM325 | hmr-miR-27a_rfam7.0 | /5AmMC6/GGCGGAACTTAGCCACTGTGAA (SEQ. ID. No. 697) |
| EAM326 | hmr-miR-296_rfam7.0 | /5AmMC6/ACAGGATTGAGGGGGGGCCCT (SEQ. ID. No. 698) |
| EAM327 | hmr-miR-299-5p_rfam7.0 | /5AmMC6/ATGTATGTGGGACGGTAAACCA (SEQ. ID. No. 699) |
| EAM328 | hmr-miR-301_rfam7.0 | /5AmMC6/GCTTTGACAATACTATTGCACTG (SEQ. ID. No. 700) |
| EAM329 | hm-miR-302a_rfam7.0 | /5AmMC6/TCACCAAAACATGGAAGCACTTA (SEQ. ID. No. 701) |
| EAM330 | hmr-miR-30a-5p_rfam7.0 | /5AmMC6/GCTTCCAGTCGAGGATGTTTACA (SEQ. ID. No. 702) |
| EAM331 | hmr-miR-30e-5p_rfam7.0 | /5AmMC6/TCCAGTCAAGGATGTTTACA (SEQ. ID. No. 703) |
| EAM332 | hmr-miR-31_rfam7.0 | /5AmMC6/CAGCTATGCCAGCATCTTGCCT (SEQ. ID. No. 704) |
| EAM333 | hmr-miR-32_rfam7.0 | /5AmMC6/GCAACTTAGTAATGTGCAATA (SEQ. ID. No. 705) |
| EAM335 | h-miR-34b_rfam7.0 | /5AmMC6/CAATCAGCTAATGACACTGCCT (SEQ. ID. No. 706) |
| EAM336 | hmr-miR-34c_rfam7.0 | /5AmMC6/GCAATCAGCTAACTACACTGCCT (SEQ. ID. No. 707) |
| EAM337 | hmr-miR-93_rfam7.0 | /5AmMC6/CTACCTGCACGAACAGCACTTTG (SEQ. ID. No. 708) |
| EAM208 | hmr-miR-141_rfam7.0 | /5AmMC6/CCATCTTTACCAGACAGTGTT (SEQ. ID. No. 709) |
| EAM207 | hmr-miR-140_rfam7.0 | /5AmMC6/CTACCATAGGGTAAAACCACT (SEQ. ID. No. 710) |
| J_LA222 | hmr-miR-139_rfam7.0 | /5AmMC6/TGGAGACACGTGCACTGTAGA (SEQ. ID. No. 711) |
| J_LA220 | hmr-miR-138_rfam7.0 | /5AmMC6/CCTGATTCACAACACCAGCTG (SEQ. ID. No. 712) |
| EAM203 | hmr-miR-135a_rfam7.0 | /5AmMC6/TTCACATAGGAATAAAAAGCCATA (SEQ. ID. No. 713) |
| EAM200 | hmr-miR-133a_rfam7.0 | /5AmMC6/ACAGCTGGTTGAAGGGGACCAA (SEQ. ID. No. 714) |
| EAM195 | hmr-miR-128b_rfam7.0 | /5AmMC6/GAAAGAGACCGGTTCACTGTGA (SEQ. ID. No. 715) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| EAM 194 | hmr-miR-1 28a_rfam7.0 | /5AmMC6/AAAAGAGACCGGTTCACTGTGA (SEQ. ID. No. 716) |
| EAM254 | hmr-miR-21 9_rfam7.0 | /5AmMC6/AGAATTGCGTTTGGACAATCA (SEQ. ID. No. 717) |
| EAM257 | hmr-miR-221_rfam7.0 | /5AmMC6/GAAACCCAGCAGACAATGTAGCT (SEQ. ID. No. 718) |
| EAM258 | hmr-miR-222_rfam7.0 | /5AmMC6/GAGACCCAGTAGCCAGATGTAGCT (SEQ. ID. No. 719) |
| EAM259 | hmr-miR-223_rfam7.0 | /5AmMC6/GGGGTATTTGACAAACTGACA (SEQ. ID. No. 720) |
| JLA21 1 | m-miR-434-5p_rfam7.0 | /5AmMC6/GGTTCAAACCATGAGTCGAGCT (SEQ. ID. No. 721) |
| JLA21 2 | m-miR-434-3p_rfam7.0 | /5AmMC6/GGAGTCGAGTGATGGTTCAAA (SEQ. ID. No. 722) |
| JLA21 3 | m-miR-433-5p_rfam7.0 | /5AmMC6/GAATAATGACAGGCTCACCGTA (SEQ. ID. No. 723) |
| JLA2 | hsa-miR-522 | /5AmMC6/ACACTCTAAAGGGAACCATTTT (SEQ. ID. No. 724) |
| JLA3 | hsa-miR-495 | /5AmMC6/AAAGAAGTGCACCATGTTTGTTT (SEQ. ID. No. 725) |
| JLA200 | r-miR-297_rfam7.0 | /5AmMC6/CATGCATACATGCACACATACAT (SEQ. ID. No. 726) |
| JLA6 | hsa-miR-51 8e | /5AmMC6/AACACTCTGAAGGGAAGCGC (SEQ. ID. No. 727) |
| JLA7 | hsa-miR-5 1 9a | /5AmMC6/CACTCTAAAAGGATGCACTTT (SEQ. ID. No. 728) |
| JLA8 | hsa-mir-527* | /5AmMC6/TTCACCAAAGGGAAGCACTTT (SEQ. ID. No. 729) |
| JLA72 | hmr-miR-1 40*_rfam7.0 | /5AmMC6/GTCCGTGGTTCTACCCTGTGG (SEQ. ID. No. 730) |
| JLA1 0 | hsa-miR-521 | /5AmMC6/ACACTCTAAAGGGAAGTGCGTT (SEQ. ID. No. 731) |
| JLA1 2 | hsa-miR-362 | /5AmMC6/CTCACACCTAGGTTCCAAGGATT (SEQ. ID. No. 732) |
| JLA74 | hsa-mir-1 8* | /5AmMC6/CCAGAAGGAGCACTTAGGGCAG (SEQ. ID. No. 733) |
| JLA1 4 | hm-miR-363 | /5AmMC6/TTACAGATGGATACCGTGCAATT (SEQ. ID. No. 734) |
| JLA77 | hsa-mir-1 9b-1 * | /5AmMC6/GCTGGATGCAAACCTGCAAAAC (SEQ. ID. No. 735) |
| JLA1 7 | hsa-mir-520c, b, f | /5AmMC6/CCTCTAAAAGGAAGCACTTTCT (SEQ. ID. No. 736) |
| JLA79 | hsa-mir-23a* | /5AmMC6/AATCCCATCCCCAGGAACCC (SEQ. ID. No. 737) |
| JLA20 | hsa-miR-369-5p | /5AmMC6/CGAATATAACACGGTCGATCT (SEQ. ID. No. 738) |
| JLA81 | hsa-mir-339* | /5AmMC6/CGGCTCTGTCGTCGAGGCGC (SEQ. ID. No. 739) |
| JLA23 | hsa-mir-342* | /5AmMC6/TCAATCACAGATAGCACCCCT (SEQ. ID. No. 740) |
| JLA24 | hsa-mir-1 9a* | /5AmMC6/GTAGTGCAACTATGCAAAACT (SEQ. ID. No. 741) |
| JLA26 | hsa-miR-51 7a, b | /5AmMC6/ACACTCTAAAGGGATGCACGAT (SEQ. ID. No. 742) |
| JLA27 | hsa-miR-51 6-5p | /5AmMC6/AAAGTGCTTCTTACCTCCAGAT (SEQ. ID. No. 743) |
| JLA28 | hsa-miR-51 8b | /5AmMC6/ACCTCTAAAGGGGAGCGCTT (SEQ. ID. No. 744) |
| JLA29 | hsa-miR-51 9d | /5AmMC6/ACACTCTAAAGGGAGGCACTTT (SEQ. ID. No. 745) |
| JLA73 | hr-mir-1 51 * | /5AmMC6/ATACTAGACTGTGAGCTCCTCGA (SEQ. ID. No. 746) |
| JLA31 | hsa-mir-28* | /5AmMC6/TCCAGGAGCTCACAATCTAGTG (SEQ. ID. No. 747) |
| JLA33 | hsa-mir-51 9a-2* | /5AmMC6/AGAAAGCGCTTCCCTGTAGAG (SEQ. ID. No. 748) |
| JLA34 | hsa-mir-26b* | /5AmMC6/AGCCAAGTAATGGAGAACAGG (SEQ. ID. No. 749) |
| JLA35 | hsa-miR-526c | /5AmMC6/AGAAAGCGCTTCCCTCTAGAG (SEQ. ID. No. 750) |
| JLA36 | hsa-miR-527 | /5AmMC6/ACAGAAAGGGCTTCCCTTTGC (SEQ. ID. No. 751) |

TABLE 5-continued miRNA detection probes
ProbeID: Unique identifier for each probe sequence.
Annotation: miRNAs recognized by the probe, based on miRBASE release 7.0. "h" stands for human, "m" for mouse and "r" for rat.
Sequence: sequence of probe./5AmMC6/indicates 5' amino modification.

| Probe | Annotation | Sequence |
|---|---|---|
| JLA38 | hsa-mir-29b-2* | /5AmMC6/TCTAAGCCACCATGTGAAACCA (SEQ. ID. No. 752) |
| JLA39 | hsa-let-7g* | /5AmMC6/GCAAGGCAGTGGCCTGTACA (SEQ. ID. No. 753) |
| JLA40 | hsa-miR-518a | /5AmMC6/TCCAGCAAAGGGAAGCGCTT (SEQ. ID. No. 754) |
| JLA41 | hsa-miR-523 | /5AmMC6/ACCCTCTATAGGGAAGCGCGT (SEQ. ID. No. 755) |
| JLA44 | hsa-miR-515-3p | /5AmMC6/AACGCTCCAAAAGAAGGCACT (SEQ. ID. No. 756) |
| JLA45 | hsa-mir-146b* | /5AmMC6/ACCAGAACTGAGTCCACAGGG (SEQ. ID. No. 757) |
| JLA49 | hsa-mir-222* | /5AmMC6/ATCTACACTGGCTACTGAGCC (SEQ. ID. No. 758) |
| JLA53 | hsa-mir-24* | /5AmMC6/ACTGTGTTTCAGCTCAGTAGGCA (SEQ. ID. No. 759) |
| JLA55 | hsa-miR-503 | /5AmMC6/ACTGCAGAACTGTTCCCGCTG (SEQ. ID. No. 760) |
| JLA57 | hsa-mir-505 | /5AmMC6/AGAGGAAACCAGCAAGTGTTGA (SEQ. ID. No. 761) |
| JLA82 | hsa-mir-423* | /5AmMC6/AAAGTCTCGCTCTCTGCCCCT (SEQ. ID. No. 762) |
| JLA66 | hsa-miR-432 | /5AmMC6/CCACCCAATGACCTACTCCAAG (SEQ. ID. No. 763) |
| JLA83 | hsa-mir-425* | /5AmMC6/TCAACGGGAGTGATCGTGTCAT (SEQ. ID. No. 764) |
| JLA84 | hsa-mir-92-1 * | /5AmMC6/AGCATTGCAACCGATCCCAAC (SEQ. ID. No. 765) |
| JLA69 | hsa-mir-193* | /5AmMC6/TCATCTCGCCCGCAAAGACC (SEQ. ID. No. 766) |
| JLA70 | hsa-miR-515-5p | /5AmMC6/AGAAAGTGCTTTCTTTTGGAGAA (SEQ. ID. No. 767) |
| JLA71 | hsa-mir-516-1 * | /5AmMC6/GAAAGTGCTTCTTTCCTCGAGAA (SEQ. ID. No. 768) |
| JLA85 | hsa-mir-30d* | /5AmMC6/GCAGCAAACATCTGACTGAAAG (SEQ. ID. No. 769) |
| JLA125 | h-miR-20b_rfam7.0 | /5AmMC6/CTACCTGCACTATGAGCACTTTG (SEQ. ID. No. 770) |
| JLA198 | h-miR-191 *_rfam7.0 | /5AmMC6/GGGGACGAAATCCAAGCGCAGC (SEQ. ID. No. 771) |
| JLA199 | h-miR-154*_rfam7.0 | /5AmMC6/AATAGGTCAACCGTGTATGATT (SEQ. ID. No. 772) |
| EAM316 | h-miR-147_rfam7.0 | /5AmMC6/GCAGAAGCATTTCCACACAC (SEQ. ID. No. 773) |
| EAM317 | h-miR-155_rfam7.0 | /5AmMC6/CCCCTATCACGATTAGCATTAA (SEQ. ID. No. 774) |
| EAM318 | h-miR-17-3p_rfam7.0 | /5AmMC6/ACAAGTGCCTTCACTGCAGT (SEQ. ID. No. 775) |
| JLA195 | h-miR-200a*_rfam7.0 | /5AmMC6/TCCAGCACTGTCCGGTAAGATG (SEQ. ID. No. 776) |
| JLA196 | h-miR-302a*_rfam7.0 | /5AmMC6/AAAGCAAGTACATCCACGTTTA (SEQ. ID. No. 777) |
| JLA197 | h-miR-299-3p_rfam7.0 | /5AmMC6/AAGCGGTTTACCATCCCACATA (SEQ. ID. No. 778) |
| EAM319 | h-miR-182*_rfam7.0 | /5AmMC6/TAGTTGGCAAGTCTAGAACCA (SEQ. ID. No. 779) |
| EAM405 | h-miR-302b_rfam7.0 | /5AmMC6/CTACTAAAACATGGAAGCACTTA (SEQ. ID. No. 780) |
| EAM406 | h-miR-302b*_rfam7.0 | /5AmMC6/AGAAAGCACTTCCATGTTAAAGT (SEQ. ID. No. 781) |
| EAM392 | r-miR-352_rfam7.0 | /5AmMC6/TACTATGCAACCTACTACTCT (SEQ. ID. No. 782) |
| JLA123 | h-miR-423_rfam7.0 | /5AmMC6/CTGAGGGGCCTCAGACCGAGCT (SEQ. ID. No. 783) |
| JLA124 | h-miR-18b_rfam7.0 | /5AmMC6/TAACTGCACTAGATGCACCTTA (SEQ. ID. No. 784) |

TABLE 6

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| ProbeID | Description | MEP_1 | MEP_2 | MEP_3 | MEP_4 | MEP_5 | MEP_6 | MEP_7 | MEP_8 | ERY1_1 |
|---|---|---|---|---|---|---|---|---|---|---|
| EAM 190 | h-miR-10b | 6.00 | 6.78 | 6.00 | 6.00 | 6.44 | 6.00 | 6.06 | 6.00 | 6.00 |
| EAM 187 | hmr-miR-107 | 7.17 | 6.00 | 6.65 | 6.88 | 6.00 | 7.44 | 6.00 | 6.97 | 6.85 |
| EAM185 | hmr-miR-103 | 7.59 | 6.00 | 7.28 | 7.38 | 6.00 | 7.94 | 6.00 | 7.60 | 7.26 |
| EAM181 | hmr-let-7f | 9.18 | 9.82 | 10.08 | 10.11 | 9.68 | 9.80 | 9.61 | 8.96 | 9.40 |
| EAM 179 | hmr-let-7d | 7.47 | 9.56 | 8.99 | 9.45 | 8.89 | 9.76 | 9.10 | 9.03 | 8.76 |
| EAM 177 | mr-miR-101b | 6.00 | 6.00 | 6.00 | 6.00 | 6.00 | 6.00 | 6.00 | 6.00 | 6.00 |
| EAM175 | hmr-miR-320 | 9.41 | 8.52 | 8.86 | 9.14 | 9.42 | 9.49 | 9.67 | 9.85 | 9.17 |
| EAM 168 | hmr-let-7e | 6.00 | 6.39 | 6.35 | 6.00 | 6.00 | 6.00 | 6.00 | 6.00 | 6.19 |
| EAM 161 | hmr-miR-28 | 6.00 | 6.00 | 6.00 | 6.00 | 6.00 | 6.00 | 7.60 | 6.00 | 6.00 |
| EAM160 | hmr-miR-26b | 8.92 | 8.03 | 9.08 | 9.13 | 8.76 | 8.24 | 8.82 | 7.56 | 8.36 |
| EAM 155 | hmr-miR-136 | 6.00 | 6.00 | 6.00 | 6.00 | 6.00 | 6.00 | 6.00 | 6.00 | 6.00 |
| EAM283 | mr-miR-211 | 6.00 | 6.00 | 6.00 | 6.00 | 6.00 | 6.00 | 6.00 | 6.00 | 6.00 |
| EAM282 | m-miR-199b | 6.00 | 6.00 | 6.00 | 6.00 | 6.00 | 6.00 | 6.00 | 6.00 | 6.00 |
| EAM281 | mr-miR-217 | 6.00 | 6.00 | 6.00 | 6.00 | 6.00 | 6.00 | 6.00 | 6.00 | 6.00 |
| EAM280 | hmr-miR-30a-3p | 6.00 | 6.00 | 6.00 | 6.00 | 6.00 | 6.00 | 6.00 | 6.00 | 6.00 |
| EAM279 | hmr-miR-29c | 6.00 | 6.98 | 6.00 | 6.00 | 6.00 | 6.00 | 6.00 | 6.00 | 6.00 |
| EAM278 | hmr-miR-98 | 6.00 | 7.19 | 7.59 | 6.00 | 7.17 | 6.00 | 6.00 | 6.00 | 6.74 |
| EAM270 | hmr-miR-30b | 7.89 | 7.61 | 8.70 | 9.14 | 8.89 | 9.10 | 9.01 | 9.49 | 8.81 |
| EAM 159 | hmr-miR-130a | 7.76 | 8.35 | 8.79 | 8.49 | 8.39 | 8.29 | 8.96 | 9.53 | 8.41 |
| EAM 163 | hmr-miR-142-3p | 6.00 | 6.00 | 6.00 | 6.42 | 6.00 | 7.29 | 6.77 | 6.00 | 6.39 |
| EAM 171 | hmr-miR-137 | 6.00 | 6.00 | 6.00 | 6.00 | 6.00 | 6.00 | 6.00 | 6.00 | 6.00 |
| EAM306 | m-miR-201 | 6.00 | 6.00 | 6.00 | 6.00 | 6.00 | 6.00 | 6.00 | 6.00 | 6.00 |
| EAM307 | m-miR-202 | 6.00 | 6.00 | 6.00 | 6.00 | 6.42 | 6.00 | 6.00 | 6.00 | 6.00 |
| EAM308 | hmr-miR-206 | 6.00 | 6.00 | 6.00 | 6.00 | 6.00 | 6.00 | 6.00 | 6.00 | 6.00 |
| EAM309 | m-miR-207 | 6.00 | 6.00 | 6.00 | 6.00 | 6.00 | 6.00 | 6.00 | 6.00 | 6.00 |
| EAM310 | hmr-miR-208 | 6.00 | 6.00 | 6.00 | 6.00 | 6.00 | 6.00 | 6.00 | 6.00 | 6.00 |
| EAM247 | hmr-miR-212 | 6.00 | 6.00 | 6.00 | 6.00 | 6.00 | 6.00 | 6.00 | 6.00 | 6.00 |
| EAM251 | hmr-miR-216 | 6.00 | 6.00 | 6.00 | 6.00 | 6.00 | 6.00 | 6.00 | 6.00 | 6.00 |
| EAM253 | hmr-miR-218 | 6.00 | 6.00 | 6.00 | 6.00 | 6.00 | 6.00 | 6.00 | 6.00 | 6.00 |
| EAM275 | hmr-miR-34a | 6.00 | 6.00 | 6.00 | 6.00 | 6.00 | 6.00 | 6.00 | 6.00 | 6.00 |
| EAM246 | h-miR-211 | 6.00 | 6.00 | 6.00 | 6.00 | 6.00 | 6.00 | 6.00 | 6.00 | 6.00 |
| EAM250 | h-miR-215 | 6.00 | 6.00 | 6.00 | 6.00 | 6.00 | 6.00 | 6.00 | 6.00 | 6.00 |
| EAM252 | h-miR-217 | 6.00 | 6.00 | 6.00 | 6.00 | 6.00 | 6.00 | 6.00 | 6.00 | 6.00 |
| EAM224 | hmr-miR-17-5p | 11.37 | 11.51 | 11.39 | 10.79 | 11.11 | 11.33 | 11.35 | 11.44 | 11.52 |
| EAM225 | hmr-miR-18a | 6.00 | 6.00 | 6.00 | 7.67 | 6.07 | 6.00 | 6.00 | 8.32 | 8.14 |
| EAM226 | hmr-miR-181a | 6.26 | 8.16 | 7.40 | 8.99 | 9.49 | 8.48 | 8.90 | 7.90 | 8.54 |
| EAM227 | hmr-miR-181b | 6.00 | 6.00 | 8.18 | 8.18 | 6.59 | 7.95 | 7.59 | 9.07 | 7.76 |
| EAM234 | hmr-miR-199a | 6.00 | 6.00 | 6.00 | 6.00 | 6.00 | 6.00 | 6.00 | 6.00 | 6.00 |
| EAM235 | h-miR-199b | 6.00 | 6.00 | 6.00 | 6.00 | 6.00 | 6.00 | 6.00 | 6.00 | 6.00 |
| EAM236 | hmr-miR-19a | 7.89 | 7.04 | 8.46 | 8.23 | 8.32 | 7.24 | 7.94 | 7.49 | 8.65 |
| EAM241 | hmr-miR-203 | 6.00 | 6.00 | 6.00 | 6.00 | 6.00 | 6.00 | 6.00 | 6.00 | 6.00 |
| EAM242 | hmr-miR-204 | 6.00 | 6.00 | 6.00 | 6.00 | 6.00 | 6.00 | 6.00 | 6.00 | 6.00 |
| EAM243 | hmr-miR-205 | 6.00 | 6.00 | 6.00 | 6.00 | 6.00 | 6.00 | 6.00 | 6.00 | 6.00 |
| EAM245 | hmr-miR-210 | 6.00 | 6.00 | 6.00 | 6.00 | 6.00 | 6.00 | 6.00 | 6.00 | 6.00 |
| EAM249 | hmr-miR-214 | 6.00 | 6.00 | 6.00 | 6.00 | 6.00 | 6.00 | 6.00 | 6.00 | 6.00 |
| EAM184 | hmr-miR-100 | 6.00 | 6.00 | 6.26 | 6.00 | 6.00 | 6.00 | 6.00 | 6.00 | 6.00 |
| EAM186 | h-miR-106a | 11.10 | 11.31 | 11.28 | 10.79 | 10.90 | 11.00 | 11.02 | 11.32 | 11.22 |
| EAM 189 | hmr-miR-10a | 8.48 | 7.98 | 7.43 | 7.74 | 7.44 | 6.44 | 7.37 | 6.00 | 7.48 |
| EAM 191 | hmr-miR-122a | 6.00 | 6.00 | 6.00 | 6.00 | 6.00 | 6.00 | 6.00 | 6.00 | 6.00 |
| EAM 192 | hmr-miR-126* | 7.32 | 6.00 | 7.66 | 6.20 | 6.62 | 6.00 | 6.76 | 7.63 | 7.39 |
| EAM 198 | hmr-miR-130b | 6.00 | 6.00 | 6.36 | 6.44 | 6.68 | 6.00 | 6.00 | 6.68 | 6.00 |
| EAM202 | hmr-miR-134 | 6.00 | 6.00 | 6.00 | 6.00 | 6.00 | 6.00 | 6.00 | 6.00 | 6.00 |
| EAM209 | hmr-miR-142-5p | 6.00 | 7.72 | 7.42 | 6.95 | 8.16 | 6.62 | 7.29 | 7.92 | 6.00 |
| EAM221 | m-miR-155 | 7.57 | 8.58 | 7.87 | 7.76 | 7.43 | 7.79 | 7.65 | 7.47 | 7.97 |
| EAM223 | hmr-miR-15b | 10.67 | 8.82 | 10.83 | 10.79 | 10.29 | 10.53 | 10.47 | 9.94 | 10.59 |
| EAM228 | hmr-miR-181c | 6.00 | 6.00 | 6.00 | 6.00 | 6.00 | 6.00 | 6.00 | 6.00 | 6.00 |
| EAM222 | hm-miR-15a | 8.94 | 6.00 | 8.11 | 9.87 | 8.82 | 8.92 | 8.20 | 8.39 | 8.30 |
| EAM111 | hm-let-7g | 10.22 | 9.62 | 10.09 | 10.09 | 9.76 | 10.06 | 9.73 | 9.61 | 9.34 |
| EAM131 | hmr-miR-92 | 11.06 | 11.53 | 11.55 | 10.98 | 11.69 | 11.74 | 11.75 | 11.88 | 11.30 |
| EAM139 | hmr-miR-146a | 9.03 | 9.70 | 6.00 | 9.07 | 9.31 | 6.00 | 8.53 | 9.49 | 9.22 |
| EAM145 | hmr-let-7c | 9.28 | 9.27 | 9.03 | 9.67 | 9.39 | 9.04 | 9.24 | 9.14 | 8.71 |
| EAM 109 | hmr-miR-7 | 6.00 | 6.00 | 6.00 | 6.00 | 6.00 | 6.00 | 6.00 | 6.00 | 6.00 |
| EAM 152 | hm-miR-9* | 6.00 | 6.00 | 6.00 | 6.00 | 6.00 | 6.00 | 6.00 | 6.00 | 6.00 |
| JLA215 | hmr-let-7i | 9.03 | 8.00 | 8.07 | 8.44 | 7.26 | 8.38 | 8.85 | 7.71 | 9.25 |
| EAM153 | hmr-let-7a | 11.22 | 10.91 | 10.80 | 10.07 | 11.01 | 10.77 | 11.09 | 10.93 | 10.63 |
| EAM147 | hmr-let-7b | 9.07 | 6.31 | 9.13 | 8.64 | 9.00 | 9.63 | 10.04 | 9.43 | 7.66 |
| EAM 137 | hmr-miR-132 | 6.00 | 6.00 | 6.00 | 6.00 | 6.34 | 6.00 | 6.00 | 6.00 | 6.00 |
| EAM 133 | hmr-miR-324-5p | 7.74 | 6.00 | 6.00 | 6.00 | 6.00 | 6.00 | 6.00 | 6.00 | 6.00 |
| EAM 103 | hmr-miR-124a | 6.00 | 6.00 | 6.00 | 6.00 | 6.00 | 6.00 | 6.00 | 6.00 | 6.00 |
| EAM 105 | hmr-miR-125b | 6.00 | 7.69 | 7.56 | 8.05 | 8.75 | 8.32 | 6.81 | 7.30 | 8.45 |
| EAM 121 | hmr-miR-99a | 6.00 | 6.00 | 6.00 | 6.00 | 6.00 | 6.00 | 6.00 | 6.00 | 6.00 |
| EAM115 | hmr-miR-16 | 12.32 | 12.42 | 12.31 | 11.40 | 11.87 | 12.30 | 11.83 | 11.81 | 12.08 |
| EAM119 | hmr-miR-29b | 6.00 | 6.00 | 6.00 | 6.93 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | | | | |
|---|---|---|---|---|---|---|---|---|---|---|
| EAM311 | hmr-miR-101 | 6.00 | 6.00 | 6.00 | 6.00 | 6.00 | 6.00 | 6.39 | 6.00 | 6.00 |
| EAM312 | h-miR-105 | 6.00 | 6.00 | 6.00 | 6.00 | 6.00 | 6.00 | 6.00 | 6.00 | 6.00 |
| EAM313 | hmr-miR-106b | 9.31 | 9.44 | 8.80 | 9.39 | 9.18 | 9.09 | 8.34 | 8.86 | 8.75 |
| EAM314 | hmr-miR-126 | 8.75 | 9.89 | 8.72 | 10.12 | 9.41 | 8.10 | 9.63 | 8.69 | 10.57 |
| EAM315 | hmr-miR-127 | 6.00 | 6.00 | 6.00 | 6.00 | 6.00 | 6.00 | 6.00 | 6.00 | 6.00 |
| EAM320 | hm-miR-189 | 6.00 | 6.00 | 6.00 | 6.00 | 6.00 | 6.00 | 6.00 | 6.00 | 6.00 |
| JLA216 | hmr-miR-200c | 6.00 | 6.00 | 6.00 | 6.00 | 6.00 | 6.00 | 8.00 | 6.00 | 7.19 |
| EAM323 | h-miR-224 | 6.00 | 6.00 | 6.00 | 6.00 | 6.00 | 6.00 | 6.00 | 6.00 | 6.00 |
| EAM324 | hmr-miR-25 | 6.00 | 9.01 | 6.41 | 7.40 | 8.30 | 7.82 | 8.26 | 8.59 | 7.82 |
| EAM386 | r-miR-336 | 6.00 | 6.00 | 6.00 | 6.00 | 6.00 | 6.00 | 6.00 | 6.00 | 6.00 |
| JLA218 | r-miR-343 | 6.00 | 6.00 | 6.00 | 6.00 | 6.00 | 6.00 | 6.00 | 6.00 | 6.00 |
| EAM388 | r-miR-344 | 6.00 | 6.00 | 6.00 | 6.00 | 6.00 | 6.00 | 6.00 | 6.00 | 6.00 |
| EAM338 | h-miR-95 | 6.00 | 6.00 | 6.00 | 6.00 | 6.00 | 6.00 | 6.00 | 6.00 | 6.00 |
| JLA214 | hmr-miR-129 | 6.00 | 6.00 | 6.00 | 6.00 | 6.00 | 6.00 | 6.00 | 6.00 | 6.00 |
| EAM340 | mr-let-7d* | 7.71 | 6.00 | 6.00 | 6.00 | 6.00 | 7.41 | 6.00 | 6.00 | 6.00 |
| EAM341 | m-miR-106a | 10.34 | 11.12 | 10.40 | 9.97 | 10.46 | 10.70 | 10.47 | 10.68 | 10.60 |
| EAM342 | hmr-miR-135b | 6.00 | 6.00 | 6.00 | 6.00 | 6.00 | 6.00 | 6.00 | 6.00 | 6.00 |
| EAM343 | mr-miR-151 | 6.00 | 6.00 | 6.00 | 6.00 | 6.00 | 6.00 | 6.00 | 6.00 | 6.00 |
| EAM344 | m-miR-17-3p | 6.00 | 6.00 | 6.00 | 6.00 | 6.00 | 6.00 | 6.00 | 6.00 | 6.00 |
| EAM345 | m-miR-224 | 6.00 | 6.00 | 6.00 | 6.00 | 6.00 | 6.00 | 6.00 | 6.00 | 6.00 |
| EAM346 | mr-miR-290 | 6.00 | 6.00 | 6.00 | 6.00 | 6.00 | 6.00 | 6.00 | 6.00 | 6.00 |
| EAM347 | mr-miR-291-3p | 6.00 | 6.00 | 6.00 | 6.00 | 6.00 | 6.00 | 6.00 | 6.00 | 6.00 |
| EAM348 | mr-miR-291-5p | 6.00 | 6.00 | 6.00 | 6.00 | 6.00 | 6.00 | 6.00 | 6.00 | 6.00 |
| EAM349 | mr-miR-292-3p | 6.00 | 6.00 | 6.00 | 6.00 | 6.00 | 6.00 | 6.00 | 6.00 | 6.00 |
| EAM350 | mr-miR-292-5p | 6.00 | 6.00 | 6.00 | 6.00 | 6.00 | 6.00 | 6.00 | 6.00 | 6.00 |
| EAM351 | m-miR-293 | 6.00 | 6.00 | 6.00 | 6.00 | 6.00 | 6.00 | 6.00 | 6.00 | 6.00 |
| EAM352 | m-miR-294 | 6.00 | 6.00 | 6.00 | 6.00 | 6.00 | 6.00 | 6.00 | 6.00 | 6.00 |
| EAM353 | m-miR-295 | 6.00 | 6.00 | 6.00 | 6.00 | 6.00 | 6.00 | 6.00 | 6.00 | 6.00 |
| EAM354 | m-miR-297 | 6.00 | 6.00 | 6.00 | 6.00 | 6.00 | 6.00 | 6.00 | 6.00 | 6.00 |
| EAM355 | mr-miR-298 | 6.00 | 6.00 | 6.00 | 6.00 | 6.00 | 6.00 | 6.00 | 6.00 | 6.00 |
| EAM356 | mr-miR-300 | 6.00 | 6.00 | 6.00 | 6.00 | 6.00 | 6.00 | 6.00 | 6.00 | 6.00 |
| EAM358 | hmr-miR-323 | 6.00 | 6.00 | 6.00 | 6.00 | 6.00 | 6.00 | 6.00 | 6.00 | 6.00 |
| EAM359 | hmr-miR-324-3p | 6.00 | 6.00 | 6.00 | 6.00 | 6.00 | 6.00 | 6.00 | 7.59 | 6.00 |
| EAM360 | mr-miR-325 | 7.36 | 6.93 | 6.00 | 6.00 | 6.00 | 6.00 | 6.00 | 6.00 | 6.00 |
| EAM361 | hmr-miR-326 | 6.00 | 6.00 | 6.00 | 6.00 | 6.00 | 6.00 | 6.00 | 6.00 | 6.00 |
| EAM362 | hmr-miR-328 | 6.00 | 6.00 | 6.98 | 6.00 | 6.00 | 6.00 | 6.00 | 6.00 | 6.00 |
| EAM363 | mr-miR-329 | 6.00 | 6.00 | 6.00 | 6.00 | 6.00 | 6.00 | 6.00 | 6.00 | 6.00 |
| EAM365 | hmr-miR-331 | 6.00 | 6.00 | 6.00 | 6.00 | 6.00 | 6.00 | 6.00 | 6.00 | 6.00 |
| EAM366 | mr-miR-337 | 6.00 | 6.00 | 6.00 | 6.00 | 6.00 | 6.00 | 6.00 | 6.00 | 6.00 |
| EAM367 | hmr-miR-338 | 6.00 | 6.00 | 6.00 | 6.00 | 6.00 | 6.00 | 6.00 | 6.00 | 6.00 |
| EAM368 | hmr-miR-339 | 6.00 | 6.00 | 6.00 | 6.00 | 6.10 | 6.00 | 6.00 | 6.00 | 6.00 |
| EAM369 | hmr-miR-340 | 6.00 | 6.00 | 6.00 | 6.00 | 6.00 | 6.00 | 6.00 | 6.00 | 6.00 |
| EAM370 | mr-miR-341 | 6.00 | 6.00 | 6.00 | 6.00 | 6.00 | 6.00 | 6.00 | 6.00 | 6.00 |
| EAM371 | hmr-miR-342 | 9.66 | 9.70 | 6.00 | 10.47 | 9.48 | 9.58 | 10.06 | 9.41 | 8.70 |
| EAM372 | m-miR-344 | 6.00 | 6.00 | 6.00 | 6.00 | 6.00 | 6.00 | 6.00 | 6.00 | 6.00 |
| EAM373 | mr-miR-345 | 6.00 | 6.00 | 6.00 | 6.00 | 6.00 | 6.00 | 6.00 | 6.00 | 6.00 |
| EAM374 | m-miR-346 | 6.00 | 6.00 | 6.00 | 6.00 | 6.00 | 6.00 | 6.00 | 6.00 | 6.00 |
| EAM375 | mr-miR-34b | 6.00 | 6.00 | 6.00 | 6.00 | 6.00 | 6.00 | 6.00 | 6.00 | 6.00 |
| JLA217 | mr-miR-350 | 6.00 | 6.00 | 6.00 | 6.00 | 6.00 | 6.00 | 6.00 | 6.00 | 6.00 |
| EAM377 | mr-miR-351 | 6.00 | 6.00 | 6.00 | 6.00 | 6.00 | 6.00 | 6.00 | 6.00 | 6.00 |
| EAM378 | mr-miR-7b | 6.00 | 6.00 | 6.00 | 6.00 | 6.00 | 6.00 | 6.00 | 6.00 | 6.00 |
| EAM382 | r-miR-20* | 6.00 | 6.00 | 6.00 | 6.00 | 6.00 | 6.00 | 6.00 | 6.00 | 6.00 |
| EAM383 | r-miR-327 | 6.00 | 6.00 | 6.00 | 6.00 | 6.00 | 6.00 | 6.00 | 6.00 | 6.00 |
| EAM384 | r-miR-333 | 6.00 | 6.00 | 6.00 | 6.00 | 6.00 | 6.00 | 6.00 | 6.00 | 6.00 |
| EAM385 | hmr-miR-335 | 6.91 | 7.60 | 8.50 | 7.99 | 7.28 | 6.00 | 7.20 | 7.07 | 7.65 |
| EAM393 | r-miR-7* | 6.00 | 6.00 | 6.00 | 6.00 | 6.00 | 6.00 | 6.00 | 6.00 | 6.00 |
| EAM304 | hmr-miR-200a | 6.00 | 6.00 | 6.00 | 6.00 | 6.00 | 6.00 | 6.00 | 6.00 | 6.00 |
| EAM298 | hmr-miR-194 | 6.00 | 6.00 | 6.00 | 6.00 | 6.00 | 6.00 | 6.00 | 6.00 | 6.00 |
| JLA221 | hmr-miR-191 | 7.79 | 6.44 | 7.74 | 8.72 | 8.73 | 8.28 | 8.34 | 8.43 | 7.85 |
| EAM295 | hmr-miR-190 | 6.00 | 6.00 | 6.00 | 6.00 | 6.00 | 6.00 | 6.00 | 6.00 | 6.00 |
| EAM292 | hmr-miR-186 | 6.00 | 6.00 | 6.00 | 6.00 | 6.00 | 6.00 | 6.00 | 6.00 | 6.00 |
| JLA219 | hmr-miR-185 | 6.00 | 6.00 | 6.00 | 6.07 | 7.36 | 7.59 | 6.40 | 6.00 | 6.00 |
| EAM290 | hmr-miR-184 | 6.00 | 6.00 | 6.00 | 6.00 | 6.00 | 6.00 | 6.00 | 6.00 | 6.00 |
| EAM402 | hm-miR-133b | 6.00 | 6.00 | 6.00 | 6.00 | 6.00 | 6.00 | 6.00 | 6.00 | 6.00 |
| EAM403 | h-miR-151 | 6.00 | 6.00 | 6.00 | 6.00 | 6.00 | 6.00 | 6.00 | 6.00 | 6.00 |
| EAM404 | hmr-miR-196b | 6.00 | 6.00 | 6.00 | 6.52 | 6.00 | 6.00 | 6.00 | 6.00 | 6.00 |
| EAM418 | hm-miR-370 | 6.00 | 6.00 | 6.00 | 6.00 | 6.00 | 6.00 | 6.00 | 6.00 | 6.00 |
| EAM419 | h-miR-371 | 6.00 | 6.00 | 6.00 | 6.00 | 6.00 | 6.00 | 6.00 | 6.00 | 6.00 |
| EAM420 | h-miR-372 | 6.00 | 6.00 | 6.00 | 6.00 | 6.00 | 6.00 | 6.00 | 6.00 | 6.00 |
| EAM421 | h-miR-373 | 6.00 | 6.00 | 6.00 | 6.00 | 6.00 | 6.00 | 6.00 | 6.00 | 6.00 |
| EAM422 | h-miR-373* | 6.00 | 6.00 | 6.00 | 6.00 | 6.00 | 6.00 | 6.00 | 6.00 | 6.00 |
| EAM423 | h-miR-374 | 6.00 | 6.69 | 6.19 | 7.70 | 7.86 | 6.00 | 6.69 | 6.60 | 7.31 |
| EAM426 | m-miR-215 | 6.00 | 6.00 | 6.00 | 6.00 | 6.00 | 6.00 | 6.00 | 6.00 | 6.00 |
| EAM427 | hm-miR-409-3p | 6.00 | 6.00 | 6.00 | 6.00 | 6.00 | 6.00 | 6.00 | 6.00 | 6.00 |
| EAM428 | hm-miR-410 | 6.00 | 6.00 | 6.00 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | | | | |
|---|---|---|---|---|---|---|---|---|---|---|
| EAM429 | m-miR-376b | 6.00 | 6.00 | 6.00 | 6.00 | 6.00 | 6.00 | 6.00 | 6.00 | 6.00 |
| EAM430 | m-miR-376a | 6.00 | 6.00 | 6.00 | 6.00 | 6.00 | 6.00 | 6.00 | 6.00 | 6.00 |
| EAM431 | m-miR-411 | 6.00 | 6.00 | 6.00 | 6.00 | 6.00 | 6.00 | 6.00 | 6.00 | 6.00 |
| EAM432 | m-miR-380-3p | 6.00 | 6.00 | 6.00 | 6.00 | 6.00 | 6.00 | 6.00 | 6.00 | 6.00 |
| EAM433 | hm-miR-412 | 6.00 | 6.00 | 6.00 | 6.00 | 6.00 | 6.00 | 6.00 | 6.00 | 6.00 |
| EAM264 | hmr-miR-27b | 7.18 | 6.00 | 6.78 | 7.56 | 8.20 | 6.00 | 6.00 | 6.80 | 7.55 |
| EAM263 | hmr-miR-26a | 9.87 | 9.50 | 10.10 | 9.97 | 9.68 | 9.23 | 9.40 | 10.04 | 10.07 |
| EAM262 | hmr-miR-24 | 6.00 | 6.25 | 6.00 | 6.94 | 6.00 | 6.00 | 6.00 | 6.00 | 7.29 |
| EAM261 | hmr-miR-23b | 7.42 | 7.66 | 7.78 | 8.90 | 8.11 | 7.19 | 9.17 | 8.50 | 7.90 |
| EAM260 | hmr-miR-23a | 7.78 | 8.15 | 7.85 | 9.30 | 7.94 | 8.13 | 8.87 | 8.83 | 8.09 |
| EAM256 | h-miR-220 | 6.00 | 6.00 | 6.00 | 6.00 | 6.00 | 6.00 | 6.00 | 6.00 | 6.00 |
| EAM255 | hmr-miR-22 | 6.00 | 6.24 | 6.00 | 6.00 | 6.00 | 6.00 | 6.00 | 6.00 | 6.00 |
| EAM248 | hmr-miR-213 | 6.00 | 6.00 | 6.00 | 6.00 | 6.00 | 6.00 | 6.00 | 6.00 | 6.00 |
| EAM244 | hmr-miR-21 | 6.39 | 7.99 | 8.45 | 8.89 | 8.32 | 9.27 | 8.02 | 7.77 | 7.86 |
| EAM240 | hmr-miR-20a | 11.36 | 11.38 | 11.87 | 11.08 | 11.27 | 11.19 | 11.27 | 11.27 | 11.50 |
| EAM237 | hmr-miR-19b | 8.88 | 7.38 | 9.64 | 9.13 | 8.68 | 8.34 | 8.68 | 8.09 | 9.38 |
| EAM233 | hmr-miR-196a | 6.00 | 6.00 | 6.00 | 6.00 | 6.00 | 6.00 | 6.00 | 6.00 | 6.00 |
| EAM214 | hm-miR-148a | 6.00 | 6.00 | 6.00 | 6.00 | 6.00 | 6.00 | 6.00 | 6.00 | 6.00 |
| EAM212 | hmr-miR-145 | 6.00 | 6.00 | 6.00 | 6.00 | 6.00 | 6.00 | 6.00 | 6.00 | 6.00 |
| EAM211 | hmr-miR-144 | 9.13 | 7.29 | 6.00 | 6.37 | 6.88 | 7.86 | 6.00 | 6.00 | 6.00 |
| EAM210 | hmr-miR-143 | 6.00 | 6.00 | 6.00 | 6.00 | 6.00 | 6.00 | 6.00 | 6.00 | 6.00 |
| EAM389 | r-miR-346 | 6.00 | 6.00 | 6.00 | 6.00 | 6.00 | 6.00 | 6.00 | 6.00 | 6.00 |
| EAM390 | r-miR-347 | 6.00 | 6.00 | 6.00 | 6.00 | 6.00 | 6.00 | 6.00 | 6.00 | 6.00 |
| EAM391 | r-miR-349 | 6.00 | 6.00 | 6.00 | 6.00 | 6.00 | 6.00 | 6.00 | 6.00 | 6.00 |
| JLA223 | hmr-miR-33 | 6.00 | 6.00 | 6.00 | 6.00 | 6.00 | 6.00 | 6.00 | 6.00 | 6.00 |
| EAM277 | hmr-miR-96 | 6.00 | 6.00 | 6.00 | 6.00 | 6.00 | 6.00 | 6.00 | 6.00 | 6.00 |
| EAM276 | hmr-miR-9 | 6.00 | 6.00 | 6.00 | 6.00 | 6.00 | 6.00 | 6.00 | 6.00 | 6.00 |
| EAM272 | hmr-miR-30d | 7.05 | 6.00 | 7.40 | 8.82 | 8.29 | 8.37 | 8.23 | 8.50 | 8.82 |
| EAM288 | mr-miR-10b | 6.74 | 8.16 | 6.94 | 6.48 | 7.41 | 6.00 | 6.56 | 6.00 | 6.00 |
| EAM293 | hm-miR-188 | 6.00 | 6.00 | 6.00 | 6.00 | 6.00 | 6.00 | 6.00 | 6.00 | 6.00 |
| EAM297 | hmr-miR-193a | 6.00 | 6.00 | 6.00 | 6.00 | 6.00 | 6.00 | 6.00 | 6.00 | 6.00 |
| EAM301 | h-miR-198 | 6.00 | 6.00 | 6.00 | 6.00 | 6.00 | 6.00 | 6.00 | 6.00 | 6.00 |
| EAM232 | hmr-miR-192 | 6.11 | 6.00 | 6.00 | 6.00 | 6.00 | 6.00 | 6.00 | 6.00 | 6.00 |
| EAM231 | hmr-miR-187 | 6.00 | 6.00 | 6.00 | 6.00 | 6.00 | 6.00 | 6.00 | 6.00 | 6.00 |
| EAM230 | hmr-miR-183 | 6.00 | 6.00 | 6.00 | 6.00 | 6.29 | 6.00 | 6.00 | 6.00 | 6.00 |
| EAM229 | hm-miR-182 | 6.00 | 6.00 | 6.00 | 6.00 | 6.00 | 6.00 | 6.00 | 6.00 | 6.00 |
| EAM220 | hmr-miR-154 | 6.00 | 6.00 | 6.00 | 6.00 | 6.00 | 6.00 | 6.00 | 6.00 | 6.00 |
| EAM219 | hmr-miR-153 | 6.00 | 6.00 | 6.00 | 6.00 | 6.00 | 6.00 | 6.00 | 6.00 | 6.00 |
| EAM218 | hmr-miR-152 | 6.00 | 6.00 | 6.00 | 6.00 | 6.00 | 6.00 | 6.00 | 6.00 | 6.00 |
| EAM217 | hmr-miR-150 | 6.00 | 7.22 | 6.00 | 6.00 | 6.00 | 7.52 | 6.00 | 6.00 | 6.78 |
| EAM216 | hm-miR-149 | 6.00 | 6.00 | 6.00 | 6.00 | 6.00 | 6.00 | 6.00 | 6.00 | 6.00 |
| EAM215 | hmr-miR-148b | 6.00 | 6.00 | 6.00 | 6.00 | 6.00 | 6.00 | 6.00 | 6.00 | 6.00 |
| EAM271 | hmr-miR-30c | 7.66 | 7.76 | 8.70 | 9.30 | 9.01 | 9.25 | 9.17 | 9.58 | 8.66 |
| EAM268 | hmr-miR-29a | 6.19 | 7.88 | 6.00 | 6.00 | 6.00 | 6.68 | 6.00 | 6.00 | 6.90 |
| EAM305 | hmr-miR-200b | 6.00 | 6.00 | 6.00 | 6.00 | 6.28 | 6.00 | 7.02 | 6.00 | 6.46 |
| EAM303 | hm-miR-199a* | 6.00 | 6.00 | 6.00 | 6.00 | 6.00 | 6.00 | 6.00 | 6.00 | 6.00 |
| EAM300 | h-miR-197 | 7.59 | 6.00 | 6.82 | 7.62 | 8.19 | 7.13 | 6.99 | 8.12 | 8.11 |
| EAM299 | hmr-miR-195 | 9.34 | 9.94 | 9.20 | 8.70 | 8.93 | 9.57 | 8.49 | 8.73 | 9.15 |
| JLA91 | hmr-miR-99b | 9.43 | 8.63 | 6.00 | 9.99 | 7.89 | 8.23 | 7.06 | 7.31 | 6.00 |
| JLA92 | hmr-miR-433 | 6.00 | 6.00 | 6.00 | 6.00 | 6.00 | 6.00 | 6.00 | 6.00 | 6.00 |
| JLA93 | hmr-miR-431 | 6.00 | 6.00 | 6.00 | 6.00 | 6.00 | 6.00 | 6.00 | 6.00 | 6.00 |
| JLA94 | hmr-miR-365 | 8.38 | 6.00 | 8.96 | 7.30 | 7.15 | 6.00 | 6.43 | 6.00 | 6.00 |
| JLA95 | hmr-miR-450 | 6.00 | 6.00 | 6.00 | 6.00 | 6.00 | 6.00 | 6.00 | 6.00 | 6.00 |
| JLA96 | hmr-miR-449 | 6.00 | 6.00 | 6.00 | 6.00 | 6.00 | 6.00 | 6.00 | 6.00 | 6.00 |
| JLA99 | hmr-miR-448 | 6.00 | 6.00 | 6.00 | 6.00 | 6.00 | 6.00 | 6.00 | 6.00 | 6.00 |
| JLA103 | hmr-miR-424 | 6.00 | 6.20 | 6.81 | 7.28 | 6.00 | 6.00 | 6.66 | 6.00 | 7.64 |
| JLA105 | hm-miR-361 | 6.00 | 6.01 | 6.00 | 7.74 | 7.07 | 7.28 | 7.99 | 6.00 | 7.46 |
| JLA106 | hm-miR-375 | 6.00 | 6.00 | 6.00 | 6.00 | 6.00 | 6.00 | 6.00 | 6.00 | 6.00 |
| JLA107 | hm-miR-377 | 6.00 | 6.00 | 6.00 | 6.00 | 6.00 | 6.00 | 6.00 | 6.00 | 6.00 |
| JLA108 | hm-miR-378 | 6.00 | 6.00 | 6.00 | 6.00 | 6.00 | 6.00 | 6.00 | 6.00 | 6.00 |
| JLA109 | hm-miR-379 | 6.00 | 6.00 | 6.00 | 6.00 | 6.00 | 6.00 | 6.00 | 6.00 | 6.00 |
| JLA110 | hm-miR-380-5p | 6.00 | 6.00 | 6.00 | 6.00 | 6.00 | 6.00 | 6.00 | 6.00 | 6.00 |
| JLA111 | hm-miR-381 | 6.00 | 6.00 | 6.00 | 6.00 | 6.00 | 6.00 | 6.00 | 6.00 | 6.00 |
| JLA112 | hm-miR-382 | 6.00 | 6.00 | 6.00 | 6.00 | 6.00 | 6.00 | 6.00 | 6.00 | 6.00 |
| JLA115 | hm-miR-384 | 6.00 | 6.00 | 6.00 | 6.00 | 6.00 | 6.00 | 6.00 | 6.00 | 6.00 |
| JLA116 | hm-miR-425 | 6.00 | 6.00 | 6.00 | 6.00 | 6.00 | 6.00 | 6.00 | 6.00 | 6.00 |
| JLA117 | hm-miR-452 | 6.00 | 6.00 | 6.00 | 6.00 | 6.00 | 6.00 | 6.00 | 6.00 | 6.00 |
| JLA118 | hm-miR-30e-3p | 6.00 | 6.00 | 6.00 | 6.00 | 6.00 | 6.00 | 6.00 | 6.00 | 6.00 |
| JLA104 | mr-miR-129-3p | 9.27 | 6.00 | 9.25 | 6.00 | 8.52 | 6.00 | 7.63 | 7.12 | 6.00 |
| JLA98 | mr-miR-429 | 6.00 | 6.00 | 6.00 | 6.00 | 6.00 | 6.00 | 6.00 | 6.00 | 6.00 |
| JLA101 | mr-miR-330 | 6.00 | 6.00 | 6.00 | 6.00 | 6.00 | 6.00 | 6.00 | 6.00 | 6.00 |
| JLA102 | mr-miR-322 | 6.00 | 6.00 | 6.00 | 6.00 | 6.00 | 6.00 | 6.00 | 6.00 | 6.00 |
| JLA114 | m-miR-383 | 6.00 | 6.00 | 6.00 | 6.00 | 6.00 | 6.00 | 6.00 | 6.00 | 6.00 |
| JLA5 | hmr-miR-451 | 9.95 | 8.32 | 6.00 | 6.85 | 9.54 | 8.59 | 6.00 | 6.33 | 6.00 |
| JLA201 | r-miR-421 | 6.00 | 6.00 | 6.00 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | | | | |
|---|---|---|---|---|---|---|---|---|---|---|
| JLA202 | m-miR-463 | 6.00 | 6.00 | 6.00 | 6.00 | 6.00 | 6.00 | 6.00 | 6.00 | 6.00 |
| JLA203 | m-miR-464 | 6.00 | 6.00 | 6.00 | 6.00 | 6.00 | 6.00 | 6.00 | 6.00 | 6.00 |
| JLA204 | m-miR-465 | 6.00 | 6.00 | 6.00 | 6.00 | 6.00 | 6.00 | 6.00 | 6.00 | 6.00 |
| JLA205 | m-miR-466 | 7.94 | 6.00 | 6.00 | 6.00 | 6.00 | 6.00 | 6.00 | 6.00 | 6.00 |
| JLA206 | m-miR-467 | 8.36 | 6.00 | 6.00 | 6.00 | 6.00 | 6.00 | 6.00 | 6.00 | 6.00 |
| JLA207 | m-miR-468 | 6.05 | 6.00 | 6.00 | 6.00 | 6.00 | 6.00 | 6.00 | 6.00 | 6.00 |
| JLA208 | m-miR-469 | 6.00 | 6.00 | 6.00 | 6.00 | 6.00 | 6.00 | 6.00 | 6.00 | 6.00 |
| JLA209 | m-miR-470 | 6.00 | 6.00 | 6.00 | 6.00 | 6.00 | 6.00 | 6.00 | 6.00 | 6.00 |
| JLA210 | m-miR-471 | 6.00 | 6.00 | 6.00 | 6.00 | 6.00 | 6.00 | 6.00 | 6.00 | 6.00 |
| EAM325 | hmr-miR-27a | 8.16 | 6.00 | 7.67 | 8.75 | 8.56 | 6.00 | 6.00 | 7.93 | 8.44 |
| EAM326 | hmr-miR-296 | 6.00 | 6.00 | 6.00 | 6.00 | 6.00 | 6.00 | 6.00 | 6.00 | 6.00 |
| EAM327 | hmr-miR-299-5p | 6.00 | 6.00 | 6.00 | 6.00 | 6.00 | 6.00 | 6.00 | 6.00 | 6.00 |
| EAM328 | hmr-miR-301 | 6.25 | 6.00 | 6.00 | 6.00 | 6.00 | 6.00 | 6.00 | 6.56 | 6.16 |
| EAM329 | hm-miR-302a | 6.00 | 6.00 | 6.00 | 6.00 | 6.00 | 6.00 | 6.00 | 6.00 | 6.00 |
| EAM330 | hmr-miR-30a-5p | 6.00 | 6.01 | 6.00 | 7.29 | 6.25 | 6.55 | 6.00 | 6.78 | 7.23 |
| EAM331 | hmr-miR-30e-5p | 6.00 | 6.21 | 6.00 | 6.00 | 6.00 | 6.00 | 6.00 | 6.00 | 6.00 |
| EAM332 | hmr-miR-31 | 6.00 | 6.00 | 6.00 | 6.00 | 6.00 | 6.00 | 6.00 | 6.00 | 6.00 |
| EAM333 | hmr-miR-32 | 7.38 | 6.00 | 6.21 | 6.00 | 6.00 | 6.00 | 6.00 | 6.00 | 6.00 |
| EAM335 | h-miR-34b | 6.00 | 6.00 | 6.00 | 6.00 | 6.00 | 6.00 | 6.00 | 6.00 | 6.00 |
| EAM336 | hmr-miR-34c | 6.00 | 6.00 | 6.00 | 6.00 | 6.00 | 6.00 | 6.00 | 6.00 | 6.00 |
| EAM337 | hmr-miR-93 | 8.93 | 9.74 | 9.14 | 9.92 | 8.36 | 10.06 | 10.35 | 9.58 | 10.28 |
| EAM208 | hmr-miR-141 | 6.00 | 6.00 | 6.00 | 6.00 | 6.00 | 6.00 | 6.00 | 6.00 | 6.00 |
| EAM207 | hmr-miR-140 | 6.00 | 6.00 | 6.00 | 6.00 | 6.00 | 6.00 | 6.00 | 6.00 | 6.00 |
| JLA222 | hmr-miR-139 | 6.00 | 6.00 | 6.00 | 6.00 | 6.00 | 6.00 | 6.00 | 6.00 | 6.00 |
| JLA220 | hmr-miR-138 | 6.00 | 6.00 | 6.00 | 6.00 | 6.00 | 6.00 | 6.00 | 6.00 | 6.00 |
| EAM203 | hmr-miR-135a | 6.00 | 6.00 | 6.00 | 6.00 | 6.00 | 6.00 | 6.00 | 6.00 | 6.00 |
| EAM200 | hmr-miR-133a | 6.00 | 6.00 | 6.00 | 6.00 | 6.00 | 6.00 | 6.00 | 6.00 | 6.00 |
| EAM | hmr-miR-128b | 6.00 | 6.00 | 6.00 | 6.00 | 6.00 | 6.00 | 6.00 | 6.00 | 6.00 |
| EAM | hmr-miR-128a | 6.00 | 6.00 | 6.00 | 6.00 | 6.00 | 6.00 | 6.00 | 6.00 | 6.00 |
| EAM254 | hmr-miR-219 | 6.00 | 6.00 | 6.00 | 6.00 | 6.00 | 6.00 | 6.00 | 6.00 | 6.00 |
| EAM257 | hmr-miR-221 | 7.93 | 6.55 | 6.23 | 6.00 | 6.00 | 6.00 | 6.00 | 6.00 | 6.29 |
| EAM258 | hmr-miR-222 | 6.00 | 8.99 | 9.28 | 8.07 | 8.88 | 8.98 | 9.45 | 8.55 | 8.72 |
| EAM259 | hmr-miR-223 | 7.82 | 7.94 | 7.94 | 8.62 | 7.50 | 8.85 | 8.28 | 8.36 | 8.42 |
| JLA211 | m-miR-434-5p | 6.65 | 6.49 | 6.00 | 6.00 | 6.00 | 6.00 | 6.00 | 6.00 | 6.00 |
| JLA212 | m-miR-434-3p | 6.00 | 6.00 | 6.00 | 6.00 | 6.00 | 6.00 | 6.00 | 6.00 | 6.00 |
| JLA213 | m-miR-433-5p | 6.00 | 6.00 | 6.00 | 6.00 | 6.00 | 6.00 | 6.00 | 6.00 | 6.00 |
| JLA2 | hsa-miR-522 | 6.00 | 6.00 | 6.00 | 6.00 | 6.00 | 6.00 | 6.00 | 6.00 | 6.00 |
| JLA3 | hsa-miR-495 | 6.00 | 6.00 | 6.00 | 6.00 | 6.00 | 6.00 | 6.00 | 6.00 | 6.00 |
| JLA200 | r-miR-297 | 6.00 | 6.00 | 6.00 | 6.00 | 6.00 | 6.00 | 6.00 | 6.00 | 6.00 |
| JLA6 | hsa-miR-518e | 6.00 | 6.00 | 6.00 | 6.00 | 6.00 | 6.00 | 6.00 | 6.00 | 6.00 |
| JLA7 | hsa-miR-519a | 6.00 | 6.00 | 6.00 | 6.00 | 6.00 | 6.00 | 6.00 | 6.00 | 6.00 |
| JLA8 | hsa-mir-527* | 6.00 | 6.00 | 6.00 | 6.00 | 6.00 | 6.00 | 6.00 | 6.00 | 6.00 |
| JLA72 | hmr-miR-140* | 8.13 | 6.00 | 6.00 | 7.81 | 7.88 | 6.14 | 6.00 | 6.44 | 6.00 |
| JLA10 | hsa-miR-521 | 6.00 | 6.00 | 6.00 | 6.00 | 6.00 | 6.00 | 6.00 | 6.00 | 6.00 |
| JLA12 | hsa-miR-362 | 6.00 | 6.00 | 6.00 | 6.00 | 6.00 | 6.00 | 6.00 | 6.00 | 6.00 |
| JLA74 | hsa-mir-18* | 6.00 | 6.00 | 6.00 | 6.00 | 6.00 | 6.00 | 6.00 | 6.00 | 6.00 |
| JLA14 | hm-miR-363 | 6.31 | 6.77 | 6.00 | 7.17 | 6.26 | 6.00 | 6.00 | 7.78 | 6.35 |
| JLA77 | hsa-mir-19b-1* | 6.00 | 6.00 | 6.00 | 6.00 | 6.00 | 6.00 | 6.00 | 6.00 | 6.00 |
| JLA17 | hsa-mir-520c,b,f | 6.00 | 6.00 | 6.00 | 6.00 | 6.00 | 6.00 | 6.00 | 6.00 | 6.00 |
| JLA79 | hsa-mir-23a* | 6.00 | 7.27 | 6.00 | 6.00 | 6.00 | 6.00 | 6.00 | 6.00 | 6.00 |
| JLA20 | hsa-miR-369-5p | 6.00 | 6.00 | 6.00 | 6.00 | 6.00 | 6.00 | 6.00 | 6.00 | 6.00 |
| JLA81 | hsa-mir-339* | 6.00 | 6.00 | 6.00 | 6.00 | 6.00 | 6.00 | 6.00 | 6.00 | 6.00 |
| JLA23 | hsa-mir-342* | 6.00 | 6.00 | 6.00 | 6.00 | 6.00 | 6.00 | 6.00 | 6.10 | 6.00 |
| JLA24 | hsa-mir-19a* | 6.00 | 6.00 | 6.00 | 6.00 | 6.00 | 6.00 | 6.00 | 6.00 | 6.00 |
| JLA26 | hsa-miR-517a,b | 6.00 | 6.00 | 6.00 | 6.00 | 6.00 | 6.00 | 6.00 | 6.00 | 7.45 |
| JLA27 | hsa-miR-516-5p | 6.00 | 6.00 | 6.00 | 6.00 | 6.00 | 6.00 | 6.00 | 6.00 | 6.26 |
| JLA28 | hsa-miR-518b | 6.00 | 6.00 | 6.00 | 6.00 | 6.00 | 6.00 | 6.00 | 6.00 | 6.00 |
| JLA29 | hsa-miR-519d | 6.00 | 6.00 | 6.00 | 6.00 | 6.00 | 6.00 | 6.00 | 6.00 | 6.43 |
| JLA73 | hr-mir-151* | 7.12 | 6.00 | 6.00 | 6.00 | 7.45 | 7.00 | 7.48 | 6.00 | 6.35 |
| JLA31 | hsa-mir-28* | 6.00 | 6.00 | 6.00 | 6.31 | 6.00 | 6.00 | 6.00 | 6.00 | 6.00 |
| JLA33 | hsa-mir-519a-2* | 6.00 | 6.00 | 6.00 | 6.00 | 6.00 | 6.00 | 6.00 | 6.00 | 6.00 |
| JLA34 | hsa-mir-26b* | 6.00 | 6.00 | 6.00 | 6.00 | 6.00 | 6.00 | 6.00 | 6.00 | 6.00 |
| JLA35 | hsa-miR-526c | 6.00 | 6.00 | 6.00 | 6.00 | 6.00 | 6.00 | 6.00 | 6.00 | 6.00 |
| JLA36 | hsa-miR-527 | 6.00 | 6.00 | 6.00 | 6.00 | 6.00 | 6.00 | 6.00 | 6.00 | 6.00 |
| JLA38 | hsa-mir-29b-2* | 6.00 | 6.00 | 6.00 | 6.00 | 6.00 | 6.00 | 6.00 | 6.00 | 6.00 |
| JLA39 | hsa-let-7g* | 6.00 | 6.00 | 6.00 | 6.00 | 6.00 | 6.00 | 6.00 | 6.00 | 6.00 |
| JLA40 | hsa-miR-518a | 6.00 | 6.00 | 6.00 | 6.00 | 6.00 | 6.00 | 6.00 | 6.00 | 6.00 |
| JLA41 | hsa-miR-523 | 6.00 | 6.00 | 6.00 | 6.00 | 6.00 | 6.00 | 6.00 | 6.00 | 6.00 |
| JLA44 | hsa-mir-515-3p | 6.00 | 6.00 | 6.00 | 6.00 | 6.00 | 6.00 | 6.00 | 6.00 | 6.00 |
| JLA45 | hsa-mir-146b* | 6.00 | 6.00 | 6.00 | 6.00 | 6.00 | 6.00 | 6.00 | 6.00 | 6.00 |
| JLA49 | hsa-mir-222* | 6.00 | 6.00 | 6.00 | 6.00 | 6.00 | 6.00 | 6.00 | 6.00 | 6.00 |
| JLA53 | hsa-mir-24* | 6.00 | 6.00 | 6.00 | 6.00 | 6.00 | 6.00 | 6.00 | 6.00 | 6.00 |
| JLA55 | hsa-miR-503 | 6.00 | 6.00 | 6.00 | 6.00 | 6.00 | 6.00 | 6.00 | 6.00 | 6.00 |
| JLA57 | hsa-mir-505 | 6.00 | 6.00 | 6.00 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | | | |
|---|---|---|---|---|---|---|---|---|---|
| JLA82 | hsa-mir-423* | 10.00 | 10.80 | 10.94 | 10.76 | 10.93 | 10.75 | 10.65 | 10.87 | 10.46 |
| JLA66 | hsa-miR-432 | 6.00 | 6.00 | 6.00 | 6.00 | 6.00 | 6.00 | 6.00 | 6.00 | 6.00 |
| JLA83 | hsa-mir-425* | 6.00 | 6.00 | 6.77 | 7.81 | 8.68 | 7.65 | 7.36 | 6.86 | 6.00 |
| JLA84 | hsa-mir-92-1* | 6.00 | 6.00 | 6.00 | 7.03 | 6.00 | 6.00 | 6.00 | 6.00 | 6.00 |
| JLA69 | hsa-mir-193* | 6.00 | 6.00 | 6.00 | 6.00 | 6.00 | 6.00 | 6.00 | 6.00 | 6.00 |
| JLA70 | hsa-miR-515-5p | 6.00 | 6.00 | 6.00 | 6.00 | 6.00 | 6.00 | 6.00 | 6.00 | 6.00 |
| JLA71 | hsa-mir-516-1* | 6.00 | 6.00 | 6.00 | 6.00 | 6.00 | 6.00 | 6.00 | 6.00 | 6.00 |
| JLA85 | hsa-mir-30d* | 6.00 | 6.00 | 6.00 | 6.00 | 6.00 | 6.00 | 6.00 | 6.00 | 6.00 |
| JLA125 | h-miR-20b | 10.18 | 10.08 | 10.29 | 9.65 | 9.78 | 10.07 | 9.95 | 10.22 | 10.08 |
| JLA198 | h-miR-191* | 6.00 | 6.00 | 6.00 | 6.00 | 6.00 | 6.36 | 6.00 | 6.00 | 6.00 |
| JLA199 | h-miR-154* | 6.00 | 6.00 | 6.00 | 6.00 | 6.00 | 6.00 | 6.00 | 6.00 | 6.00 |
| EAM316 | h-miR-147 | 6.00 | 6.00 | 6.00 | 6.00 | 6.00 | 6.00 | 6.00 | 6.00 | 6.00 |
| EAM317 | h-miR-155 | 9.59 | 10.47 | 9.67 | 10.45 | 9.61 | 9.58 | 9.48 | 9.42 | 9.75 |
| EAM318 | h-miR-17-3p | 6.00 | 6.00 | 6.00 | 6.00 | 6.00 | 6.00 | 6.00 | 7.19 | 6.00 |
| JLA195 | h-miR-200a* | 6.00 | 6.00 | 6.00 | 6.00 | 6.00 | 6.00 | 6.00 | 6.00 | 6.00 |
| JLA196 | h-miR-302a* | 6.00 | 6.00 | 6.00 | 6.00 | 6.00 | 6.00 | 6.00 | 6.00 | 6.00 |
| JLA197 | h-miR-299-3p | 6.00 | 6.00 | 6.00 | 6.00 | 6.00 | 6.00 | 6.00 | 6.00 | 7.25 |
| EAM319 | h-miR-182* | 6.00 | 6.00 | 6.00 | 6.00 | 6.00 | 6.00 | 6.00 | 6.00 | 6.00 |
| EAM405 | h-miR-302b | 6.00 | 6.00 | 6.00 | 6.00 | 6.00 | 6.00 | 6.00 | 6.00 | 6.00 |
| EAM406 | h-miR-302b* | 6.00 | 6.00 | 6.00 | 6.00 | 6.00 | 6.00 | 6.00 | 6.00 | 6.00 |
| EAM392 | r-miR-352 | 6.25 | 7.91 | 7.30 | 8.16 | 7.22 | 8.24 | 7.61 | 7.55 | 7.24 |
| JLA123 | h-miR-423 | 6.00 | 6.00 | 6.00 | 6.00 | 6.00 | 6.00 | 6.00 | 6.00 | 6.00 |
| JLA124 | h-miR-18b | 6.00 | 6.00 | 6.00 | 7.59 | 6.00 | 6.00 | 6.00 | 8.06 | 8.14 |

| ProbeID | Description | ERY1_2 | ERY1_3 | ERY1_4 | ERY2_1 | ERY2_2 | ERY2_3 |
|---|---|---|---|---|---|---|---|
| EAM 190 | h-miR-10b | 6.00 | 6.99 | 6.75 | 6.00 | 6.00 | 7.96 |
| EAM 187 | hmr-miR-107 | 8.25 | 6.00 | 7.84 | 6.00 | 7.81 | 6.90 |
| EAM 185 | hmr-miR-103 | 8.79 | 6.00 | 8.39 | 6.00 | 8.34 | 7.93 |
| EAM181 | hmr-let-7f | 7.95 | 8.58 | 8.86 | 9.12 | 9.72 | 6.00 |
| EAM 179 | hmr-let-7d | 7.02 | 7.49 | 8.73 | 7.65 | 9.88 | 8.43 |
| EAM 177 | mr-miR-101b | 6.00 | 6.00 | 6.00 | 6.00 | 6.00 | 6.00 |
| EAM175 | hmr-miR-320 | 9.89 | 9.23 | 8.71 | 8.40 | 10.08 | 7.51 |
| EAM 168 | hmr-let-7e | 6.00 | 6.93 | 6.00 | 6.00 | 6.62 | 6.00 |
| EAM 161 | hmr-miR-28 | 6.00 | 6.00 | 6.00 | 6.00 | 6.08 | 6.00 |
| EAM160 | hmr-miR-26b | 8.10 | 8.96 | 9.69 | 9.37 | 9.42 | 7.41 |
| EAM 155 | hmr-miR-136 | 6.00 | 6.00 | 6.00 | 6.00 | 6.00 | 6.00 |
| EAM283 | mr-miR-211 | 6.00 | 6.00 | 6.00 | 6.00 | 6.00 | 6.00 |
| EAM282 | m-miR-199b | 6.00 | 6.00 | 6.00 | 6.00 | 6.00 | 6.00 |
| EAM281 | mr-miR-217 | 6.00 | 6.00 | 6.00 | 6.00 | 6.00 | 6.00 |
| EAM280 | hmr-miR-30a-3p | 6.00 | 6.00 | 6.00 | 6.00 | 6.00 | 6.00 |
| EAM279 | hmr-miR-29c | 6.00 | 6.00 | 6.00 | 6.00 | 6.00 | 6.00 |
| EAM278 | hmr-miR-98 | 6.00 | 6.00 | 6.00 | 6.25 | 6.00 | 6.00 |
| EAM270 | hmr-miR-30b | 8.99 | 7.63 | 8.95 | 8.53 | 9.45 | 7.95 |
| EAM159 | hmr-miR-130a | 8.43 | 8.44 | 7.06 | 6.00 | 8.49 | 9.20 |
| EAM 163 | hmr-miR-142-3p | 6.00 | 6.00 | 6.00 | 6.00 | 6.00 | 6.00 |
| EAM 171 | hmr-miR-137 | 6.00 | 6.00 | 6.00 | 6.00 | 6.00 | 6.00 |
| EAM306 | m-miR-201 | 6.00 | 6.00 | 6.00 | 6.00 | 6.00 | 6.00 |
| EAM307 | m-miR-202 | 6.00 | 6.00 | 6.00 | 6.00 | 6.00 | 7.33 |
| EAM308 | hmr-miR-206 | 6.00 | 6.00 | 6.00 | 6.00 | 6.00 | 6.00 |
| EAM309 | m-miR-207 | 6.00 | 6.00 | 6.00 | 7.37 | 6.00 | 6.00 |
| EAM310 | hmr-miR-208 | 6.00 | 6.00 | 6.00 | 6.00 | 6.00 | 6.00 |
| EAM247 | hmr-miR-212 | 6.00 | 6.37 | 6.00 | 6.00 | 6.00 | 6.00 |
| EAM251 | hmr-miR-216 | 6.00 | 6.00 | 6.00 | 6.00 | 6.00 | 6.00 |
| EAM253 | hmr-miR-218 | 6.00 | 6.00 | 6.00 | 6.00 | 6.00 | 6.00 |
| EAM275 | hmr-miR-34a | 6.00 | 6.00 | 6.00 | 6.00 | 6.00 | 6.00 |
| EAM246 | h-miR-211 | 6.00 | 6.00 | 6.00 | 6.00 | 6.00 | 6.00 |
| EAM250 | h-miR-215 | 6.00 | 6.00 | 6.92 | 6.00 | 6.00 | 6.00 |
| EAM252 | h-miR-217 | 6.00 | 6.00 | 6.00 | 6.00 | 6.00 | 6.00 |
| EAM224 | hmr-miR-17-5p | 11.52 | 10.93 | 10.34 | 10.89 | 10.35 | 11.50 |
| EAM225 | hmr-miR-18a | 7.13 | 7.50 | 6.00 | 6.00 | 6.00 | 7.18 |
| EAM226 | hmr-miR-181a | 7.91 | 9.01 | 7.64 | 6.00 | 8.20 | 6.00 |
| EAM227 | hmr-miR-181b | 6.95 | 7.06 | 6.00 | 6.00 | 7.97 | 6.00 |
| EAM234 | hmr-miR-199a | 6.00 | 6.00 | 6.00 | 6.00 | 6.00 | 6.00 |
| EAM235 | h-miR-199b | 6.00 | 6.00 | 6.00 | 6.00 | 6.00 | 6.00 |
| EAM236 | hmr-miR-19a | 7.76 | 8.02 | 7.53 | 8.50 | 7.41 | 7.49 |
| EAM241 | hmr-miR-203 | 6.00 | 6.00 | 6.00 | 6.00 | 6.00 | 6.00 |
| EAM242 | hmr-miR-204 | 6.00 | 6.00 | 6.00 | 6.00 | 6.00 | 6.00 |
| EAM243 | hmr-miR-205 | 6.00 | 6.00 | 6.00 | 6.00 | 6.00 | 6.00 |
| EAM245 | hmr-miR-210 | 6.00 | 6.00 | 6.48 | 6.00 | 6.00 | 6.00 |
| EAM249 | hmr-miR-214 | 6.00 | 6.00 | 6.00 | 6.00 | 6.00 | 6.00 |
| EAM184 | hmr-miR-100 | 6.00 | 6.00 | 6.00 | 6.00 | 6.00 | 6.00 |
| EAM186 | h-miR-106a | 11.18 | 10.83 | 10.11 | 10.62 | 10.16 | 11.33 |
| EAM189 | hmr-miR-10a | 6.00 | 7.49 | 9.10 | 6.00 | 6.43 | 6.00 |
| EAM191 | hmr-miR-122a | 6.00 | 6.00 | 7.20 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM192 | hmr-miR-126* | 7.58 | 8.43 | 8.67 | 6.00 | 6.00 | 6.00 |
| EAM198 | hmr-miR-130b | 6.00 | 6.01 | 6.00 | 6.00 | 7.44 | 6.00 |
| EAM202 | hmr-miR-134 | 6.00 | 6.00 | 6.00 | 6.00 | 6.00 | 6.00 |
| EAM209 | hmr-miR-142-5p | 8.13 | 6.00 | 6.75 | 6.77 | 7.48 | 8.09 |
| EAM221 | m-miR-155 | 7.36 | 7.54 | 6.00 | 6.59 | 7.89 | 6.00 |
| EAM223 | hmr-miR-15b | 10.30 | 9.57 | 10.03 | 11.29 | 10.88 | 11.16 |
| EAM228 | hmr-miR-181c | 6.00 | 6.00 | 6.00 | 6.00 | 6.00 | 6.00 |
| EAM222 | hm-miR-15a | 7.27 | 8.26 | 6.00 | 8.36 | 9.42 | 10.08 |
| EAM111 | hm-let-7g | 8.71 | 9.39 | 9.63 | 9.43 | 10.51 | 10.13 |
| EAM131 | hmr-miR-92 | 11.87 | 11.49 | 9.87 | 11.68 | 11.05 | 9.45 |
| EAM139 | hmr-miR-146a | 7.16 | 9.30 | 8.85 | 6.00 | 9.34 | 10.46 |
| EAM145 | hmr-let-7c | 8.87 | 10.13 | 10.11 | 9.49 | 9.50 | 9.31 |
| EAM109 | hmr-miR-7 | 6.00 | 6.00 | 6.00 | 6.00 | 6.00 | 6.00 |
| EAM152 | hm-miR-9* | 6.00 | 6.00 | 6.00 | 6.00 | 6.00 | 6.00 |
| JLA215 | hmr-let-7i | 6.00 | 6.35 | 9.31 | 7.17 | 8.40 | 9.25 |
| EAM153 | hmr-let-7a | 10.73 | 11.16 | 12.01 | 10.47 | 10.87 | 11.26 |
| EAM147 | hmr-let-7b | 7.57 | 9.14 | 8.77 | 9.57 | 9.66 | 6.51 |
| EAM137 | hmr-miR-132 | 6.00 | 6.00 | 6.00 | 6.00 | 6.00 | 6.00 |
| EAM133 | hmr-miR-324-5p | 6.00 | 6.00 | 6.00 | 6.00 | 6.00 | 6.00 |
| EAM103 | hmr-miR-124a | 6.00 | 6.00 | 6.00 | 6.00 | 6.00 | 6.21 |
| EAM105 | hmr-miR-125b | 7.21 | 7.24 | 7.48 | 6.00 | 6.34 | 6.00 |
| EAM121 | hmr-miR-99a | 6.00 | 6.00 | 6.00 | 6.00 | 6.00 | 6.00 |
| EAM115 | hmr-miR-16 | 12.08 | 12.26 | 12.61 | 12.97 | 12.35 | 12.37 |
| EAM119 | hmr-miR-29b | 6.00 | 6.00 | 6.00 | 6.00 | 6.00 | 6.00 |
| EAM311 | hmr-miR-101 | 6.00 | 6.24 | 6.18 | 6.00 | 6.00 | 6.00 |
| EAM312 | h-miR-105 | 6.00 | 6.00 | 6.00 | 6.00 | 6.00 | 6.00 |
| EAM313 | hmr-miR-106b | 8.64 | 8.72 | 9.09 | 9.65 | 7.84 | 9.00 |
| EAM314 | hmr-miR-126 | 10.18 | 11.18 | 11.85 | 7.84 | 9.11 | 6.00 |
| EAM315 | hmr-miR-127 | 6.00 | 6.00 | 6.00 | 6.00 | 6.00 | 6.00 |
| EAM320 | hm-miR-189 | 6.00 | 6.00 | 6.00 | 6.00 | 6.00 | 6.00 |
| JLA216 | hmr-miR-200c | 6.00 | 6.00 | 6.00 | 6.00 | 7.88 | 6.00 |
| EAM323 | h-miR-224 | 6.00 | 6.00 | 6.00 | 6.00 | 6.00 | 6.00 |
| EAM324 | hmr-miR-25 | 8.01 | 8.81 | 6.04 | 7.43 | 8.29 | 6.00 |
| EAM386 | r-miR-336 | 6.00 | 6.00 | 6.00 | 6.00 | 6.00 | 6.00 |
| JLA218 | r-miR-343 | 6.00 | 6.00 | 6.00 | 6.00 | 6.00 | 6.00 |
| EAM388 | r-miR-344 | 6.00 | 6.00 | 6.00 | 6.00 | 6.00 | 6.00 |
| EAM338 | h-miR-95 | 6.00 | 6.00 | 6.00 | 6.00 | 6.00 | 6.00 |
| JLA214 | hmr-miR-129 | 6.00 | 6.00 | 6.00 | 6.00 | 6.00 | 6.00 |
| EAM340 | mr-let-7d* | 6.00 | 7.18 | 6.00 | 6.00 | 6.00 | 6.00 |
| EAM341 | m-miR-106a | 10.77 | 10.26 | 10.07 | 10.38 | 9.39 | 10.73 |
| EAM342 | hmr-miR-135b | 6.00 | 6.00 | 6.00 | 6.00 | 6.00 | 6.00 |
| EAM343 | mr-miR-151 | 6.00 | 6.00 | 6.00 | 6.00 | 6.00 | 6.00 |
| EAM344 | m-miR-17-3p | 6.00 | 6.00 | 6.00 | 6.00 | 6.00 | 6.00 |
| EAM345 | m-miR-224 | 6.00 | 6.00 | 6.00 | 6.00 | 6.00 | 6.00 |
| EAM346 | mr-miR-290 | 6.00 | 6.00 | 6.00 | 6.00 | 6.00 | 6.00 |
| EAM347 | mr-miR-291-3p | 6.00 | 6.00 | 6.00 | 6.00 | 6.00 | 6.00 |
| EAM348 | mr-miR-291-5p | 6.00 | 6.00 | 6.00 | 6.00 | 6.00 | 6.00 |
| EAM349 | mr-miR-292-3p | 6.00 | 6.00 | 7.71 | 6.00 | 6.00 | 6.00 |
| EAM350 | mr-miR-292-5p | 6.00 | 6.00 | 6.00 | 6.00 | 6.00 | 6.00 |
| EAM351 | m-miR-293 | 6.00 | 6.00 | 6.00 | 8.36 | 6.00 | 6.45 |
| EAM352 | m-miR-294 | 6.00 | 6.00 | 6.00 | 6.00 | 6.00 | 6.00 |
| EAM353 | m-miR-295 | 6.00 | 6.00 | 6.00 | 6.00 | 6.00 | 6.00 |
| EAM354 | m-miR-297 | 6.00 | 6.00 | 6.00 | 6.00 | 6.00 | 6.00 |
| EAM355 | mr-miR-298 | 6.00 | 6.00 | 6.00 | 6.00 | 6.00 | 6.00 |
| EAM356 | mr-miR-300 | 6.00 | 6.00 | 6.00 | 6.00 | 6.00 | 6.00 |
| EAM358 | hmr-miR-323 | 6.00 | 6.00 | 6.00 | 6.00 | 6.00 | 6.00 |
| EAM359 | hmr-miR-324-3p | 6.00 | 6.00 | 6.00 | 6.00 | 6.00 | 6.00 |
| EAM360 | mr-miR-325 | 6.00 | 6.00 | 7.44 | 6.00 | 6.00 | 6.39 |
| EAM361 | hmr-miR-326 | 6.00 | 6.00 | 6.00 | 6.00 | 6.00 | 6.00 |
| EAM362 | hmr-miR-328 | 6.00 | 6.00 | 6.00 | 6.00 | 6.00 | 6.00 |
| EAM363 | mr-miR-329 | 6.00 | 6.00 | 6.00 | 6.00 | 6.00 | 6.00 |
| EAM365 | hmr-miR-331 | 6.00 | 6.00 | 6.00 | 6.00 | 6.00 | 6.00 |
| EAM366 | mr-miR-337 | 6.00 | 6.00 | 6.00 | 6.00 | 6.00 | 6.00 |
| EAM367 | hmr-miR-338 | 6.00 | 6.00 | 6.00 | 6.00 | 6.00 | 6.00 |
| EAM368 | hmr-miR-339 | 6.00 | 6.00 | 6.00 | 6.00 | 6.00 | 6.00 |
| EAM369 | hmr-miR-340 | 6.00 | 6.00 | 6.00 | 6.00 | 6.00 | 6.00 |
| EAM370 | mr-miR-341 | 6.00 | 6.00 | 6.00 | 6.00 | 6.00 | 6.00 |
| EAM371 | hmr-miR-342 | 7.83 | 6.00 | 6.00 | 9.42 | 10.64 | 9.88 |
| EAM372 | m-miR-344 | 6.00 | 6.00 | 6.00 | 6.00 | 6.00 | 6.00 |
| EAM373 | mr-miR-345 | 6.00 | 6.00 | 6.00 | 6.00 | 6.00 | 6.00 |
| EAM374 | m-miR-346 | 6.00 | 6.00 | 6.00 | 6.00 | 6.00 | 6.00 |
| EAM375 | mr-miR-34b | 6.00 | 6.00 | 6.00 | 6.00 | 6.00 | 6.00 |
| JLA217 | mr-miR-350 | 6.00 | 6.00 | 6.00 | 6.00 | 6.00 | 6.00 |
| EAM377 | mr-miR-351 | 6.00 | 6.00 | 6.00 | 6.00 | 6.00 | 6.00 |
| EAM378 | mr-miR-7b | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM382 | r-miR-20* | 6.00 | 6.00 | 6.00 | 6.00 | 6.00 | 6.00 |
| EAM383 | r-miR-327 | 6.00 | 6.00 | 6.00 | 6.00 | 6.00 | 6.00 |
| EAM384 | r-miR-333 | 6.00 | 6.00 | 6.00 | 6.00 | 6.00 | 6.00 |
| EAM385 | hmr-miR-335 | 7.14 | 6.00 | 6.00 | 6.00 | 6.00 | 6.00 |
| EAM393 | r-miR-7* | 6.00 | 6.00 | 6.00 | 6.00 | 6.00 | 6.00 |
| EAM304 | hmr-miR-200a | 6.00 | 6.00 | 6.00 | 6.00 | 6.00 | 6.00 |
| EAM298 | hmr-miR-194 | 6.07 | 6.00 | 6.00 | 6.00 | 6.00 | 6.00 |
| JLA221 | hmr-miR-191 | 8.31 | 6.00 | 6.60 | 8.62 | 7.95 | 7.15 |
| EAM295 | hmr-miR-190 | 6.00 | 6.00 | 6.00 | 6.00 | 6.00 | 6.00 |
| EAM292 | hmr-miR-186 | 6.00 | 6.00 | 6.00 | 6.00 | 6.00 | 6.00 |
| JLA219 | hmr-miR-185 | 6.00 | 7.21 | 6.00 | 6.54 | 7.12 | 6.00 |
| EAM290 | hmr-miR-184 | 6.00 | 6.21 | 6.00 | 6.00 | 6.00 | 6.00 |
| EAM402 | hm-miR-133b | 6.00 | 6.00 | 7.29 | 6.00 | 6.00 | 6.00 |
| EAM403 | h-miR-151 | 6.00 | 6.00 | 6.00 | 6.00 | 6.00 | 6.00 |
| EAM404 | hmr-miR-196b | 6.00 | 6.00 | 6.00 | 6.00 | 6.00 | 6.00 |
| EAM418 | hm-miR-370 | 6.00 | 6.00 | 6.00 | 6.00 | 6.00 | 6.00 |
| EAM419 | h-miR-371 | 6.00 | 6.00 | 6.00 | 6.00 | 6.00 | 6.00 |
| EAM420 | h-miR-372 | 6.00 | 6.00 | 6.00 | 6.00 | 6.00 | 6.00 |
| EAM421 | h-miR-373 | 6.00 | 6.00 | 6.00 | 6.00 | 6.00 | 6.00 |
| EAM422 | h-miR-373* | 6.00 | 6.00 | 6.00 | 6.00 | 6.00 | 6.00 |
| EAM423 | h-miR-374 | 6.00 | 7.19 | 7.18 | 6.25 | 7.10 | 6.61 |
| EAM426 | m-miR-215 | 6.00 | 6.00 | 6.00 | 6.00 | 6.00 | 6.00 |
| EAM427 | hm-miR-409-3p | 6.54 | 6.00 | 6.00 | 6.00 | 6.00 | 6.00 |
| EAM428 | hm-miR-410 | 6.00 | 6.00 | 6.00 | 6.00 | 6.00 | 6.00 |
| EAM429 | m-miR-376b | 6.00 | 6.00 | 6.00 | 6.00 | 6.00 | 6.00 |
| EAM430 | m-miR-376a | 6.00 | 6.00 | 6.00 | 6.00 | 6.00 | 6.00 |
| EAM431 | m-miR-411 | 6.00 | 6.00 | 6.00 | 6.00 | 6.00 | 6.00 |
| EAM432 | m-miR-380-3p | 6.00 | 6.00 | 6.00 | 6.00 | 6.00 | 6.00 |
| EAM433 | hm-miR-412 | 6.00 | 6.00 | 6.00 | 6.00 | 6.00 | 6.00 |
| EAM264 | hmr-miR-27b | 6.00 | 6.00 | 8.78 | 6.80 | 6.95 | 8.02 |
| EAM263 | hmr-miR-26a | 9.27 | 9.43 | 9.90 | 9.27 | 9.26 | 8.54 |
| EAM262 | hmr-miR-24 | 6.00 | 6.00 | 8.39 | 7.36 | 6.00 | 6.00 |
| EAM261 | hmr-miR-23b | 7.59 | 8.64 | 8.06 | 7.72 | 8.59 | 8.34 |
| EAM260 | hmr-miR-23a | 8.42 | 9.19 | 8.03 | 8.11 | 8.60 | 8.55 |
| EAM256 | h-miR-220 | 6.00 | 6.00 | 6.00 | 6.00 | 6.00 | 6.00 |
| EAM255 | hmr-miR-22 | 6.00 | 6.00 | 6.00 | 6.00 | 6.00 | 6.00 |
| EAM248 | hmr-miR-213 | 6.00 | 6.00 | 6.00 | 6.00 | 6.00 | 6.00 |
| EAM244 | hmr-miR-21 | 8.34 | 8.60 | 6.73 | 6.00 | 8.29 | 7.93 |
| EAM240 | hmr-miR-20a | 11.40 | 11.35 | 9.92 | 11.02 | 10.86 | 12.04 |
| EAM237 | hmr-miR-19b | 8.65 | 9.13 | 8.54 | 9.35 | 8.39 | 8.54 |
| EAM233 | hmr-miR-196a | 6.00 | 6.00 | 6.00 | 6.00 | 6.00 | 6.00 |
| EAM214 | hm-miR-148a | 6.00 | 6.00 | 6.00 | 6.00 | 6.00 | 6.00 |
| EAM212 | hmr-miR-145 | 6.00 | 6.00 | 6.00 | 6.00 | 6.00 | 6.00 |
| EAM211 | hmr-miR-144 | 6.00 | 6.00 | 6.00 | 8.80 | 6.00 | 8.40 |
| EAM210 | hmr-miR-143 | 6.00 | 6.00 | 6.00 | 6.00 | 6.00 | 6.00 |
| EAM389 | r-miR-346 | 6.00 | 6.00 | 6.00 | 6.00 | 6.00 | 6.00 |
| EAM390 | r-miR-347 | 6.00 | 6.00 | 6.00 | 6.00 | 6.00 | 6.00 |
| EAM391 | r-miR-349 | 6.00 | 6.00 | 6.00 | 6.00 | 6.00 | 6.00 |
| JLA223 | hmr-miR-33 | 6.00 | 6.00 | 6.00 | 6.00 | 6.00 | 6.00 |
| EAM277 | hmr-miR-96 | 6.00 | 6.00 | 6.00 | 6.00 | 6.00 | 6.00 |
| EAM276 | hmr-miR-9 | 6.00 | 6.00 | 6.00 | 6.00 | 6.00 | 6.00 |
| EAM272 | hmr-miR-30d | 8.59 | 6.70 | 8.78 | 7.19 | 8.38 | 6.00 |
| EAM288 | mr-miR-10b | 6.00 | 6.00 | 7.04 | 6.00 | 6.00 | 7.72 |
| EAM293 | hm-miR-188 | 6.00 | 6.00 | 6.00 | 6.00 | 6.00 | 6.00 |
| EAM297 | hmr-miR-193a | 6.00 | 6.00 | 6.00 | 6.00 | 6.00 | 6.00 |
| EAM301 | h-miR-198 | 6.00 | 6.00 | 6.00 | 6.00 | 6.00 | 6.00 |
| EAM232 | hmr-miR-192 | 6.00 | 6.00 | 6.00 | 6.00 | 6.00 | 6.00 |
| EAM231 | hmr-miR-187 | 6.00 | 6.00 | 6.00 | 6.00 | 6.00 | 6.00 |
| EAM230 | hmr-miR-183 | 6.00 | 6.00 | 6.00 | 6.00 | 6.00 | 6.00 |
| EAM229 | hm-miR-182 | 6.00 | 6.00 | 6.00 | 6.39 | 6.00 | 6.00 |
| EAM220 | hmr-miR-154 | 6.00 | 6.00 | 6.00 | 6.00 | 6.00 | 6.00 |
| EAM219 | hmr-miR-153 | 6.00 | 6.00 | 6.00 | 6.00 | 6.00 | 6.00 |
| EAM218 | hmr-miR-152 | 6.00 | 6.00 | 6.00 | 6.00 | 6.00 | 6.00 |
| EAM217 | hmr-miR-150 | 6.00 | 6.00 | 8.16 | 6.79 | 9.98 | 6.00 |
| EAM216 | hm-miR-149 | 6.00 | 6.00 | 6.00 | 6.00 | 6.00 | 6.00 |
| EAM215 | hmr-miR-148b | 6.00 | 6.83 | 6.00 | 6.00 | 6.00 | 6.00 |
| EAM271 | hmr-miR-30c | 9.13 | 7.46 | 8.56 | 8.72 | 9.62 | 7.65 |
| EAM268 | hmr-miR-29a | 6.00 | 6.00 | 6.85 | 6.00 | 6.20 | 6.00 |
| EAM305 | hmr-miR-200b | 6.00 | 6.00 | 6.00 | 6.00 | 7.01 | 6.00 |
| EAM303 | hm-miR-199a* | 6.00 | 6.00 | 6.00 | 6.00 | 6.00 | 6.00 |
| EAM300 | h-miR-197 | 8.29 | 8.88 | 7.83 | 8.40 | 8.70 | 6.00 |
| EAM299 | hmr-miR-195 | 9.77 | 9.49 | 9.17 | 10.48 | 9.03 | 9.81 |
| JLA91 | hmr-miR-99b | 10.42 | 6.63 | 8.77 | 6.00 | 6.00 | 6.00 |
| JLA92 | hmr-miR-433 | 6.00 | 6.00 | 6.00 | 6.00 | 6.00 | 6.00 |
| JLA93 | hmr-miR-431 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| JLA94 | hmr-miR-365 | 6.06 | 7.03 | 7.03 | 6.00 | 6.00 | 8.39 |
| JLA95 | hmr-miR-450 | 6.00 | 6.00 | 6.00 | 6.00 | 6.00 | 6.00 |
| JLA96 | hmr-miR-449 | 6.00 | 6.00 | 6.00 | 6.00 | 6.00 | 6.00 |
| JLA99 | hmr-miR-448 | 6.00 | 6.00 | 6.00 | 6.00 | 6.00 | 6.00 |
| JLA103 | hmr-miR-424 | 6.00 | 9.39 | 9.21 | 6.98 | 6.00 | 6.00 |
| JLA105 | hm-miR-361 | 6.00 | 8.25 | 6.00 | 6.00 | 6.00 | 6.00 |
| JLA106 | hm-miR-375 | 6.00 | 6.00 | 6.00 | 6.00 | 6.00 | 6.00 |
| JLA107 | hm-miR-377 | 6.00 | 6.00 | 6.00 | 6.00 | 6.00 | 6.00 |
| JLA108 | hm-miR-378 | 6.00 | 6.00 | 6.00 | 6.00 | 6.00 | 6.00 |
| JLA109 | hm-miR-379 | 6.00 | 6.00 | 6.00 | 6.00 | 6.00 | 6.00 |
| JLA110 | hm-miR-380-5p | 6.00 | 6.00 | 6.00 | 6.00 | 6.00 | 6.00 |
| JLA111 | hm-miR-381 | 6.00 | 6.00 | 6.00 | 6.00 | 6.00 | 6.00 |
| JLA112 | hm-miR-382 | 8.83 | 6.00 | 6.00 | 6.00 | 7.08 | 6.00 |
| JLA115 | hm-miR-384 | 6.00 | 6.00 | 6.00 | 6.00 | 6.00 | 6.00 |
| JLA116 | hm-miR-425 | 6.00 | 6.00 | 6.00 | 6.00 | 6.00 | 6.00 |
| JLA117 | hm-miR-452 | 6.00 | 6.00 | 6.00 | 6.00 | 6.00 | 6.00 |
| JLA118 | hm-miR-30e-3p | 6.00 | 6.00 | 6.00 | 6.00 | 6.00 | 6.00 |
| JLA104 | mr-miR-129-3p | 7.18 | 6.00 | 6.00 | 6.24 | 6.00 | 7.62 |
| JLA98 | mr-miR-429 | 6.00 | 6.00 | 6.00 | 6.00 | 6.00 | 6.00 |
| JLA101 | mr-miR-330 | 6.00 | 6.00 | 6.00 | 6.00 | 6.00 | 6.00 |
| JLA102 | mr-miR-322 | 6.00 | 6.00 | 6.00 | 6.00 | 6.00 | 6.00 |
| JLA114 | m-miR-383 | 6.00 | 6.00 | 6.00 | 6.00 | 6.00 | 6.00 |
| JLA5 | hmr-miR-451 | 6.00 | 6.15 | 7.06 | 9.77 | 7.29 | 6.77 |
| JLA201 | r-miR-421 | 6.00 | 6.00 | 6.00 | 6.00 | 6.00 | 6.00 |
| JLA202 | m-miR-463 | 6.00 | 6.00 | 6.00 | 6.00 | 6.00 | 6.00 |
| JLA203 | m-miR-464 | 6.00 | 6.00 | 6.00 | 6.00 | 6.00 | 6.00 |
| JLA204 | m-miR-465 | 6.00 | 6.00 | 6.00 | 6.00 | 6.00 | 6.00 |
| JLA205 | m-miR-466 | 6.00 | 6.00 | 6.00 | 6.00 | 6.00 | 7.54 |
| JLA206 | m-miR-467 | 6.00 | 6.00 | 6.00 | 6.00 | 6.00 | 6.00 |
| JLA207 | m-miR-468 | 6.00 | 6.00 | 6.00 | 6.00 | 6.00 | 6.00 |
| JLA208 | m-miR-469 | 6.00 | 6.00 | 6.00 | 6.00 | 6.00 | 6.00 |
| JLA209 | m-miR-470 | 6.00 | 6.00 | 6.00 | 6.00 | 6.00 | 6.00 |
| JLA210 | m-miR-471 | 6.00 | 6.00 | 6.00 | 6.00 | 6.00 | 6.00 |
| EAM325 | hmr-miR-27a | 6.00 | 6.00 | 8.84 | 7.51 | 7.75 | 9.09 |
| EAM326 | hmr-miR-296 | 6.00 | 6.00 | 6.00 | 6.00 | 6.00 | 6.00 |
| EAM327 | hmr-miR-299- | 6.00 | 6.00 | 6.00 | 6.00 | 6.00 | 6.00 |
| EAM328 | hmr-miR-301 | 6.00 | 6.00 | 6.00 | 6.09 | 6.00 | 6.00 |
| EAM329 | hm-miR-302a | 6.00 | 6.00 | 6.00 | 6.00 | 6.00 | 6.00 |
| EAM330 | hmr-miR-30a- | 6.05 | 6.84 | 8.16 | 6.64 | 6.71 | 6.00 |
| EAM331 | hmr-miR-30e- | 6.00 | 6.00 | 6.00 | 6.00 | 6.00 | 6.00 |
| EAM332 | hmr-miR-31 | 6.00 | 6.00 | 6.00 | 6.00 | 6.00 | 6.00 |
| EAM333 | hmr-miR-32 | 6.00 | 7.53 | 6.00 | 6.00 | 6.00 | 6.00 |
| EAM335 | h-miR-34b | 6.00 | 6.00 | 6.00 | 6.00 | 6.00 | 6.00 |
| EAM336 | hmr-miR-34c | 6.00 | 6.00 | 6.00 | 6.00 | 6.00 | 6.00 |
| EAM337 | hmr-miR-93 | 9.86 | 7.32 | 6.00 | 9.38 | 9.47 | 8.20 |
| EAM208 | hmr-miR-141 | 6.00 | 6.00 | 6.00 | 6.00 | 6.00 | 6.00 |
| EAM207 | hmr-miR-140 | 6.00 | 6.00 | 6.00 | 6.00 | 6.00 | 6.00 |
| JLA222 | hmr-miR-139 | 6.00 | 6.00 | 6.00 | 6.00 | 6.00 | 6.00 |
| JLA220 | hmr-miR-138 | 6.00 | 6.00 | 6.00 | 6.00 | 6.00 | 6.00 |
| EAM203 | hmr-miR-135a | 6.00 | 6.00 | 6.00 | 6.00 | 6.00 | 6.00 |
| EAM200 | hmr-miR-133a | 6.00 | 6.00 | 7.18 | 6.00 | 6.00 | 6.00 |
| EAM | hmr-miR-128b | 6.00 | 6.00 | 6.00 | 6.00 | 6.00 | 6.00 |
| EAM | hmr-miR-128a | 6.00 | 6.00 | 6.00 | 6.00 | 6.00 | 6.00 |
| EAM254 | hmr-miR-219 | 6.00 | 6.00 | 6.00 | 6.00 | 6.00 | 6.00 |
| EAM257 | hmr-miR-221 | 6.00 | 7.88 | 6.00 | 6.00 | 6.00 | 6.00 |
| EAM258 | hmr-miR-222 | 6.90 | 7.15 | 7.46 | 7.68 | 8.11 | 6.00 |
| EAM259 | hmr-miR-223 | 8.26 | 6.46 | 6.31 | 9.11 | 8.85 | 8.89 |
| JLA211 | m-miR-434-5p | 6.00 | 6.00 | 6.00 | 6.00 | 6.00 | 6.00 |
| JLA212 | m-miR-434-3p | 6.00 | 6.00 | 6.00 | 6.00 | 6.00 | 6.00 |
| JLA213 | m-miR-433-5p | 6.00 | 6.00 | 6.00 | 6.00 | 6.00 | 6.00 |
| JLA2 | hsa-miR-522 | 6.00 | 6.00 | 6.86 | 6.00 | 6.00 | 6.00 |
| JLA3 | hsa-miR-495 | 6.00 | 6.00 | 6.00 | 6.00 | 6.00 | 6.00 |
| JLA200 | r-miR-297 | 6.00 | 6.00 | 6.00 | 6.00 | 6.00 | 6.00 |
| JLA6 | hsa-miR-518e | 6.00 | 6.00 | 6.00 | 6.00 | 6.00 | 6.00 |
| JLA7 | hsa-miR-519a | 6.00 | 6.80 | 7.83 | 6.00 | 6.00 | 6.00 |
| JLA8 | hsa-mir-527* | 6.00 | 6.00 | 6.00 | 6.00 | 6.00 | 6.00 |
| JLA72 | hmr-miR-140* | 6.00 | 6.00 | 6.01 | 6.00 | 8.10 | 6.00 |
| JLA10 | hsa-miR-521 | 6.00 | 6.00 | 6.00 | 6.00 | 6.00 | 6.00 |
| JLA12 | hsa-miR-362 | 6.00 | 6.00 | 6.00 | 6.00 | 6.00 | 6.00 |
| JLA74 | hsa-mir-18* | 6.00 | 6.00 | 6.00 | 6.00 | 6.00 | 6.00 |
| JLA14 | hm-miR-363 | 6.00 | 6.00 | 6.00 | 6.00 | 6.00 | 6.00 |
| JLA77 | hsa-mir-19b-1* | 6.00 | 6.00 | 6.00 | 6.00 | 6.00 | 6.00 |
| JLA17 | hsa-mir-520c,b,f | 6.00 | 6.00 | 6.69 | 6.00 | 6.00 | 6.00 |
| JLA79 | hsa-mir-23a* | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| JLA20 | hsa-miR-369-5p | 6.00 | 6.00 | 6.00 | 6.00 | 6.00 | 6.00 |
| JLA81 | hsa-mir-339* | 6.00 | 6.00 | 6.00 | 6.00 | 6.00 | 6.00 |
| JLA23 | hsa-mir-342* | 7.31 | 6.00 | 6.00 | 6.00 | 6.00 | 6.00 |
| JLA24 | hsa-mir-19a* | 6.00 | 6.00 | 6.00 | 6.00 | 6.00 | 6.00 |
| JLA26 | hsa-miR-517a,b | 9.19 | 9.68 | 9.88 | 6.00 | 6.00 | 6.00 |
| JLA27 | hsa-miR-516-5p | 8.01 | 7.22 | 8.30 | 6.00 | 6.00 | 6.00 |
| JLA28 | hsa-miR-518b | 6.00 | 6.00 | 6.10 | 6.00 | 6.00 | 6.00 |
| JLA29 | hsa-miR-519d | 6.00 | 8.31 | 9.35 | 6.00 | 6.00 | 6.00 |
| JLA73 | hr-mir-151* | 8.47 | 6.00 | 6.00 | 6.00 | 7.04 | 6.00 |
| JLA31 | hsa-mir-28* | 6.00 | 6.00 | 6.00 | 6.00 | 6.00 | 6.00 |
| JLA33 | hsa-mir-519a-2* | 6.00 | 6.00 | 6.00 | 6.00 | 6.00 | 6.00 |
| JLA34 | hsa-mir-26b* | 6.00 | 6.00 | 6.00 | 6.00 | 6.00 | 6.00 |
| JLA35 | hsa-miR-526c | 6.00 | 6.00 | 6.00 | 6.00 | 6.00 | 6.00 |
| JLA36 | hsa-miR-527 | 6.00 | 6.00 | 6.00 | 6.00 | 6.00 | 6.00 |
| JLA38 | hsa-mir-29b-2* | 6.00 | 6.00 | 6.00 | 6.00 | 6.00 | 6.00 |
| JLA39 | hsa-let-7g* | 6.00 | 6.00 | 6.00 | 6.00 | 6.00 | 6.00 |
| JLA40 | hsa-miR-518a | 6.00 | 6.00 | 6.00 | 6.00 | 6.00 | 6.00 |
| JLA41 | hsa-miR-523 | 6.00 | 6.00 | 6.00 | 6.00 | 6.00 | 6.00 |
| JLA44 | hsa-miR-515-3p | 6.00 | 6.00 | 6.00 | 6.00 | 6.00 | 6.00 |
| JLA45 | hsa-mir-146b* | 6.00 | 6.00 | 6.00 | 6.00 | 6.00 | 6.00 |
| JLA49 | hsa-mir-222* | 6.00 | 6.00 | 6.00 | 6.00 | 6.00 | 6.00 |
| JLA53 | hsa-mir-24* | 6.00 | 6.00 | 6.00 | 6.00 | 6.00 | 6.00 |
| JLA55 | hsa-miR-503 | 6.00 | 6.00 | 6.00 | 6.00 | 6.00 | 6.00 |
| JLA57 | hsa-mir-505 | 6.00 | 6.00 | 6.00 | 6.00 | 6.00 | 6.00 |
| JLA82 | hsa-mir-423* | 10.59 | 11.08 | 10.84 | 10.71 | 10.99 | 9.16 |
| JLA66 | hsa-miR-432 | 6.00 | 6.00 | 6.00 | 6.00 | 6.00 | 6.00 |
| JLA83 | hsa-mir-425* | 6.69 | 9.11 | 6.64 | 8.35 | 7.69 | 6.00 |
| JLA84 | hsa-mir-92-1* | 6.00 | 6.00 | 6.00 | 6.00 | 6.00 | 6.00 |
| JLA69 | hsa-mir-193* | 6.00 | 6.00 | 6.00 | 6.00 | 6.00 | 6.88 |
| JLA70 | hsa-miR-515-5p | 6.00 | 6.00 | 6.00 | 6.00 | 6.00 | 6.00 |
| JLA71 | hsa-mir-516-1* | 6.00 | 6.00 | 6.00 | 6.00 | 6.00 | 6.00 |
| JLA85 | hsa-mir-30d* | 6.00 | 6.00 | 6.00 | 6.00 | 6.00 | 6.00 |
| JLA125 | h-miR-20b | 10.33 | 10.27 | 8.32 | 9.68 | 9.66 | 11.07 |
| JLA198 | h-miR-191* | 6.30 | 6.00 | 6.00 | 7.24 | 6.00 | 6.58 |
| JLA199 | h-miR-154* | 6.00 | 6.00 | 6.00 | 6.00 | 6.00 | 6.00 |
| EAM316 | h-miR-147 | 6.00 | 6.00 | 6.00 | 6.00 | 6.00 | 6.00 |
| EAM317 | h-miR-155 | 8.97 | 9.50 | 7.69 | 8.48 | 9.68 | 7.96 |
| EAM318 | h-miR-17-3p | 6.00 | 6.00 | 6.00 | 6.00 | 6.00 | 6.00 |
| JLA195 | h-miR-200a* | 6.00 | 6.00 | 6.00 | 6.00 | 6.00 | 6.00 |
| JLA196 | h-miR-302a* | 6.00 | 6.00 | 6.00 | 6.00 | 6.00 | 6.00 |
| JLA197 | h-miR-299-3p | 6.41 | 6.00 | 6.82 | 6.00 | 6.78 | 7.18 |
| EAM319 | h-miR-182* | 6.00 | 6.00 | 6.00 | 6.00 | 6.00 | 6.00 |
| EAM405 | h-miR-302b | 6.00 | 6.00 | 6.00 | 6.00 | 6.00 | 6.00 |
| EAM406 | h-miR-302b* | 6.00 | 6.00 | 6.00 | 6.00 | 6.00 | 6.00 |
| EAM392 | r-miR-352 | 6.00 | 6.00 | 6.96 | 6.00 | 8.26 | 7.14 |
| JLA123 | h-miR-423 | 6.00 | 6.00 | 6.00 | 6.00 | 6.00 | 6.00 |
| JLA124 | h-miR-18b | 7.00 | 7.20 | 6.00 | 6.00 | 6.00 | 7.50 |

| ProbeID | Description | ERY3_1 | ERY3_2 | MEGA1_1 | MEGA1_2 | MEGA1_3 | MEGA1_4 |
|---|---|---|---|---|---|---|---|
| EAM 190 | h-miR-10b | 6.06 | 6.00 | 6.00 | 6.00 | 6.00 | 6.00 |
| EAM 187 | hmr-miR-107 | 6.00 | 7.49 | 8.75 | 6.30 | 6.68 | 6.79 |
| EAM 185 | hmr-miR-103 | 6.00 | 7.79 | 9.02 | 6.76 | 7.19 | 7.67 |
| EAM181 | hmr-let-7f | 9.09 | 8.47 | 9.80 | 9.53 | 8.57 | 10.11 |
| EAM179 | hmr-let-7d | 9.02 | 9.01 | 9.57 | 9.31 | 8.27 | 8.89 |
| EAM177 | mr-miR-101b | 6.00 | 6.00 | 6.00 | 6.00 | 6.00 | 6.00 |
| EAM175 | hmr-miR-320 | 6.66 | 7.03 | 8.58 | 8.34 | 8.72 | 8.73 |
| EAM 168 | hmr-let-7e | 6.00 | 6.00 | 6.00 | 6.00 | 6.00 | 8.34 |
| EAM 161 | hmr-miR-28 | 6.00 | 6.00 | 7.52 | 7.96 | 6.00 | 8.29 |
| EAM 160 | hmr-miR-26b | 8.32 | 7.48 | 9.69 | 9.65 | 8.59 | 9.78 |
| EAM 155 | hmr-miR-136 | 6.00 | 6.00 | 6.00 | 6.00 | 6.00 | 6.00 |
| EAM283 | mr-miR-211 | 6.00 | 6.00 | 6.00 | 6.00 | 6.00 | 6.00 |
| EAM282 | m-miR-199b | 6.00 | 6.00 | 6.00 | 6.00 | 6.00 | 6.00 |
| EAM281 | mr-miR-217 | 6.00 | 6.00 | 6.00 | 6.00 | 6.00 | 6.00 |
| EAM280 | hmr-miR-30a-3p | 6.00 | 6.00 | 6.00 | 6.00 | 6.00 | 6.00 |
| EAM279 | hmr-miR-29c | 6.00 | 6.00 | 6.00 | 6.56 | 6.00 | 6.00 |
| EAM278 | hmr-miR-98 | 6.00 | 6.00 | 6.00 | 8.00 | 7.69 | 7.32 |
| EAM270 | hmr-miR-30b | 7.36 | 6.00 | 9.58 | 8.74 | 8.82 | 9.46 |
| EAM 159 | hmr-miR-130a | 6.00 | 6.00 | 9.15 | 7.39 | 8.91 | 6.79 |
| EAM 163 | hmr-miR-142-3p | 6.00 | 6.00 | 7.47 | 7.43 | 6.00 | 7.89 |
| EAM 171 | hmr-miR-137 | 6.00 | 6.00 | 6.00 | 6.00 | 6.00 | 6.00 |
| EAM306 | m-miR-201 | 6.00 | 6.00 | 6.00 | 6.00 | 6.00 | 6.00 |
| EAM307 | m-miR-202 | 6.67 | 6.00 | 6.00 | 6.00 | 6.00 | 6.00 |
| EAM308 | hmr-miR-206 | 6.00 | 6.00 | 6.00 | 6.00 | 6.00 | 6.00 |
| EAM309 | m-miR-207 | 6.00 | 6.00 | 6.00 | 6.00 | 6.00 | 7.57 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM310 | hmr-miR-208 | 6.00 | 6.00 | 6.00 | 6.00 | 6.00 | 6.00 |
| EAM247 | hmr-miR-212 | 6.00 | 6.00 | 6.00 | 6.00 | 6.00 | 6.00 |
| EAM251 | hmr-miR-216 | 6.00 | 6.00 | 6.00 | 6.00 | 6.00 | 6.00 |
| EAM253 | hmr-miR-218 | 6.00 | 6.00 | 6.00 | 6.00 | 6.00 | 6.00 |
| EAM275 | hmr-miR-34a | 6.00 | 6.00 | 6.00 | 6.00 | 6.00 | 6.00 |
| EAM246 | h-miR-211 | 6.00 | 6.00 | 6.00 | 6.00 | 6.00 | 6.00 |
| EAM250 | h-miR-215 | 6.40 | 7.44 | 6.00 | 6.00 | 6.00 | 6.00 |
| EAM252 | h-miR-217 | 6.00 | 6.00 | 6.00 | 6.00 | 6.00 | 6.00 |
| EAM224 | hmr-miR-17-5p | 10.47 | 10.31 | 10.24 | 10.44 | 11.27 | 9.91 |
| EAM225 | hmr-miR-18a | 6.00 | 6.00 | 6.00 | 7.40 | 6.00 | 6.00 |
| EAM226 | hmr-miR-181a | 6.00 | 6.00 | 8.26 | 7.87 | 8.68 | 7.08 |
| EAM227 | hmr-miR-181b | 6.00 | 6.00 | 6.00 | 6.79 | 7.49 | 6.00 |
| EAM234 | hmr-miR-199a | 6.00 | 6.00 | 6.00 | 6.00 | 6.00 | 6.00 |
| EAM235 | h-miR-199b | 6.00 | 6.00 | 6.00 | 6.00 | 6.00 | 6.00 |
| EAM236 | hmr-miR-19a | 6.00 | 7.84 | 7.23 | 7.70 | 8.90 | 8.55 |
| EAM241 | hmr-miR-203 | 6.00 | 6.00 | 6.00 | 6.00 | 8.15 | 6.99 |
| EAM242 | hmr-miR-204 | 6.00 | 6.00 | 6.00 | 6.00 | 6.00 | 6.00 |
| EAM243 | hmr-miR-205 | 6.00 | 6.00 | 6.69 | 6.00 | 6.00 | 6.00 |
| EAM245 | hmr-miR-210 | 6.00 | 6.00 | 6.00 | 6.00 | 6.00 | 6.00 |
| EAM249 | hmr-miR-214 | 6.00 | 6.00 | 6.00 | 6.00 | 6.00 | 6.00 |
| EAM 184 | hmr-miR-100 | 6.00 | 6.00 | 6.00 | 6.00 | 6.00 | 6.00 |
| EAM 186 | h-miR-106a | 10.18 | 10.13 | 10.04 | 10.31 | 10.92 | 9.89 |
| EAM 189 | hmr-miR-10a | 6.00 | 6.00 | 6.54 | 7.74 | 8.59 | 8.29 |
| EAM 191 | hmr-miR-122a | 6.00 | 6.00 | 6.00 | 6.00 | 6.00 | 6.00 |
| EAM192 | hmr-miR-126* | 6.00 | 6.00 | 8.11 | 6.82 | 7.25 | 6.18 |
| EAM 198 | hmr-miR-130b | 6.00 | 7.98 | 6.00 | 6.27 | 6.21 | 6.00 |
| EAM202 | hmr-miR-134 | 6.00 | 6.00 | 6.00 | 6.00 | 6.00 | 6.00 |
| EAM209 | hmr-miR-142-5p | 6.00 | 6.00 | 9.02 | 7.81 | 7.04 | 7.93 |
| EAM221 | m-miR-155 | 6.00 | 6.00 | 6.00 | 7.17 | 8.01 | 7.16 |
| EAM223 | hmr-miR-15b | 11.83 | 11.90 | 11.05 | 10.50 | 10.40 | 9.74 |
| EAM228 | hmr-miR-181c | 6.00 | 6.00 | 6.00 | 6.00 | 6.00 | 6.00 |
| EAM222 | hm-miR-15a | 10.72 | 9.83 | 8.88 | 9.52 | 9.67 | 6.00 |
| EAM111 | hm-let-7g | 6.00 | 9.81 | 10.39 | 10.55 | 10.12 | 10.44 |
| EAM131 | hmr-miR-92 | 11.53 | 11.40 | 8.71 | 10.50 | 11.33 | 9.41 |
| EAM139 | hmr-miR-146a | 6.82 | 6.00 | 10.20 | 9.47 | 10.48 | 8.86 |
| EAM145 | hmr-let-7c | 8.41 | 8.87 | 8.35 | 8.69 | 9.07 | 9.10 |
| EAM 109 | hmr-miR-7 | 6.00 | 6.00 | 6.00 | 6.00 | 6.00 | 6.00 |
| EAM 152 | hm-miR-9* | 6.00 | 6.00 | 6.00 | 6.00 | 6.00 | 6.00 |
| JLA215 | hmr-let-7i | 6.00 | 7.09 | 8.55 | 8.71 | 8.89 | 9.07 |
| EAM153 | hmr-let-7a | 10.78 | 11.14 | 10.70 | 10.98 | 10.75 | 11.12 |
| EAM147 | hmr-let-7b | 7.43 | 7.57 | 8.10 | 8.34 | 7.17 | 10.57 |
| EAM 137 | hmr-miR-132 | 6.00 | 6.00 | 6.00 | 6.00 | 6.95 | 6.00 |
| EAM133 | hmr-miR-324-5p | 6.00 | 6.00 | 6.00 | 6.00 | 6.00 | 6.00 |
| EAM 103 | hmr-miR-124a | 6.00 | 6.00 | 6.00 | 6.00 | 6.00 | 6.00 |
| EAM 105 | hmr-miR-125b | 6.00 | 6.23 | 6.00 | 6.00 | 7.61 | 6.00 |
| EAM 121 | hmr-miR-99a | 6.00 | 6.00 | 6.00 | 6.00 | 6.00 | 6.00 |
| EAM115 | hmr-miR-16 | 13.12 | 12.85 | 12.67 | 12.56 | 12.12 | 13.06 |
| EAM119 | hmr-miR-29b | 6.00 | 6.00 | 6.00 | 6.00 | 6.00 | 6.91 |
| EAM311 | hmr-miR-101 | 6.00 | 6.00 | 6.00 | 6.00 | 6.00 | 6.00 |
| EAM312 | h-miR-105 | 6.00 | 6.00 | 6.00 | 6.00 | 6.00 | 6.00 |
| EAM313 | hmr-miR-106b | 8.32 | 8.32 | 8.32 | 8.85 | 9.53 | 9.17 |
| EAM314 | hmr-miR-126 | 6.00 | 6.00 | 7.96 | 9.23 | 10.02 | 9.48 |
| EAM315 | hmr-miR-127 | 6.00 | 6.00 | 6.00 | 6.00 | 6.00 | 6.00 |
| EAM320 | hm-miR-189 | 6.00 | 6.00 | 6.00 | 6.00 | 6.00 | 6.00 |
| JLA216 | hmr-miR-200c | 6.00 | 6.00 | 6.00 | 6.00 | 6.00 | 6.00 |
| EAM323 | h-miR-224 | 6.00 | 6.00 | 6.49 | 6.00 | 6.00 | 6.00 |
| EAM324 | hmr-miR-25 | 6.00 | 8.55 | 7.79 | 6.85 | 8.56 | 6.00 |
| EAM386 | r-miR-336 | 6.00 | 6.00 | 6.00 | 6.00 | 6.00 | 6.00 |
| JLA218 | r-miR-343 | 6.00 | 6.00 | 6.00 | 6.00 | 6.00 | 6.00 |
| EAM388 | r-miR-344 | 6.00 | 6.00 | 6.00 | 6.00 | 6.00 | 6.00 |
| EAM338 | h-miR-95 | 6.00 | 6.00 | 6.00 | 6.00 | 6.00 | 6.00 |
| JLA214 | hmr-miR-129 | 6.00 | 6.00 | 6.00 | 6.00 | 6.00 | 6.00 |
| EAM340 | mr-let-7d* | 6.00 | 8.01 | 6.00 | 6.00 | 6.00 | 6.00 |
| EAM341 | m-miR-106a | 9.85 | 9.85 | 9.54 | 9.43 | 10.30 | 9.16 |
| EAM342 | hmr-miR-135b | 6.00 | 6.00 | 6.00 | 6.00 | 6.00 | 6.00 |
| EAM343 | mr-miR-151 | 6.00 | 6.00 | 6.00 | 6.00 | 6.00 | 6.00 |
| EAM344 | m-miR-17-3p | 6.00 | 6.00 | 6.00 | 6.00 | 6.00 | 6.00 |
| EAM345 | m-miR-224 | 6.00 | 6.00 | 6.00 | 6.00 | 6.00 | 6.00 |
| EAM346 | mr-miR-290 | 6.00 | 6.00 | 6.00 | 6.00 | 6.00 | 6.00 |
| EAM347 | mr-miR-291-3p | 6.00 | 6.00 | 6.00 | 6.00 | 6.00 | 6.00 |
| EAM348 | mr-miR-291-5p | 6.00 | 6.00 | 6.00 | 6.00 | 6.00 | 6.00 |
| EAM349 | mr-miR-292-3p | 6.00 | 6.00 | 6.00 | 6.00 | 6.00 | 6.00 |
| EAM350 | mr-miR-292-5p | 6.00 | 6.00 | 6.00 | 6.00 | 6.00 | 6.00 |
| EAM351 | m-miR-293 | 6.69 | 6.00 | 6.00 | 6.00 | 6.00 | 6.00 |
| EAM352 | m-miR-294 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM353 | m-miR-295 | 6.00 | 6.00 | 6.00 | 6.00 | 6.00 | 6.00 |
| EAM354 | m-miR-297 | 6.00 | 6.00 | 6.00 | 6.00 | 6.00 | 6.00 |
| EAM355 | mr-miR-298 | 10.24 | 6.00 | 6.00 | 6.00 | 6.00 | 6.00 |
| EAM356 | mr-miR-300 | 6.00 | 6.00 | 6.00 | 6.00 | 6.00 | 6.00 |
| EAM358 | hmr-miR-323 | 6.00 | 6.00 | 6.00 | 6.00 | 6.00 | 6.49 |
| EAM359 | hmr-miR-324-3p | 6.00 | 6.00 | 6.00 | 6.00 | 6.00 | 6.00 |
| EAM360 | mr-miR-325 | 6.00 | 6.00 | 6.00 | 6.00 | 6.63 | 6.00 |
| EAM361 | hmr-miR-326 | 6.00 | 6.00 | 6.00 | 6.00 | 6.00 | 6.00 |
| EAM362 | hmr-miR-328 | 6.00 | 6.00 | 6.00 | 6.00 | 6.00 | 6.00 |
| EAM363 | mr-miR-329 | 6.00 | 6.00 | 6.00 | 6.00 | 6.00 | 6.00 |
| EAM365 | hmr-miR-331 | 6.00 | 6.00 | 6.00 | 6.00 | 6.00 | 6.00 |
| EAM366 | mr-miR-337 | 6.00 | 6.00 | 6.00 | 6.00 | 6.00 | 6.00 |
| EAM367 | hmr-miR-338 | 6.00 | 6.00 | 6.00 | 6.00 | 6.00 | 6.00 |
| EAM368 | hmr-miR-339 | 6.00 | 6.00 | 6.00 | 6.00 | 6.00 | 6.00 |
| EAM369 | hmr-miR-340 | 6.00 | 6.00 | 6.00 | 6.00 | 6.00 | 6.00 |
| EAM370 | mr-miR-341 | 6.00 | 6.00 | 6.00 | 6.00 | 6.00 | 6.00 |
| EAM371 | hmr-miR-342 | 6.00 | 9.57 | 10.38 | 11.21 | 8.81 | 10.24 |
| EAM372 | m-miR-344 | 6.00 | 6.00 | 6.00 | 6.00 | 6.00 | 6.00 |
| EAM373 | mr-miR-345 | 7.09 | 6.00 | 6.00 | 6.00 | 6.00 | 6.00 |
| EAM374 | m-miR-346 | 6.00 | 6.00 | 6.00 | 6.00 | 6.00 | 6.00 |
| EAM37 | mr-miR-34b | 6.00 | 6.00 | 6.00 | 6.00 | 6.00 | 6.00 |
| JLA217 | mr-miR-350 | 6.00 | 6.00 | 6.00 | 6.00 | 6.00 | 6.00 |
| EAM37 | mr-miR-351 | 6.00 | 6.00 | 6.00 | 6.00 | 6.00 | 6.00 |
| EAM37 | mr-miR-7b | 6.00 | 6.00 | 6.00 | 6.00 | 6.00 | 6.00 |
| EAM38 | r-miR-20* | 6.00 | 6.00 | 6.00 | 6.00 | 6.00 | 6.00 |
| EAM38 | r-miR-327 | 6.00 | 6.00 | 6.00 | 6.00 | 6.00 | 6.00 |
| EAM38 | r-miR-333 | 6.00 | 6.00 | 6.00 | 6.00 | 6.00 | 6.00 |
| EAM38 | hmr-miR-335 | 6.00 | 6.00 | 6.00 | 7.18 | 7.80 | 6.00 |
| EAM39 | r-miR-7* | 6.00 | 6.00 | 6.00 | 6.00 | 6.00 | 6.00 |
| EAM30 | hmr-miR-200a | 6.00 | 6.00 | 6.00 | 6.00 | 6.00 | 6.00 |
| EAM29 | hmr-miR-194 | 6.00 | 6.00 | 6.48 | 6.00 | 6.22 | 6.00 |
| JLA221 | hmr-miR-191 | 8.30 | 8.00 | 8.50 | 8.20 | 7.45 | 8.85 |
| EAM29 | hmr-miR-190 | 6.00 | 6.00 | 6.00 | 6.00 | 6.00 | 6.00 |
| EAM29 | hmr-miR-186 | 6.00 | 6.00 | 6.00 | 6.00 | 6.00 | 6.00 |
| JLA219 | hmr-miR-185 | 7.47 | 9.59 | 6.23 | 6.00 | 6.00 | 6.00 |
| EAM29 | hmr-miR-184 | 6.00 | 6.00 | 6.00 | 6.00 | 6.00 | 6.00 |
| EAM40 | hm-miR-133b | 6.00 | 6.00 | 6.00 | 6.00 | 6.00 | 6.00 |
| EAM40 | h-miR-151 | 6.00 | 6.00 | 6.00 | 6.00 | 6.00 | 6.00 |
| EAM40 | hmr-miR-196b | 6.00 | 6.00 | 6.00 | 6.00 | 6.00 | 6.00 |
| EAM41 | hm-miR-370 | 6.00 | 6.00 | 6.00 | 6.00 | 6.00 | 6.00 |
| EAM41 | h-miR-371 | 6.00 | 6.00 | 6.00 | 6.00 | 6.00 | 6.00 |
| EAM42 | h-miR-372 | 6.00 | 6.00 | 6.00 | 6.00 | 6.00 | 6.00 |
| EAM42 | h-miR-373 | 6.00 | 6.00 | 6.00 | 6.00 | 6.00 | 6.00 |
| EAM42 | h-miR-373* | 6.00 | 6.00 | 6.00 | 6.00 | 6.00 | 6.00 |
| EAM42 | h-miR-374 | 6.00 | 6.00 | 6.70 | 6.00 | 7.84 | 6.58 |
| EAM42 | m-miR-215 | 6.00 | 6.00 | 6.00 | 6.00 | 6.00 | 6.00 |
| EAM42 | hm-miR-409-3p | 6.00 | 6.00 | 6.00 | 6.80 | 6.00 | 6.00 |
| EAM42 | hm-miR-410 | 6.00 | 6.00 | 6.00 | 6.00 | 6.00 | 6.00 |
| EAM42 | m-miR-376b | 6.00 | 6.00 | 6.00 | 6.00 | 6.00 | 6.00 |
| EAM43 | m-miR-376a | 6.00 | 6.00 | 6.00 | 6.00 | 6.00 | 6.00 |
| EAM43 | m-miR-411 | 6.00 | 6.00 | 6.00 | 6.00 | 6.00 | 6.00 |
| EAM43 | m-miR-380-3p | 6.00 | 6.00 | 6.00 | 6.00 | 6.00 | 6.00 |
| EAM43 | hm-miR-412 | 6.00 | 6.00 | 6.00 | 6.00 | 6.00 | 6.00 |
| EAM26 | hmr-miR-27b | 6.00 | 7.45 | 8.57 | 6.46 | 8.12 | 7.01 |
| EAM26 | hmr-miR-26a | 8.77 | 8.20 | 10.49 | 10.10 | 10.36 | 9.80 |
| EAM26 | hmr-miR-24 | 6.00 | 6.00 | 6.00 | 6.06 | 6.00 | 6.00 |
| EAM26 | hmr-miR-23b | 6.92 | 7.59 | 8.07 | 8.76 | 8.71 | 8.23 |
| EAM26 | hmr-miR-23a | 6.00 | 6.00 | 8.15 | 8.70 | 9.13 | 8.70 |
| EAM25 | h-miR-220 | 6.00 | 6.00 | 6.00 | 6.00 | 6.00 | 6.00 |
| EAM25 | hmr-miR-22 | 6.00 | 6.00 | 6.46 | 6.00 | 6.00 | 6.00 |
| EAM24 | hmr-miR-213 | 6.00 | 6.00 | 6.00 | 6.00 | 6.00 | 6.00 |
| EAM24 | hmr-miR-21 | 6.00 | 6.00 | 9.48 | 8.75 | 9.03 | 10.40 |
| EAM24 | hmr-miR-20a | 10.43 | 10.13 | 10.28 | 11.01 | 11.25 | 10.42 |
| EAM23 | hmr-miR-19b | 6.00 | 8.44 | 7.57 | 7.94 | 9.23 | 8.64 |
| EAM23 | hmr-miR-196a | 6.00 | 6.00 | 6.00 | 6.00 | 6.00 | 6.00 |
| EAM | hm-miR-148a | 6.00 | 6.00 | 6.00 | 6.00 | 6.00 | 6.00 |
| EAM21 | hmr-miR-145 | 6.00 | 6.00 | 6.40 | 6.00 | 6.16 | 6.00 |
| EAM21 | hmr-miR-144 | 11.13 | 10.47 | 7.05 | 7.20 | 6.00 | 6.00 |
| EAM | hmr-miR-143 | 6.00 | 6.00 | 6.00 | 6.00 | 6.00 | 6.00 |
| EAM38 | r-miR-346 | 6.00 | 6.00 | 6.00 | 6.00 | 6.00 | 6.00 |
| EAM39 | r-miR-347 | 6.00 | 6.00 | 6.00 | 6.00 | 6.00 | 6.00 |
| EAM39 | r-miR-349 | 6.00 | 6.00 | 6.00 | 6.00 | 6.00 | 6.00 |
| JLA223 | hmr-miR-33 | 6.00 | 6.00 | 6.00 | 6.00 | 6.00 | 6.00 |
| EAM27 | hmr-miR-96 | 6.00 | 6.00 | 6.00 | 6.00 | 6.00 | 6.00 |
| EAM27 | hmr-miR-9 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM27 | hmr-miR-30d | 6.00 | 6.04 | 8.35 | 7.77 | 7.93 | 7.87 |
| EAM28 | mr-miR-10b | 6.00 | 6.98 | 6.00 | 7.30 | 7.23 | 6.00 |
| EAM29 | hm-miR-188 | 6.00 | 6.00 | 6.00 | 6.00 | 6.00 | 6.00 |
| EAM29 | hmr-miR-193a | 6.00 | 6.00 | 6.00 | 6.00 | 6.00 | 6.00 |
| EAM30 | h-miR-198 | 6.00 | 6.00 | 6.00 | 6.00 | 6.00 | 6.00 |
| EAM23 | hmr-miR-192 | 7.14 | 7.65 | 6.00 | 6.00 | 6.00 | 6.00 |
| EAM23 | hmr-miR-187 | 6.00 | 6.00 | 6.00 | 6.00 | 6.00 | 6.00 |
| EAM23 | hmr-miR-183 | 6.00 | 6.00 | 6.00 | 6.00 | 6.00 | 6.00 |
| EAM22 | hm-miR-182 | 6.00 | 6.00 | 6.00 | 6.00 | 6.00 | 6.00 |
| EAM | hmr-miR-154 | 6.00 | 6.00 | 6.00 | 6.00 | 6.00 | 6.00 |
| EAM | hmr-miR-153 | 6.00 | 6.00 | 6.00 | 6.00 | 6.00 | 6.00 |
| EAM | hmr-miR-152 | 6.00 | 6.00 | 6.74 | 6.00 | 6.00 | 6.00 |
| EAM21 | hmr-miR-150 | 6.00 | 6.15 | 10.77 | 11.16 | 6.00 | 9.51 |
| EAM | hm-miR-149 | 6.00 | 6.00 | 6.00 | 6.00 | 6.00 | 6.00 |
| EAM | hmr-miR-148b | 6.00 | 6.00 | 7.49 | 6.00 | 6.00 | 6.00 |
| EAM | hmr-miR-30c | 7.67 | 6.00 | 9.52 | 8.38 | 8.74 | 9.34 |
| EAM26 | hmr-miR-29a | 6.00 | 6.00 | 6.00 | 8.05 | 6.00 | 6.00 |
| EAM30 | hmr-miR-200b | 6.00 | 6.00 | 6.00 | 6.00 | 6.23 | 6.00 |
| EAM30 | hm-miR-199a* | 6.00 | 6.00 | 6.00 | 6.00 | 6.00 | 6.00 |
| EAM30 | h-miR-197 | 6.00 | 6.84 | 7.76 | 7.57 | 6.00 | 6.61 |
| EAM29 | hmr-miR-195 | 10.31 | 9.58 | 9.72 | 8.90 | 8.67 | 10.18 |
| JLA91 | hmr-miR-99b | 6.00 | 6.00 | 6.00 | 6.00 | 6.00 | 9.02 |
| JLA92 | hmr-miR-433 | 6.00 | 6.00 | 6.00 | 6.00 | 6.00 | 6.00 |
| JLA93 | hmr-miR-431 | 6.00 | 6.00 | 6.00 | 6.00 | 6.00 | 6.00 |
| JLA94 | hmr-miR-365 | 6.22 | 6.53 | 8.13 | 6.77 | 6.53 | 6.00 |
| JLA95 | hmr-miR-450 | 6.00 | 6.00 | 6.00 | 6.00 | 6.00 | 6.00 |
| JLA96 | hmr-miR-449 | 6.00 | 6.00 | 6.00 | 6.00 | 6.00 | 6.00 |
| JLA99 | hmr-miR-448 | 6.00 | 6.00 | 6.00 | 6.00 | 6.00 | 6.00 |
| JLA103 | hmr-miR-424 | 6.00 | 6.00 | 6.00 | 7.35 | 7.34 | 6.00 |
| JLA105 | hm-miR-361 | 6.00 | 6.00 | 6.00 | 6.00 | 6.98 | 7.83 |
| JLA106 | hm-miR-375 | 6.00 | 6.00 | 6.00 | 6.00 | 6.00 | 6.00 |
| JLA107 | hm-miR-377 | 6.00 | 6.00 | 6.00 | 6.00 | 6.78 | 6.00 |
| JLA108 | hm-miR-378 | 6.00 | 6.00 | 6.00 | 6.00 | 6.00 | 6.00 |
| JLA109 | hm-miR-379 | 6.00 | 6.00 | 6.00 | 6.00 | 6.00 | 6.00 |
| JLA110 | hm-miR-380-5p | 6.00 | 6.00 | 6.00 | 6.00 | 6.00 | 6.00 |
| JLA111 | hm-miR-381 | 6.00 | 6.00 | 6.00 | 6.00 | 6.00 | 6.00 |
| JLA112 | hm-miR-382 | 6.00 | 6.00 | 6.00 | 6.00 | 6.00 | 6.00 |
| JLA115 | hm-miR-384 | 6.00 | 6.00 | 6.00 | 6.00 | 6.00 | 6.00 |
| JLA116 | hm-miR-425 | 6.00 | 6.00 | 6.00 | 6.00 | 6.00 | 6.00 |
| JLA117 | hm-miR-452 | 6.00 | 6.00 | 6.00 | 6.00 | 6.00 | 6.00 |
| JLA118 | hm-miR-30e-3p | 6.00 | 6.00 | 6.00 | 6.00 | 6.00 | 6.00 |
| JLA104 | mr-miR-129-3p | 8.58 | 7.16 | 7.12 | 8.05 | 6.65 | 6.00 |
| JLA98 | mr-miR-429 | 6.00 | 6.00 | 6.00 | 6.00 | 6.00 | 6.00 |
| JLA101 | mr-miR-330 | 6.00 | 6.00 | 6.00 | 6.00 | 6.00 | 6.00 |
| JLA102 | mr-miR-322 | 6.00 | 6.00 | 6.00 | 6.00 | 6.00 | 6.00 |
| JLA114 | m-miR-383 | 6.00 | 6.00 | 6.00 | 6.00 | 6.00 | 6.00 |
| JLA5 | hmr-miR-451 | 11.41 | 12.04 | 6.79 | 8.40 | 6.00 | 6.13 |
| JLA201 | r-miR-421 | 6.00 | 6.00 | 6.00 | 6.00 | 6.00 | 6.00 |
| JLA202 | m-miR-463 | 6.00 | 6.00 | 6.00 | 6.00 | 6.00 | 6.00 |
| JLA203 | m-miR-464 | 6.00 | 6.00 | 6.00 | 6.00 | 6.00 | 6.00 |
| JLA204 | m-miR-465 | 6.00 | 6.00 | 6.00 | 6.00 | 6.00 | 6.00 |
| JLA205 | m-miR-466 | 6.48 | 6.00 | 6.00 | 6.00 | 6.00 | 6.00 |
| JLA206 | m-miR-467 | 6.00 | 6.00 | 6.00 | 6.00 | 6.00 | 6.00 |
| JLA207 | m-miR-468 | 6.00 | 6.00 | 6.00 | 6.00 | 6.00 | 6.00 |
| JLA208 | m-miR-469 | 6.00 | 6.00 | 6.00 | 6.00 | 6.00 | 6.00 |
| JLA209 | m-miR-470 | 6.00 | 6.00 | 6.00 | 6.00 | 6.00 | 6.00 |
| JLA210 | m-miR-471 | 6.00 | 6.00 | 6.00 | 6.00 | 6.00 | 6.00 |
| EAM325 | hmr-miR-27a | 6.00 | 6.80 | 9.54 | 7.10 | 8.39 | 6.53 |
| EAM326 | hmr-miR-296 | 6.00 | 6.00 | 6.00 | 6.00 | 6.00 | 6.00 |
| EAM327 | hmr-miR-299-5p | 6.00 | 6.00 | 6.00 | 6.00 | 6.00 | 6.00 |
| EAM328 | hmr-miR-301 | 6.00 | 6.00 | 6.00 | 6.00 | 6.00 | 6.00 |
| EAM329 | hm-miR-302a | 6.00 | 6.00 | 6.00 | 6.00 | 6.00 | 6.00 |
| EAM330 | hmr-miR-30a-5p | 6.00 | 6.00 | 6.62 | 6.00 | 6.00 | 6.00 |
| EAM331 | hmr-miR-30e-5p | 6.00 | 6.00 | 6.00 | 6.00 | 7.15 | 6.00 |
| EAM332 | hmr-miR-31 | 6.00 | 6.00 | 6.00 | 6.00 | 6.00 | 6.00 |
| EAM333 | hmr-miR-32 | 6.00 | 6.00 | 6.00 | 6.00 | 6.00 | 6.00 |
| EAM335 | h-miR-34b | 6.00 | 6.00 | 6.00 | 6.00 | 6.00 | 6.00 |
| EAM336 | hmr-miR-34c | 6.00 | 6.00 | 6.00 | 6.00 | 6.00 | 6.00 |
| EAM337 | hmr-miR-93 | 7.82 | 10.69 | 8.89 | 8.55 | 9.94 | 9.41 |
| EAM208 | hmr-miR-141 | 6.00 | 6.00 | 6.00 | 6.00 | 6.00 | 6.00 |
| EAM207 | hmr-miR-140 | 6.00 | 6.00 | 6.00 | 6.00 | 6.00 | 6.00 |
| JLA222 | hmr-miR-139 | 6.00 | 6.00 | 6.00 | 6.00 | 6.00 | 6.00 |
| JLA220 | hmr-miR-138 | 6.00 | 6.00 | 6.00 | 6.00 | 6.00 | 6.00 |
| EAM203 | hmr-miR-135a | 6.00 | 6.00 | 6.00 | 6.00 | 6.00 | 6.00 |
| EAM200 | hmr-miR-133a | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM195 | hmr-miR-128b | 6.00 | 6.00 | 6.00 | 6.00 | 6.00 | 6.00 |
| EAM194 | hmr-miR-128a | 6.00 | 6.00 | 6.00 | 6.00 | 6.00 | 6.00 |
| EAM254 | hmr-miR-219 | 6.45 | 6.00 | 6.00 | 6.00 | 6.00 | 6.00 |
| EAM257 | hmr-miR-221 | 8.25 | 6.00 | 8.79 | 7.37 | 7.46 | 6.00 |
| EAM258 | hmr-miR-222 | 6.00 | 6.00 | 8.38 | 8.32 | 7.76 | 6.95 |
| EAM259 | hmr-miR-223 | 6.00 | 6.00 | 8.82 | 8.60 | 8.36 | 9.22 |
| JLA211 | m-miR-434-5p | 6.00 | 6.00 | 6.00 | 6.00 | 6.00 | 6.00 |
| JLA212 | m-miR-434-3p | 6.00 | 6.00 | 6.00 | 6.00 | 6.00 | 6.00 |
| JLA213 | m-miR-433-5p | 6.00 | 6.00 | 6.00 | 6.00 | 6.00 | 6.00 |
| JLA2 | hsa-miR-522 | 6.00 | 6.00 | 6.00 | 6.00 | 6.00 | 6.00 |
| JLA3 | hsa-miR-495 | 6.00 | 6.00 | 6.00 | 6.00 | 6.00 | 6.00 |
| JLA200 | r-miR-297 | 6.00 | 6.00 | 6.00 | 6.00 | 6.00 | 6.00 |
| JLA6 | hsa-miR-518e | 6.58 | 6.67 | 6.00 | 6.00 | 6.00 | 6.00 |
| JLA7 | hsa-miR-519a | 6.68 | 6.53 | 6.00 | 6.00 | 6.00 | 6.00 |
| JLA8 | hsa-mir-527* | 6.19 | 6.07 | 6.00 | 6.00 | 6.00 | 6.00 |
| JLA72 | hmr-miR-140* | 6.71 | 7.22 | 7.30 | 6.03 | 6.02 | 6.00 |
| JLA10 | hsa-miR-521 | 6.00 | 6.00 | 6.00 | 6.00 | 6.00 | 6.00 |
| JLA12 | hsa-miR-362 | 6.00 | 6.00 | 6.00 | 6.00 | 6.00 | 6.00 |
| JLA74 | hsa-mir-18* | 6.00 | 6.00 | 6.00 | 6.00 | 6.00 | 6.00 |
| JLA14 | hm-miR-363 | 6.00 | 6.00 | 6.00 | 6.00 | 6.00 | 7.63 |
| JLA77 | hsa-mir-19b-1* | 6.00 | 6.00 | 6.00 | 6.00 | 6.00 | 6.00 |
| JLA17 | hsa-mir-520c,b,f | 6.00 | 6.00 | 6.00 | 6.00 | 6.00 | 6.00 |
| JLA79 | hsa-mir-23a* | 6.00 | 6.00 | 6.00 | 6.00 | 6.00 | 6.00 |
| JLA20 | hsa-miR-369-5p | 6.00 | 6.00 | 6.00 | 6.00 | 6.00 | 6.00 |
| JLA81 | hsa-mir-339* | 6.00 | 6.00 | 6.00 | 6.00 | 6.00 | 6.00 |
| JLA23 | hsa-mir-342* | 6.00 | 6.00 | 8.07 | 6.00 | 6.81 | 6.00 |
| JLA24 | hsa-mir-19a* | 6.00 | 6.00 | 6.00 | 6.00 | 6.00 | 6.00 |
| JLA26 | hsa-miR-517a,b | 6.00 | 6.00 | 6.00 | 6.00 | 6.00 | 6.00 |
| JLA27 | hsa-miR-516-5p | 6.00 | 6.00 | 6.00 | 6.00 | 6.00 | 6.00 |
| JLA28 | hsa-miR-518b | 6.00 | 6.00 | 6.00 | 6.00 | 6.00 | 6.00 |
| JLA29 | hsa-miR-519d | 6.00 | 6.00 | 6.00 | 6.00 | 6.00 | 6.00 |
| JLA73 | hr-mir-151* | 6.03 | 8.07 | 7.32 | 7.22 | 6.01 | 7.57 |
| JLA31 | hsa-mir-28* | 6.00 | 6.00 | 6.00 | 6.00 | 6.00 | 6.00 |
| JLA33 | hsa-mir-519a-2* | 6.00 | 6.00 | 6.00 | 6.00 | 6.00 | 6.00 |
| JLA34 | hsa-mir-26b* | 6.00 | 6.00 | 6.00 | 6.00 | 6.00 | 6.00 |
| JLA35 | hsa-miR-526c | 6.00 | 6.00 | 6.00 | 6.00 | 6.00 | 6.00 |
| JLA36 | hsa-miR-527 | 6.00 | 6.00 | 6.00 | 6.00 | 6.00 | 6.00 |
| JLA38 | hsa-mir-29b-2* | 6.00 | 6.00 | 6.00 | 6.00 | 6.00 | 6.00 |
| JLA39 | hsa-let-7g* | 6.00 | 6.00 | 6.00 | 6.00 | 6.00 | 6.00 |
| JLA40 | hsa-miR-518a | 6.00 | 6.00 | 6.00 | 6.00 | 6.00 | 6.00 |
| JLA41 | hsa-miR-523 | 6.00 | 6.00 | 6.00 | 6.00 | 6.00 | 6.00 |
| JLA44 | hsa-miR-515-3p | 6.00 | 6.00 | 6.00 | 6.00 | 6.00 | 6.00 |
| JLA45 | hsa-mir-146b* | 6.00 | 6.00 | 6.00 | 6.00 | 6.00 | 6.00 |
| JLA49 | hsa-mir-222* | 6.00 | 6.00 | 6.00 | 6.00 | 6.00 | 6.00 |
| JLA53 | hsa-mir-24* | 6.00 | 6.00 | 6.00 | 6.00 | 6.00 | 6.00 |
| JLA55 | hsa-miR-503 | 6.00 | 6.00 | 6.00 | 6.00 | 6.00 | 6.00 |
| JLA57 | hsa-mir-505 | 6.00 | 6.00 | 6.00 | 6.00 | 6.00 | 6.00 |
| JLA82 | hsa-mir-423* | 12.28 | 11.26 | 10.01 | 10.16 | 9.82 | 9.90 |
| JLA66 | hsa-miR-432 | 6.00 | 6.00 | 6.00 | 6.00 | 7.28 | 6.00 |
| JLA83 | hsa-mir-425* | 6.09 | 6.00 | 8.19 | 7.93 | 7.46 | 6.00 |
| JLA84 | hsa-mir-92-1* | 6.00 | 6.00 | 6.00 | 6.00 | 6.00 | 6.00 |
| JLA69 | hsa-mir-193* | 7.72 | 6.00 | 6.00 | 6.00 | 6.00 | 6.00 |
| JLA70 | hsa-miR-515-5p | 6.00 | 6.00 | 6.00 | 6.00 | 6.00 | 6.00 |
| JLA71 | hsa-mir-516-1* | 6.00 | 6.00 | 6.00 | 6.00 | 6.00 | 6.00 |
| JLA85 | hsa-mir-30d* | 6.00 | 6.00 | 6.00 | 6.00 | 6.00 | 6.00 |
| JLA125 | h-miR-20b | 9.22 | 8.63 | 8.99 | 9.71 | 9.91 | 8.67 |
| JLA198 | h-miR-191* | 6.63 | 6.11 | 6.26 | 6.00 | 6.00 | 6.74 |
| JLA199 | h-miR-154* | 6.00 | 6.00 | 6.00 | 6.00 | 6.00 | 6.00 |
| EAM316 | h-miR-147 | 6.00 | 6.00 | 6.00 | 6.00 | 6.00 | 6.00 |
| EAM317 | h-miR-155 | 6.18 | 6.00 | 6.00 | 8.85 | 9.85 | 8.50 |
| EAM318 | h-miR-17-3p | 6.00 | 6.00 | 6.00 | 6.00 | 6.00 | 6.00 |
| JLA195 | h-miR-200a* | 6.00 | 6.00 | 6.00 | 6.00 | 6.00 | 6.00 |
| JLA196 | h-miR-302a* | 6.00 | 6.00 | 6.00 | 6.00 | 6.00 | 6.00 |
| JLA197 | h-miR-299-3p | 6.47 | 6.00 | 6.00 | 6.00 | 6.00 | 6.00 |
| EAM319 | h-miR-182* | 6.00 | 6.00 | 6.00 | 6.00 | 6.00 | 6.00 |
| EAM405 | h-miR-302b | 6.00 | 6.00 | 6.00 | 6.00 | 6.00 | 6.00 |
| EAM406 | h-miR-302b* | 6.00 | 6.00 | 6.00 | 6.00 | 6.00 | 6.00 |
| EAM392 | r-miR-352 | 6.72 | 7.48 | 7.86 | 7.72 | 6.58 | 7.71 |
| JLA123 | h-miR-423 | 6.00 | 6.39 | 6.00 | 6.00 | 6.00 | 6.00 |
| JLA124 | h-miR-18b | 6.00 | 6.00 | 6.00 | 7.19 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| ProbeID | Description | MEGA2_1 | MEGA2_2 | MEGA2_3 | MEGA2_4 | MEGA2_5 | MEGA2_6 |
|---|---|---|---|---|---|---|---|
| EAM 190 | h-miR-10b | 6.00 | 6.00 | 6.66 | 6.00 | 6.00 | 7.22 |
| EAM 187 | hmr-miR-107 | 6.00 | 6.00 | 8.32 | 7.63 | 6.92 | 8.79 |
| EAM 185 | hmr-miR-103 | 6.44 | 6.00 | 8.54 | 8.04 | 7.13 | 9.39 |
| EAM181 | hmr-let-7f | 6.73 | 8.73 | 9.75 | 8.60 | 9.07 | 9.57 |
| EAM179 | hmr-let-7d | 9.64 | 9.34 | 9.91 | 9.61 | 9.83 | 9.79 |
| EAM177 | mr-miR-101b | 6.00 | 6.00 | 6.00 | 6.00 | 6.00 | 6.00 |
| EAM175 | hmr-miR-320 | 8.11 | 8.87 | 8.50 | 8.70 | 7.50 | 7.51 |
| EAM 168 | hmr-let-7e | 6.65 | 6.00 | 6.00 | 6.00 | 6.00 | 7.50 |
| EAM 161 | hmr-miR-28 | 8.44 | 8.09 | 8.01 | 7.47 | 6.00 | 8.47 |
| EAM 160 | hmr-miR-26b | 8.86 | 9.24 | 9.38 | 9.23 | 8.61 | 8.95 |
| EAM 155 | hmr-miR-136 | 6.00 | 6.00 | 6.00 | 6.00 | 6.00 | 6.00 |
| EAM283 | mr-miR-211 | 6.00 | 6.00 | 6.00 | 6.00 | 6.00 | 6.00 |
| EAM282 | m-miR-199b | 6.00 | 6.00 | 6.00 | 6.00 | 6.00 | 6.00 |
| EAM281 | mr-miR-217 | 6.00 | 6.00 | 6.00 | 6.00 | 6.00 | 6.00 |
| EAM280 | hmr-miR-30a-3p | 6.00 | 6.00 | 6.00 | 6.00 | 6.00 | 6.00 |
| EAM279 | hmr-miR-29c | 6.00 | 6.16 | 8.18 | 7.23 | 6.00 | 6.00 |
| EAM278 | hmr-miR-98 | 8.11 | 6.00 | 6.00 | 7.17 | 9.06 | 6.50 |
| EAM270 | hmr-miR-30b | 8.10 | 8.74 | 9.66 | 9.54 | 6.00 | 9.43 |
| EAM 159 | hmr-miR-130a | 8.20 | 7.67 | 7.48 | 6.87 | 6.00 | 6.00 |
| EAM 163 | hmr-miR-142-3p | 7.56 | 6.00 | 7.79 | 7.27 | 8.56 | 6.00 |
| EAM 171 | hmr-miR-137 | 6.00 | 6.00 | 6.00 | 6.00 | 6.00 | 6.00 |
| EAM306 | m-miR-201 | 6.00 | 6.00 | 6.00 | 6.00 | 6.00 | 6.00 |
| EAM307 | m-miR-202 | 7.21 | 6.00 | 6.00 | 6.00 | 7.05 | 6.00 |
| EAM308 | hmr-miR-206 | 6.00 | 6.00 | 6.00 | 6.00 | 6.00 | 6.00 |
| EAM309 | m-miR-207 | 6.00 | 6.00 | 6.00 | 6.00 | 6.00 | 6.00 |
| EAM310 | hmr-miR-208 | 6.00 | 6.00 | 6.00 | 6.00 | 6.00 | 6.00 |
| EAM247 | hmr-miR-212 | 6.00 | 6.00 | 6.00 | 6.00 | 6.00 | 6.00 |
| EAM251 | hmr-miR-216 | 6.00 | 6.00 | 6.00 | 6.00 | 6.00 | 6.00 |
| EAM253 | hmr-miR-218 | 6.00 | 6.00 | 6.00 | 6.00 | 6.00 | 6.00 |
| EAM275 | hmr-miR-34a | 6.00 | 6.00 | 6.00 | 6.00 | 6.00 | 6.00 |
| EAM246 | h-miR-211 | 6.00 | 6.00 | 6.00 | 6.00 | 6.00 | 6.00 |
| EAM250 | h-miR-215 | 6.00 | 6.00 | 6.00 | 6.00 | 7.32 | 6.00 |
| EAM252 | h-miR-217 | 6.00 | 6.00 | 6.00 | 6.00 | 6.00 | 6.00 |
| EAM224 | hmr-miR-17-5p | 10.39 | 8.79 | 10.13 | 10.33 | 9.48 | 9.88 |
| EAM225 | hmr-miR-18a | 6.00 | 6.00 | 6.00 | 6.00 | 6.00 | 6.00 |
| EAM226 | hmr-miR-181a | 6.00 | 8.81 | 6.84 | 9.72 | 6.00 | 6.56 |
| EAM227 | hmr-miR-181b | 6.00 | 6.00 | 6.00 | 7.54 | 6.00 | 6.00 |
| EAM234 | hmr-miR-199a | 6.00 | 6.00 | 6.00 | 6.00 | 6.00 | 6.00 |
| EAM235 | h-miR-199b | 6.00 | 6.00 | 6.00 | 6.00 | 6.00 | 6.00 |
| EAM236 | hmr-miR-19a | 6.00 | 7.14 | 6.00 | 7.61 | 8.19 | 6.60 |
| EAM241 | hmr-miR-203 | 6.00 | 6.00 | 6.00 | 6.00 | 8.16 | 6.00 |
| EAM242 | hmr-miR-204 | 6.00 | 6.00 | 6.00 | 6.00 | 6.00 | 6.00 |
| EAM243 | hmr-miR-205 | 6.00 | 6.00 | 6.00 | 6.00 | 6.00 | 6.00 |
| EAM245 | hmr-miR-210 | 6.00 | 6.00 | 6.00 | 6.00 | 6.00 | 6.00 |
| EAM249 | hmr-miR-214 | 6.00 | 6.00 | 6.00 | 6.00 | 6.00 | 6.12 |
| EAM 184 | hmr-miR-100 | 6.00 | 6.00 | 6.00 | 6.00 | 7.20 | 6.00 |
| EAM186 | h-miR-106a | 10.11 | 8.23 | 10.12 | 10.01 | 9.48 | 9.71 |
| EAM 189 | hmr-miR-10a | 6.00 | 6.00 | 6.00 | 6.72 | 6.00 | 6.00 |
| EAM 191 | hmr-miR-122a | 6.00 | 6.00 | 6.00 | 6.00 | 6.00 | 6.00 |
| EAM192 | hmr-miR-126* | 6.97 | 6.00 | 6.00 | 6.00 | 6.00 | 7.21 |
| EAM 198 | hmr-miR-130b | 6.00 | 6.00 | 6.00 | 6.00 | 6.00 | 6.00 |
| EAM202 | hmr-miR-134 | 6.00 | 6.00 | 6.00 | 6.00 | 6.00 | 6.00 |
| EAM209 | hmr-miR-142-5p | 7.90 | 6.86 | 8.66 | 8.37 | 9.90 | 7.87 |
| EAM221 | m-miR-155 | 6.00 | 6.00 | 7.48 | 6.00 | 6.00 | 7.03 |
| EAM223 | hmr-miR-15b | 11.50 | 11.22 | 10.39 | 10.79 | 11.03 | 11.04 |
| EAM228 | hmr-miR-181c | 6.00 | 6.00 | 6.00 | 6.00 | 6.00 | 6.00 |
| EAM222 | hm-miR-15a | 9.33 | 6.00 | 8.87 | 10.18 | 10.57 | 8.69 |
| EAM111 | hm-let-7g | 8.32 | 9.39 | 11.19 | 10.14 | 10.65 | 10.03 |
| EAM131 | hmr-miR-92 | 9.74 | 11.07 | 9.10 | 10.74 | 9.01 | 10.31 |
| EAM139 | hmr-miR-146a | 6.00 | 8.51 | 9.66 | 8.61 | 6.00 | 8.90 |
| EAM145 | hmr-let-7c | 7.53 | 9.60 | 7.46 | 6.68 | 9.21 | 7.82 |
| EAM 109 | hmr-miR-7 | 6.00 | 6.00 | 6.00 | 6.00 | 6.00 | 6.00 |
| EAM 152 | hm-miR-9* | 6.00 | 6.00 | 6.00 | 6.00 | 6.00 | 6.00 |
| JLA215 | hmr-let-7i | 9.12 | 8.59 | 8.08 | 9.20 | 10.60 | 9.03 |
| EAM153 | hmr-let-7a | 10.65 | 11.41 | 10.93 | 10.44 | 11.51 | 11.17 |
| EAM147 | hmr-let-7b | 6.00 | 6.58 | 6.09 | 6.78 | 9.59 | 6.11 |
| EAM 137 | hmr-miR-132 | 6.00 | 6.00 | 6.00 | 6.00 | 6.00 | 6.00 |
| EAM133 | hmr-miR-324-5p | 6.00 | 6.00 | 6.00 | 7.17 | 6.00 | 6.00 |
| EAM 103 | hmr-miR-124a | 6.00 | 6.00 | 6.00 | 6.00 | 6.00 | 6.00 |
| EAM 105 | hmr-miR-125b | 6.00 | 6.00 | 6.00 | 6.00 | 6.00 | 6.00 |
| EAM 121 | hmr-miR-99a | 6.00 | 6.00 | 6.00 | 6.00 | 7.94 | 6.00 |
| EAM115 | hmr-miR-16 | 12.43 | 12.37 | 12.79 | 12.11 | 13.02 | 12.69 |
| EAM119 | hmr-miR-29b | 6.00 | 6.00 | 6.00 | 7.01 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| EAM311 | hmr-miR-101 | 6.00 | 6.00 | 6.00 | 6.00 | 6.00 | 6.00 |
|---|---|---|---|---|---|---|---|
| EAM312 | h-miR-105 | 6.00 | 6.00 | 6.00 | 6.00 | 6.00 | 6.00 |
| EAM313 | hmr-miR-106b | 8.97 | 8.11 | 9.38 | 8.94 | 7.61 | 8.82 |
| EAM314 | hmr-miR-126 | 8.22 | 6.00 | 8.38 | 8.42 | 6.00 | 8.73 |
| EAM315 | hmr-miR-127 | 6.00 | 6.00 | 6.00 | 6.00 | 6.00 | 6.00 |
| EAM320 | hm-miR-189 | 6.00 | 6.00 | 6.00 | 6.00 | 6.00 | 6.00 |
| JLA216 | hmr-miR-200c | 6.96 | 6.00 | 7.14 | 6.52 | 7.22 | 6.00 |
| EAM323 | h-miR-224 | 6.00 | 6.00 | 6.00 | 6.00 | 6.00 | 6.00 |
| EAM324 | hmr-miR-25 | 6.00 | 7.38 | 6.00 | 7.51 | 6.00 | 6.00 |
| EAM386 | r-miR-336 | 6.00 | 6.00 | 6.00 | 6.00 | 6.00 | 6.00 |
| JLA218 | r-miR-343 | 6.00 | 6.00 | 6.00 | 6.00 | 6.00 | 6.00 |
| EAM388 | r-miR-344 | 6.00 | 6.00 | 6.00 | 6.00 | 6.00 | 6.00 |
| EAM338 | h-miR-95 | 6.00 | 6.00 | 6.00 | 6.00 | 6.00 | 6.00 |
| JLA214 | hmr-miR-129 | 6.00 | 6.00 | 6.00 | 6.00 | 6.00 | 6.00 |
| EAM340 | mr-let-7d* | 6.99 | 6.00 | 6.00 | 6.00 | 6.00 | 6.00 |
| EAM341 | m-miR-106a | 9.99 | 8.43 | 9.69 | 9.84 | 7.93 | 9.04 |
| EAM342 | hmr-miR-135b | 6.00 | 6.00 | 6.00 | 6.00 | 6.00 | 6.00 |
| EAM343 | mr-miR-151 | 6.00 | 6.00 | 6.00 | 6.00 | 6.00 | 6.00 |
| EAM344 | m-miR-17-3p | 6.00 | 6.00 | 6.00 | 6.00 | 6.00 | 6.00 |
| EAM345 | m-miR-224 | 6.00 | 6.00 | 6.00 | 6.00 | 6.00 | 6.00 |
| EAM346 | mr-miR-290 | 6.00 | 6.00 | 6.00 | 6.00 | 6.00 | 6.00 |
| EAM347 | mr-miR-291-3p | 6.00 | 6.00 | 6.00 | 6.00 | 6.00 | 6.00 |
| EAM348 | mr-miR-291-5p | 6.00 | 6.00 | 6.00 | 6.00 | 6.00 | 6.00 |
| EAM349 | mr-miR-292-3p | 6.00 | 6.00 | 6.00 | 6.00 | 6.00 | 6.00 |
| EAM350 | mr-miR-292-5p | 6.00 | 6.00 | 6.00 | 6.00 | 6.00 | 6.00 |
| EAM351 | m-miR-293 | 6.00 | 6.00 | 6.00 | 6.00 | 6.00 | 6.00 |
| EAM352 | m-miR-294 | 6.00 | 6.00 | 6.00 | 6.00 | 6.00 | 6.00 |
| EAM353 | m-miR-295 | 6.00 | 6.00 | 6.00 | 6.00 | 6.00 | 6.00 |
| EAM354 | m-miR-297 | 6.00 | 6.00 | 6.00 | 6.00 | 6.00 | 6.00 |
| EAM355 | mr-miR-298 | 6.00 | 6.00 | 7.52 | 6.00 | 6.00 | 6.00 |
| EAM356 | mr-miR-300 | 6.00 | 6.00 | 6.00 | 6.00 | 6.00 | 6.00 |
| EAM358 | hmr-miR-323 | 6.00 | 6.00 | 6.00 | 6.00 | 6.00 | 6.00 |
| EAM359 | hmr-miR-324-3p | 6.00 | 6.00 | 6.00 | 6.00 | 6.00 | 6.00 |
| EAM360 | mr-miR-325 | 6.00 | 6.00 | 6.00 | 6.00 | 6.00 | 6.00 |
| EAM361 | hmr-miR-326 | 6.00 | 6.00 | 6.00 | 6.00 | 6.00 | 6.00 |
| EAM362 | hmr-miR-328 | 6.00 | 6.00 | 6.00 | 6.00 | 6.00 | 6.00 |
| EAM363 | mr-miR-329 | 6.00 | 6.00 | 6.00 | 6.00 | 6.00 | 6.00 |
| EAM365 | hmr-miR-331 | 6.00 | 6.00 | 6.00 | 6.00 | 6.00 | 6.00 |
| EAM366 | mr-miR-337 | 6.00 | 6.00 | 6.00 | 6.00 | 6.00 | 6.00 |
| EAM367 | hmr-miR-338 | 6.00 | 6.00 | 6.00 | 6.00 | 6.00 | 6.00 |
| EAM368 | hmr-miR-339 | 6.00 | 6.00 | 6.00 | 6.00 | 6.00 | 6.00 |
| EAM369 | hmr-miR-340 | 6.00 | 6.00 | 6.00 | 6.00 | 6.00 | 6.00 |
| EAM370 | mr-miR-341 | 6.00 | 6.00 | 6.00 | 6.00 | 6.00 | 6.00 |
| EAM371 | hmr-miR-342 | 11.01 | 11.98 | 10.79 | 11.69 | 11.33 | 11.20 |
| EAM372 | m-miR-344 | 6.00 | 6.00 | 6.00 | 6.00 | 6.00 | 6.00 |
| EAM373 | mr-miR-345 | 6.00 | 6.00 | 6.00 | 6.00 | 6.00 | 6.00 |
| EAM374 | m-miR-346 | 6.00 | 6.00 | 6.00 | 6.00 | 6.00 | 6.00 |
| EAM37 | mr-miR-34b | 6.19 | 6.00 | 6.00 | 6.00 | 6.00 | 6.00 |
| JLA217 | mr-miR-350 | 6.00 | 6.00 | 6.00 | 6.00 | 6.00 | 6.00 |
| EAM37 | mr-miR-351 | 6.00 | 6.00 | 6.00 | 6.00 | 6.00 | 6.00 |
| EAM37 | mr-miR-7b | 6.00 | 6.00 | 6.00 | 6.00 | 6.00 | 6.00 |
| EAM38 | r-miR-20* | 6.00 | 6.00 | 6.00 | 6.00 | 6.00 | 6.00 |
| EAM38 | r-miR-327 | 6.00 | 6.00 | 6.00 | 6.00 | 6.00 | 6.00 |
| EAM38 | r-miR-333 | 6.00 | 6.00 | 6.00 | 6.00 | 6.00 | 6.00 |
| EAM38 | hmr-miR-335 | 6.00 | 6.00 | 6.42 | 6.00 | 6.00 | 6.00 |
| EAM39 | r-miR-7* | 6.00 | 6.00 | 6.00 | 6.00 | 6.00 | 6.00 |
| EAM30 | hmr-miR-200a | 6.00 | 6.00 | 6.00 | 6.00 | 6.00 | 6.00 |
| EAM29 | hmr-miR-194 | 6.00 | 6.00 | 6.00 | 6.00 | 6.00 | 6.00 |
| JLA221 | hmr-miR-191 | 7.58 | 8.83 | 7.67 | 8.32 | 8.13 | 8.89 |
| EAM29 | hmr-miR-190 | 6.00 | 6.00 | 6.00 | 6.00 | 6.00 | 6.00 |
| EAM29 | hmr-miR-186 | 6.00 | 6.00 | 6.00 | 6.00 | 6.00 | 6.00 |
| JLA219 | hmr-miR-185 | 6.00 | 6.00 | 6.00 | 7.40 | 6.00 | 6.00 |
| EAM29 | hmr-miR-184 | 6.00 | 6.00 | 6.00 | 7.33 | 6.00 | 6.00 |
| EAM40 | hm-miR-133b | 6.94 | 6.00 | 6.00 | 6.00 | 6.00 | 6.00 |
| EAM40 | h-miR-151 | 6.00 | 6.00 | 6.00 | 6.00 | 6.00 | 6.00 |
| EAM40 | hmr-miR-196b | 6.00 | 6.00 | 6.00 | 6.00 | 6.00 | 6.00 |
| EAM41 | hm-miR-370 | 6.00 | 6.00 | 6.00 | 6.00 | 6.00 | 6.00 |
| EAM41 | h-miR-371 | 6.00 | 6.00 | 6.00 | 6.00 | 6.00 | 6.00 |
| EAM42 | h-miR-372 | 6.00 | 6.00 | 6.00 | 6.00 | 6.00 | 6.00 |
| EAM42 | h-miR-373 | 6.00 | 6.00 | 6.00 | 6.00 | 6.00 | 6.00 |
| EAM42 | h-miR-373* | 6.00 | 6.00 | 6.00 | 6.00 | 6.00 | 6.00 |
| EAM42 | h-miR-374 | 6.50 | 6.70 | 6.78 | 7.50 | 6.00 | 6.82 |
| EAM42 | m-miR-215 | 6.00 | 6.00 | 6.00 | 6.00 | 6.00 | 6.00 |
| EAM42 | hm-miR-409-3p | 6.00 | 6.00 | 6.00 | 6.00 | 6.00 | 6.00 |
| EAM42 | hm-miR-410 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| EAM42 | m-miR-376b | 6.00 | 6.00 | 6.00 | 6.00 | 6.00 | 6.00 |
| EAM43 | m-miR-376a | 6.00 | 6.00 | 6.00 | 6.00 | 6.00 | 6.00 |
| EAM43 | m-miR-411 | 6.00 | 6.00 | 6.00 | 6.00 | 6.00 | 6.00 |
| EAM43 | m-miR-380-3p | 6.00 | 6.00 | 6.00 | 6.00 | 6.00 | 6.00 |
| EAM43 | hm-miR-412 | 6.00 | 6.00 | 6.00 | 6.00 | 6.00 | 6.00 |
| EAM26 | hmr-miR-27b | 7.72 | 6.00 | 6.48 | 6.42 | 6.00 | 6.00 |
| EAM26 | hmr-miR-26a | 10.53 | 10.61 | 10.61 | 10.21 | 9.69 | 10.16 |
| EAM26 | hmr-miR-24 | 6.00 | 8.19 | 6.00 | 7.34 | 6.00 | 7.32 |
| EAM26 | hmr-miR-23b | 9.80 | 9.82 | 8.30 | 9.41 | 7.07 | 9.69 |
| EAM26 | hmr-miR-23a | 9.58 | 9.49 | 7.88 | 9.15 | 7.55 | 9.76 |
| EAM25 | h-miR-220 | 6.00 | 6.00 | 6.00 | 6.00 | 6.11 | 6.00 |
| EAM25 | hmr-miR-22 | 6.00 | 6.00 | 6.00 | 6.82 | 6.00 | 6.00 |
| EAM24 | hmr-miR-213 | 6.00 | 6.00 | 6.00 | 6.00 | 6.00 | 6.00 |
| EAM24 | hmr-miR-21 | 10.10 | 6.00 | 9.43 | 9.46 | 8.42 | 9.73 |
| EAM24 | hmr-miR-20a | 10.12 | 8.35 | 10.58 | 9.97 | 10.81 | 10.61 |
| EAM23 | hmr-miR-19b | 6.80 | 7.05 | 6.00 | 8.35 | 8.53 | 7.39 |
| EAM23 | hmr-miR-196a | 6.00 | 6.00 | 6.00 | 6.00 | 6.00 | 6.00 |
| EAM | hm-miR-148a | 6.00 | 6.00 | 6.05 | 6.00 | 6.00 | 6.00 |
| EAM21 | hmr-miR-145 | 7.14 | 6.00 | 6.00 | 6.00 | 6.00 | 6.00 |
| EAM21 | hmr-miR-144 | 7.46 | 6.88 | 6.00 | 6.17 | 9.44 | 7.76 |
| EAM | hmr-miR-143 | 6.00 | 6.00 | 6.00 | 6.00 | 6.00 | 6.00 |
| EAM38 | r-miR-346 | 6.00 | 6.00 | 6.00 | 6.00 | 6.00 | 6.00 |
| EAM39 | r-miR-347 | 6.00 | 6.00 | 6.00 | 6.00 | 6.00 | 6.00 |
| EAM39 | r-miR-349 | 6.00 | 6.00 | 6.00 | 6.00 | 6.00 | 6.00 |
| JLA223 | hmr-miR-33 | 6.00 | 6.00 | 6.00 | 6.00 | 6.00 | 6.00 |
| EAM27 | hmr-miR-96 | 6.00 | 6.00 | 6.00 | 6.00 | 6.00 | 6.00 |
| EAM27 | hmr-miR-9 | 6.00 | 6.00 | 6.00 | 6.00 | 6.00 | 6.00 |
| EAM27 | hmr-miR-30d | 7.45 | 7.53 | 6.00 | 8.04 | 7.48 | 6.00 |
| EAM28 | mr-miR-10b | 6.00 | 6.00 | 7.97 | 6.00 | 6.00 | 7.89 |
| EAM29 | hm-miR-188 | 6.00 | 6.00 | 6.00 | 6.00 | 6.00 | 6.00 |
| EAM29 | hmr-miR-193a | 6.00 | 6.00 | 6.00 | 6.00 | 6.00 | 6.00 |
| EAM30 | h-miR-198 | 6.00 | 6.00 | 6.00 | 6.00 | 6.00 | 6.00 |
| EAM23 | hmr-miR-192 | 6.00 | 6.00 | 6.00 | 6.00 | 8.50 | 6.00 |
| EAM23 | hmr-miR-187 | 6.00 | 6.00 | 6.00 | 6.00 | 6.00 | 6.00 |
| EAM23 | hmr-miR-183 | 6.00 | 6.00 | 6.00 | 6.00 | 8.16 | 6.00 |
| EAM22 | hm-miR-182 | 6.00 | 6.00 | 6.00 | 6.00 | 6.00 | 6.48 |
| EAM | hmr-miR-154 | 6.39 | 6.00 | 6.00 | 6.00 | 6.00 | 6.00 |
| EAM | hmr-miR-153 | 6.00 | 6.00 | 6.00 | 6.00 | 6.00 | 6.00 |
| EAM | hmr-miR-152 | 6.00 | 6.00 | 6.00 | 6.00 | 6.00 | 6.00 |
| EAM21 | hmr-miR-150 | 11.36 | 12.16 | 11.59 | 11.15 | 9.72 | 10.24 |
| EAM | hm-miR-149 | 6.00 | 6.00 | 6.00 | 6.00 | 6.00 | 6.00 |
| EAM | hmr-miR-148b | 6.00 | 6.00 | 7.27 | 6.00 | 6.00 | 6.00 |
| EAM | hmr-miR-30c | 8.39 | 8.71 | 9.24 | 9.92 | 6.00 | 9.42 |
| EAM26 | hmr-miR-29a | 6.00 | 7.29 | 9.38 | 8.34 | 6.29 | 6.00 |
| EAM30 | hmr-miR-200b | 6.00 | 6.00 | 6.51 | 6.00 | 6.00 | 6.00 |
| EAM30 | hm-miR-199a* | 6.00 | 6.00 | 6.00 | 6.00 | 6.00 | 6.00 |
| EAM30 | h-miR-197 | 8.15 | 10.15 | 6.98 | 9.26 | 7.21 | 8.36 |
| EAM29 | hmr-miR-195 | 9.61 | 9.73 | 9.28 | 8.75 | 10.26 | 9.42 |
| JLA91 | hmr-miR-99b | 6.00 | 6.00 | 6.00 | 7.63 | 9.71 | 6.00 |
| JLA92 | hmr-miR-433 | 6.00 | 6.00 | 6.00 | 6.00 | 6.00 | 6.00 |
| JLA93 | hmr-miR-431 | 7.98 | 6.00 | 6.00 | 6.00 | 6.00 | 6.00 |
| JLA94 | hmr-miR-365 | 9.78 | 6.00 | 6.79 | 6.00 | 6.00 | 9.08 |
| JLA95 | hmr-miR-450 | 6.00 | 6.00 | 6.00 | 6.00 | 6.00 | 6.00 |
| JLA96 | hmr-miR-449 | 6.00 | 6.00 | 6.00 | 6.00 | 6.00 | 6.00 |
| JLA99 | hmr-miR-448 | 6.00 | 6.00 | 6.00 | 6.00 | 6.00 | 6.00 |
| JLA103 | hmr-miR-424 | 6.00 | 7.82 | 6.00 | 6.20 | 6.00 | 7.17 |
| JLA105 | hm-miR-361 | 6.00 | 6.00 | 6.23 | 7.28 | 6.00 | 6.00 |
| JLA106 | hm-miR-375 | 6.00 | 6.00 | 6.00 | 6.00 | 6.00 | 6.00 |
| JLA107 | hm-miR-377 | 6.00 | 6.00 | 6.00 | 6.19 | 6.00 | 6.00 |
| JLA108 | hm-miR-378 | 6.00 | 6.00 | 6.00 | 6.00 | 6.00 | 6.00 |
| JLA109 | hm-miR-379 | 6.00 | 6.00 | 6.00 | 6.00 | 6.00 | 6.00 |
| JLA110 | hm-miR-380-5p | 6.00 | 6.00 | 6.00 | 6.00 | 6.00 | 6.00 |
| JLA111 | hm-miR-381 | 6.00 | 6.00 | 6.00 | 6.00 | 6.00 | 6.00 |
| JLA112 | hm-miR-382 | 7.52 | 6.00 | 6.00 | 7.61 | 6.00 | 6.00 |
| JLA115 | hm-miR-384 | 6.00 | 6.00 | 6.00 | 6.00 | 6.00 | 6.00 |
| JLA116 | hm-miR-425 | 6.00 | 6.00 | 6.00 | 6.00 | 6.00 | 6.00 |
| JLA117 | hm-miR-452 | 6.00 | 6.00 | 6.00 | 6.00 | 6.00 | 6.00 |
| JLA118 | hm-miR-30e-3p | 6.00 | 6.00 | 6.36 | 6.00 | 6.00 | 6.00 |
| JLA104 | mr-miR-129-3p | 10.17 | 6.00 | 6.00 | 6.00 | 9.32 | 7.47 |
| JLA98 | mr-miR-429 | 6.00 | 6.00 | 6.00 | 6.00 | 6.00 | 6.00 |
| JLA101 | mr-miR-330 | 6.00 | 6.00 | 6.00 | 6.00 | 6.00 | 6.00 |
| JLA102 | mr-miR-322 | 6.00 | 6.00 | 6.00 | 6.00 | 6.00 | 6.00 |
| JLA114 | m-miR-383 | 6.00 | 6.00 | 6.00 | 6.00 | 6.00 | 6.00 |
| JLA5 | hmr-miR-451 | 7.43 | 9.12 | 9.14 | 7.74 | 7.56 | 7.28 |
| JLA201 | r-miR-421 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| JLA202 | m-miR-463 | 6.00 | 6.00 | 6.00 | 6.00 | 6.00 | 6.00 |
| JLA203 | m-miR-464 | 6.00 | 6.00 | 6.00 | 6.00 | 6.00 | 6.00 |
| JLA204 | m-miR-465 | 6.00 | 6.00 | 6.00 | 6.00 | 6.00 | 6.00 |
| JLA205 | m-miR-466 | 6.00 | 6.00 | 6.00 | 6.00 | 6.00 | 6.00 |
| JLA206 | m-miR-467 | 6.00 | 6.00 | 6.00 | 6.00 | 6.00 | 6.00 |
| JLA207 | m-miR-468 | 6.00 | 6.00 | 6.00 | 6.00 | 6.00 | 6.00 |
| JLA208 | m-miR-469 | 6.00 | 6.00 | 6.00 | 6.00 | 6.00 | 6.00 |
| JLA209 | m-miR-470 | 6.00 | 6.00 | 6.00 | 6.00 | 6.00 | 6.00 |
| JLA210 | m-miR-471 | 6.00 | 6.00 | 6.00 | 6.00 | 6.00 | 6.00 |
| EAM325 | hmr-miR-27a | 8.76 | 6.00 | 6.63 | 7.02 | 6.00 | 6.84 |
| EAM326 | hmr-miR-296 | 6.00 | 6.00 | 6.00 | 6.00 | 6.00 | 6.00 |
| EAM327 | hmr-miR-299-5p | 6.00 | 6.00 | 6.00 | 6.00 | 6.00 | 6.00 |
| EAM328 | hmr-miR-301 | 6.00 | 6.00 | 6.00 | 6.09 | 6.00 | 6.00 |
| EAM329 | hm-miR-302a | 6.00 | 6.00 | 6.00 | 6.00 | 6.00 | 6.00 |
| EAM330 | hmr-miR-30a-5p | 6.00 | 6.00 | 6.29 | 6.00 | 6.00 | 6.00 |
| EAM331 | hmr-miR-30e-5p | 6.00 | 6.00 | 7.02 | 6.00 | 6.00 | 6.00 |
| EAM332 | hmr-miR-31 | 6.00 | 6.00 | 6.00 | 6.00 | 6.00 | 6.00 |
| EAM333 | hmr-miR-32 | 6.00 | 6.00 | 6.00 | 6.00 | 6.00 | 6.00 |
| EAM335 | h-miR-34b | 6.00 | 6.00 | 6.00 | 6.00 | 6.00 | 6.00 |
| EAM336 | hmr-miR-34c | 6.00 | 6.00 | 6.00 | 6.00 | 6.00 | 6.00 |
| EAM337 | hmr-miR-93 | 7.91 | 6.00 | 9.76 | 9.69 | 8.17 | 8.93 |
| EAM208 | hmr-miR-141 | 6.00 | 6.00 | 6.00 | 6.00 | 6.00 | 6.00 |
| EAM207 | hmr-miR-140 | 6.00 | 6.00 | 6.00 | 6.00 | 6.00 | 6.00 |
| JLA222 | hmr-miR-139 | 6.00 | 6.00 | 6.00 | 6.00 | 6.00 | 6.00 |
| JLA220 | hmr-miR-138 | 6.00 | 6.00 | 6.00 | 6.00 | 6.00 | 6.00 |
| EAM203 | hmr-miR-135a | 6.00 | 6.00 | 6.00 | 6.00 | 6.00 | 6.00 |
| EAM200 | hmr-miR-133a | 6.99 | 6.00 | 6.00 | 6.00 | 6.00 | 6.00 |
| EAM195 | hmr-miR-128b | 6.00 | 6.00 | 6.00 | 6.00 | 6.00 | 6.00 |
| EAM194 | hmr-miR-128a | 6.00 | 6.00 | 6.00 | 6.00 | 6.00 | 6.00 |
| EAM254 | hmr-miR-219 | 6.00 | 6.00 | 6.00 | 6.00 | 6.00 | 6.00 |
| EAM257 | hmr-miR-221 | 8.97 | 8.93 | 6.00 | 6.00 | 6.00 | 6.00 |
| EAM258 | hmr-miR-222 | 8.78 | 6.00 | 6.00 | 6.83 | 6.00 | 6.00 |
| EAM259 | hmr-miR-223 | 9.19 | 8.58 | 8.02 | 8.85 | 6.64 | 9.70 |
| JLA211 | m-miR-434-5p | 6.00 | 6.00 | 6.00 | 6.00 | 6.00 | 6.00 |
| JLA212 | m-miR-434-3p | 6.00 | 6.00 | 6.00 | 6.00 | 6.00 | 6.00 |
| JLA213 | m-miR-433-5p | 6.00 | 6.00 | 6.00 | 6.00 | 6.00 | 6.00 |
| JLA2 | hsa-miR-522 | 6.00 | 6.00 | 6.00 | 6.00 | 6.00 | 6.00 |
| JLA3 | hsa-miR-495 | 6.00 | 6.00 | 6.00 | 6.00 | 6.00 | 6.00 |
| JLA200 | r-miR-297 | 6.00 | 6.00 | 6.00 | 6.00 | 6.00 | 6.00 |
| JLA6 | hsa-miR-518e | 6.00 | 6.00 | 6.00 | 6.00 | 6.00 | 6.00 |
| JLA7 | hsa-miR-519a | 6.00 | 6.00 | 6.00 | 6.00 | 6.00 | 6.00 |
| JLA8 | hsa-mir-527* | 6.00 | 6.00 | 6.00 | 6.00 | 6.00 | 6.00 |
| JLA72 | hmr-miR-140* | 8.06 | 6.00 | 6.93 | 7.57 | 6.48 | 6.93 |
| JLA10 | hsa-miR-521 | 6.00 | 6.00 | 6.00 | 6.00 | 6.00 | 6.00 |
| JLA12 | hsa-miR-362 | 6.00 | 6.00 | 6.00 | 6.00 | 6.00 | 6.00 |
| JLA74 | hsa-mir-18* | 6.39 | 6.00 | 6.00 | 6.00 | 6.00 | 6.00 |
| JLA14 | hm-miR-363 | 6.00 | 6.00 | 6.00 | 7.63 | 6.00 | 6.00 |
| JLA77 | hsa-mir-19b-1* | 6.00 | 6.00 | 6.00 | 6.00 | 6.00 | 6.00 |
| JLA17 | hsa-mir-520c,b,f | 6.00 | 6.00 | 6.00 | 6.00 | 6.00 | 6.00 |
| JLA79 | hsa-mir-23a* | 6.00 | 6.00 | 6.57 | 6.00 | 6.00 | 7.64 |
| JLA20 | hsa-miR-369-5p | 6.00 | 6.00 | 6.00 | 6.00 | 6.00 | 6.00 |
| JLA81 | hsa-mir-339* | 6.00 | 6.00 | 6.00 | 6.00 | 6.00 | 6.00 |
| JLA23 | hsa-mir-342* | 8.42 | 7.43 | 6.00 | 6.00 | 7.48 | 6.00 |
| JLA24 | hsa-mir-19a* | 6.00 | 6.00 | 6.00 | 6.00 | 6.00 | 6.00 |
| JLA26 | hsa-miR-517a,b | 6.00 | 6.00 | 6.00 | 6.00 | 6.00 | 6.00 |
| JLA27 | hsa-miR-516-5p | 6.00 | 6.00 | 6.00 | 6.00 | 6.00 | 6.00 |
| JLA28 | hsa-miR-518b | 6.00 | 6.00 | 6.00 | 6.00 | 6.00 | 6.00 |
| JLA29 | hsa-miR-519d | 6.00 | 6.00 | 6.00 | 6.00 | 6.00 | 6.00 |
| JLA73 | hr-mir-151* | 6.87 | 8.90 | 7.45 | 7.30 | 6.00 | 7.78 |
| JLA31 | hsa-mir-28* | 6.00 | 6.00 | 6.00 | 6.00 | 6.00 | 6.00 |
| JLA33 | hsa-mir-519a-2* | 6.00 | 6.00 | 6.00 | 6.00 | 6.00 | 6.00 |
| JLA34 | hsa-mir-26b* | 6.00 | 6.00 | 6.00 | 6.00 | 6.00 | 6.00 |
| JLA35 | hsa-miR-526c | 6.00 | 6.00 | 6.00 | 6.00 | 6.00 | 6.00 |
| JLA36 | hsa-miR-527 | 6.00 | 6.00 | 6.00 | 6.00 | 6.00 | 6.00 |
| JLA38 | hsa-mir-29b-2* | 6.00 | 6.00 | 6.00 | 6.00 | 6.00 | 6.00 |
| JLA39 | hsa-let-7g* | 6.00 | 6.00 | 6.00 | 6.00 | 6.00 | 6.00 |
| JLA40 | hsa-miR-518a | 6.00 | 6.00 | 6.00 | 6.00 | 6.00 | 6.00 |
| JLA41 | hsa-miR-523 | 6.00 | 6.00 | 6.00 | 6.00 | 6.00 | 6.00 |
| JLA44 | hsa-miR-515-3p | 6.00 | 6.00 | 6.00 | 6.00 | 6.00 | 6.00 |
| JLA45 | hsa-mir-146b* | 6.00 | 6.00 | 6.00 | 6.00 | 6.00 | 6.00 |
| JLA49 | hsa-mir-222* | 6.00 | 6.00 | 6.00 | 6.00 | 6.00 | 6.00 |
| JLA53 | hsa-mir-24* | 6.00 | 6.00 | 6.00 | 6.00 | 6.00 | 6.00 |
| JLA55 | hsa-miR-503 | 6.00 | 6.00 | 6.00 | 6.00 | 6.00 | 6.00 |
| JLA57 | hsa-mir-505 | 6.00 | 6.00 | 6.00 | 6.00 | 6.00 | 6.00 |

TABLE 6-continued

Normalized miRNA expression profiling data for MEP, ERY and MEGA samples Data were normalized, log2-transformed and thresholded at 6. Readings for samples are in columns and readings for miRNAs are in rows. Due to page limitation, every page lists only a subset of samples and miRNAs. The data will also be available online.

| | | | | | | | |
|---|---|---|---|---|---|---|---|
| JLA82 | hsa-mir-423* | 11.38 | 12.04 | 10.39 | 11.13 | 9.84 | 11.00 |
| JLA66 | hsa-miR-432 | 6.00 | 6.00 | 6.00 | 6.00 | 6.00 | 6.00 |
| JLA83 | hsa-mir-425* | 6.51 | 6.00 | 6.89 | 7.58 | 6.00 | 8.04 |
| JLA84 | hsa-mir-92-1* | 6.00 | 6.00 | 6.00 | 6.00 | 6.00 | 6.00 |
| JLA69 | hsa-mir-193* | 6.00 | 6.00 | 6.00 | 6.00 | 6.00 | 6.00 |
| JLA70 | hsa-miR-515-5p | 6.00 | 6.00 | 6.00 | 6.00 | 6.00 | 6.00 |
| JLA71 | hsa-mir-516-1* | 6.00 | 6.00 | 6.00 | 6.00 | 6.00 | 6.00 |
| JLA85 | hsa-mir-30d* | 6.00 | 6.00 | 6.00 | 6.00 | 6.00 | 6.00 |
| JLA125 | h-miR-20b | 8.72 | 8.40 | 8.95 | 9.35 | 10.04 | 9.35 |
| JLA198 | h-miR-191* | 6.36 | 6.15 | 6.00 | 6.00 | 7.19 | 6.00 |
| JLA199 | h-miR-154* | 6.00 | 6.00 | 6.00 | 6.00 | 6.00 | 6.00 |
| EAM316 | h-miR-147 | 6.00 | 6.00 | 6.00 | 6.00 | 6.00 | 6.00 |
| EAM317 | h-miR-155 | 6.00 | 6.00 | 8.82 | 7.46 | 6.00 | 8.90 |
| EAM318 | h-miR-17-3p | 6.00 | 6.00 | 6.00 | 6.00 | 6.00 | 6.00 |
| JLA195 | h-miR-200a* | 6.00 | 6.00 | 6.00 | 6.00 | 6.00 | 6.00 |
| JLA196 | h-miR-302a* | 6.00 | 6.00 | 6.00 | 6.00 | 6.00 | 6.00 |
| JLA197 | h-miR-299-3p | 6.23 | 6.00 | 6.00 | 6.00 | 6.00 | 7.60 |
| EAM319 | h-miR-182* | 6.00 | 6.00 | 6.00 | 6.00 | 6.00 | 6.00 |
| EAM405 | h-miR-302b | 6.00 | 6.00 | 6.00 | 6.00 | 6.00 | 6.19 |
| EAM406 | h-miR-302b* | 6.00 | 6.00 | 6.00 | 6.00 | 6.00 | 6.00 |
| EAM392 | r-miR-352 | 8.32 | 7.78 | 8.00 | 8.07 | 8.34 | 8.37 |
| JLA123 | h-miR-423 | 6.00 | 6.00 | 6.00 | 6.00 | 6.00 | 6.00 |
| JLA124 | h-miR-18b | 6.00 | 6.00 | 6.00 | 6.00 | 6.00 | 6.00 |

What is claimed:

1. A method of treating anemia in a host in need thereof, the method comprising administering an effective amount of an agent that inhibits miR-150 in a cell to a host, wherein the agent is a nucleic acid sequence that is at least 90% identical to SEQ. ID. No. 3.

2. The method of claim 1, wherein the cell is a progenitor cell.

3. The method of claim 2, wherein the progenitor cell is a hematopoietic progenitor cell.

4. The method of claim 1, wherein the agent is an antagomir of miR-150, an anti-miR-150 oligonucleotide, an antisense oligonucleotide to miR-150 or a locked nucleic acid that anneals to miR-150.

5. A method of treating anemia in a host in need thereof, the method comprising:
   a. obtaining a sample of hematopoietic progenitor cells from said host;
   b. contacting the hematopoietic progenitor cells with a vector comprising a nucleic acid sequence that is at least 90% identical to SEQ. ID. No. 3; and
   c. introducing the cell from step b into the same host.

* * * * *

UNITED STATES PATENT AND TRADEMARK OFFICE
CERTIFICATE OF CORRECTION

| | | Page 1 of 1 |
|---|---|---|
| PATENT NO. | : 8,530,443 B2 | |
| APPLICATION NO. | : 13/652672 | |
| DATED | : September 10, 2013 | |
| INVENTOR(S) | : Lu et al. | |

It is certified that error appears in the above-identified patent and that said Letters Patent is hereby corrected as shown below:

In the Specification

Please replace Column 1, Lines 18 - 20:

GOVERNMENT SUPPORT

"This invention was made with Government support under No. 219335 awarded by the National Institute of Health. The Government has certain rights in the invention."

with the following text which should read:

--This invention was made with Government support under Grant No. HL081030 awarded by the National Institutes of Health. The government has certain rights in this invention.--

Signed and Sealed this
Twenty-ninth Day of July, 2014

Michelle K. Lee
*Deputy Director of the United States Patent and Trademark Office*